(12) United States Patent
Yao et al.

US010813930B2

(10) Patent No.: US 10,813,930 B2
(45) Date of Patent: Oct. 27, 2020

(54) SUBSTITUTED IMIDAZOPYRIDAZINES AND BENZIMIDAZOLES AS INHIBITORS OF FGFR3

(71) Applicants: Incyte Corporation, Wilmington, DE (US); Incyte Holdings Corporation, Wilmington, DE (US)

(72) Inventors: Wenqing Yao, Chadds Ford, PA (US); Colin Zhang, Berwyn, PA (US); Meizhong Xu, Hockessin, DE (US); Jincong Zhuo, Garnet Valley, PA (US); Chunhong He, Boothwyn, PA (US)

(73) Assignees: Incyte Corporation, Wilmington, DE (US); Incyte Holdings Corporation, Wilmington, DE (US)

( * ) Notice: Subject to any disclaimer, the term of this patent is extended or adjusted under 35 U.S.C. 154(b) by 0 days.

(21) Appl. No.: 16/238,277

(22) Filed: Jan. 2, 2019

(65) Prior Publication Data

US 2019/0240220 A1    Aug. 8, 2019

Related U.S. Application Data

(60) Continuation of application No. 15/359,012, filed on Nov. 22, 2016, now Pat. No. 10,213,427, which is a division of application No. 14/267,139, filed on May 1, 2014, now Pat. No. 9,533,954, which is a continuation of application No. 13/333,021, filed on Dec. 21, 2011, now Pat. No. 8,754,114.

(60) Provisional application No. 61/426,273, filed on Dec. 22, 2010.

(51) Int. Cl.
| C07D 401/12 | (2006.01) |
| A61K 31/5025 | (2006.01) |
| C07D 401/14 | (2006.01) |
| C07D 403/12 | (2006.01) |
| C07D 405/12 | (2006.01) |
| C07D 405/14 | (2006.01) |
| C07D 407/12 | (2006.01) |
| C07D 487/04 | (2006.01) |
| C07D 235/06 | (2006.01) |
| C07D 403/04 | (2006.01) |
| A61K 31/5377 | (2006.01) |

(52) U.S. Cl.
CPC ...... *A61K 31/5025* (2013.01); *A61K 31/5377* (2013.01); *C07D 235/06* (2013.01); *C07D 401/12* (2013.01); *C07D 401/14* (2013.01); *C07D 403/04* (2013.01); *C07D 403/12* (2013.01); *C07D 405/12* (2013.01); *C07D 405/14* (2013.01); *C07D 407/12* (2013.01); *C07D 487/04* (2013.01)

(58) Field of Classification Search
CPC .................................................. A61K 31/5025
See application file for complete search history.

(56) References Cited

U.S. PATENT DOCUMENTS

| 850,370 A | 4/1907 | Hynes |
| 3,894,021 A | 7/1975 | Denzel et al. |
| 4,271,074 A | 6/1981 | Lohmann et al. |
| 4,339,267 A | 7/1982 | Levitt |
| 4,347,348 A | 8/1982 | Chernikhov et al. |
| 4,402,878 A | 9/1983 | D'Alelio et al. |
| 4,405,519 A | 9/1983 | D'Alelio et al. |
| 4,405,520 A | 9/1983 | D'Alelio et al. |
| 4,405,786 A | 9/1983 | D'Alelio et al. |
| 4,460,773 A | 7/1984 | Suzuki et al. |
| 4,874,803 A | 10/1989 | Baron et al. |
| 4,940,705 A | 7/1990 | Boshagen et al. |
| 5,159,054 A | 10/1992 | Keller |
| 5,240,941 A | 8/1993 | Bruneau |
| 5,480,887 A | 1/1996 | Hornback et al. |
| 5,536,725 A | 7/1996 | Cullen et al. |
| 5,541,324 A | 7/1996 | TenBrink et al. |
| 5,783,577 A | 7/1998 | Houghten et al. |
| 5,845,025 A | 12/1998 | Garito et al. |
| 5,994,364 A | 11/1999 | Njoroge et al. |
| 6,465,484 B1 | 10/2002 | Bilodeau et al. |
| 6,998,408 B2 | 2/2006 | Pinto |
| 7,074,801 B1 | 7/2006 | Yoshida et al. |
| 7,125,880 B1 | 10/2006 | Chen |
| 7,618,975 B2 | 11/2009 | Cai et al. |
| 7,642,255 B2 | 1/2010 | Sim |
| 8,754,114 B2 | 6/2014 | Yao et al. |
| 8,889,711 B2 | 11/2014 | Bedjeguelal |
| 9,266,892 B2 | 2/2016 | Zhuo et al. |
| 9,388,185 B2 | 7/2016 | Lu et al. |
| 9,533,954 B2 | 1/2017 | Yao et al. |
| 9,533,984 B2 | 1/2017 | Sun et al. |
| 9,580,423 B2 | 2/2017 | Lu et al. |
| 9,611,267 B2 | 4/2017 | Wu et al. |
| 9,708,318 B2 | 7/2017 | Lu et al. |
| 9,745,311 B2 | 8/2017 | Lu et al. |
| 9,801,889 B2 | 10/2017 | Lu et al. |
| 9,890,156 B2 | 2/2018 | Lu et al. |
| 10,016,348 B2 | 7/2018 | Lu et al. |
| 10,040,790 B2 | 8/2018 | Sun et al. |
| 10,131,667 B2 | 11/2018 | Wu et al. |
| 10,213,427 B2 | 2/2019 | Yao et al. |
| 10,214,528 B2 | 2/2019 | Lu et al. |
| 10,251,892 B2 | 4/2019 | Sokolsky et al. |
| 10,450,313 B2 | 10/2019 | Lu et al. |

(Continued)

FOREIGN PATENT DOCUMENTS

| CL | 2014003355 | 6/2015 |
| CL | 201702117 | 6/2018 |

(Continued)

OTHER PUBLICATIONS

McMahon et al. (2000).*

(Continued)

*Primary Examiner* — Paul V Ward
(74) *Attorney, Agent, or Firm* — Fish & Richardson P.C.

(57) ABSTRACT

The present invention relates to substituted imidazopyridazines and substituted benzimidazoles, as well as pharmaceutical compositions comprising the same, which are FGFR3 inhibitors useful in the treatment of cancer and other diseases.

42 Claims, No Drawings

(56) References Cited

U.S. PATENT DOCUMENTS

| | | |
|---|---|---|
| 2003/0078255 A1 | 4/2003 | Pinto |
| 2003/0078277 A1 | 4/2003 | Hibi et al. |
| 2003/0181622 A1 | 9/2003 | Chin et al. |
| 2004/0044012 A1 | 3/2004 | Dobrusin et al. |
| 2004/0067948 A1 | 4/2004 | Hallett |
| 2004/0097493 A1 | 5/2004 | Chen et al. |
| 2004/0122029 A1 | 6/2004 | Liu et al. |
| 2004/0204427 A1 | 10/2004 | Chen et al. |
| 2005/0070542 A1 | 3/2005 | Hodgetts et al. |
| 2005/0148603 A1 | 7/2005 | Jimenez et al. |
| 2005/0197340 A1 | 9/2005 | Arora et al. |
| 2006/0222637 A1 | 10/2006 | Bamdad |
| 2006/0270849 A1 | 11/2006 | Nishino et al. |
| 2007/0116984 A1 | 5/2007 | Park et al. |
| 2007/0197510 A1 | 8/2007 | Ohmoto et al. |
| 2007/0280943 A1 | 12/2007 | Friedman et al. |
| 2008/0249301 A1 | 10/2008 | Hornberger et al. |
| 2009/0098086 A1 | 4/2009 | Zask et al. |
| 2009/0099165 A1 | 4/2009 | Hurley et al. |
| 2009/0099190 A1 | 4/2009 | Flynn et al. |
| 2009/0105233 A1 | 4/2009 | Chua et al. |
| 2009/0131467 A1 | 5/2009 | Kanazawa et al. |
| 2009/0163545 A1 | 6/2009 | Goldfarb |
| 2009/0246198 A1 | 10/2009 | Dong et al. |
| 2010/0032626 A1 | 2/2010 | Akino |
| 2010/0099684 A1 | 4/2010 | Cook, II et al. |
| 2010/0105661 A1 | 4/2010 | Shirakami et al. |
| 2010/0143547 A1 | 6/2010 | Kriegel et al. |
| 2010/0204235 A1 | 8/2010 | Lizos |
| 2010/0210636 A1 | 8/2010 | Ishikawa et al. |
| 2010/0239496 A1 | 9/2010 | Gangadharmath et al. |
| 2011/0045511 A1 | 2/2011 | Graus Porta et al. |
| 2011/0159604 A1 | 6/2011 | Fan et al. |
| 2011/0160203 A1 | 6/2011 | Liu et al. |
| 2011/0195968 A1 | 8/2011 | Greul et al. |
| 2011/0212077 A1 | 9/2011 | Noronha et al. |
| 2011/0224155 A1 | 9/2011 | Tachdjian et al. |
| 2011/0262525 A1 | 10/2011 | Wang et al. |
| 2011/0313003 A1 | 12/2011 | Shi et al. |
| 2012/0135997 A1 | 5/2012 | Kato et al. |
| 2012/0165305 A1 | 6/2012 | Yao et al. |
| 2012/0295881 A1 | 11/2012 | Lange et al. |
| 2012/0319095 A1 | 12/2012 | Tada et al. |
| 2013/0078731 A1 | 3/2013 | George et al. |
| 2013/0200356 A1 | 8/2013 | Jung et al. |
| 2013/0338134 A1 | 12/2013 | Wu et al. |
| 2014/0045814 A1 | 2/2014 | Lu et al. |
| 2014/0054564 A1 | 2/2014 | Kim et al. |
| 2014/0080892 A1 | 3/2014 | Bhanot et al. |
| 2014/0088100 A1 | 3/2014 | Bifulco, Jr. et al. |
| 2014/0103325 A1 | 4/2014 | Shin et al. |
| 2014/0117318 A1 | 5/2014 | Choi et al. |
| 2014/0148548 A1 | 5/2014 | Yamanaka et al. |
| 2014/0171405 A1 | 6/2014 | Zhuo et al. |
| 2014/0187559 A1 | 7/2014 | Miduturu |
| 2014/0243308 A1 | 8/2014 | Yao et al. |
| 2014/0296233 A1 | 10/2014 | D'Agostino et al. |
| 2014/0315902 A1 | 10/2014 | Sun et al. |
| 2014/0374722 A1 | 12/2014 | Kim et al. |
| 2014/0378468 A1 | 12/2014 | Aichholz et al. |
| 2014/0378481 A1 | 12/2014 | Bifulco, Jr. et al. |
| 2014/0378483 A1 | 12/2014 | Benazet et al. |
| 2015/0011548 A1 | 1/2015 | Linnanen et al. |
| 2015/0011560 A1 | 1/2015 | Legeai-Mallet |
| 2015/0011579 A1 | 1/2015 | Clary-Ceccato et al. |
| 2015/0197519 A1 | 7/2015 | Bifulco |
| 2016/0115164 A1 | 4/2016 | Wu et al. |
| 2016/0244448 A1 | 8/2016 | Lu et al. |
| 2016/0244449 A1 | 8/2016 | Lu et al. |
| 2016/0244450 A1 | 8/2016 | Lu et al. |
| 2016/0280713 A1 | 9/2016 | Lu et al. |
| 2017/0107216 A1 | 4/2017 | Wu et al. |
| 2017/0119782 A1 | 5/2017 | Lu et al. |
| 2017/0137424 A1 | 5/2017 | Wu et al. |
| 2017/0145025 A1 | 5/2017 | Li et al. |
| 2017/0165263 A1 | 6/2017 | Yao et al. |
| 2017/0166564 A1 | 6/2017 | Sun et al. |
| 2017/0174671 A1 | 6/2017 | Wu et al. |
| 2017/0174679 A1 | 6/2017 | Lajkiewicz et al. |
| 2017/0290839 A1 | 10/2017 | Lu et al. |
| 2017/0320875 A1 | 11/2017 | Li et al. |
| 2017/0320877 A1 | 11/2017 | Wu et al. |
| 2017/0342060 A1 | 11/2017 | Lu et al. |
| 2017/0362253 A1 | 12/2017 | Xiao et al. |
| 2018/0008610 A1 | 1/2018 | Lu et al. |
| 2018/0016260 A1 | 1/2018 | Yu et al. |
| 2018/0244672 A1 | 8/2018 | Lu et al. |
| 2019/0055237 A1 | 2/2019 | Pan et al. |
| 2019/0062327 A1 | 2/2019 | Sun et al. |
| 2019/0127376 A1 | 5/2019 | Wu et al. |
| 2019/0241560 A1 | 8/2019 | Lu et al. |
| 2019/0269693 A1 | 9/2019 | Lu et al. |
| 2019/0284187 A1 | 9/2019 | Wu et al. |
| 2019/0337948 A1 | 11/2019 | Frietze et al. |

FOREIGN PATENT DOCUMENTS

| | | |
|---|---|---|
| CN | 1863774 | 11/2006 |
| CN | 101007778 | 8/2007 |
| CN | 102399220 | 4/2012 |
| CN | 102399233 | 4/2012 |
| CN | 103571502 | 2/2014 |
| CN | 103588771 | 2/2014 |
| CN | 104262330 | 1/2015 |
| DE | 2156720 | 5/1973 |
| DE | 2934578 | 3/1981 |
| DE | 3432983 | 4/1985 |
| DE | 280853 | 7/1990 |
| DE | 3937633 | 5/1991 |
| DE | 4119767 | 12/1992 |
| DE | 19912638 | 9/2000 |
| EP | 0466452 | 1/1992 |
| EP | 0995751 | 4/2000 |
| EP | 1199070 | 4/2002 |
| EP | 1217000 | 6/2002 |
| EP | 1388541 | 2/2004 |
| EP | 2651404 | 10/2015 |
| FR | 2428654 | 1/1980 |
| FR | 2876582 | 4/2006 |
| FR | 2983196 | 5/2013 |
| FR | 2983199 | 5/2013 |
| FR | 2983200 | 5/2013 |
| JP | 62273979 | 11/1987 |
| JP | 63017882 | 1/1988 |
| JP | S 6310630 | 1/1988 |
| JP | 02009895 | 1/1990 |
| JP | H 0348656 | 3/1991 |
| JP | H 03275669 | 12/1991 |
| JP | 04179576 | 6/1992 |
| JP | H 04158084 | 6/1992 |
| JP | H 04328121 | 11/1992 |
| JP | H 05320173 | 12/1993 |
| JP | H 05320515 | 12/1993 |
| JP | H 09188812 | 7/1997 |
| JP | H 1060426 | 3/1998 |
| JP | H 11171865 | 6/1999 |
| JP | 2000123973 | 4/2000 |
| JP | 2001265031 | 9/2001 |
| JP | 2002516327 | 6/2002 |
| JP | 2002296731 | 10/2002 |
| JP | 2003335788 | 11/2003 |
| JP | 2004203749 | 7/2004 |
| JP | 2004346145 | 12/2004 |
| JP | 2005015395 | 1/2005 |
| JP | 2005320288 | 11/2005 |
| JP | 200628027 | 2/2006 |
| JP | 2006514624 | 5/2006 |
| JP | 2006284843 | 10/2006 |
| JP | 2006522756 | 10/2006 |
| JP | 2006316054 | 11/2006 |
| JP | 2007500725 | 1/2007 |
| JP | 2008198769 | 8/2008 |
| JP | 2009537520 | 10/2009 |

(56) References Cited

FOREIGN PATENT DOCUMENTS

| | | |
|---|---|---|
| JP | 2010180147 | 8/2010 |
| JP | 2010248429 | 11/2010 |
| JP | 2010267847 | 11/2010 |
| JP | 2010270245 | 12/2010 |
| JP | 2010272618 | 12/2010 |
| JP | 2010272727 | 12/2010 |
| JP | 2010278114 | 12/2010 |
| JP | 20119348 | 1/2011 |
| JP | 201144637 | 3/2011 |
| JP | 2011116840 | 6/2011 |
| JP | 2011222650 | 11/2011 |
| JP | 2012116825 | 6/2012 |
| JP | 2012136476 | 7/2012 |
| JP | 5120580 | 1/2013 |
| JP | 201349251 | 3/2013 |
| JP | 2013179181 | 9/2013 |
| JP | 2015517376 | 6/2015 |
| JP | 2018507214 | 3/2018 |
| JP | 2018511573 | 4/2018 |
| KR | 20080045536 | 5/2008 |
| KR | 20110023190 | 3/2011 |
| KR | 20110043270 | 4/2011 |
| KR | 20120052034 | 5/2012 |
| KR | 20120078303 | 7/2012 |
| KR | 20130043460 | 4/2013 |
| KR | 20140090411 | 7/2014 |
| KR | 20140099105 | 8/2014 |
| WO | WO 1988/03025 | 5/1988 |
| WO | WO 1991/09835 | 7/1991 |
| WO | WO 1991/10172 | 7/1991 |
| WO | WO 1992/06078 | 4/1992 |
| WO | WO 1992/22552 | 12/1992 |
| WO | WO 1993/24488 | 12/1993 |
| WO | WO 1994/13669 | 6/1994 |
| WO | WO 1994/15995 | 7/1994 |
| WO | WO 1994/25438 | 11/1994 |
| WO | WO 1995/20965 | 8/1995 |
| WO | WO 1996/15128 | 5/1996 |
| WO | WO 1996/40707 | 12/1996 |
| WO | WO 1997/47601 | 12/1997 |
| WO | WO 1998/05661 | 2/1998 |
| WO | WO 1998/06703 | 2/1998 |
| WO | WO 1998/11438 | 3/1998 |
| WO | WO 1998/18781 | 5/1998 |
| WO | WO 1998/28281 | 7/1998 |
| WO | WO 1998/33798 | 8/1998 |
| WO | WO 1998/46609 | 10/1998 |
| WO | WO 1998/54156 | 12/1998 |
| WO | WO 1999/06422 | 2/1999 |
| WO | WO 1999/07732 | 2/1999 |
| WO | WO 1999/09030 | 2/1999 |
| WO | WO 1999/42442 | 8/1999 |
| WO | WO 1999/59975 | 11/1999 |
| WO | WO 1999/61444 | 12/1999 |
| WO | WO 1999/64400 | 12/1999 |
| WO | WO 2000/24744 | 5/2000 |
| WO | WO 2000/68186 | 11/2000 |
| WO | WO 2001/02369 | 1/2001 |
| WO | WO 2001/22938 | 4/2001 |
| WO | WO 2001/23386 | 4/2001 |
| WO | WO 2001/29041 | 4/2001 |
| WO | WO 2001/29042 | 4/2001 |
| WO | WO 2001/42247 | 6/2001 |
| WO | WO 2001/47892 | 7/2001 |
| WO | WO 2001/53273 | 7/2001 |
| WO | WO 2001/55148 | 8/2001 |
| WO | WO 2001/57037 | 8/2001 |
| WO | WO 2001/57038 | 8/2001 |
| WO | WO 2001/58899 | 8/2001 |
| WO | WO 2001/66099 | 9/2001 |
| WO | WO 2001/68647 | 9/2001 |
| WO | WO 2001/83472 | 11/2001 |
| WO | WO 2001/85722 | 11/2001 |
| WO | WO 2002/00655 | 1/2002 |
| WO | WO 2002/12442 | 2/2002 |
| WO | WO 2002/14315 | 2/2002 |
| WO | WO 2002/20011 | 3/2002 |
| WO | WO 2002/051831 | 7/2002 |
| WO | WO 2002/055082 | 7/2002 |
| WO | WO 2002/066481 | 8/2002 |
| WO | WO 2002/74754 | 9/2002 |
| WO | WO 2002/076953 | 10/2002 |
| WO | WO 2002/088095 | 11/2002 |
| WO | WO 2002/094825 | 11/2002 |
| WO | WO 2002/096873 | 12/2002 |
| WO | WO 2002/102793 | 12/2002 |
| WO | WO 2003/000187 | 1/2003 |
| WO | WO 2003/000688 | 1/2003 |
| WO | WO 2003/000690 | 1/2003 |
| WO | WO 2003/009852 | 2/2003 |
| WO | WO 2003/014083 | 2/2003 |
| WO | WO 2003/037891 | 5/2003 |
| WO | WO 2003/040131 | 5/2003 |
| WO | WO 2003/049542 | 6/2003 |
| WO | WO 2003/062236 | 7/2003 |
| WO | WO 2003/075836 | 9/2003 |
| WO | WO 2003/082871 | 10/2003 |
| WO | WO 2003/097609 | 11/2003 |
| WO | WO 2003/099818 | 12/2003 |
| WO | WO 2003/101985 | 12/2003 |
| WO | WO 2004/002986 | 1/2004 |
| WO | WO 2004/011465 | 2/2004 |
| WO | WO 2004/014382 | 2/2004 |
| WO | WO 2004/014907 | 2/2004 |
| WO | WO 2004/018472 | 3/2004 |
| WO | WO 2004/020441 | 3/2004 |
| WO | WO 2004/041821 | 5/2004 |
| WO | WO 2004/041822 | 5/2004 |
| WO | WO 2004/041823 | 5/2004 |
| WO | WO 2004/043367 | 5/2004 |
| WO | WO 2004/046152 | 6/2004 |
| WO | WO 2004/048343 | 6/2004 |
| WO | WO 2004/052291 | 6/2004 |
| WO | WO 2004/052862 | 6/2004 |
| WO | WO 2004/056822 | 7/2004 |
| WO | WO 2004/056830 | 7/2004 |
| WO | WO 2004/065378 | 8/2004 |
| WO | WO 2004/083177 | 9/2004 |
| WO | WO 2004/087053 | 10/2004 |
| WO | WO 2004/089955 | 10/2004 |
| WO | WO 2004/094420 | 11/2004 |
| WO | WO 2004/099209 | 11/2004 |
| WO | WO 2004/108139 | 11/2004 |
| WO | WO 2004/110487 | 12/2004 |
| WO | WO 2004/112793 | 12/2004 |
| WO | WO 2004/113307 | 12/2004 |
| WO | WO 2005/007653 | 1/2005 |
| WO | WO 2005/011597 | 2/2005 |
| WO | WO 2005/021533 | 3/2005 |
| WO | WO 2005/028434 | 3/2005 |
| WO | WO 2005/028478 | 3/2005 |
| WO | WO 2005/028480 | 3/2005 |
| WO | WO 2005/040119 | 5/2005 |
| WO | WO 2005/047289 | 5/2005 |
| WO | WO 2005/056524 | 6/2005 |
| WO | WO 2005/063768 | 6/2005 |
| WO | WO 2005/066162 | 7/2005 |
| WO | WO 2005/070430 | 8/2005 |
| WO | WO 2005/070929 | 8/2005 |
| WO | WO 2005/072412 | 8/2005 |
| WO | WO 2005/073232 | 8/2005 |
| WO | WO 2005/080393 | 9/2005 |
| WO | WO 2005/082903 | 9/2005 |
| WO | WO 2005/085210 | 9/2005 |
| WO | WO 2005/085248 | 9/2005 |
| WO | WO 2005/085249 | 9/2005 |
| WO | WO 2005/087765 | 9/2005 |
| WO | WO 2005/092901 | 10/2005 |
| WO | WO 2005/105097 | 11/2005 |
| WO | WO 2005/113536 | 12/2005 |
| WO | WO 2005/116035 | 12/2005 |
| WO | WO 2005/121130 | 12/2005 |
| WO | WO 2005/121142 | 12/2005 |
| WO | WO 2006/000420 | 1/2006 |

(56) References Cited

FOREIGN PATENT DOCUMENTS

| | | |
|---|---|---|
| WO | WO 2006/024486 | 3/2006 |
| WO | WO 2006/024487 | 3/2006 |
| WO | WO 2006/024834 | 3/2006 |
| WO | WO 2006/028289 | 3/2006 |
| WO | WO 2006/030031 | 3/2006 |
| WO | WO 2006/038112 | 4/2006 |
| WO | WO 2006/050076 | 5/2006 |
| WO | WO 2006/050162 | 5/2006 |
| WO | WO 2006/052712 | 5/2006 |
| WO | WO 2006/055752 | 5/2006 |
| WO | WO 2006/024524 | 6/2006 |
| WO | WO 2006/058120 | 6/2006 |
| WO | WO 2006/062465 | 6/2006 |
| WO | WO 2006/065703 | 6/2006 |
| WO | WO 2006/074293 | 7/2006 |
| WO | WO 2006/087230 | 8/2006 |
| WO | WO 2006/092691 | 9/2006 |
| WO | WO 2006/102588 | 9/2006 |
| WO | WO 2006/102610 | 9/2006 |
| WO | WO 2006/105448 | 10/2006 |
| WO | WO 2006/107644 | 10/2006 |
| WO | WO 2006/112666 | 10/2006 |
| WO | WO 2006/119504 | 11/2006 |
| WO | WO 2006/124462 | 11/2006 |
| WO | WO 2006/124731 | 11/2006 |
| WO | WO 2006/135821 | 12/2006 |
| WO | WO 2006/136442 | 12/2006 |
| WO | WO 2007/013964 | 2/2007 |
| WO | WO 2007/017096 | 2/2007 |
| WO | WO 2007/021795 | 2/2007 |
| WO | WO 2007/022268 | 2/2007 |
| WO | WO 2007/023105 | 3/2007 |
| WO | WO 2007/025949 | 3/2007 |
| WO | WO 2007/030366 | 3/2007 |
| WO | WO 2007/032466 | 3/2007 |
| WO | WO 2007/033780 | 3/2007 |
| WO | WO 2007/038209 | 4/2007 |
| WO | WO 2007/044698 | 4/2007 |
| WO | WO 2007/044729 | 4/2007 |
| WO | WO 2007/048802 | 5/2007 |
| WO | WO 2007/053135 | 5/2007 |
| WO | WO 2007/053452 | 5/2007 |
| WO | WO 2007/053498 | 5/2007 |
| WO | WO 2007/055418 | 5/2007 |
| WO | WO 2007/056023 | 5/2007 |
| WO | WO 2007/056075 | 5/2007 |
| WO | WO 2007/056170 | 5/2007 |
| WO | WO 2007/058392 | 5/2007 |
| WO | WO 2007/058626 | 5/2007 |
| WO | WO 2007/059108 | 5/2007 |
| WO | WO 2007/061554 | 5/2007 |
| WO | WO 2007/064883 | 6/2007 |
| WO | WO 2007/064931 | 6/2007 |
| WO | WO 2007/066189 | 6/2007 |
| WO | WO 2007/067444 | 6/2007 |
| WO | WO 2007/071752 | 6/2007 |
| WO | WO 2007/084314 | 7/2007 |
| WO | WO 2007/088999 | 8/2007 |
| WO | WO 2007/092879 | 8/2007 |
| WO | WO 2007/093901 | 8/2007 |
| WO | WO 2007/109334 | 9/2007 |
| WO | WO 2007/110868 | 10/2007 |
| WO | WO 2007/112347 | 10/2007 |
| WO | WO 2007/120097 | 10/2007 |
| WO | WO 2007/120339 | 10/2007 |
| WO | WO 2007/125351 | 11/2007 |
| WO | WO 2007/125405 | 11/2007 |
| WO | WO 2007/126841 | 11/2007 |
| WO | WO 2007/134259 | 11/2007 |
| WO | WO 2007/136465 | 11/2007 |
| WO | WO 2007/140957 | 12/2007 |
| WO | WO 2007/143600 | 12/2007 |
| WO | WO 2007/147217 | 12/2007 |
| WO | WO 2008/001070 | 1/2008 |
| WO | WO 2008/003766 | 1/2008 |
| WO | WO 2008/005877 | 1/2008 |
| WO | WO 2008/008234 | 1/2008 |
| WO | WO 2008/008747 | 1/2008 |
| WO | WO 2008/012635 | 1/2008 |
| WO | WO 2008/021389 | 2/2008 |
| WO | WO 2008/021851 | 2/2008 |
| WO | WO 2008/025556 | 3/2008 |
| WO | WO 2008/033858 | 3/2008 |
| WO | WO 2008/033999 | 3/2008 |
| WO | WO 2008/034859 | 3/2008 |
| WO | WO 2008/034860 | 3/2008 |
| WO | WO 2008/042639 | 4/2008 |
| WO | WO 2008/052898 | 5/2008 |
| WO | WO 2008/052934 | 5/2008 |
| WO | WO 2008/060907 | 5/2008 |
| WO | WO 2008/063583 | 5/2008 |
| WO | WO 2008/063609 | 5/2008 |
| WO | WO 2008/071455 | 6/2008 |
| WO | WO 2008/074068 | 6/2008 |
| WO | WO 2008/075068 | 6/2008 |
| WO | WO 2008/076278 | 6/2008 |
| WO | WO 2008/078091 | 7/2008 |
| WO | WO 2008/078100 | 7/2008 |
| WO | WO 2008/079460 | 7/2008 |
| WO | WO 2008/079933 | 7/2008 |
| WO | WO 2008/085942 | 7/2008 |
| WO | WO 2008/089105 | 7/2008 |
| WO | WO 2008/099075 | 8/2008 |
| WO | WO 2008/107436 | 9/2008 |
| WO | WO 2008/107544 | 9/2008 |
| WO | WO 2008/109181 | 9/2008 |
| WO | WO 2008/109943 | 9/2008 |
| WO | WO 2008/115974 | 9/2008 |
| WO | WO 2008/117269 | 10/2008 |
| WO | WO 2008/118454 | 10/2008 |
| WO | WO 2008/123755 | 10/2008 |
| WO | WO 2008/128141 | 10/2008 |
| WO | WO 2008/130584 | 10/2008 |
| WO | WO 2008/131972 | 11/2008 |
| WO | WO 2008/141065 | 11/2008 |
| WO | WO 2008/142720 | 11/2008 |
| WO | WO 2008/144253 | 11/2008 |
| WO | WO 2008/151184 | 12/2008 |
| WO | WO 2008/153207 | 12/2008 |
| WO | WO 2008/153852 | 12/2008 |
| WO | WO 2008/154221 | 12/2008 |
| WO | WO 2009/013335 | 1/2009 |
| WO | WO 2009/013354 | 1/2009 |
| WO | WO 2009/097446 | 1/2009 |
| WO | WO 2009/016253 | 2/2009 |
| WO | WO 2009/019518 | 2/2009 |
| WO | WO 2009/021083 | 2/2009 |
| WO | WO 2009/029473 | 3/2009 |
| WO | WO 2009/029625 | 3/2009 |
| WO | WO 2009/030871 | 3/2009 |
| WO | WO 2009/032861 | 3/2009 |
| WO | WO 2009/036012 | 3/2009 |
| WO | WO 2009/044788 | 4/2009 |
| WO | WO 2009/046606 | 4/2009 |
| WO | WO 2009/047255 | 4/2009 |
| WO | WO 2009/047506 | 4/2009 |
| WO | WO 2009/047522 | 4/2009 |
| WO | WO 2009/047993 | 4/2009 |
| WO | WO 2009/049018 | 4/2009 |
| WO | WO 2009/053737 | 4/2009 |
| WO | WO 2009/055828 | 4/2009 |
| WO | WO 2009/056886 | 5/2009 |
| WO | WO 2009/071535 | 6/2009 |
| WO | WO 2009/073153 | 6/2009 |
| WO | WO 2009/086130 | 7/2009 |
| WO | WO 2009/086509 | 7/2009 |
| WO | WO 2009/087238 | 7/2009 |
| WO | WO 2009/092764 | 7/2009 |
| WO | WO 2009/093209 | 7/2009 |
| WO | WO 2009/093210 | 7/2009 |
| WO | WO 2009/094528 | 7/2009 |
| WO | WO 2009/099982 | 8/2009 |
| WO | WO 2009/103652 | 8/2009 |
| WO | WO 2009/105717 | 8/2009 |

(56) References Cited

FOREIGN PATENT DOCUMENTS

| | | |
|---|---|---|
| WO | WO 2009/108332 | 9/2009 |
| WO | WO 2009/108827 | 9/2009 |
| WO | WO 2009/112826 | 9/2009 |
| WO | WO 2009/114870 | 9/2009 |
| WO | WO 2009/114874 | 9/2009 |
| WO | WO 2009/122180 | 10/2009 |
| WO | WO 2009/123967 | 10/2009 |
| WO | WO 2009/125808 | 10/2009 |
| WO | WO 2009/125809 | 10/2009 |
| WO | WO 2009/126584 | 10/2009 |
| WO | WO 2009/128520 | 10/2009 |
| WO | WO 2009/131687 | 10/2009 |
| WO | WO 2009/131926 | 10/2009 |
| WO | WO 2009/132980 | 11/2009 |
| WO | WO 2009/133127 | 11/2009 |
| WO | WO 2009/141386 | 11/2009 |
| WO | WO 2009/144205 | 12/2009 |
| WO | WO 2009/144302 | 12/2009 |
| WO | WO 2009/146034 | 12/2009 |
| WO | WO 2009/150150 | 12/2009 |
| WO | WO 2009/150240 | 12/2009 |
| WO | WO 2009/151997 | 12/2009 |
| WO | WO 2009/153592 | 12/2009 |
| WO | WO 2009/157423 | 12/2009 |
| WO | WO 2010/006947 | 1/2010 |
| WO | WO 2010/007099 | 1/2010 |
| WO | WO 2010/007116 | 1/2010 |
| WO | WO 2010/009155 | 1/2010 |
| WO | WO 2010/009195 | 1/2010 |
| WO | WO 2010/009207 | 1/2010 |
| WO | WO 2010/015643 | 2/2010 |
| WO | WO 2010/017047 | 2/2010 |
| WO | WO 2010/019210 | 2/2010 |
| WO | WO 2010/019899 | 2/2010 |
| WO | WO 2010/030027 | 3/2010 |
| WO | WO 2010/038081 | 4/2010 |
| WO | WO 2010/045371 | 4/2010 |
| WO | WO 2010/049731 | 5/2010 |
| WO | WO 2010/051043 | 5/2010 |
| WO | WO 2010/052448 | 5/2010 |
| WO | WO 2010/059552 | 5/2010 |
| WO | WO 2010/059658 | 5/2010 |
| WO | WO 2010/064621 | 6/2010 |
| WO | WO 2010/064875 | 6/2010 |
| WO | WO 2010/067886 | 6/2010 |
| WO | WO 2010/067888 | 6/2010 |
| WO | WO 2010/077647 | 7/2010 |
| WO | WO 2010/077680 | 7/2010 |
| WO | WO 2010/078421 | 7/2010 |
| WO | WO 2010/078427 | 7/2010 |
| WO | WO 2010/080503 | 7/2010 |
| WO | WO 2010/080712 | 7/2010 |
| WO | WO 2010/083145 | 7/2010 |
| WO | WO 2010/083283 | 7/2010 |
| WO | WO 2010/086089 | 8/2010 |
| WO | WO 2010/092181 | 8/2010 |
| WO | WO 2010/099938 | 9/2010 |
| WO | WO 2010/103306 | 9/2010 |
| WO | WO 2010/104047 | 9/2010 |
| WO | WO 2010/107765 | 9/2010 |
| WO | WO 2010/107768 | 9/2010 |
| WO | WO 2010/111303 | 9/2010 |
| WO | WO 2010/111573 | 9/2010 |
| WO | WO 2010/115279 | 10/2010 |
| WO | WO 2010/117425 | 10/2010 |
| WO | WO 2010/119284 | 10/2010 |
| WO | WO 2010/119285 | 10/2010 |
| WO | WO 2010/117323 | 11/2010 |
| WO | WO 2010/125216 | 11/2010 |
| WO | WO 2010/126960 | 11/2010 |
| WO | WO 2010/127212 | 11/2010 |
| WO | WO 2010/129509 | 11/2010 |
| WO | WO 2010/136031 | 12/2010 |
| WO | WO 2010/142801 | 12/2010 |
| WO | WO 2010/151689 | 12/2010 |
| WO | WO 2011/002038 | 1/2011 |
| WO | WO 2011/007819 | 1/2011 |
| WO | WO 2011/011597 | 1/2011 |
| WO | WO 2011/012816 | 2/2011 |
| WO | WO 2011/014535 | 2/2011 |
| WO | WO 2011/015037 | 2/2011 |
| WO | WO 2011/016472 | 2/2011 |
| WO | WO 2011/016528 | 2/2011 |
| WO | WO 2011/018894 | 2/2011 |
| WO | WO 2011/022439 | 2/2011 |
| WO | WO 2011/026579 | 3/2011 |
| WO | WO 2011/028947 | 3/2011 |
| WO | WO 2011/031740 | 3/2011 |
| WO | WO 2011/032050 | 3/2011 |
| WO | WO 2011/039344 | 4/2011 |
| WO | WO 2011/041143 | 4/2011 |
| WO | WO 2011/042389 | 4/2011 |
| WO | WO 2011/042474 | 4/2011 |
| WO | WO 2011/045344 | 4/2011 |
| WO | WO 2011/049825 | 4/2011 |
| WO | WO 2011/049988 | 4/2011 |
| WO | WO 2011/050245 | 4/2011 |
| WO | WO 2011/051425 | 5/2011 |
| WO | WO 2011/054843 | 5/2011 |
| WO | WO 2011/055911 | 5/2011 |
| WO | WO 2011/057022 | 5/2011 |
| WO | WO 2011/060295 | 5/2011 |
| WO | WO 2011/062253 | 5/2011 |
| WO | WO 2011/062885 | 5/2011 |
| WO | WO 2011/063159 | 5/2011 |
| WO | WO 2011/068899 | 6/2011 |
| WO | WO 2011/071821 | 6/2011 |
| WO | WO 2011/075515 | 6/2011 |
| WO | WO 2011/075620 | 6/2011 |
| WO | WO 2011/077043 | 6/2011 |
| WO | WO 2011/077044 | 6/2011 |
| WO | WO 2011/079231 | 6/2011 |
| WO | WO 2011/080755 | 7/2011 |
| WO | WO 2011/082234 | 7/2011 |
| WO | WO 2011/082266 | 7/2011 |
| WO | WO 2011/082267 | 7/2011 |
| WO | WO 2011/082488 | 7/2011 |
| WO | WO 2011/087776 | 7/2011 |
| WO | WO 2011/090666 | 7/2011 |
| WO | WO 2011/090738 | 7/2011 |
| WO | WO 2011/090760 | 7/2011 |
| WO | WO 2011/093672 | 8/2011 |
| WO | WO 2011/094890 | 8/2011 |
| WO | WO 2011/097717 | 8/2011 |
| WO | WO 2011/101806 | 8/2011 |
| WO | WO 2011/102441 | 8/2011 |
| WO | WO 2011/103196 | 8/2011 |
| WO | WO 2011/103441 | 8/2011 |
| WO | WO 2011/103460 | 8/2011 |
| WO | WO 2011/103557 | 8/2011 |
| WO | WO 2011/105161 | 9/2011 |
| WO | WO 2011/109237 | 9/2011 |
| WO | WO 2011/111880 | 9/2011 |
| WO | WO 2011/112687 | 9/2011 |
| WO | WO 2011/112995 | 9/2011 |
| WO | WO 2011/115725 | 9/2011 |
| WO | WO 2011/119894 | 9/2011 |
| WO | WO 2011/120327 | 10/2011 |
| WO | WO 2011/123493 | 10/2011 |
| WO | WO 2011/128403 | 10/2011 |
| WO | WO 2011/130390 | 10/2011 |
| WO | WO 2011/133722 | 10/2011 |
| WO | WO 2011/133750 | 10/2011 |
| WO | WO 2011/133888 | 10/2011 |
| WO | WO 2011/135376 | 11/2011 |
| WO | WO 2011/137313 | 11/2011 |
| WO | WO 2011/140338 | 11/2011 |
| WO | WO 2011/141756 | 11/2011 |
| WO | WO 2011/141848 | 11/2011 |
| WO | WO 2011/143033 | 11/2011 |
| WO | WO 2011/143318 | 11/2011 |
| WO | WO 2011/143430 | 11/2011 |
| WO | WO 2011/147198 | 12/2011 |
| WO | WO 2011/147199 | 12/2011 |

(56) References Cited

FOREIGN PATENT DOCUMENTS

| | | |
|---|---|---|
| WO | WO 2011/151360 | 12/2011 |
| WO | WO 2011/153553 | 12/2011 |
| WO | WO 2011/155983 | 12/2011 |
| WO | WO 2011/156610 | 12/2011 |
| WO | WO 2012/000103 | 1/2012 |
| WO | WO 2012/003544 | 1/2012 |
| WO | WO 2012/004217 | 1/2012 |
| WO | WO 2012/004731 | 1/2012 |
| WO | WO 2012/004732 | 1/2012 |
| WO | WO 2012/008563 | 1/2012 |
| WO | WO 2012/008564 | 1/2012 |
| WO | WO 2012/008999 | 1/2012 |
| WO | WO 2012/009258 | 1/2012 |
| WO | WO 2012/009309 | 1/2012 |
| WO | WO 2012/013619 | 2/2012 |
| WO | WO 2012/015274 | 2/2012 |
| WO | WO 2012/019093 | 2/2012 |
| WO | WO 2012/020133 | 2/2012 |
| WO | WO 2012/027236 | 3/2012 |
| WO | WO 2012/027239 | 3/2012 |
| WO | WO 2012/030990 | 3/2012 |
| WO | WO 2012/031004 | 3/2012 |
| WO | WO 2012/032031 | 3/2012 |
| WO | WO 2012/032065 | 3/2012 |
| WO | WO 2012/032067 | 3/2012 |
| WO | WO 2012/032334 | 3/2012 |
| WO | WO 2012/035996 | 3/2012 |
| WO | WO 2012/036233 | 3/2012 |
| WO | WO 2012/038743 | 3/2012 |
| WO | WO 2012/047699 | 4/2012 |
| WO | WO 2012/054364 | 4/2012 |
| WO | WO 2012/057260 | 5/2012 |
| WO | WO 2012/058211 | 5/2012 |
| WO | WO 2012/061337 | 5/2012 |
| WO | WO 2012/062462 | 5/2012 |
| WO | WO 2012/063207 | 5/2012 |
| WO | WO 2012/064715 | 5/2012 |
| WO | WO 2012/065297 | 5/2012 |
| WO | WO 2012/065546 | 5/2012 |
| WO | WO 2012/066578 | 5/2012 |
| WO | WO 2012/068343 | 5/2012 |
| WO | WO 2012/073017 | 6/2012 |
| WO | WO 2012/080727 | 6/2012 |
| WO | WO 2012/080729 | 6/2012 |
| WO | WO 2012/083866 | 6/2012 |
| WO | WO 2012/083953 | 6/2012 |
| WO | WO 2012/083954 | 6/2012 |
| WO | WO 2012/087784 | 6/2012 |
| WO | WO 2012/088266 | 6/2012 |
| WO | WO 2012/091240 | 7/2012 |
| WO | WO 2012/093731 | 7/2012 |
| WO | WO 2012/098068 | 7/2012 |
| WO | WO 2012/101239 | 8/2012 |
| WO | WO 2012/106995 | 8/2012 |
| WO | WO 2012/112961 | 8/2012 |
| WO | WO 2012/112965 | 8/2012 |
| WO | WO 2012/116237 | 8/2012 |
| WO | WO 2012/125812 | 9/2012 |
| WO | WO 2012/127012 | 9/2012 |
| WO | WO 2012/134943 | 10/2012 |
| WO | WO 2012/138975 | 10/2012 |
| WO | WO 2012/140114 | 10/2012 |
| WO | WO 2012/158704 | 11/2012 |
| WO | WO 2012/158795 | 11/2012 |
| WO | WO 2012/158994 | 11/2012 |
| WO | WO 2012/161812 | 11/2012 |
| WO | WO 2012/167247 | 12/2012 |
| WO | WO 2012/173370 | 12/2012 |
| WO | WO 2013/016197 | 1/2013 |
| WO | WO 2013/024002 | 2/2013 |
| WO | WO 2013/024895 | 2/2013 |
| WO | WO 2013/033981 | 3/2013 |
| WO | WO 2013/039854 | 3/2013 |
| WO | WO 2013/049352 | 4/2013 |
| WO | WO 2013/063000 | 5/2013 |
| WO | WO 2013/063003 | 5/2013 |
| WO | WO 2013/108809 | 7/2013 |
| WO | WO 2013/109027 | 7/2013 |
| WO | WO 2013/124316 | 8/2013 |
| WO | WO 2013/136249 | 9/2013 |
| WO | WO 2013/144339 | 10/2013 |
| WO | WO 2014/007951 | 1/2014 |
| WO | WO 2014/011284 | 1/2014 |
| WO | WO 2014/011900 | 1/2014 |
| WO | WO 2014/019186 | 2/2014 |
| WO | WO 2014/022528 | 2/2014 |
| WO | WO 2014/026125 | 2/2014 |
| WO | WO 2014/044846 | 3/2014 |
| WO | WO 2014/048878 | 4/2014 |
| WO | WO 2014/062454 | 4/2014 |
| WO | WO 2014/085216 | 5/2014 |
| WO | WO 2014/089913 | 6/2014 |
| WO | WO 2014/105849 | 7/2014 |
| WO | WO 2014/113191 | 7/2014 |
| WO | WO 2014/136972 | 9/2014 |
| WO | WO 2014/138485 | 9/2014 |
| WO | WO 2014/140184 | 9/2014 |
| WO | WO 2014/144737 | 9/2014 |
| WO | WO 2014/160160 | 10/2014 |
| WO | WO 2014/160478 | 10/2014 |
| WO | WO 2014/160521 | 10/2014 |
| WO | WO 2014/162039 | 10/2014 |
| WO | WO 2014/170063 | 10/2014 |
| WO | WO 2014/171755 | 10/2014 |
| WO | WO 2014/172644 | 10/2014 |
| WO | WO 2014/174307 | 10/2014 |
| WO | WO 2014/182829 | 11/2014 |
| WO | WO 2014/198942 | 12/2014 |
| WO | WO 2014/206343 | 12/2014 |
| WO | WO 2014/206344 | 12/2014 |
| WO | WO 2015/000715 | 1/2015 |
| WO | WO 2015/006492 | 1/2015 |
| WO | WO 2015/006754 | 1/2015 |
| WO | WO 2015/030021 | 3/2015 |
| WO | WO 2015/057938 | 4/2015 |
| WO | WO 2015/057963 | 4/2015 |
| WO | WO 2015/059668 | 4/2015 |
| WO | WO 2015/061572 | 4/2015 |
| WO | WO 2015/066452 | 5/2015 |
| WO | WO 2015/108992 | 7/2015 |
| WO | WO 2016/064960 | 4/2016 |
| WO | WO 2016/134314 | 8/2016 |

OTHER PUBLICATIONS

Pinedo et al. (2000).*
Neidle et al., Cancer Drug Design & Discovery. (2008).*
Australian Office Action in Australian Application No. 2018208772, dated Jul. 1, 2018, 5 pages.
Australian Office Action in Australian Application No. 2016219822, dated Jul. 8, 2019, 4 pages.
Australian Office Action in Australian Application No. 2016219816, dated Aug. 26, 2019, 3 pages.
Chilean Office Action in Chilean Application No. 2122-2017, dated Apr. 22, 2019, 25 pages.
Costa Rican Office Action in Costa Rican Application No. 2014-0577, dated Jun. 13, 2019, 17 pages.
Desnoyers et al., "Targeting FGF19 inhibits tumor growth in colon cancer xenograft and FGF19 transgenic hepatocellular carcinoma models," Oncogene, 2008, 27:85-97.
Ding et al., "Somatic mutations affect key pathways in lung adenocarcinoma," Nature., Oct. 23, 2008, 455:1069-1075.
Heinle C, et al., "Differential Effects of Polymorphic Alleles of FGF Receptor 4 on Colon Cancer Growth and Metastasis," Cancer Research, Nov. 2012, 72(22):5767-5777.
Ho et al., "Fibroblast growth factor receptor 4 regulates proliferation, anti apoptosis and alpha-fetoprotein secretion during hepatocellular carcinoma progression and represents a potential target for therapeutic intervention," J Hepatol, 2009, 50:118-127.

(56) References Cited

OTHER PUBLICATIONS

Hu and Cong, "Fibroblast growth factor 19 is correlated with an unfavorable prognosis and promotes progression by activating fibroblast growth factor receptor 4 in advanced-stage serous ovarian cancer," Oncol Rep., Aug. 20, 2015, 34(5):2683-2691.
Japanese Office Action in Japanese Application No. 2018-228352, dated Aug. 20, 2019, 6 pages.
Korean Office Action in Korean Application No. 10-2015-7000701, dated Aug. 26, 2019, 19 pages.
Marks et al., "Mutational Analysis of EGFR and Related Signaling Pathway Genes in Lung Adenocarcinomas Identifies a Novel Somatic Kinase Domain Mutation in FGFR4," PLoS ONE, May 9, 2007, 2:e426.
Philippine Office Action in Philippine Application No. 1/2015/502383, dated Jul. 8, 2019, 7 pages.
Seitzer et al., "A single nucleotide change in the mouse genome accelerates breast cancer progression," Cancer Res., Jan. 2010, 70(2):802-812.
Tang et al., "Role of fibroblast growth factor receptor 4 in cancer," Cancer Science, Oct. 2018, 109(10):3024-3031.
Thussbas et al., "FGFR4 Arg388 Allele Is Associated With Resistance to Adjuvant Therapy in Primary Breast Cancer," J. Clin. Oncol., Aug. 10, 2006, 23:3747-3755.
Turkington et al., "Fibroblast growth factor receptor 4 (FGFR4): a targetable regulator of drug resistance in colorectal cancer," Cell Death Dis., Feb. 6, 2014, 5:e1046.
Wang et al., "The fibroblast growth factor receptor-4 Arg388 allele is associated with prostate cancer initiation and progression," Clin Cancer Res. 2004, 10:6169-6178.
Yu et al., "FGFR-4 Arg(3)(8)(8) enhances prostate cancer progression via extracellular signal-related kinase and serum response factor signaling," Clin Cancer Res., Jul. 2011, 17:4355-4366.
Ying et al., "Genome-wide screening for genetic alterations in esophageal cancer by aCGH identifies 11q13 amplification oncogenes associated with nodal metastasis," PLoS One, Jun. 25, 2012, 7:e39797.
"Sabiosciences.com" [online]. "FGF Pathway," 2000-2012, [retrieved on Jun. 23, 2015]. Retrieved from the Internet: URL <http://www.sabiosciences.com/pathway.php?sn=FGF_Signaling>, 3 pages.
"Substance Record for SID 240993001," Feb. 13, 2015, pp. 1-8.
Acevedo et al., "Inducible FGFR-1 Activation Leads to Irreversible Prostate Adenocarcinoma and an Epithelial-to-Mesenchymal Transition," Cancer Cell, Dec. 2007, 12: 559-571.
Ali et al., "Synthesis and structure activity relationship of substituted N,6-diphenyl-5,6-dihydrobenzo[h]quinazolin-2-amine as inhibitors of fibroblast growth factor receptors (FGFR)" Cancer Res, Apr. 15, 2012, 72; 3905.
Angevin et al., "TKI258 (dovitinib lactate) in metastatic renal cell carcinoma (mRCC) patients refractory to approved targeted therapies: A phase I/II dose finding and biomarker study," Journal of Clinical Oncology, May 20, 2009, 27:15S, 1 page.
Antonios-McCrea et al., "LHMDS mediated tandem acylation-cyclization of 2-aminobenzenecarbonitriles with 2-benzymidazol-2-ylacetates: a short and efficient route to the synthesis of 4-amino-3-benzimidazol-2-ylhydroquinolin-2-ones," Tetrahedron Letters, 2006, 657-660.
Arai et al., "Characterization of the cell or origin and propagation potential of the fibroblast growth factor 9-induced mouse model of lung adenocarcinoma," J. Pathol., Mar. 2015, 235(4): 593-605.
Ash and Ash, "Handbook of Pharmaceutical Additives," Gower Publishing Company, 2007, 3rd ed, \*\*\*\*\*\*\*\*\*\*\*too voluminous to provide\*\*\*\*\*\*\*\*\*.
Australian Office Action in Australian Application No. 2013287176, dated Sep. 12, 2017, 4 pages.
Australian Office Action in Australian Application No. 2014253798, dated Jul. 31, 2017, 4 pages.
Avet-Loiseau et al., "Impact of high-risk cytogenetics and prior therapy on outcomes in patients with advanced relapsed or refractory multiple myeloma treated with lenalidomide plus dexamethasone," Leukemia, 2010, 623-628.

Bai et al., "GP369, an FGFR2-IIIb specific antibody, exhibits potent antitumor activity against human cancers driven by activated FGFR2 signaling," Am. Assoc. for Cancer Research, Aug. 17, 2010, 30 pages.
Bansal et al., "Specific inhibitor of FGF receptor signaling: FGF-2-mediated effects on proliferation, differentiation, and MAPK activation are inhibited by PD173074 in oligodendrocyte-lineage cells," J. Neurosci. Res., 2003, 74: 486.
Beekman et al., "New Molecular Targets and Novel Agents in the Treatment of Advanced Urothelial Cancer," Semin Oncol, 2007, 34: 154-164.
Bello et al., "E-3810 is a potent dual inhibitor of VEGFR and FGFR that exerts antitumor activity in multiple preclinical models," Cancer Res, 2011.
Bello et al., "E-3810 is a potent dual inhibitor of VEGFR and FGFR that exerts antitumor activity in multiple preclinical models," Cancer Res, 2011, Supplemental figures, 4 pages.
Bello et al., "E-3810 is a potent dual inhibitor of VEGFR and FGFR that exerts antitumor activity in multiple preclinical models," Cancer Res, 2011, Supplemental table, 3 pages.
Bello et al., "E-3810 is a potent dual inhibitor of VEGFR and FGFR that exerts antitumor activity in multiple preclinical models," Cancer Res, 2011, Supplementary data, 4 pages.
Benet-pp. et al., "An FGF23 missense mutation causes familial tumoral calcinosis with hyperphosphatemia," Human Molecular Genetics, 2005, 14(3):385-390.
Berge et al., "Pharmaceutical Salts", Journal of Pharmaceutical Science, 66(2):1-19 (1977).
Bergwitz and Juppner, "Regulation of Phosphate Homeostasis by PTH, Vitamin D, and FGF23," Annu. Rev. Med., 2010, 61:91-104.
Bhide et al., "Discovery and Preclinical Studies of (R )-1-(4-(4-Fluoro-2-methyl-1H-indol-5-yloxy)-5-methylpyrrolo[2,f][1,2,4]triazin-6-yloxy)propan-2-ol (BMS-540215), an In Vivo Active Potent VEGFR-2 Inhibitor," Journal of Medicinal Chemistry, 2006, 49(7): 2143-2146.
Billerey et al., "Frequent FGFR3 Mutations in Papillary Non-Invasive Bladder (pTa) Tumors," American Journal of Pathology, Jun. 2001, 158(6): 1955-1959.
Billottet et al., "Targets of Fibroblast Growth Factor 1 (FGF-1) and FGF-2 Signaling Involved in the Invasive and Tumorigenic Behavior of Carchinoma Cells," Molecular Biology of the Cell, Oct. 2004, 15: 4725-4734.
BioCentury, Week of Nov. 10, 2014, 52 pages.
Bisping et al., "Bortezomib, Dexamethasone, and Fibroblast Growth Factor Receptor 3-Specific Tyrosine Kinase Inhibitor in t(4;14) Myeloma," Clin Cancer Res, Jan. 2009, 15(2):520-531.
Black et al., "Targeted therapies in bladder cancer—an update," Urologic Oncology: Seminars and Original Investigations, 2007, 433-438.
Blom et al., "Optimizing Preparative LC-MS Configurations and Methods for Parallel Synthesis Purification", J. Combi Chem., 5, 670 (2003).
Blom et al., Preparative LC-MS Purification: Improved Compound Specific Method Optimization, J. Combi. Chem. 2004, 6(6), 874-883.
Blom, K., "Two-Pump At col. Dilution Configuration for Preparative LC-MS", J. Combi Chem., 4, 295 (2002).
Bonaventure et al., "Common Mutations in the Fibroblast Growth Factor Receptor 3 (FRFR3) Gene Account for Achondroplasia, Hypochondroplasia and Thanatophoric Dwarfism," Clin Pediatr Endocrinol, 1997, 105-113.
Bono et al., "Inhibition of Tumor Angiogenesis and Growth by a Small-Molecule Multi-FGF Receptor Blocker with Allosteric Properties," Cancer Cell, Apr. 2013, 477-488.
Brooks et al., "Fibroblast growth factor signaling: a new therapeutic opportunity in cancer," Clinical Cancer Research, 2012, 1-23.
Cancer [online], [retrieved on Jul. 6, 2007] Retrieved from the Internet, URL: http://www.nlm.nih.gov/medlineplus/cancer.html.
Cappellen et al., "Frequent activating mutations of FGFR3 in human bladder and cervix carcinomas," Nature Genetics, Sep. 1999, 23: 18-20.

(56) References Cited

OTHER PUBLICATIONS

Capelletti et al., "Identification of Recurrent FGFR3-TACC3 Fusion Oncogenes from Lung Adenocarcinoma," AACR Journals, 2014, 6551-6558.

Carmichael et al., "Familial Tumoral Calcinosis: A Forty-Year Follow-up on One Family," The Journal of Bone & Joint Surgery, 2009, 664-671.

Cha et al., "Aberrant Receptor Internalization and Enhanced FRS2-dependent Signaling Contribute to the Transforming Activity of the Fibroblast Growth Factor Receptor 2 IIIb C3 Isoform," The Journal of Biological Chemistry, Mar. 2009, 284(10): 6227-6240.

Chandrani et al., "Drug-sensitive FGFR3 mutations in lung adenocarcinoma," Annals of Oncology, 2017, 28: 597-603.

Chase et al., "Activity of TKI258 against primary cells and cell lines with FGFR1 fusion genes associated with the 8p11 myeloproliferative syndryome," Blood, 2007, 110:3729-3734.

Chefetz and Sprecher, "Familial tumoral calcinosis and the role of O-glycosylation in the maintenance of phosphate homeostasis," Biochimica et Biophysica Acta, 2009, 847-852.

Chefetz et al., "A novel homozygous missense mutation in FGF23 causes Familial Tumoral Calcinosis associated with disseminated visceral calcification," Hum Genet, 2005, 118:261-266.

Chell et al., "Tumour cell responses to new fibroblast growth factor receptor tyrosine kinase inhibitors and identification of a gatekeeper mutation in FGFR3 as a mechanism of acquired resistance," Oncogene, 2012, 1-12.

Chen et al., "Acenaphtho[1,2-b]pyrrole-Based Selective Fibroblast Growth Factor Receptors 1 (FRGR1) Inhibitors: Design, Synthesis, and Biological Activity," Jounal of Medicinal Chemistry, 2011, 54: 3732-3745.

Chen et al., "FGFR3 as a therapeutic target of the small molecule inhibitor PKC412 in hematopoietic malignancies," Oncogene, 2005, 24: 8259-8267.

Chen et al., "Genome-Wide Loss of Heterozygosity and DNA Copy Number Aberration in HPV-Negative Oral Squamous Cell Carcinoma and Their Associations with Disease-Specific Survival," PLOS ONE, Aug. 2015, 23 pages.

Chesi et al., "Activated fibroblast growth factor receptor 3 is an oncogene that contributes to tumor progression in multiple myeloma," Blood, 2001, 97:729-736.

Chesi et al., "Frequent translocation t(4;14)(p16.3;q32.3) in multiple myeloma is associated with increased expression and activating mutations of fibroblast growth factor receptor 3," Nature Genetics, 1997, 260-264.

Chilean Office Action in Chilean Application No. 2015-003089, dated Apr. 24, 2017, 13 pages. (English Summary).

Chilean Office Action in Chilean Application No. 3355-2014, dated Jan. 18, 2017, 17 pages. (with English translation).

Chilean Opposition in Chilean Application No. 3355-2014, received Feb. 3, 2017, 3 pages. (English translation only).

Chilean Office Action in Chilean Application No. 2015-003089, dated Jan. 23, 2018, 8 pages.

Chinese Office Action in Chinese Application No. 201380041027.9, dated Feb. 13, 2017, 10 pages. (with English translation).

Chinese Office Action in Chinese Application No. 201380041027.9, dated Jul. 12, 2016, 11 pages. (with English translation).

Chinese Office Action in Chinese Application No. 201380041027.9, dated Oct. 28, 2015, 17 pages. (with English translation).

Chinese Office Action in Chinese Application No. 201480028858.7, dated Aug. 19, 2016, 18 pages. (English Translation).

Chinese Office Action in Chinese Application No. 201480028858.7, dated Jul. 12, 2017, 10 pages. (English Translation).

Chng et al., "Translocation t(4;14) retains prognostic significance even in the setting of high-risk molecular signature," Leukemia, 2008, 2: 459-461.

Chuaqui et al., "Interaction Profiles of Protein Kinase—Inhibitor Complexes and Their Application to Virtual Screening," J. Med. Chem., 2005, 48: 121-133.

Cole et al "Inhibition of FGFR2 and FGFR1 increases cisplatin sensitivity in ovarian cancer,", Cancer Biol. Therapy, Sep. 1, 2010, 10(5):495-504.

Coleman, "Positive and negative regulation of cellular sensitivity to anti-cancer drugs by FGF-2," Drug Resistance Updates, 2003, 85-94.

Colombian Office Action in Colombian Application No. 14-275934-6, dated May 31, 2016, 3 pages. (English translation only).

Colombian Office Action in Colombian Application No. 14-275934-6, dated Nov. 17, 2015, 12 pages. (English translation only).

Colombian Office Action in Colombian Application No. 16100866, dated Aug. 10, 2017, 9 pages.

Colombian Office Action in Colombian Application No. NC2017/0008795, dated Aug. 29, 2017, 2 pages.

Colombian Office Action in Colombian Application No. NC2017/0008795, dated Nov. 29, 2018, 8 pages.

Colombian Office Action in Colombian Application No. NC2017/0008824, dated Aug. 31, 2017, 3 pages.

Colombian Office Action in Colombian Application No. NC2017/0008824, dated Nov. 29, 2018, 8 pages.

Corre et al., "Synthesis and biological evaluation of a triazole-based library of pyrido [2,3-d]pyrimidines as FGFR3 tyrosine kinase inhibitors," Organic & Biomolecular Chemistry, 2010, 8:2164-2173.

Costa Rican Opposition in Costa Rican Application No. PCT/US2013/045309, dated Jun. 29, 2015, 14 pages. (English Translation).

Covic et al., "Vascular calcification in chronic kidney disease," Clinical Science, 2010, 119: 111-121.

Crose et al., "FGFR4 Blockade Exerts Distinct Antitumorigenic Effects in Human Embryonal versus Alveolar Rhabdomyosarcoma," Clin Cancer Res., 2012, 18:3780-3790.

Dailey et al., "Mechanisms underlying differential responses to FGF signaling," Cytokine & Growth Factor Reviews, 2005, 233-247.

Dash et al., "A Role for Neoadjuvant Gemcitabine Plus Cisplatin in Muscle-Invasive Urothelial Carcinoma o the Bladder: A Retrospective Experience," Cancer, 2008, 113(9): 2471-2477.

Dey et al., "Targeting Fibroblast Growth Factor Receptors Blocks PI3K/AKT Signaling, Induces Apoptosis, and Impairs Mammary Tumor Outgrowth and Metastasis," Cancer Research, 2010, 4151-4162.

Dieci et al., "Fibroblast Growth Factor Receptor Inhibitors as a Cancer Treatment: From a Biologic Rationale to Medical Perspectives," Cancer Discovery, 2013, 1-16.

Dienstmann et al., "Genomic aberrations in the FGFR pathway: opportunities for targeted therapies in solid tumors," Annals of Oncology, 2013, 1-12.

Diller and Li, "Kinases, Homology Models, and High Throughput Docking," J. Med. Chem., 2003, 46: 4638-4647.

Dimopoulos et al., "Lenalidomide plus Dexamethasone for Relapsed or Refractory Multiple Myeloma," The New England Journal of Medicine, 2007, 357:2123-2132.

Dovedi and Davies, "Emerging targeted therapies for bladder cancer: a disease waiting for a drug," Cancer Metastasis Rev, 2009, 28:355-367.

Dring et al., "A Global Expression-based Analysis of the Consequences of the t(4;14) Translocation in Myeloma," Clinical Cancer Research, Sep. 2004, 10: 5692-5701.

Dutt et al., "Drug-sensitive FGFR2 mutations in endometrial carcinoma," PNAS, Jun. 24, 2008, 105(25):8713-8717.

Dutt et al., "Drug-sensitive FGFR2 mutations in endometrial carcinoma," Supporting Information, Jun. 2008, 8 pages.

Eissa, "Synthesis and evaluation of some surface active agents from long chain fatty amine," Spanish National Research Council, Jan. 2007, 58(4):379-389.

Elsheikh et al., "FGFR1 amplification in breast carcinomas: a chromogenic in situ hybridisation analysis," Breast Cancer Research, Mar. 2007, 9(2): 1-12.

Eskens and Verweij, "The clinical toxicity profile of vascular endothelial growth factor (VEGF) and vascular endothelial growth factor receptor (VEGFR) targeting angiogenesis inhibitors; A review," European Journal of Cancer, 2006, 3127-3139.

(56) References Cited

OTHER PUBLICATIONS

Eswarakumar and Schlessinger, "Cellular signaling by fibroblast growth factor receptors," Cytokine & Growth Factor Reviews, 2005, 139-149.
Eurasian Office Aciton in Eurasian Application No. 201590005, dated Oct. 21, 2015, 6 pages.
European Communication pursuant to Article 94(3) EPC in European Application No. 13783125.1, dated Jan. 26, 2016, 4 pages.
European search report in European Application No. 16203866.5, dated Mar. 1, 2017, 7 pages.
European Search Report in European Application No. 17199421.3, dated Jul. 12, 2018, 15 pages.
European Search Report in European Application No. 17199421.3, dated Mar. 12, 2018, 14 pages.
Faul et al., "FGF23 induces left ventricular hypertrophy," The Journal of Clinical Investigation, 2010, 1-16.
Feng et al., "Guidance to rational use of pharmaceuticals in gallbladder sarcomatoid carcinoma using patient-derived cancer cells and whole exome sequencing," Oncotarget, 2017, 8(3): 5349-5360.
Feng et al., "Targeting Fibroblast Growth Factor Receptor Signaling Inhibits Prostate Cancer Progression," Clinical Cancer Research, 2012, 1-9.
Ferrera et al., "Bevacizumab (Avastin), a humanized anti-VEGF monoclonal antibody for cancer therapy," Biochemical and Biophysical Research Communications, 2005, 328-335.
Fillmore et al., "Estrogen expands breast cancer stem-like cells through paracrine FGF/Tbx3 signaling," PNAS, 2010, 1-6.
Fischer et al., "Fibroblast growth factor receptor-mediated signals contribute to the malignant phenotype of non-small cel lung cancer cells: therapeutic implications and synergism with epidermal growth factor receptor inhibition," Mol Cancer Therapy, 2008, 3408-3419.
French et al., "Targeting FGFR4 Inhibits Hepatocellular Carcinoma in Preclinical Mouse Models," PLoS ONE, 2012, 7(5):e36713, 1-12.
Frishberg et al., "Hypertosis-Hyperphosphatemia Syndrome: A Congenital Disorder of O-Glycosylation Associated With Augmented Processing of Fibroblast Growth Factor 23," Journal of Bone and Mineral Research, 2007, 22(2): 235-242.
Frishberg et al., "Identification of a recurrent mutation in GALNT3 demonstrates that hyperostosis-hyperphosphatemia syndrome and familial tumoral calcinosis are allelic disorders," J Mol Med, 2005, 83:33-38.
Fukumoto and Yamashita, "FGF23 is a hormone-regulating phophate metabolism—Unique biological characteristics of FGF23," Bone, 2007, 1190-1195.
Galdemard et al., "Regulation of FGF-3 Gene Expression in Tumorigenic and Non-tumorigenic Clones of a Human Colon Carcinoma Cell Line," The Journal of Biological Chemistry, 2000, 275(23): 17364-17373.
Garringer et al., "Molecular genetic and biochemical analyses of FGF23 mutations in familial tumoral calcinosis," Am J Physiol Endocrinol Metab, 2008, 929-937.
Gattineni et al., "FGF23 decreases renal NaPi-2a and NaPi-2c expression and induces hypophosphatemia in vivo predominantly via FGF receptor 1," Am J Physiol Renal Physiol, 2009, 297: 282-291.
Gavine et al., "AZD4547: An Orally Bioavailable, Potent, and Selective Inhibitor of the Fibroblast Growth Factor Receptor Tyrosine Kinase Family," American Association for Cancer Research, Apr. 2012, 72(8): 2045-2056.
Gerby et al., "2-Arylidenedihydroindole-3-ones: Design, synthesis, and biological activity on bladder carcinoma cell lines," Bioorganic & Medicinal Chemistry Letters, 2007, 208-213.
Ghorab et al., "Synthesis of some sulfur containing Tetrahydrobenzoabuthieno [b] Thieno(Pyridines, Quinolines, Oxazins and Pyrimidines) as possible radioprotective and Antineoplastic agents," Phosphorus, Sulfur and Silicon, Jan. 1998, 134/135:57-76.
Gibson, "Pharmaceutical Preformulation and Formulation," CRC Press LLC, 2009, 2nd ed ********Too Voluminous to provide**********.

Goetz et al., "Isolated C-terminal tail of FGF23 alleviates hypophosphatemia by inhibiting FGF23-FGFR-Klotho complex formation," PNAS, Jan. 2010, 107(1): 407-412.
Golub et al., "Molecular Classification of Cancer: Class Discovery and Class Prediction by Gene Expression Monitoring," Science, 1999, 286: 531-537.
Gomez-Rivera et al., "The Tyrosine Kinase Inhibitor, AZD2171, Inhibits Vascular Endothelial Growth Factor Receptor Signaling and Growth of Anaplastic Thyroid Cancer in an Orthotopic Nude Mouse Model," Clin Cancer Res, Aug. 2007, 4519-4527.
Govindan, "Summary of Presentations from the Ninth Annual Targeted Therapies in Lung Cancer Symposium," Journal of Thoracic Oncology, Nov. 2009, 4(11): 1045-1089.
Gozgit et al., "Ponatinib (AP24534), a Multitargeted Pan-FGFR Inhibitor with Activity in Multiple FGFR-Amplified or Mutated Cancer Models," Mol Cancer Ther, 2012, 11: 690-699.
Granberg et al., "Strong FGFR3 staining is a marker for FGFR3 fusions in diffuse gliomas," Neuro-Oncology, 2017, 19(9): 1206-1216.
Grand et al., "Targeting FGFR3 in multiple myeloma inhibition of t(4;14)-positive cells by SU5402 and PD173074," Leukemia, 2004, 18: 962-966.
Greene, T. W. and Wuts, P. G. M., "Protective Groups in Organic Synthesis", 3rd Ed., Wiley & Sons, Inc., New York (1999) **Too Voluminous to Provide.
Greulich and Pollock, "Targeting mutant fibroblast growth factor receptors in cancer," Cell Press, May 2011, 17(5): 283-292.
Grose and Dickson, "Fibroblast growth factor signaling in tumorigenesis," Cytokine & Growth Factor Reviews, 2005, 179-186.
Gu et al., "Phosphotyrosine profiling identifies the KG-1 cell line as a model for the study of FGFR1 fusions in acute myeloid leukemia," Blood, Dec. 15, 2006, 108(13):4202-42040.
Guagnano et al., "Discovery of 3-(2,6-Dichloro-3,5-dimethoxyphenyl)-1-{6-[4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase," J. Med. Chem., 2011, 54: 7066-7083.
Guan et al., "Design and synthesis of aminopropyl tetrahydroindole-based indolin-2-ones as selective and potent inhibitors of Src and Yes tyrosine kinase," Bioorganic & Medicinal Chemistry Letters, 2004, 187-190.
Gust et al., "Fibroblast Growth Factor Receptor 3 Is a Rational Therapeutic Target in Bladder Cancer," Molecular Cancer Therapeutics, Jul. 2013, 12(7): 1245-1254.
Hackam, et al. JAMA, 296(14), 2006, 1731-1732.
Hafner et al., "High Frequency of FGFR3 Mutations in Adenoid Seborrheic Keratoses," Journal of Investigative Dermatology, 2006, 126: 2404-2407.
Hafner, "Seborrheic keratoses and epidermal nevi: new pathogenetic insights and therapeutic implications," Expert Rev Dermatol, 2006, 1(6): 759-761.
Hagel et al., "First Selective Small Molecule Inhibitor of FGFR4 for the Treatment of Hepatocellular Carcinomas with an Activated FGFR4 Signaling Pathway," Cancer Discovery, Apr. 2015, 1-14.
Hara and Saito, "CARD9 versus CARMA1 in innate and adaptive immunity," Cell Press, 2009, 234-242.
Heinzle et al., "Is fibroblast growth factor receptor 4 a suitable target of cancer therapy?," Cur. Pharm. Des. 2014, 20:2881-98.
Heinzle et al., "Targeting fibroblast-growth-factor-receptor-dependent signaling for cancer therapy," Expert Opinion, 2011, 1-18.
Helsten et al., "The FGFR Landscape in Cancer: Analysis of 4,853 Tumors by Next-Generation Sequencing," Clin. Cancer Res , Jan. 2016, 259-267.
Hideshima and Anderson, "Preclinical Studies of Novel Targeted Therapies," Hematol Oncol Clin N Am, 2007, 1071-1091.
Honigberg et al., "The Bruton tyrosine kinase inhibitor PCI-32765 blocks B-cell activation and is efficacious in models of autoimmune disease and B-cell malignancy," Supporting Information, PNAS, Jul. 20, 2010, 107:29.

(56) References Cited

OTHER PUBLICATIONS

Hruska et al., "The Pathogenesis of Vascular Calcification in the Chronic Kidney Disease Mineral Bone Disorder (CKD-MBD): The Links Between Bone and Vasculature," Semin Nephrol, Mar. 2009, 29(2): 156-165.
Huynh, "Tyrosine kinase inhibitors to treat liver cancer," Expert Opinion, 2010, 13-26.
Hynes and Dey, "Potential for Targeting the Fibroblast Growth Factor Receptors in Breast Cancer," Cancer Res, 2010, 70:5199-5202.
Ichikawa et al., "A homozygous missense mutation in human KLOTHO causes severe tumoral calcinosis," The Journal of Clinical Investigation, Sep. 2007, 117(9): 2684-2691.
Ichikawa et al., "A Novel GALNT3 Mutation in a Pseudoautosomal Dominant Form of Tumoral Calcinosis: Evidence That the Disorder Is Autosomal Recessive," J. Clin. Endocrinol. Metab., 2005, 90:2420-2423.
Ichikawa et al., "Clinical Variability of Familial Tumoral Calcinosis Caused by Novel GALNT3 Mutations," American Journal of Medical Genetics, 2009, 896-903.
Ichikawa et al., "Novel GALNT3 Mutations Causing Hyperostosis-Hyperphosphatemia Syndrome Result in Low Intact Fibroblast Growth Factor 23 Concentrations," J. Clin. Endocrinol. Metab., 2007, 92:1943-1947.
Ichikawa et al., "Tumoral Calcinosis Presenting with Eyelid Calcifications due to Novel Missense Mutations in the Glycosyl Transferase Domain of the GALNT3 Gene," J. Clin. Endocrinol. Metab., 2006, 91: 4472-4475.
ICH Harmonised Tripartite Guideline, "Specifications:Test Procedures and Acceptance Criteria for New Drug Substances and New Drug Products Chemical Substances," ICHTRRPHU, Oct. 6, 1999, 35 pages.
Indian Office Action in Indian Application No. 10665/DELNP/2014, dated Jun. 25, 2018, 8 pages.
Inokuchi et al., "Therapeutic targeting of fibroblast growth factor receptors in gastric cancer," Gastroenterol Res Pract., Apr. 27, 2015, 2015:796380, 8 pages.
International Preliminary Report on Patentability and Written Opinion in International Application No. PCT/US2011/066473, dated Jun. 25, 2013, 10 pages.
International Preliminary Report on Patentability in International Application No. PCT/US2013/045309, dated Dec. 24, 2014, 11 pages.
International Preliminary Report on Patentability in International Application No. PCT/US2013/054361, dated Feb. 19, 2015, 7 pages.
International Preliminary Report on Patentability in International Application No. PCT/US2014/034662, dated Oct. 29, 2015, 12 pages.
International Preliminary Report on Patentability in International Application No. PCT/US2015/056583, dated Apr. 25, 2017, 7 pages.
International Preliminary Report on Patentability in International Application No. PCT/US2016/018737, dated Aug. 31, 2017, 8 pages.
International Preliminary Report on Patentability in International Application No. PCT/US2016/018770, dated Aug. 22, 2017, 10 pages.
International Preliminary Report on Patentability in International Application No. PCT/US2016/018787, dated Aug. 22, 2017, 7 pages.
International Search Report and Written Opinion for International Application No. PCT/US2015/056583, dated Dec. 15, 2015, 10 pages.
International Search Report and Written Opinion in International Application No. PCT/US2013/045309, dated Jan. 22, 2014, 19 pages.
International Search Report and Written Opinion in International Application No. PCT/US2013/054361, dated Oct. 16, 2013, 12 pages.
International Search Report and Written Opinion in International Application No. PCT/US2014/034662, dated Oct. 24, 2014, 18 pages.
International Search Report and Written Opinion in International Application No. PCT/US2016/018737, dated Jun. 2, 2016, 12 pages.
International Search Report and Written Opinion in International Application No. PCT/US2016/018770, dated Jun. 2, 2016, 14 pages.
International Search Report and Written Opinion in International Application No. PCT/US2016/018787, dated Jun. 2, 2016, 12 pages.
International Search Report dated Jun. 19, 2012 for International Appln. No. PCT/US2011/066473 (15 pgs.).
International Search Report and Written Opinion in International Application No. PCT/US2018/034559, dated Mar. 8, 2019, 14 pages.
Invitation to Pay Additional Fees and, Where Applicable, Protest Fee in International Application No. PCT/US2013/045309, mailed Nov. 25, 2013, 5 pages.
Isakova et al., "Fibroblast Growth Factor 23 and Risks of Mortality and End-Stage Renal Disease in Patients With Chronic Kidney Disease," JAMA, Jun. 15, 2011, 305:23, 2432-2439.
Ishikawa et al., "Accelerated proliferation of myeloma cells by interleukin-6 cooperating with fibroblast growth factor receptor 3-mediated signals," Oncogene, 2005, 24:6328-6332.
Israeli Office Action in Israeli Application No. 236,078 dated Mar. 21, 2017, 10 pages. (English Translation).
Jan de Beur, "Tumoral Calcinosis: A Look into the Metabolic Mirror of Phosphate Homeostasis," The Journal of Clinical Endocrinology & Metabolism, 2005, 90: 2469-2471.
Japanese Office Action in Japanese Application No. 2015-517376, dated Feb. 21, 2017, 5 pages. (with English translation).
Jebar et al., "FGFR3 and Ras gene mutations are mutually exclusive genetic events in urothelial cell carcinoma," Oncogene, 2005, 24: 5218-5225.
Javidi-Sharifi et al., "Crosstalk between KIT and FGFR3 Promotes Gastrointestinal Stromal Tumor Cell Growth and Drug Resistance," Cancer Research, Mar. 2015, 75(5): 880-892.
Jiang et al., "miR-99a promotes proliferation targeting FGFR3 in human epithelial ovarian cancer cells," Biomedicine & Pharmacotherapy, 2014, 68: 163-169.
Johnson et al., "Pharmacological and Functional Comparison of the Polo-like Kinase Family: Insight into Inhibitor and Substrate Specificity," Biochemistry, 2007, 46: 9551-9563.
Jonker et al., "A phase I study to determine the safety, pharmacokinetics and pharmacodynamics of a dual VEGFR and FGFR inhibitor, brivanib, in patients with advanced or metastatic solid tumors," Annals of Oncology, 2010, 1-7.
Jordan, V.C. Nature Reviews: Drug Discovery, 2, 2003, 205.
Kang et al., FGFR3 Activates RSK2 to Mediate Hematopoietic Transformation through Tyrosine Phosphorylation of RSK2 and Activation of the MEK/EEK Pathway, Cancer Cell, Sep. 2007, 12:201-214.
Kassack et al., "Structure-activity relationships of analogues of NF449 confirm NF449 as the most potent and selective known $P2X_1$ receptor antagonist," European Journal of Medicinal Chemisty, 2004, 345-357.
Katoh and Katoh, "FGF signaling network in the gastrointestinal tract (Review)," International Journal of Oncology, 2006, 29: 163-168.
Keats et al., "Ten years and counting: so what do we know about t(4;14) (p16;q32) multiple myeloma," Leukemia & Lymphoma, Nov. 2006, 47(11): 2289-2300.
Keer et al., "Enrolling a Rare Patient Population: Establishing Proof of Concept for FP-1039, an FGF "Trap," in Endometrial Cancer Patients with the S252W FGFR2 Mutation," Journal of Clinical Oncology, 2010 ASCO Annual Meeting Abstracts, 28:15, May 20 Supplement, 1 page.
Kim et al., "Phase I/II and Pharmacodynamic Study of Dovitinib (TKI258), an Inhibitor of Fibroblast Growth Factor Receptors and VEGF Receptors, in Patients with Advanced Melanoma," Clin Cancer Res, 2011, 17: 7451-7461.

(56) References Cited

OTHER PUBLICATIONS

Kim et al.' "The design, synthesis, and biological evaluation of potent receptor tyrosine kinase inhibitors," Bioorganic & Medicinal Chemistry Letters, 2012, 4979-4985.
Klein et al., "FGFR1 Kinase Inhibitors: Close Regioisomers Adopt Divergent Binding Modes and Display Distinct Biophysical Signatures," American Chemical Society, 2014, 166-171.
Knights and Cook, "De-regulated FGF receptors as therapeutic targets in cancer," Pharmacology & Therapeutics, 2010, 125:105-117.
Kompier et al., "Bladder cancer: Novel molecular characteristics, diagnostic, and therapeutic implications," Urologic Oncology: Seminars and Original Investigations, 2010, 91-96.
Kompier et al., "FGFR3, HRAS, KRAS, NRAS and PIK3CA Mutations in Bladder Cancer and Their Potential as Biomarkers for Surveillance and Therapy," PLoS ONE, Nov. 2010, 5(11): 1-13.
Kono et al., "The fibroblast growth factor receptor signaling pathway as a mediator of intrinsic resistance to EGFR-specific tyrosine kinase inhibitors in non-small cell lung cancer," Drug Resistance Updates, 2009, 95-102.
Koziczak and Hynes, "Cooperation between Fibroblast Growth Factor Receptor-4 and ErbB2 in Regulation of Cyclin D1 Translation," The Journal of Biological Chemistry, 2004, 279(48): 50004-50011.
Koziczak et al., "Blocking of FGFR signaling inhibits breast cancer cell proliferation through downregulation of D-type cyclins," Oncogene, 2004, 23:3501-3508.
Krejci et al., "Molecular pathology of the fibroblast growth factor family," Hum Mutat, Sep. 2009, 30(9): 1245-1255.
Krejci et al., "NF449 Is a Novel Inhibitor of Fibroblast Growth Factor Receptor 3 (FGFR3) Signaling Active in Chondrocytes and Multiple Myeloma Cells," The Journal of Biological Chemistry, Jul. 2010, 285(27): 20644-20653.
Krejci et al., "NF449 is a novel inhibitor of fibroblast growth factor receptor 3 (FGFR3) signaling active in chondrocytes and multiple myeloma cells," The American Society for Biochemistry and Molecular Biology, 2010, 1-20.
Kunii et al., "FGFR2-Amplified Gastric Cancer Cell Lines Require FGFR2 and Erbb3 Signaling for Growth and Survival," Cancer Res., Apr. 1, 2008, 68(7):2340-2348.
Kunii et al., "FGFR2-Amplified Gastric Cancer Cell Lines Require FGFR2 and Erbb3 Signaling for Growth and Survival," Cancer Res., Apr. 1, 2008, Supplemental figures, 11 pages.
Kuroso et al., "Immunohistochemical Detection of Fibroblast Growth Factor Receptor 3 in Human Breast Cancer: Correlation with Clinicopathological/Molecular Pammeteres and Prognosis," Pathobiology, Mar. 2010, 77: 231-240.
Kurosu et al., "Regulation of Fibroblast Growth Factor-23 Signaling by Klotho," The Journal of Biological Chemistry, Mar. 2006, 281(10): 6120-6123.
Lala et al., "Role of nitric oxide in tumor progression: Lessons from experimental tumors," Cancer and Metastasis Reviews, 1998, 17: 91-106.
Lammoglia and Mericq, "Familial Tumoral Calcinosis Caused by a Novel FGF23 Mutation: Response to Induction of Tubular Renal Acidosis with Acetazolamide and the Non-Calcium Phosphate Binder Sevelamer," Horm Res, 2009, 71:178-184.
Lamont et al., "Small molecule FGF receptor inhibitors block FGFR-dependent urothelial carcinoma growth in vitro and in vivo," Br. J Cancer, 2010, 1-8.
Lamont et al., "Small molecule FGF receptor inhibitors block FGFR-dependent urothelial carcinoma growth in vitro and in vivo," Br. J Cancer, 2011, 104:75-82.
Le Corre et al., "Synthesis and biological evaluation of a triazole-based library of pyrido [2,3-d]pyrimidines as FGFR3 tyrosine kinase inhibitors," Org. Biomol. Chem., 2010, 8, 2164-2173.
Lee et al., "In vivo Target Modulation and Biological Activity of CHIR-258, a Multitargeted Growth Factor Receptor Kinase Inhibitor, in Colon Cancer Models," Clin Cancer Res, May 2005, 3633-3641.

L'Hote and Knowles, "Cell responses to FGFR3 signalling: growth, differentiation and apoptosis," Experimental Cell Research, 2005, 417-431.
Li et al., "Compound deletion of Fgfr3 and Fgfr4 partially rescues the Hyp mouse phenotype," Am. J. Physiology—Endocrinol Metab, Dec. 7, 2010, 300:3, 29 pages.
Liang et al., "Anticancer molecules targeting fibroblast growth factor receptors," Cell Press, 2012, 11 pages.
Liu et al., "Developing Irreversible Inhibitors of the Protein Kinase Cysteinome," Chemistry & Biology, Feb. 2013, 146-159.
Liu et al., "FRFR3 and FRFR4 Do not Mediate Renal Effects of FGF23," J Am Soc Nephrol, 2008, 19:2342-2350.
Liu et al., "Pathogenic role of Fgf23 in Hyp mice," Am J Physiol Endocrinol Metab 291, Jan. 31, 2006, E38-E49.
Lopes de Menezes et al., "CHIR-258: A Potent Inhibitor of FLT3 Kinase in Experimental Tumor Xenograft Models of Human Acute Myelogenous Leukemia," Clin Cancer Res, Jul. 2005, 5281-5291.
Luo et al., "Deficiency of metabolic regulator FGFR4 delays breast cancer progression through systemic and microenvironmental metabolic alterations," Cancer & Metabolism, 2013, 20 pages.
Maeda et al., "Transforming property of TEL-FGFR3 mediated through PI3-K in a T-cell lymphoma that subsequently progressed to AML," Blood, Mar. 2005, 105(5): 2115-2123.
Marek et al., "Fibroblast Growth Factor (FGF) and FGF Receptor-Mediated Autocrine Signaling in Non-Small-Cell Lung Cancer Cells," Molecular Pharmacology, 2009, 75:196-207.
Marfe and Stefano, "In vitro Anti-leukaemia Activity of Pyrrolo[1,2-b][1,2,5]benzothiadiaze-pines (PBTDs)," Recent Patents on Anti-Cancer Drug Discovery, 2010, 58-68.
Marshall et al., "Fibroblast Growth Factor Receptors are Components of Autocrine Signaling Networks in Head and Neck Squamous Cell Carcinoma Cells," Clin Cancer Res., 2011, 17:5016-5025.
Martino et al., "Mutant fibroblast growth factor receptor 3 induces intracellular signaling and cellular transformation in a cell type- and mutation-specific manner," Oncogene, 2009, 28: 4306-4316.
Martinez-Torrecuadrada et al., "Targeting the Extracellular Domain of Fibroblast Growth Factor Receptor 3 with Human Single-Chain Fv Antibodies Inhibits Bladder Carcinoma Cell Line Proliferation," Clin Cancer Res, Sep. 2005, 6280-6290.
Matsuda et al., "Fibroblast Growth Factor Receptor 2 IIIc as a Therapeutic Target for Colorectal Cancer Cells," Mol Cancer Ther., 2012, 52 pages.
McConkey et al., "Molecular genetics of bladder cancer: Emerging mechanisms of tumor initiation and progression," Urologic Oncology: Seminars and Original Investigations, 2010, 429-440.
McMahon, "VEGF Receptor Signaling in Tumor Angiogenesis," Oncologist, 2000, 5(suppl 1):3-10.
Meijer et al., "Fibroblast growth factor receptor 4 predicts failure on tamoxifen therapy in patients with recurrent breast cancer," Endocrine-Related Cancer, 2008, 15:101-111.
Mellor, "Targeted inhibition of the FGF19-FGFR4 pathway in hepatocellular carcinoma; translational safety considerations," Liver International, 2013, 1-9.
Memon et al., "Does Fgf23-klotho activity influence vascular and soft tissue calcification through regulating phosphate homeostasis," Kidney Int., 2008, 74(5): 566-570.
Metzner, "Fibroblast Growth Factor Receptors as Therapeutic Targets in Human Melanoma: Synergism with BRAF Inhibition," J Investigative Dermatol., 2011, 131:2087-2095.
Miyake et al., "1-tert-Butyl-3-[6-(3,5-dimethoxy-phenyl)-2-(4-diethylamino-butylamino)-pyrido[2,3-d]pyrimidin-7-yl]-urea (PD173074), a Selective Tyrosine Kinase Inhibitor of Fibroblast Growth Factor Receptor-3 (FGFR3), Inhibits Cell Proliferation of Bladder Cancer Carrying the FGFR3 Gene Mutation along with Up-Regulation of p27/Kipl and $G_1/G_0$ Arrest," The Journal of Pharmacology and Experimental Therapeutics, 2010, 332(3):795-802.
Mohammadi et al., "Crystal structure of an angiogenesis inhibitor bound to the FGF receptor tyrosine kinase domain," The EMBO Journal, 1998, 5896-5904.
Mohammadi et al., "Structures of the Tyrosine Kinase Domain of Fibroblast Growth Factor Receptor in Complex with Inhibitors," Science, May 1997, 276:955-960.

(56) References Cited

OTHER PUBLICATIONS

Murphy et al., "Evidence for distinct alterations in the FGF axis in prostate cancer progression to an aggressive clinical phenotype," J Pathol., 2010, 220:452-460.
Naito et al., "Progressive tumoral calcinosis as the presenting feature of sarcoidosis in a patient on haemodialysis treatment," Nephrol Dial Transplant, 1999, 14:2716-2719.
Nakatani et al., "In vivo genetic evidence for klotho-dependent, fibroblast growth factor 23 (Fgf23)—mediated regulation of systemic phosphate homeostasis," The FASEB Journal, Feb. 2009, 23:433-441.
Natajaran et al., "p38 MAP kinase inhibitors. Part 3: SAR on 3,4-dihydropyrimido-[4,5-d]pyrimidin-2-ones and 3,4-dihydropyrido[4,3-d]-pyrimidin-2-ones," Bioorgan. Med. Chem. Lett., 2006, 4400-4404.
New Zealand Office Action in New Zealand Application No. 743274, dated Jul. 19, 2018, 5 pages.
New Zealand Examination Report in New Zealand Application No. 743274, dated Jul. 18, 2018, 4 pages.
New Zealand Office Action in New Zealand Application No. 702747, dated Sep. 16, 2016, 3 pages.
New Zealand Office Action in New Zealand Application No. 702747, dated Mar. 8, 2019, 2 pages.
Nitta, "Relationship between Fibroblast Growth Factor-23 and Mineral Metabolism in Chronic Kidney Disease," International Journal of Nephrology, 2010, 1-7.
Nomura et al., "FGF10/FGFR20 signal induces cell migration and invasion in pancreatic cancer," Br. J Cancer, 2008, 99:305-313.
Norman et al., "Protein-Ligand Crystal Structures Can Guide the Design of Selective Inhibitors of the FGFR Tyrosine Kinase," J. Med. Chem., 2012, 55(11):5003-5012.
Office Action from the Intellectual Property Office of the Philippines in Application No. 1-2014-502772, dated Mar. 17, 2016, 3 pages.
Ornitz et al., "Receptor Specificity of the Fibroblast Growth Factor Family," The Journal of Biological Chemistry, 1996, 271(25): 15292-15297.
Pai et al., "Antibody-Mediated Inhibition of Fibroblast Growth Factor 19 Results in Increased Bile Acids Synthesis and Ileal Malabsortion of Bile Acides in Cynomolgus Monkeys," Toxicological Sciences, 2012, 126(2): 446-456.
Pan et al., "MK-2461, a Novel Multitargeted Kinase Inhibitor, Preferentially Inhibits the Activated c-Met Receptor," Cancer Res, Feb. 2010, 1524-1533.
Pandith et al., "Oncogenic role of fibroblast growth factor receptor 3 in tumorigenesis of urinary bladder cancer," Urologic Oncology: Seminars and Original Investigations, 2010, 1-9.
Pandith et al., "Oncogenic role of fibroblast growth factor receptor 3 in tumorigenesis of urinary bladder cancer," Urologic Oncology: Seminars and Original Investigations, 2013, 31: 398-406.
Pardo et al., "The Fibroblast Growth Factor Receptor Inhibitor PD173074 Blocks Small Cell Lung Cancer Growth In vitro and In vivo," Cancer Res, Nov. 2009, 8645-8651.
Paterson et al., "Preclinical studies of fibroblast growth factor receptor 3 as a therapeutic target in multiple myeloma," British Journal of Haematology, 2004, 124:595-603.
Piazza et al., "Towards a new age in the treatment of multiple myeloma," Ann Hematol, 2007, 86:159-172.
Pinedo and Slamon, "Translational Research: The Role of VEGF in Tumor Angiogenesis," Oncologist, 2000, 5(suppl 1):1-2.
Platt et al., "Spectrum of Phosphatidylinositol 3-Kinase Pathway Gene Alterations in Bladder Cancer," Clin Cancer Res, Oct. 2009, 6008-6017.
Pliarchopoulou et al., "Current chemotherapeutic options for the treatment of advanced bladder cancer: A review," Urologic Oncology: Seminars and Original Investigations, 2010, 1-9.
Plowright et al., "Ectopic expression of fibroblast growth factor receptor 3 promotes myeloma cell proliferation and prevents apoptosis," Blood, Feb. 2000, 95(3): 992-998.
Podar et al., "Emerging therapies for multiple myeloma," Expert Opin. Emerging Drugs, 2009, 14(1):9-127.
Podar et al., "Targeting signalling pathways for the treatment of multiple myeloma," Expert Opin. Ther. Targets, 2005, 359-381.
Pollett et al., "Overexpression of the myeloma-associated oncogene fibroblast growth factor receptor 3 confers dexamethasone resistance," Blood, Nov. 2002, 100(10): 3819-3821.
Pollock et al., "Frequent activating FGFR2 mutations in endometrial carcinomas parallel germline mutations associated with craniosynostosis and skeletal dysplasia syndromes," Oncogene, 2007, 26:7158-7162.
Propper et al., "Phase I and Pharmacokinetic Study of PKC412, an Inhibitor of Protein Kinase C," J Clin Oncol, 2001, 19(5):1485-1492.
Qian et al., "Targeting Tumor Angiogenesis with Histone Deacetylase Inhibitors: the Hydroxamic Acid Derivative LBH589," Clin Cancer Res, Jan. 2006, 634-642.
Qing et al., "Antibody-based targeting of FGFR3 in bladder carcinoma and t(4;14)-positive multiple myeloma in mice," The Journal of Clinical Investigation, May 2009, 119(5): 1216-1229.
Qing et al., "Antibody-based targeting of FGFR3 in bladder carcinoma and t(4;14)-positive multiple myeloma in mice," The Journal of Clinical Investigation, May 2009, Supplemental Table 1: Summary of crystallographic analysis, 21 pages.
Qiu et al., "Over-expression of fibroblast growth factor receptor 3 in human hepatocellular carcinoma," World J Gastroenterol, 2005, 11(34): 5266-5272.
Raab et al., "Multiple myeloma," Lancet, 2009, 374: 324-339.
Ravindranathan et al., "Discovery of Novel Fibroblast Growth Factor Receptor 1 Kinase Inhibitors by Structure-Based Virtual Screening," J. Med. Chem., 2010, 53: 1662-1672.
Razzaque, "FGF23-mediated regulation of systemic phosphate homeostasis: is Klotho an essential player?," Am J Physiol Renal Physiol, 2009, 470-476.
Reimers et al., "NoBP, a Nuclear Fibroblast Growth Factor 3 Binding Protein, Is Cell Cycle Regulated and Promotes Cell Growth," Molecular and Cellular Biology, Aug. 2001, 21(15): 4996-5007.
Reis-Filho et al., "FGFR1 Emerges as a Potential Therapeutic Target for Lobular Breast Carcinomas," Clin Cancer Res, Nov. 2006, 6652-6662.
Reiter et al., "Consistent Fusion of ZNF198 to the Fibroblast Growth Factor Receptor-1 in the t(8;13)(p11;q12) Myeloproliferative Syndrome," Blood, Sep. 1998, 92(5): 1735-1742.
Remington's Pharmaceutical Sciences, 17th ed., Mack Publishing Company, Easton, Pa., 1985, p. 1418*.
Remington, "The Science and Practice of Pharmacy," Lippincott Williams & Wilkins, 2005, 21st edition *************Too voluminous to provide************.
Renhowe et al., "Design, Structure—Activity Relationships and in Vivo Characterization of 4-Amino-3-benzimidazol-2-ylhydroquinolin-2-ones: A Novel Class of Receptor Tyrosine Kinase Inhibitors," J. Med. Chem., 2009, 52: 278-292.
Ribatti et al., "The discovery of basic fibroblast growth factor/fibroblast growth factor-2 and its role in haematological malignancies," Cytokine & Growth Factor Reviews, 2007, 18: 327-334.
Ribatti, "Tyrosine Kinase Inhibitors as Antiangiogenic Drugs in Multiple Myeloma," Pharmaceuticals, 2010, 3: 1225-1231.
Roidl et al., "Resistance to Chemotherapy Is Associated with Fibroblast Growth Factor Receptor 4 Up-Regulation," Clin Cancer Res, Mar. 2009, 2058-2066.
Ronchetti et al., "Deregulated FGFR3 mutants in multiple myeloma cell lines with t(4;14): comparative analysis of Y373C, K650E and the novel G384D mutations," Oncogene, 2001, 20: 3553-3562.
Roumiantsev et al., "Distinct stem cell myeloproliferative/T lymphoma syndromes induced by ZNF198-FGFR1 and BCR-FGFR1 fusion genes from 8p11 translocations," Cancer Cell, Mar. 2004, 5: 287-298.
Rowe et al., "Handbook of Pharmaceutical Excipients," The Pharmaceutical Press and the American.Pharmaceutical Association, 2009, 6th Edition ****too voluminous to provide*****.
Ryan et al., "Toxicologic Pathology of Unique Biotechnology Agents and Biotherapies," Toxicologic Pathology, 1999, 27(1): 78-86.

(56) References Cited

OTHER PUBLICATIONS

Sakurai et al., "A novel angiogenesis inhibitor, Ki23057, is useful for preventing the progression of colon cancer and the spreading of cancer cells to the liver," European Journal of Cancer, 2007, 2612-2620.
Sarker et al., "A Phase I Pharmacokinetic and Pharmacodynamic Study of TKI258, an Oral, Multitargeted Receptor Tyrosine Kinase Inhibitor in Patients with Advanced Solid Tumors," Clin Cancer Res, Apr. 2008, 2075-2081.
Saxty et al., "Fragment-based drug discovery of selective inhibitors of fibroblast growth factor receptor (FGFr)," Cancer Res, Apr. 15, 2010, 70, 5778.
Schenone et al., "Small Molecules ATP-Comptetitive Inhibitors of FLT3: A Chemical Overview," Current Medicinal Chemistry, 2008, 15(29): 3113-3132.
Schlapbach et al., "A novel Pd-catalyzed cyclization rection of ureas for the synthesis of dihydroquinazolinone p38 kinase inhibitors," Bioorg. Med. Chem. Lett., 2004, 357-360.
Science IP Order 3032627, Chemical Structure Search, Science IP, Apr. 2012, 78 pages.
Science IP Order 3101926, Chemical Structure Search, Science IP, Jan. 2015, 50 pages.
Science IP Order 3101983, Chemical Structure Search, Science IP, Jan. 2015, 70 pages.
Science IP Order 3104564, Patent Chemical Structure Search, Science IP, Mar. 2015, 90 pages.
Science IP Order 3104565, Patent Chemical Structure Search, Science IP, Mar. 2015, 521 pages.
Segev et al., "Restrained chondrocyte proliferation and maturation with abnormal growth plate vascularization and ossification in human FRFR-3$^{G380R}$ trasngenic mice," Human Molecular Genetics, 2000, 9(2): 249-258.
Shariat et al., "Association of Angiogenesis Related Markers With Bladder Cancer Outcomes and Other Molecular Markers," The Journal of Urology, May 2010, 183: 1744-1750.
Sharkey et al., "PKC412 demonstrates JNK-dependent activity against human multiple myeloma cells," Blood, Feb. 2007, 109(4): 1712-1719.
Shi et al., "High Expression of FGFR4 Enhances Tumor Growth and Metastasis in Nasopharyngeal Carcinoma," Journal of Cancer, 2015, 6(12): 1245-1254.
Shinya et al., "Fgf signalling through MAPK cascade is required for development of the subpallial telencephalon in zebrafish embryos," Development, 2001, 4153-4164.
Singh et al., "Transforming Fusions of FGFR and TACC Genes in Human Glioblastoma," Science, Sep. 2012, 337:1231-1235.
Slavin et al., "Familial Tumoral Calcinosis," The American Journal of Surgical Pathology, 1993, 17(8): 188-802.
Smith et al., "Circulating αKlotho influences phosphate handling by controlling FGF23 production," The Journal of Clinical Investigation, Dec. 2012, 122(12): 4710-4715.
Song et al., "Fibroblast growth factors: An epigenetic mechanism of broad spectrum resistance to anticancer drugs," PNAS, Jul. 2000, 97(15): 8658-8663.
Sonvilla et al., "Fibroblast growth factor receptor 3-IIIc mediates colorectal cancer growth and migration," British Journal of Cancer, 2010, 1-12.
Soria, "FGFR inhibition overview of clinical development programs," Presentation, presented at TAT in Washington DC on Mar. 5-7, 2014, 54 pages.
Soverini et al., "Novel mutation and RNA splice variant of fibroblast growth factor receptor 3 in multiple myeloma patients at diagnosis," Haematologica, 2002, 87: 1036-1040.
Specktor et al., "Hyperphosphatemic familial tumoral calcinosis caused by a mutation in GALNT3 in a European kindred," J Hum Genet, 2006, 51:487-490.
Squires et al., "Development of inhibitors of the fibroblast growth factor receptor (FGFR) kinase using a fragment based approach," Cancer Res 70, Apr. 15, 2010, 3626.

Squires et al., "Development of inhibitors of the fibroblast growth factor receptor (FGFR) kinase using a fragment based approach," Cancer Res, 2008, 1 page.
Sun et al., "Design, Synthesis, and Evaluations of Substituted 3-[(3- or 4-Carboxyethylpyrrol-2-yl)methylidenyl]indolin-2-ones as Inhibitors of VEGF, FGF, and PDGF Receptor Tyrosine Kinases," J. Med. Chem., 1999, 42: 5120-5130.
Sun et al., "Identification of Substituted 3-[(4,5,6,7-Tetrahydro-1H-indol-2-yl)methylene]-1,3-dihydroindol-2-ones as Growth Factor Receptor Inhibitors for VEGF-R2 (Flk-1/KDR), FGF-R1, and PDGF-Rβ Tyrosine Kinases," J. Med. Chem., 2000, 43: 2655-2663.
Sun et al., "Synthesis and Biological Evaluations of 3-Substituated Indolin-2-ones: A Novel Class of Tyrosine Kinase Inhibitors That Exhibit Selectivity toward Particular Receptor Tyrosine Kinases," J. Med. Chem., 1998, 41: 2588-2603.
Taiwanese Office Action in Taiwan Application No. 102120946, dated Nov. 9, 2016, 9 pages. (with English translation).
Taiwanese Office Action in Taiwanese Application No. 102120946, dated Jul. 13, 2017, 7 pages. (English Translation).
Takeda et al., "AZD2171 Shows Potent Antitumor Activity Against Gastric Cancer Over-Expressing Fibroblast Growth Factor Receptor 2/Keratinocyte Growth Factor Receptor," Clin Cancer Res, May 2007, 3051-3057.
Tan et al., "Development of covalent inhibitors that can overcome resistance to first-generation FGFR kinase inhibitors," PNAS, Oct. 2014, E4869-E4877.
Taylor et al., "Identification of FGFR4-activating mutations in human rhabdomyasarcomas that promote metastasis in xenotransplanted models," J Clin Invest, Nov. 2009, 119(11): 3395-407.
Taylor, "Inhibitor PD-173074 Bound to the Tyrosine Kinase Domain of FGFR 1," Molecular & Behavioral Neuroscience Institute, Feb. 2006, 1 page.
Taylor, "Inhibitor SU-5402 Bound to the Tyrosine Kinase Domain of FGFR 1," Molecular & Behavioral Neuroscience Institute, Apr. 2006, 1 page.
Terai et al., "Vascular calcification and secondary hyperparathyroidism of severe chronic kidney disease and its relation to serum phosphate and calcium levels," British Journal of Pharmacology, 2009, 156: 1267-1278.
Thai Office Action in Thai Application No. 1401007417, dated Jun. 5, 2016, 7 pages (with English translation).
Thome and Weil, "Post-translational modifications regulate distinct functions of CARMA1 and BCL10," TRENDS in Immunology, 2007, 28(6): 281-288.
Thompson et al., "3-(3,5-Dimethoxyphenyl)-1,6-naphthyridine-2,7-diamines and Related 2-Urea Derivatives Are Potent and Selective Inhibitors of the FGF Receptor-1 Tyrosine Kinase," J. Med. Chem., 2000, 43: 4200-4211.
Thompson et al., "Photochemical Preparation of a Pyridone Containing Tetracycle: A Jak Protein Kinase Inhibitor," Bioorganic & Medicinal Chemistry Letters 12:1219-1223, 2002.
Thompson et al., "Synthesis and Structure—Activity Relationships of Soluble 7-Substituted 3-(3,5- Dimethoxyphenyl)-1,6-naphthyridin-2-amines and Related Ureas as Dual Inhibitors of the Fibroblast Growth Factor Receptor-1 and Vascular Endothelial Growth Factor Receptor-2 Tyrosine Kinases," J. Med. Chem., 2005, 48: 4628-2653.
Tolcher et al., "381 Preliminary results of a dose escalation study of the Fibroblast Growth Factor (FGF) "trap" FP-1039 (FGFR1:Fc) in patients with advanced malignancies," EJC Supplements, Nov. 2010, 8:7, p. 121.
Tomlinson et al., "FGFR3 protein expression and its relationship to mutation status and prognostic variables in bladder cancer," J Pathol, Sep. 2007, 213(1): 91-98.
Tomlinson et al., "Fibroblast Growth Factor Receptor 1 Promotes Proliferation and Survival via Activation of the Mitogen-Activated Protein Kinase Pathway in Bladder Cancer," Cancer Res, 2009, 4613-4620.
Tomlinson et al., "Knockdown by shRNA identifies S249C mutant FGFR3 as a potential therapeutic target in bladder cancer," Oncogene, 2007, 26: 5889-5899.

(56) References Cited

OTHER PUBLICATIONS

Topaz et al., "Mutations in GALNT3, encoding a protein involved in O-linked glycosylation, cause familial tumoral calcinosis," Nature Genetics, 2004, 1-3.
Traxler and Furet, "Strategies toward the Design of Novel and Selective Protein Tyrosine Kinase Inhibitors," Pharmacol. Ther., 1999, 82(2-3): 195-206.
Trudel et al., "CHIR-258, a novel, multitargeted tyrosine kinase inhibitor for the potential treatment of t(4;14) multiple myeloma," Blood, Apr. 2005, 105(7): 2941-2948.
Trudel et al., "Inhibition of fibroblast growth factor receptor 3 induces differentiation and apoptosis in t(4;14) myeloma," Blood, May 2004, 103(9):3521-3528.
Trudel et al., "The inhibitory anti-FGFR3 antibody, PRO-001, is cytotoxic to t(4;14) multiple myeloma cells," Blood, May 2006, 107(10): 4039-4046.
Trudel, "CHIR-258, a Novel Multi-targeted Tyrosine KinaseInhibitor, for the Treatment of t(4;14) Multiple Myeloma," Presentation, Presented at International Myeloma Foundation, Apr. 2005, 18 pages.
Turner and Grose, "Fibroblast growth factor signalling: from development to cancer," Nature Reviews Cancer, 2010, 10:116-129.
Turner et al., "FGFR1 Amplification Drives Endocrine Therapy Resistance and Is a Therapeutic Target in Breast Cancer," Cancer Res., Mar. 2010, 2085-2094.
Tvorogov et al., "Effective Suppression of Vascular Network Formation by Combination of Antibodies Blocking VEGFR Ligand Binding and Receptor Dimerization," Cancer Cell, Dec. 2010, 18: 630-640.
Ueno et al., "Enhanced Expression of Fibroblast Growth Factor Receptor 3 IIIc Promotes Human Esophageal Carcinoma Cell Proliferation," Journal of Histochemistry & Cytochemistry, 2016, 64(1): 7-17.
Ukraine Office Action in Ukraine Application No. a201500191, dated Dec. 13, 2016, 10 pages. (with English translation).
Ukraine Office Action in Ukraine Application No. a201511370, dated Nov. 12, 2018, 6 pages. (with English translation).
Urakawa et al., "Klotho converts canonical FGF receptor into a specific receptor for FGF23," Nature, Dec. 2006, 444: 770-774.
Uzawa et al., "Targeting fibroblast growth factor receptor 3 enhances radiosensitivity in human squamous cancer cells," Oncogene, 2011, 1-6.
van Oers et al., "FGFR3 Mutations Indicate Better Survival in Invasive Upper Urinary Tract and Bladder Tumours," European Urology, 2009, 650-658.
Våtsveen et al., "FGFR3 is expressed and is important for survival in INA-6, a human myeloma cell line without a t(4;14)," Eur. J. Haematol., 83:5, Jul. 6, 2009, 471-476.
Vietnamese Office Action in Vietnamese Application No. 1-2015-00102, dated Mar. 18, 2015, 4 pages.
von Massenhausen et al., "Evaluation of FGFR3 as a Therapeutic Target in Head and Neck Squamous Cell Carcinoma," Targ. Oncol., 2016, 11: 631-642.
Wang and Becker, "Antisense targeting of basic fibroblast growth factor and fibroblast growth factor receptor-1 in human melanomas blocks intratumoral angiogenesis and tumor growth," Nature Medicine, Aug. 1997, 887-893.
Wang and Ding, "Fibroblast growth factor receptors in breast cancer," Tumor Biology, May 2017, 1-10.
Ware et al., "Rapidly Acquired Resistance to EFGR Tyrosine Kinase Inhibitors in NSCLC Cell Lines through De-Repression of FGFR2 and FGFR3 Expression," PLoS, Nov. 2010, 5(11): 1-9.
Weiss et al., Frequent and Focal FGFR1 Amplification Associates with Therapeutically Tractable FGFR1 Dependency in Squamous Cell Lung Cancer, Sci. Transl. Med., 2010, 2(62):62ra93, pp. 1-7.
Wu, "Urothelial Tumorigenesis: A Tale of Divergent Pathways," Nature Reviews, Sep. 2005, 5: 713-725.

Wöhrle et al., "FGF Receptors Control Vitamin D and Phosphate Homeostasis by Mediating Renal FGF-23 Signaling and Regulating FGF-23 Expression in Bone," Journal of Bone and Mineral Research, Oct. 2011, 26(10): 2486-2497.
Wöhrle et al., "Pharmacological inhibition of FGFR signaling ameliorates FGF23-mediated hypophosphatemic rickets," Journal of Bone and Mineral Research, 2012, 1-36.
Xian et al., "Pleiotropic effects of FGFR1 on cell proliferation, survival, and migration in a 3D mammary epithelial cell model," JCB, 2005, 171(4): 663-673.
Xin et al., "CHIR-258 Is Efficacious in a Newly Developed Fibroblast Growth Factor Receptor 3-Expressing Orthotopic Multiple Myeloma Model in Mice," Clin Cancer Res, Aug. 2006, 4908-4915.
Xu et al., "Fibroblast growth factor receptor 4 promotes progression and correlates to poor prognosis in cholangiocarcinoma," Biochemical and Biophysical Research Communications, 2014, 446: 54-60.
Yu et al., "Analysis of the Biochemical Mechanisms for the Endocrine Actions of Firbroblast Growth Factor-23," Endocrinology, Nov. 2005, 146(11): 4647-4656.
Zaid et al., "Identification of FGFR4 as a Potential Therapeutic Target for Advanced-Stage, High-Grade Serous Ovarian Cancer," Clin Cancer Res, 2013, 19(4): 809-820.
Zhang et al., "AZD4547, a potent and selective FGF-receptor inhibitor induces tumor regressions in a human primary model of FGF-receptor 2 amplified gastric cancer and is efficacious in combination with chemotherapy," 2012.
Zhang et al., "Direct Cell Cycle Regulation by the Fibroblast Growth Factor Receptor (FGFR) Kinase through Phosphorylation-dependent Release of Cks1 from FGFR Substrate 2," The Journal of Biological Chemistry, 2004, 279(53): 55348-55354.
Zhang et al., "FP-1039 (FGFR1:Fc), A Soluble FGFR1 Receptor Antagonist, Inhibits Tumor Growth and Angiogenesis," Mol Cancer Ther, 6, Nov. 2007, B55.
Zhang et al., "Receptor Specificity of the Fibroblast Growth Factor Family," Journal of Biological Chemistry, Jun. 2006, 281(23): 15694-15700.
Zhang et al., "Translating the therapeutic potential of AZD4547 in FGFR1-amplified non-small cell lung cancer through the use of patient derived tumor xenograft (PDTX) models," Clin cancer Res, Oct. 18, 2012, 40 pages.
Zhao et al., "A Novel, Selective Inhibitor of Fibroblast Growth Factor Receptors That Shows a Potent Broad Spectrum of Antitumor Activity in Several Tumor Xenograft Models," Mol Cancer Ther, Nov. 2011, 2200-2210.
Zhao et al., "Homozygous Deletions and Chromosome Amplifications in Human Lung Carcinomas Revealed by Single Nucleotide Polymorphism Array Analysis," Cancer Res, Jul. 2005, 5561-5570.
Zhou et al., "A Structure-Guided Approach to Creating Covalent FGFR Inhibitors," Chemistry and Biology, Mar. 2010, 285-295.
Zhu et al., "Fibroblast growth factor receptor 3 inhibition by short hairpin RNAs leads to apoptosis in multiple myeloma," Mol Cancer Ther, May 2005, 787-798.
Zieger et al., "Role of Activating Fibroblast Growth Factor Receptor 3 Mutations in the Development of Bladder Tumors," Clin Cancer Res, Nov. 2005, 7709-7719.
Zingone et al., "Ectopic expression of wild-type FGFR3 cooperates with MYC to accelerate development of B-cell lineage neoplasms," Leukemia, 2010, 1171-1178.
Malaysian Office Action in Malaysian Application No. 2014003396, dated Dec. 15, 2017, 4 pages.
Mexican Office Action in Mexican Application No. MX/a/2014/015192, dated Jan. 24, 2018, 6 pages.
Japanese Office Action in Japanese Application No. 2016-509131, dated Feb. 20, 2018, 5 pages. (English Translation).
Eurasian Office Action in Eurasian Application No. 201791866, dated Feb. 19, 2018, 10 pages. (English Translation).
Eurasian Office Action in Eurasian Application No. 201590005, dated Mar. 28, 2018,.
Taiwan Office Action in Taiwan Application No. 103114284, dated Apr. 9, 2018, 4 pages. (English Search Report).
Chinese Office Action in Chinese Application No. 201480028858.7, dated Apr. 4, 2018, 10 pages. (English Translation).

(56) References Cited

OTHER PUBLICATIONS

Eurasian Office Action in Eurasian Application No. 201791867, dated Apr. 4, 2018, 4 pages. (English Translation).
Indonesian Office Action in Indonesian Application No. P00201507153, dated Apr. 27, 2018, 5 pages. (English Translation).
Williams et al., "Oncogenic FGFR3 gene fusions in bladder cancer," Hum Mol Genet, 2013, 22:795-803.
The Cancer Genome Atlas Research Network, "Comprehensivemolecular characterization of urothelial bladder carcinoma," Nature, 2014, 507: 315-22.
Piro et al., "An FGFR3 Autocrine Loop Sustains Acquired Resistance to Trastuzumab in Gastric Cancer Patients," Clinical Cancer Research, Dec. 2016, 22(24): 6164-6175.
Zhang et al., "Enhanced FGFR signalling predisposes pancreatic cancer to the effect of a potent FGFR inhibitor in preclinical models," British Journal of Cancer, 2014, 110: 320-329.
Peruvian Office Action in Peruvian Application No. 2433, dated Nov. 27, 2018, 13 pages.
Chinese Office Action in Chinese Application No. 201710874686.0, dated Feb. 25, 2019, 17 pages.
Chinese Office Action in Chinese Application No. 201710395346.X, dated Jan. 22, 2019, 17 pages.
Indian Office Action in Indian Application No. 9781/DELNP/2015, dated Jan. 18, 2019, 6 pages.
Argentina Office Action in Argentina Application No. 20140101651, dated Nov. 21, 2019, 5 pages.
Australian Office Action in Australian Application No. 2019200066, dated Aug. 27, 2019, 6 pages.
Bazyl et al., "The selective ortho-methoxylation of pentafluorobenzoic acid —a new way to tetrafluorosalicylic acid and its derivatives," J Flour Chem., Feb. 11, 1999, 94(1):11-13.
Caira, "Crystalline Polymorphism of Organic Compounds,"Topics in Current Chemistry, Jan. 1, 1998, 198:163-208.
Chilean Office Action in Chilean Application No. 1984-2017, dated Sep. 12, 2019, 9 pages.
Chinese Office Action in Chinese Application No. 201710395346.X, dated Sep. 9, 2019, 10 pages.
Chinese Office Action in Chinese Application No. 201680011348.8, dated Aug. 2, 2019, 14 pages.
Chinese Office Action in Chinese Application No. 201680011332.7, dated Aug. 5, 2019, 14 pages.
Chinese Office Action in Chinese Application No. 10874686.0, dated Oct. 8, 2019, 10 pages.
Colombian Office Action in Colombian Application No. NC2017/0008795, dated Aug. 16, 2019, 6 pages.
Heinrich et al., "Fragment-based discovery of new highly substituted 1H-pyrrolo[2,3-b]- and 3H-imidazolo[4,5-b]-pyridines as focal adhesion kinase inhibitors," J of Med Chem., Jan. 8, 2013, 56(3):1160-1170.
Heinle et al., "Is Fibroblast growth factor receptor 4 a suitable target of cancer therapy?" Cur. Pharm. Des., May 1, 2014, 20:2881-2898.
Indian Office Action in Indian Application No. 201717030267, dated Dec. 3, 2019, 7 pages.
Indian Office Action in Indian Application No. 201717030265, dated Dec. 12, 2019, 5 pages.
International Preliminary Report on Patentability in International Application No. PCT/US2018/034559, dated Nov. 26, 2019, 8 pages.
International Search Report and Written Opinion in International Application No. PCT/US2019/030633, dated Nov. 28, 2019, 21 pages.
International Invitation to Pay Fees in International Appln. No. PCT/US2019/030633, dated Aug. 12, 2019, 5 pages.
Jackson et al., "8p11 Myeloproliferative syndrome: a review," Human Pathology, Apr. 1, 2010, 41:461-476.
Japanese Office Action in Japanese Application No. 2017-543981, dated Dec. 3, 2019, 4 pages.
Japanese Office Action in Japanese Application No. 2017-544021, dated Nov. 26, 2019, 6 pages.
Philippine Office Action in Philippine Application No. 1-2017-501481, dated Oct. 29, 2019, 4 pages.
Taiwan Office Action in Taiwan Application No. 105105018, dated Oct. 22, 2019, 7 pages.
Takii et al., "Serotonin Derivative, N-(p-Coumaroyl)serotonin, Isolated from Safflower (*Carthamus tinctorius* L.) Oil Cake Augments the Proliferation of Normal Human and Mouse Fibroblasts in Synergy with Basic Fibroblast Growth Factor (bFGF) or Epidermal Growth Factor (EGF)", J Biochem., 1995, 125(5):910-915.
Ukraine Office Action in Ukraine Application No. a201709220, dated Dec. 9, 2019, 11 pages.
Wuts et al., "Greene's Protective Groups in Organic Synthesis," 4th Ed., 2006, Chapter 7, 696-926.

\* cited by examiner

SUBSTITUTED IMIDAZOPYRIDAZINES AND BENZIMIDAZOLES AS INHIBITORS OF FGFR3

CROSS REFERENCE TO RELATED APPLICATIONS

This application is a continuation of U.S. application Ser. No. 15/359,012, filed on Nov. 22, 2016, which is a divisional of U.S. application Ser. No. 14/267,139, filed on May 1, 2014, which is a continuation of U.S. application Ser. No. 13/333,021, filed on Dec. 21, 2011, which claims the benefit of U.S. Ser. No. 61/426,273, filed Dec. 22, 2010, the entireties of which are incorporated herein by reference.

FIELD OF THE INVENTION

The present invention relates to substituted imidazopyridazines and substituted benzimidazoles, as well as pharmaceutical compositions comprising the same, and which are FGFR3 inhibitors useful in the treatment of cancer and other diseases.

BACKGROUND OF THE INVENTION

The Fibroblast Growth Factor Receptors (FGFR) are receptor tyrosine kinases that bind to fibroblast growth factor (FGF) ligands. There are four FGFR proteins (FGFR1-4) that are capable of binding ligands and are involved in the regulation of many physiological processes including tissue development, angiogenesis, wound healing, and metabolic regulation. Upon ligand binding, the receptors undergo dimerization and phosphorylation leading to stimulation of the protein kinase activity and recruitment of many intracellular docking proteins. These interactions facilitate the activation of an array of intracellular signaling pathways including Ras-MAPK, AKT-PI3K, and phospholipase C that are important for cellular growth, proliferation and survival.

Aberrant activation of this pathway, either through overexpression of FGF ligands or FGFR or activating mutations in the FGFRs, can lead to tumor development, progression, and resistance to conventional cancer therapies. In human cancer, genetic alterations including gene amplification, chromosomal translocations and somatic mutations that lead to ligand-independent receptor activation have been described. Large scale DNA sequencing of thousands of tumor samples has revealed that components of the FGFR pathway are among the most frequently mutated in human cancer. Many of these activating mutations are identical to germline mutations that lead to skeletal dysplasia syndromes. Mechanisms that lead to aberrant ligand-dependent signaling in human disease include overexpression of FGFs and changes in FGFR splicing that lead to receptors with more promiscuous ligand binding abilities. Therefore, development of selective inhibitors targeting FGFR is useful in the clinical treatment of diseases that have elevated FGF or FGFR activity.

The cancer types in which FGF/FGFRs are implicated include, but are not limited to: carcinomas (e.g., bladder, breast, cervical, colorectal, endometrial, gastric, head and neck, kidney, liver, lung, ovarian, prostate); hematopoietic malignancies (e.g., multiple myeloma, chronic lymphocytic lymphoma, adult T cell leukemia, acute myelogenous leukemia, non-Hodgkin lymphoma, myeloproliferative neoplasms, and Waldenstrom's Macroglubulinemia); and other neoplasms (e.g., glioblastoma, melanoma, and rhabdosarcoma). In addition to a role in oncogenic neoplasms, FGFR activation has also been implicated in skeletal and chondrocyte disorders including but not limited to achrondroplasia and craniosynostosis syndromes.

There is a continuing need for the development of new drugs for the treatment of cancer, and the FGFR3 inhibitors described herein help address this need.

SUMMARY OF THE INVENTION

The present invention is directed to, inter alia, FGFR3 inhibitors of Formula I and II:

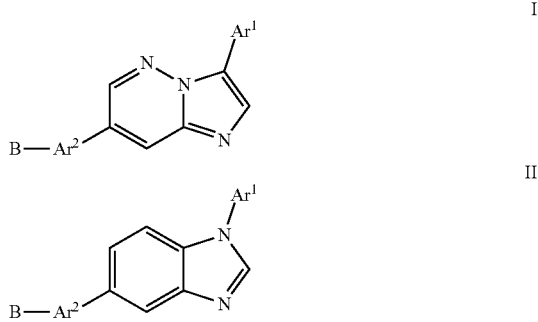

or pharmaceutically acceptable salts thereof, wherein constituent variables are defined herein.

The present invention is further directed to a pharmaceutical composition comprising a compound of Formula I or II, or a pharmaceutically acceptable salt thereof, and at least one pharmaceutically acceptable carrier.

The present invention is further directed to methods of treating the various diseases recited herein, including various cancers, myeloproliferative disorders, and skeletal or chondrocyte disorders, comprising administering to a patient a therapeutically effective amount of a compound of Formula I or II, or a pharmaceutically acceptable salt thereof.

DETAILED DESCRIPTION

The present invention is directed to, inter alia, FGFR3 inhibitors of Formula I and II:

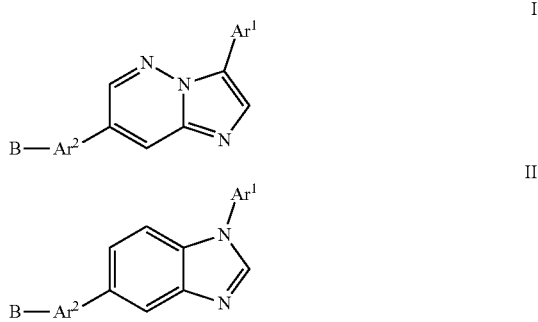

or a pharmaceutically acceptable salt thereof, wherein:

$Ar^1$ is aryl, heteroaryl, cycloalkyl, or heterocycloalkyl, each optionally substituted by 1, 2, 3, 4, or 5 independently selected $R^{41}$ groups;

$Ar^2$ is aryl, heteroaryl, cycloalkyl, or heterocycloalkyl, each optionally substituted by 1, 2, 3, or 4 independently selected $R^{42}$ groups;

B is:
(i) —(CR³R⁴)$_{m1}$—(CR¹R²)—(CR³R⁴)$_{m2}$—X;
(ii) -L¹-(CR³R⁴)$_n$-Cy¹;
(iii) -Cy²-(L²)$_a$-(CR³R⁴)$_p$-Cy³; or
(iv) -Cy⁴-L³-Y;

L¹ is C(O)NR, C(O)O, S(O)₂NR, NRC(O)NR, NRC(S)NR, S, or S(O);

L² and L³ are each independently selected from CO, C(O)O, C(O)NR, S(O)₂NR, NR, NRC(O)NR, NRC(S)NR, O, S, S(O), and S(O)₂;

X is Cy⁵, CN, C(O)NR⁵R⁶, NR⁵C(O)R⁷, NR⁵S(O)₂R⁷, NR⁵S(O)₂NR⁵R⁶, NR⁵C(O)OR⁸, or S(O)₂NR⁵R⁶;

Y is:
(1) aryl, heteroaryl, or heterocycloalkyl, each optionally substituted by 1, 2, 3, 4, or 5 independently selected $R^{B1}$ groups;
(2) $C_{3-7}$ cycloalkyl substituted by 1, 2, 3, 4, or 5 independently selected $R^{B2}$ groups; or
(3) $C_{1-6}$ alkyl or $C_{1-6}$ haloalkyl, each substituted by 1, 2, 3, 4, or 5 independently selected $R^X$ groups;

Cy¹, Cy², Cy³, Cy⁴, and Cy⁵ are each independently selected from aryl, heteroaryl, cycloalkyl, and heterocycloalkyl, each of which is optionally substituted by 1, 2, 3, 4, or 5 independently selected $R^{Cy}$ groups;

R is independently selected from H and $C_{1-4}$ alkyl;

R¹ is halo, cyano, hydroxy, $C_{1-4}$ alkyl, $C_{2-4}$ cyanoalkyl, $C_{2-4}$ alkoxyalkyl, $C_{1-4}$ haloalkyl, aryl, heteroaryl, cycloalkyl, or heterocycloalkyl, wherein said aryl, heteroaryl, cycloalkyl, or heterocycloalkyl is optionally substituted by 1, 2, 3, 4, or 5 independently selected $R^D$ groups;

R² and R⁴ are each independently selected from H, halo, hydroxy, $C_{1-4}$ alkyl, $C_{2-4}$ cyanoalkyl, $C_{2-4}$ alkoxyalkyl, and $C_{1-4}$ haloalkyl;

R³ is independently selected from H, halo, cyano, hydroxy, $C_{1-4}$ alkyl, $C_{2-4}$ cyanoalkyl, $C_{2-4}$ alkoxyalkyl, $C_{1-4}$ haloalkyl, aryl, heteroaryl, cycloalkyl, and heterocycloalkyl, wherein said aryl, heteroaryl, cycloalkyl, or heterocycloalkyl is optionally substituted by 1, 2, 3, 4, or 5 independently selected $R^D$ groups;

R⁵ is independently selected from H, $C_{1-4}$ alkyl, $C_{2-4}$ cyanoalkyl, $C_{2-4}$ alkoxyalkyl, and $C_{1-4}$ haloalkyl;

R⁶, R⁷, and R⁸ are each independently selected from H, $C_{1-4}$ alkyl, aryl, heteroaryl, cycloalkyl, and heterocycloalkyl, wherein said $C_{1-4}$ alkyl, aryl, heteroaryl, cycloalkyl, or heterocycloalkyl is optionally substituted with 1, 2, 3, 4, 5, or 6 independently selected $R^D$ groups;

or R⁵ and R⁶ together with the N atom to which they are attached form a 4-, 5-, 6-, or 7-membered heterocycloalkyl ring optionally substituted by 1, 2, 3, 4, or 5 independently selected $R^D$ groups;

each $R^{A1}$ is independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, NO₂, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$ C(=NR$^e$)R$^b$, C(=NR$^e$)NR$^c$R$^d$, NR$^c$C(=NR$^e$)NR$^c$R$^d$ NR$^c$S(O)R$^b$ NR$^c$S(O)₂R$^b$, NR$^c$S(O)₂NR$^c$R$^d$, S(O)R$^b$, S(O)NR$^c$R$^d$, S(O)₂R$^b$, and S(O)₂NR$^c$R$^d$; wherein said $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, NO₂, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(=NR$^e$)NR$^c$R$^d$, NR$^c$R$^d$, NR$^c$C(O)R$^b$, NR$^c$C(O)OR$^a$, NRC(O)NR$^c$R$^d$, NR$^c$S(O)R$^b$, NR$^c$S(O)₂R$^b$, NR$^c$S(O)₂NR$^c$R$^d$, S(O)R$^b$, S(O)NR$^c$R$^d$, S(O)₂R$^b$, and S(O)₂NR$^c$R$^d$;

each $R^{A2}$ is independently selected from halo, $C_{1-4}$ alkyl, $C_{2-4}$ alkenyl, $C_{2-4}$ alkynyl, $C_{1-4}$ haloalkyl, halosulfanyl, CN, NO₂, OR$^{a1}$, SR$^{a1}$, C(O)R$^{b1}$, C(O)NR$^{c1}$R$^{d1}$, C(O)OR$^{a1}$, OC(O)R$^{b1}$ OC(O)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, C(=NR$^{e1}$)R$^{b1}$, C(=NR$^{e1}$)NR$^{c1}$R$^{d1}$, NR$^{c1}$C(=NR$^{e1}$)NR$^{c1}$R$^{d1}$, NR$^{c1}$S(O)R$^{b1}$ NR$^{c1}$S(O)₂R$^{b1}$, NR$^{c1}$S(O)₂NR$^{c1}$R$^{d1}$ S(O)R$^{b1}$, S(O)NR$^{e1}$R$^{d1}$, S(O)₂R$^{b1}$, and S(O)₂NR$^{c1}$R$^{d1}$; wherein said $C_{1-4}$ alkyl, $C_{2-4}$ alkenyl, $C_{2-4}$ alkynyl, $C_{1-4}$ haloalkyl, aryl, cycloalkyl, heteroaryl, and heterocycloalkyl are each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, NO₂, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$ NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)₂R$^{b1}$, NR$^{c1}$S(O)₂NR$^{c1}$R$^{d1}$, S(O)R$^{b1}$, S(O)NR$^{c1}$R$^{d1}$, S(O)₂R$^{b1}$, and S(O)₂NR$^{c1}$R$^{d1}$;

each $R^{B1}$, $R^{B2}$, $R^{Cy}$, and $R^D$ is independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, NO₂, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^{e2}$)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$S(O)R$^{b2}$, NR$^{c2}$S(O)₂R$^{b2}$, NR$^{c2}$S(O)₂NR$^{c2}$R$^{d2}$, S(O)R$^{b2}$, S(O)NR$^{c2}$R$^{d2}$, S(O)₂R$^{b2}$, and S(O)₂NR$^{c2}$R$^{d2}$; wherein said $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, NO₂, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$ NR$^{c2}$C(O)OR$^{a2}$, NR$^{c2}$C(O)NR$^{c2}$R$^{d2}$, NR$^{c2}$S(O)R$^{b2}$, NR$^{c2}$S(O)₂R$^{b2}$, NR$^{c2}$S(O)₂NR$^{c2}$R$^{d2}$, S(O)R$^{b2}$ S(O)NR$^{c2}$R$^{d2}$, S(O)₂R$^{b2}$, and S(O)₂NR$^{c2}$R$^{d2}$;

each $R^X$ is independently selected from $C_{1-6}$ alkyl, $C_{2-6}$ alkenyl, $C_{2-6}$ alkynyl, aryl, cycloalkyl, heteroaryl, heterocycloalkyl, CN, NO₂, OR$^{a3}$, SR$^{a3}$, C(O)R$^{b3}$, C(O)NR$^{c3}$R$^{d3}$ C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NR$^{e3}$)NR$^{c3}$R$^{d3}$, NR$^{c3}$C(=NR$^{e3}$)NR$^{c3}$R$^{d3}$, NR$^{c3}$S(O)R$^{b3}$, NR$^{c3}$S(O)₂R$^{b3}$, NR$^{c3}$S(O)₂NR$^{c3}$R$^{d3}$, S(O)R$^{b3}$, S(O)NR$^{c3}$R$^{d3}$, S(O)₂R$^{b3}$, and S(O)₂NR$^{c3}$R$^{d3}$; wherein said $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, NO₂, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)₂R$^{b3}$, NR$^{c3}$S(O)₂NR$^{c3}$R$^{d3}$, S(O)R$^{b3}$, S(O)NR$^{c3}$R$^{d3}$, S(O)₂R$^{b3}$, and S(O)₂NR$^{c3}$R$^{d3}$;

each R$^a$, R$^b$, R$^c$, and R$^d$ is independently selected from H, $C_{1-6}$ alkyl, $C_{1-4}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl; wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-4}$ alkyl, $C_{1-4}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{f4})NR^{c4}R^{d4}$, $NR^{c4}C(=NR^{f4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

or any $R^c$ and $R^d$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{f4})NR^{c4}R^{d4}$, $NR^{c4}C(=NR^{f4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$, wherein said $C_{1-6}$ alkyl is optionally substituted by 1, 2, or 3 substituents independently selected from halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{f4})NR^{c4}R^{d4}$, $NR^{c4}C(=NR^{f4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

each $R^e$ and $R^f$ is independently selected from H, $C_{1-4}$ alkyl, CN, $OR^{a4}$, $SR^{b4}$, $S(O)_2R^{b4}$, $C(O)R^{b4}$, $S(O)_2NR^{c4}R^{d4}$, and $C(O)NR^{c4}R^{d4}$;

each $R^{a1}$, $R^{b1}$, $R^{c1}$, and $R^{d1}$ is independently selected from H, $C_{1-4}$ alkyl, $C_{2-4}$ alkenyl, $C_{2-4}$ alkynyl, aryl, cycloalkyl, heteroaryl, and heterocycloalkyl, wherein said $C_{1-4}$ alkyl, $C_{2-4}$ alkenyl, $C_{2-4}$ alkynyl, aryl, cycloalkyl, heteroaryl, or heterocycloalkyl is optionally substituted with 1, 2, or 3 substituents independently selected from $C_{1-6}$ alkyl, $C_{1-6}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{f4})NR^{c4}R^{d4}$, $NR^{c4}C(=NR^{f4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

or any $R^{c1}$ and $R^{d1}$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, $OR^{a4}SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$ $NR^{c4}C(O)R^{b4}$, $NR^{c4}C(O)NR^{c4}R^{d4}$ $NR^{c4}C(O)OR^{a4}$, $C(=NR^{f4})NR^{c4}R^{d4}$, $NR^{c4}C(=NR^{f4})NR^{c4}R^{d4}$ $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

each $R^{e1}$ and $R^{f1}$ is independently selected from H, $C_{1-4}$ alkyl, CN, $OR^{a4}$, $SR^{b4}$, $S(O)_2R^{b4}$, $C(O)R^{b4}$, $S(O)_2NR^{c4}R^{d4}$, and $C(O)NR^{c4}R^{d4}$;

each $R^{a2}$, $R^{b2}$, $R^{c2}$, and $R^{d2}$ is independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-4}$ alkyl, $C_{1-4}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$ $NR^{c4}C(O)R^{b4}$ $NR^{c4}C(O)NR^{c4}R^{d4}$ $NR^{c4}C(O)OR^{a4}$, $C(=NR^{f4})NR^{c4}R^{d4}$ $NR^{c4}C(=NR^{f4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$ and $S(O)_2NR^{c4}R^{d4}$;

or any $R^{c2}$ and $R^{d2}$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{f4})NR^{c4}R^{d4}$, $NR^{c4}C(=NR^{f4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$, wherein said $C_{1-6}$ alkyl is optionally substituted by 1, 2, or 3 substituents independently selected from halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{f4})NR^{c4}R^{d4}$, $NR^{c4}C(=NR^{f4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

each $R^{e2}$ and $R^{f2}$ is independently selected from H, $C_{1-4}$ alkyl, CN, $OR^{a4}$, $SR^{b4}$, $S(O)_2R^{b4}$, $C(O)R^{b4}$, $S(O)_2NR^{c4}R^{d4}$, and $C(O)NR^{c4}R^{d4}$;

each $R^{a3}$, $R^{b3}$, $R^{c3}$, and $R^{d3}$ is independently selected from H, $C_{1-6}$ alkyl, $C_{2-6}$ alkenyl, and $C_{2-6}$ alkynyl, wherein said $C_{1-6}$ alkyl, $C_{2-6}$ alkenyl, or $C_{2-6}$ alkynyl, is optionally substituted with 1, 2, 3, 4, or 5 substituents independently selected from $C_{1-4}$ alkyl, $C_{1-4}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$ $NR^{c4}C(O)R^{b4}$, $NR^{c4}C(O)NR^{c4}R^{d4}$, $NR^{c4}C(O)OR^{a4}$, $C(=NR^{f4})NR^{c4}R^{d4}$, $NR^{c4}C(=NR^{f4})NR^{c4}R^{d4}$ $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

or any $R^{c3}$ and $R^{d3}$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$ $NR^{c4}C(O)R^{b4}$ $NR^{c4}C(O)NR^{c4}R^{d4}$ $NR^{c4}C(O)OR^{a4}$, $C(=NR^{f4})NR^{c4}R^{d4}$, $NR^{c4}C(=NR^{f4})NR^{c4}R^{d4}$ $S(O)R^{b4}$, $S(O)NR^{c4}R^{d4}$, $S(O)_2R^{b4}$, $NR^{c4}S(O)_2R^{b4}$ $NR^{c4}S(O)_2NR^{c4}R^{d4}$, and $S(O)_2NR^{c4}R^{d4}$;

each $R^{e3}$ and $R^{f3}$ is independently selected from H, $C_{1-4}$ alkyl, CN, $OR^{a4}$, $SR^{b4}$, $S(O)_2R^{b4}$, $C(O)R^{b4}$, $S(O)_2NR^{c4}R^{d4}$, and $C(O)NR^{c4}R^{d4}$;

each $R^{a4}$, $R^{b4}$, $R^{c4}$, and $R^{d4}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{1-4}$ haloalkyl, $C_{2-4}$ alkenyl, or $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

or any $R^{c4}$ and $R^{d4}$ together with the N atom to which they are attached form a 3-, 4-, 5-, 6-, or 7-membered heterocycloalkyl group or heteroaryl group, each optionally substituted with 1, 2, or 3 substituents independently selected from OH, CN, amino, halo, $C_{1-6}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

each $R^{e4}$ and $R^{f4}$ is independently selected from H, $C_{1-4}$ alkyl, and CN;

a is 0 or 1;
m1 is 0, 1, 2, 3, or 4;
m2 is 0, 1, 2, 3, or 4;
n is 1, 2, 3, 4, 5, or 6; and
p is 1, 2, 3, 4, 5, or 6.

In some embodiments, the compounds of the invention have Formula I.

In some embodiments, the compounds of the invention have Formula II.

In some embodiments, $Ar^1$ is aryl or heteroaryl, each optionally substituted by 1, 2, 3, 4, or 5 independently selected $R^{A1}$ groups.

In some embodiments, $Ar^1$ is aryl optionally substituted by 1, 2, 3, 4, or 5 independently selected $R^{A1}$ groups.

In some embodiments, $Ar^1$ is phenyl optionally substituted by 1, 2, 3, 4, or 5 independently selected $R^{A1}$ groups.

In some embodiments, $Ar^1$ is phenyl optionally substituted by one $R^{A1}$ group.

In some embodiments, $R^{A1}$ is independently selected from $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, and $NR^cS(O)_2NR^cR^d$.

In some embodiments, at least one $R^{A1}$ is $NR^cC(O)NR^cR^d$.

In some embodiments, each $R^c$ and $R^d$ is independently selected from H and $C_{1-6}$ alkyl, wherein said $C_{1-6}$ alkyl, is optionally substituted with 1, 2, 3, 4, or 5 substituents independently selected from $C_{1-4}$ alkyl, $C_{1-4}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$ $NR^{c4}C(O)R^{b4}$ $NR^{c4}C(O)NR^{c4}R^{d4}$ $NR^{c4}C(O)OR^{a4}$, $C(=NR^{j4})NR^{c4}R^{d4}$ $NR^{c4}C(=NR^{j4})NR^{c4}R^{d4}$ $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$.

In some embodiments, each $R^c$ is H and $R^d$ is $C_{1-6}$ alkyl or $C_{1-6}$ haloalkyl.

In some embodiments, $Ar^2$ is aryl or heteroaryl, each optionally substituted by 1, 2, 3, or 4 independently selected $R^{A2}$ groups.

In some embodiments, $Ar^2$ is aryl optionally substituted by 1, 2, 3, or 4 independently selected $R^{A2}$ groups.

In some embodiments, $Ar^2$ is phenyl optionally substituted by 1, 2, 3, or 4 independently selected $R^{A2}$ groups.

In some embodiments, $Ar^2$ is phenyl.

In some embodiments, $Ar^2$ is heteroaryl optionally substituted by 1, 2, 3, or 4 independently selected $R^A$ groups.

In some embodiments, $Ar^2$ is pyrazolyl optionally substituted by 1, 2, or 3 independently selected $R^A$ groups.

In some embodiments, $Ar^2$ is pyrazolyl.

In some embodiments, $Ar^2$ is heterocycloalkyl optionally substituted by 1, 2, or 3 independently selected $R^A$ groups.

In some embodiments, $Ar^2$ is 1,2,3,4-tetrahydroisoquinolinyl optionally substituted by 1, 2, 3, or 4 independently selected $R^A$ groups.

In some embodiments, $Ar^2$ is 1,2,3,4-tetrahydroisoquinolinyl.

In some embodiments, B is $-(CR^3R^4)_{m1}-(CR^1R^2)-(CR^3R^4)_{m2}-X$.

In some embodiments, X is $Cy^5$, $C(O)NR^5R^6$, $NR^5C(O)R^7$, $NR^5S(O)_2R^7$, $NR^5S(O)_2NR^5R^6$, $NR^5C(O)OR^8$, or $S(O)_2NR^5R^6$.

In some embodiments, X is CN, $C(O)NR^5R^6$, $NR^5C(O)R^7$, $NR^5S(O)_2R^7$, $NR^5S(O)_2NR^5R^6$, $NR^5C(O)OR^8$, or $S(O)_2NR^5R^6$.

In some embodiments, X is $C(O)NR^5R^6$, $NR^5C(O)R^7$, $NR^5S(O)_2R^7$, $NR^5S(O)_2NR^5R^6$, $NR^5C(O)OR^8$, or $S(O)_2NR^5R^6$.

In some embodiments, X is $Cy^5$, CN, or $C(O)NR^5R^6$.
In some embodiments, X is $Cy^5$.
In some embodiments, X is CN.
In some embodiments, X is $C(O)NR^5R^6$.
In some embodiments, m1 is 0.

In some embodiments, $R^1$ is halo, cyano, hydroxy, $C_{1-4}$ alkyl, $C_{2-4}$ cyanoalkyl, $C_{2-4}$ alkoxyalkyl, or $C_{1-4}$ haloalkyl.

In some embodiments, $R^1$ is $C_{1-4}$ alkyl or $C_{1-4}$ haloalkyl.

In some embodiments, $R^1$ is $C_{1-4}$ alkyl.

In some embodiments, each $R^3$ is independently selected from H, halo, cyano, hydroxy, $C_{1-4}$ alkyl, $C_{2-4}$ cyanoalkyl, $C_{2-4}$ alkoxyalkyl, and $C_{1-4}$ haloalkyl.

In some embodiments, each $R^3$ is independently selected from H, halo, cyano, hydroxy, and $C_{1-4}$ alkyl.

In some embodiments, each $R^3$ is independently selected from H and $C_{1-4}$ alkyl.

In some embodiments, B is $-L^1-(CR^3R^4)_n-Cy^1$.

In some embodiments, $L^1$ is C(O)NR.

In some embodiments, n is 1 or 2.

In some embodiments, B is $-Cy^2-(L^2)_a-(CR^3R^4)_p-Cy^3$.

In some embodiments, a is 1.

In some embodiments, a is 0.

In some embodiments, p is 1 or 2.

In some embodiments, B is $-Cy^4-L^3-Y$.

In some embodiments, Y is aryl, heteroaryl, or heterocycloalkyl, each optionally substituted by 1, 2, 3, 4, or 5 independently selected $R^{B1}$ groups.

In some embodiments, Y is $C_{3-7}$ cycloalkyl substituted by 1, 2, 3, 4, or 5 independently selected $R^{B2}$ groups.

In some embodiments, Y is $C_{1-6}$ alkyl or $C_{1-6}$ haloalkyl, each substituted by 1, 2, 3, 4, or 5 independently selected $R^X$ groups.

In some embodiments, the compounds of the invention have Formula Ia or IIa:

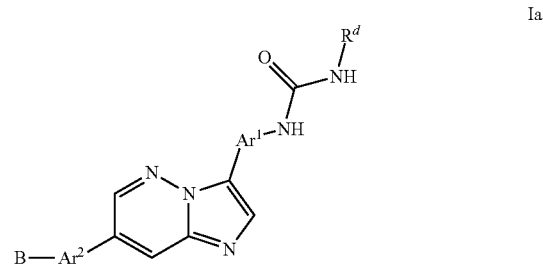

Ia

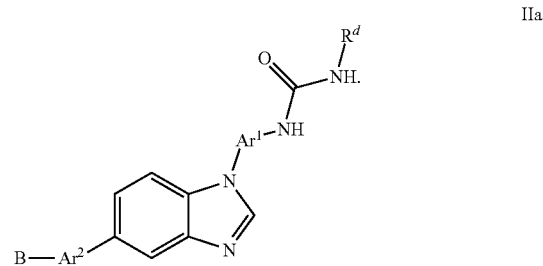

IIa

In some embodiments, $R^d$ is $C_{1-4}$ alkyl or $C_{1-4}$ haloalkyl.

In some embodiments, $R^d$ is $C_{1-4}$ haloalkyl.

In some embodiments, $Ar^1$ is aryl or heteroaryl, each optionally substituted by 1, 2, or 3 independently selected $R^{A1}$ groups.

In some embodiments, the compounds of the invention have Formula Ib or IIb:

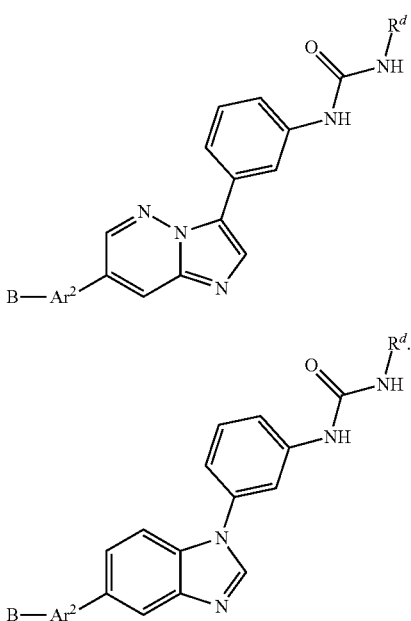

In some embodiments, Cy$^1$ is selected from aryl, heteroaryl, cycloalkyl, and heterocycloalkyl, each of which is substituted by 1, 2, 3, 4, or 5 independently selected R$^{Cy}$ groups.

In some embodiments, Cy$^5$ is selected from aryl, heteroaryl, cycloalkyl, and heterocycloalkyl, each of which is substituted by 1, 2, 3, 4, or 5 independently selected R$^{Cy}$ groups.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "C$_{1-6}$ alkyl" is specifically intended to individually disclose methyl, ethyl, C$_3$ alkyl, C$_4$ alkyl, C$_5$ alkyl, and C$_6$ alkyl.

At various places in the present specification, linking substituents are described. It is specifically intended that each linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups. For example, if the structure requires a linking group and the Markush group definition for that variable lists "alkyl" or "aryl" then it is to be understood that the "alkyl" or "aryl" represents a linking alkylene group or arylene group, respectively.

At various places in the present specification, rings are described (e.g., "a piperidine ring"). Unless otherwise specified, these rings can be attached to the rest of the molecule at any ring member as permitted by valency. For example, the term "a pyridine ring" may refer to a pyridin-2-yl, pyridin-3-yl, or pyridin-4-yl ring.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable.

For example, where a structure is described having two R groups that are simultaneously present on the same compound, the two R groups can represent different moieties independently selected from the group defined for R.

As used herein, the phrase "optionally substituted" means unsubstituted or substituted.

As used herein, the term "substituted" means that a hydrogen atom is replaced by a non-hydrogen substituent. It is to be understood that substitution at a given atom is limited by valency.

As used herein, the term "C$_{n-m}$", employed in combination with a chemical group, designates a range of the number of carbon atoms in the chemical group. For example, C$_{1-6}$ alkyl refers to an alkyl group having from 1, 2, 3, 4, 5, or 6 carbon atoms.

As used herein, the term "alkyl", employed alone or in combination with other terms, refers to a saturated hydrocarbon group that may be straight-chain or branched. In some embodiments, the alkyl group contains 1 to 6, 1 to 4 or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, n-heptyl, n-octyl, and the like. In some embodiments, the alkyl group is methyl, ethyl, or propyl.

As used herein, "alkenyl", employed alone or in combination with other terms, refers to an alkyl group having one or more carbon-carbon double bonds. In some embodiments, the alkenyl moiety contains 2 to 6, or 2 to 4 carbon atoms. Example alkenyl groups include, but are not limited to, ethenyl, n-propenyl, isopropenyl, n-butenyl, sec-butenyl, and the like.

As used herein, "alkynyl", employed alone or in combination with other terms, refers to an alkyl group having one or more carbon-carbon triple bonds. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, "halo" or "halogen", employed alone or in combination with other terms, includes fluoro, chloro, bromo, and iodo.

As used herein, the term "haloalkyl", employed alone or in combination with other terms, refers to an alkyl group having up to the full valency of halogen atoms, which may either be the same or different. In some embodiments, the halogen atoms are fluoro atoms. In some embodiments, the alkyl group has 1 to 6 or 1 to 4 carbon atoms. Example haloalkyl groups include CF$_3$, C$_2$F$_5$, CHF$_2$, CCl$_3$, CHCl$_2$, C$_2$Cl$_5$, and the like. In some embodiments, the haloalkyl group is a fluoroalkyl group.

As used herein, the term "fluoroalkyl", employed alone or in combination with other terms, refers to a haloalkyl wherein the halogen atoms are fluorines. In some embodiments, fluroalkyl is fluoromethyl, difluoromethyl, or trifluoromethyl.

As used herein, the term "alkoxy", employed alone or in combination with other terms, refers to an group of formula —O-alkyl. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, "haloalkoxy", employed alone or in combination with other terms, refers to a group of formula —O-(haloalkyl). In some embodiments, the alkyl group has 1 to 6 or 1 to 4 carbon atoms. An example haloalkoxy group is —OCF$_3$. In some embodiments, the haloalkoxy group is a fluoroalkoxy group.

As used herein, the term "fluoroalkoxy", employed alone or in combination with other terms, refers to an alkoxy group, wherein the halogen atoms are selected from fluorine.

As used herein, "amino", employed alone or in combination with other terms, refers to NH$_2$.

As used herein, the term "alkylamino", employed alone or in combination with other terms, refers to a group of formula —NH(alkyl). In some embodiments, the alkylamino group has 1 to 6 or 1 to 4 carbon atoms. Example alkylamino groups include methylamino, ethylamino, propylamino (e.g., n-propylamino and isopropylamino), and the like.

As used herein, the term "dialkylamino", employed alone or in combination with other terms, refers to a group of formula —N(alkyl)$_2$. Example dialkylamino groups include dimethylamino, diethylamino, dipropylamino (e.g., di(n-propyl)amino and di(isopropyl)amino), and the like. In some embodiments, each alkyl group independently has 1 to 6 or 1 to 4 carbon atoms.

As used herein, the term "alkylthio", employed alone or in combination with other terms, refers to a group of formula —S-alkyl. In some embodiments, the alkyl group has 1 to 6 or 1 to 4 carbon atoms.

As used herein, the term "cyano" refers to a CN group.

As used herein, the term "hydroxyl" refers to an OH group.

As used herein, the term "cyanoalkyl" refers to an alkyl group substituted by a cyano group.

As used herein, the term "alkoxyalkyl" refers to an alkyl group substituted by an alkoxy group.

As used herein, "halosulfanyl" refers to a sulfur group having one or more halogen substituents. Example halosulfanyl groups include pentahalosulfanyl groups such as SF$_5$.

As used herein, the term "cycloalkyl", employed alone or in combination with other terms, refers to a non-aromatic cyclic hydrocarbon including cyclized alkyl and alkenyl groups. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. Ring-forming carbon atoms of a cycloalkyl group can be optionally substituted by oxo. Cycloalkyl groups also include cycloalkylidenes. The term "cycloalkyl" also includes bridgehead cycloalkyl groups and spirocycloalkyl groups. As used herein, "bridgehead cycloalkyl groups" refers to non-aromatic cyclic hydrocarbon moieties containing at least one bridgehead carbon, such as admantan-1-yl. As used herein, "spirocycloalkyl groups" refers to non-aromatic hydrocarbon moieties containing at least two rings fused at a single carbon atom, such as spiro[2.5]octane and the like. In some embodiments, the cycloalkyl group has 3 to 14 ring members, 3 to 10 ring members, or 3 to 7 ring members. In some embodiments, the cycloalkyl group is monocyclic, bicyclic or tricyclic. In some embodiments, the cycloalkyl group is monocyclic. In some embodiments, the cycloalkyl group is a C$_{3-7}$ monocyclic cycloalkyl group. One or more ring-forming carbon atoms of a cycloalkyl group can be oxidized to form carbonyl linkages. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, tetrahydronaphthalenyl, octahydronaphthalenyl, indanyl, and the like. In some embodiments, the cycloalkyl group is cyclopropyl, cyclobutyl, cyclopentyl, or cyclohexyl As used herein, the term "cycloalkylalkyl", employed alone or in combination with other terms, refers to a group of formula cycloalkyl-alylene-. In some embodiments, the alkylene portion has 1 to 4, 1 to 3, 1 to 2, or 1 carbon atom(s). In some embodiments, the alkylene portion is methylene. In some embodiments, the cycloalkyl portion has 3 to 14 ring members, 3 to 10 ring members, or 3 to 7 ring members. In some embodiments, the cycloalkyl group is monocyclic or bicyclic. In some embodiments, the cycloalkyl portion is monocyclic. In some embodiments, the cycloalkyl portion is a C$_{3-7}$ monocyclic cycloalkyl group.

As used herein, the term "heterocycloalkyl", employed alone or in combination with other terms, refers to non-aromatic ring or ring system, which may optionally contain one or more alkenylene or alkynylene groups as part of the ring structure, which has at least one heteroatom ring member independently selected from nitrogen, sulfur oxygen and phosphorus.

Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic ring, for example, 1,2, 3,4-tetrahydro-quinoline and the like. Heterocycloalkyl groups can also include bridgehead heterocycloalkyl groups and spiroheterocycloalkyl groups.

As used herein, "bridgehead heterocycloalkyl group" refers to a heterocycloalkyl moiety containing at least one bridgehead atom, such as azaadmantan-1-yl and the like. As used herein, "spiroheterocycloalkyl group" refers to a heterocycloalkyl moiety containing at least two rings fused at a single atom, such as [1,4-dioxa-8-aza-spiro[4.5]decan-N-yl] and the like. In some embodiments, the heterocycloalkyl group has 3 to 20 ring-forming atoms, 3 to 14 ring-forming atoms, 3 to 10 ring-forming atoms, or about 3 to 8 ring forming atoms. In some embodiments, the heterocycloalkyl group has 2 to 20 carbon atoms, 2 to 15 carbon atoms, 2 to 10 carbon atoms, or about 2 to 8 carbon atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a C$_{2-7}$ monocyclic heterocycloalkyl group. In some embodiments, the heterocycloalkyl group is a morpholine ring, pyrrolidine ring, piperazine ring, piperdine ring, tetrahydropyran ring, azetidine ring, or tetrahydrofuran ring.

As used herein, the term "heterocycloalkylalkyl", employed alone or in combination with other terms, refers to a group of formula -alkylene-heterocycloalkyl. In some embodiments, the alkylene portion has 1 to 4, 1 to 3, 1 to 2, or 1 carbon atom(s). In some embodiments, the alkylene portion is methylene. In some embodiments, the heterocycloalkyl portion has 3 to 14 ring members, 3 to 10 ring members, or 3 to 7 ring members. In some embodiments, the heterocycloalkyl group is monocyclic or bicyclic. In some embodiments, the heterocycloalkyl portion is monocyclic. In some embodiments, the heterocycloalkyl portion is a $C_{2-7}$ monocyclic heterocycloalkyl group.

As used herein, the term "aryl", employed alone or in combination with other terms, refers to a monocyclic or polycyclic (e.g., having 2, 3 or 4 fused rings) aromatic hydrocarbon moiety, such as, but not limited to, phenyl, 1-naphthyl, 2-naphthyl, anthracenyl, phenanthrenyl, and the like. In some embodiments, aryl groups have from 6 to 20 carbon atoms, from 6 to 14 carbon atoms, from 6 to 10 carbon atoms, or 6 carbon atoms. In some embodiments, the aryl group is a monocyclic or bicyclic group. In some embodiments, the aryl group is phenyl or naphthyl.

As used herein, the term "arylalkyl", employed alone or in combination with other terms, refers to a group of formula -alkylene-aryl. In some embodiments, the alkylene portion has 1 to 4, 1 to 3, 1 to 2, or 1 carbon atom(s). In some embodiments, the alkylene portion is methylene. In some embodiments, the aryl portion is phenyl. In some embodiments, the aryl group is a monocyclic or bicyclic group. In some embodiments, the arylalkyl group is benzyl.

As used herein, the term "heteroaryl", employed alone or in combination with other terms, refers to a monocyclic or polycyclic (e.g., having 2, 3 or 4 fused rings) aromatic hydrocarbon moiety, having one or more heteroatom ring members independently selected from nitrogen, sulfur and oxygen. In some embodiments, the heteroaryl group is a monocyclic or bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, imidazo[1,2-b]thiazolyl or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In some embodiments, the heteroaryl group has from 1 to 20 carbon atoms, from 3 to 20 carbon atoms, from 3 to 15 carbon atoms, from 3 to 10 carbon atoms, from 3 to 8 carbon atoms, from 3 to 5 carbon atoms, from 1 to 5 carbon atoms, or from 5 to 10 carbon atoms. In some embodiments, the heteroaryl group contains 3 to 14, 4 to 12, 4 to 8, 9 to 10, or 5 to 6 ring-forming atoms. In some embodiments, the heteroaryl group has 1 to 4, 1 to 3, or 1 to 2 heteroatoms.

As used herein, the term "heteroarylalkyl", employed alone or in combination with other terms, refers to a group of formula -alkylene-heteroaryl. In some embodiments, the alkylene portion has 1 to 4, 1 to 3, 1 to 2, or 1 carbon atom(s). In some embodiments, the alkylene portion is methylene. In some embodiments, the heteroaryl portion is a monocyclic or bicyclic group having 1, 2, 3, or 4 heteroatoms independently selected from nitrogen, sulfur and oxygen. In some embodiments, the heteroaryl portion has 5 to 10 carbon atoms.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Other resolving agents suitable for fractional crystallization methods include stereoisomerically pure forms of methylbenzyl-amine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric iosomers, tautomers, and isotopes of the structures depicted.

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in Remington's Pharmaceutical Sciences, 17th ed., Mack Publishing Company, Easton, Pa., 1985, p. 1418 and *Journal of Pharmaceutical Science*, 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Green and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Compounds of the invention can be prepared according to numerous preparatory routes known in the literature. Example synthetic methods for preparing compounds of the invention are provided in the Schemes below.

A series of imidazo[1,2-b]pyridazine derivatives 7 can be prepared by the methods outlined in Scheme 1. Suzuki coupling of 5-chloropyridazin-3(2H)-one with a boronic acid or ester CyB(OR')$_2$ (R'=H or alkyl, Cy=cyclic moiety) provides the pyridazin-3(2H)-one derivative 2. Treatment of 2 with POX$_3$ (X=Cl or Br) affords the pyridazine 3 which can be transformed to aminopyridazine 4 by replacement with ammonia. Reaction of 4 with 2-chloroacetaldehyde can produce the imidazo[1,2-b]pyridazine 5. Iodination of the compound 5 with NIS (N-iodosuccinimide) yields the corresponding imidazo[1,2-b]pyridazine iodide 6, which can be further converted to the desired product imidazo[1,2-b]pyridazine derivatives 7 by Suzuki coupling with an aromatic boronic acid or ester ArB(OR")$_2$ (R"=H or alkyl).

Scheme 1

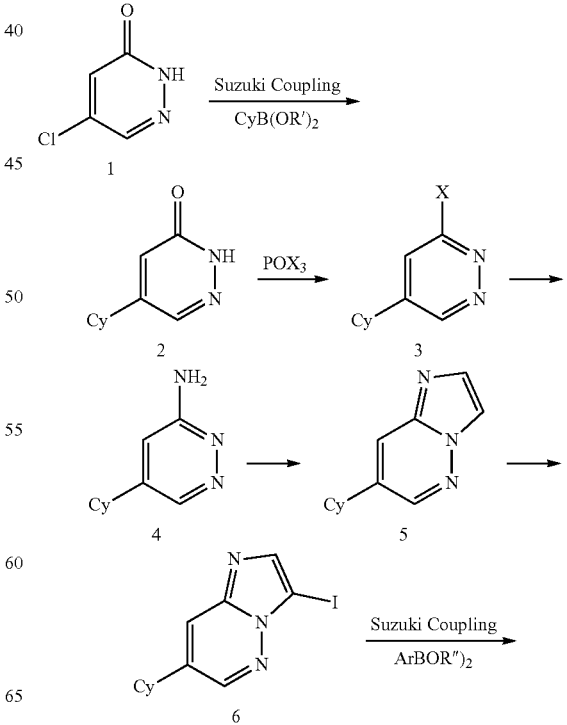

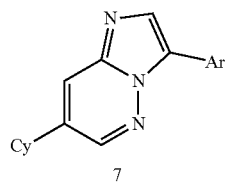

Alternatively, a series of imidazo[1,2-b]pyridazine derivatives 7 can be prepared according to the procedure outlined in Scheme 2. Cycloaddition of the pyridazine 3 with a suitable alpha-chloro-aromatic acetaldehyde 8 affords the imidazo[1,2-b]pyridazine derivatives 7.

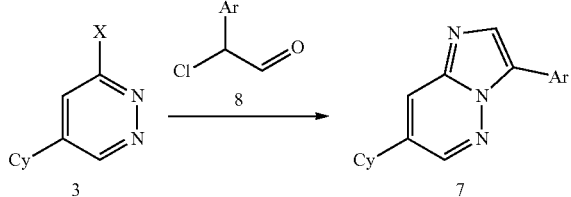

Imidazo[1,2-b]pyridazine derivatives 7 can also be prepared according to the procedure outlined in Scheme 3. Aminopyridazine 10 can be obtained by palladium catalytic amination of the dichloropyridazine 8 with diphenylmethanimine followed by hydrolysis under acidic conditions. Cycloaddition of aminopyridazine 10 with 2-chloroacetaldehyde gives the imidazo[1,2-b]pyridazine 11 which can be converted to the corresponding imidazo[1,2-b]pyridazine iodide 12 by treatment with NIS. Suzuki coupling of 12 with an aromatic boronic acid or ester ArB(OR")$_2$ affords compound 13 which can be converted to the desired product imidazo[1,2-b]pyridazine derivatives 7 by further Suzuki coupling with suitable boronic acid or ester CyB(OR')$_2$ (R'=H or alkyl).

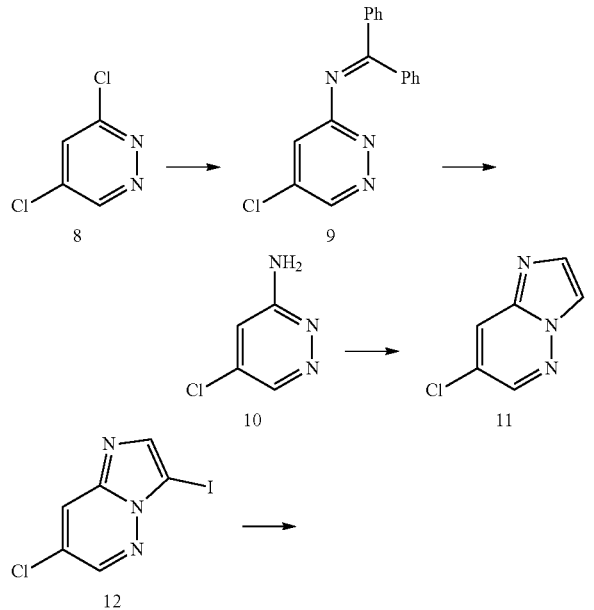

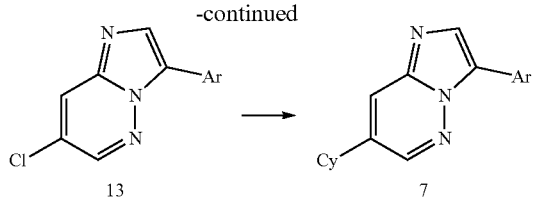

A series of imidazo[1,2-b]pyridazine derivatives 20 can be prepared according to the procedure outlined in Scheme 4. Suzuki coupling of 7-chloro-3-iodoimidazo[1,2-b]pyridazine 12 with aminophenylboronic acid produces the corresponding compound 14 which can be transformed to the corresponding urea 15 by treatment with phosgene followed by an appropriate amine ($R^c$ and $R^d$ are, e.g., independently H, alkyl, or as defined anywhere herein). Further Suzuki coupling of compound 15 with pyrazole boronic ester 16 affords the compound 17. The protecting group (PG) in compound 17 can be removed to give the compound 18 by hydrogenation in the presence of palladium on carbon in the case of PG=Cbz or by treatment with acid such as, but not limited to, trifluoroacetic acid (TFA) or HCl in a suitable solvent such as, but not limited to, dichloromethane (DCM), methanol, dioxane, or combination of two solvents, in the case of PG=Boc. Michael addition of 18 with α,β-unsaturated nitrile 19 can afford the imidazo[1,2-b]pyridazine derivatives 20 ($R^{30}$ and $R^{40}$ are, e.g., independently H, alkyl, a cyclic moiety, or substituted versions thereof).

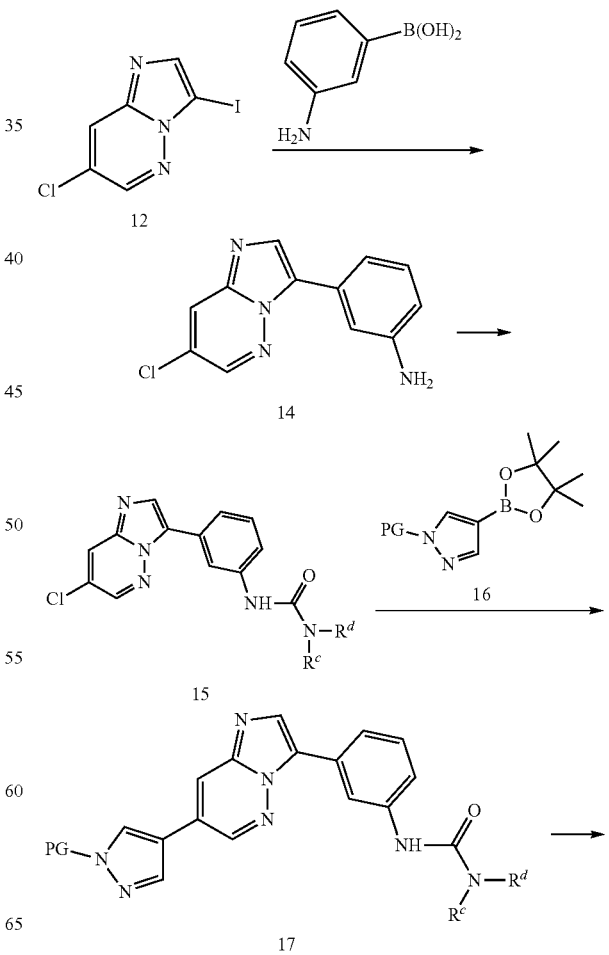

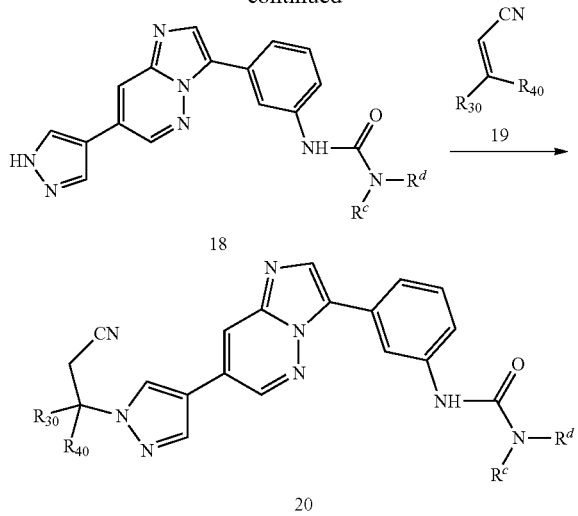

A series of imidazo[1,2-b]pyridazine derivatives 15 can also be prepared by the methods outlined in Scheme 5. Reaction of commercially available isocyanate 21 with an appropriate amine yields the corresponding urea boronic acid 22. Suzuki coupling of 22 with 7-chloro-3-iodoimidazo[1,2-b]pyridazine 12 affords the imidazo[1,2-b]pyridazine derivatives 15.

Scheme 5

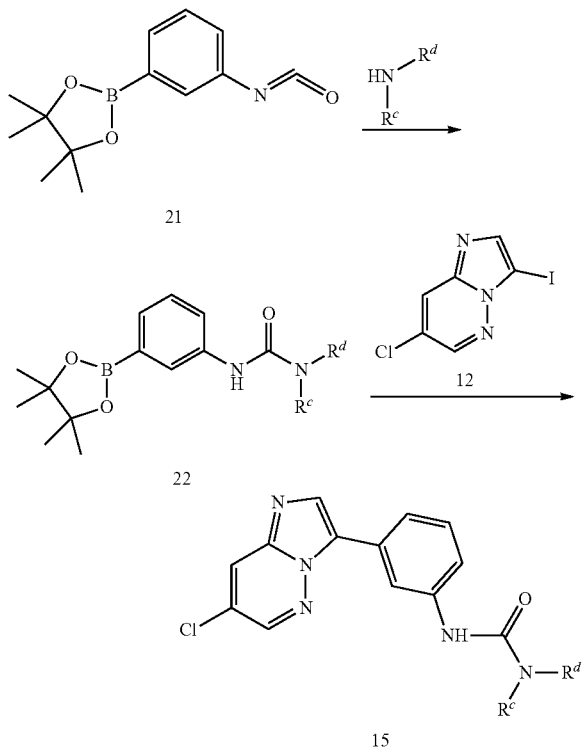

A series of urea amide derivatives 26 can be prepared according to the procedure outlined in Scheme 6. Alkylation of compound 18 with substituted 2-bromoacetic ester 23 gives the urea ester 24 (R' is, e.g., alkyl). Hydrolysis of 24 yields the acid 25 which can be converted to the corresponding urea amide 26 by coupling with an appropriate amine by using an amidation coupling reagent such as, but not limited to, (benzotriazol-1-yloxy)-tris(dimethylamino)phosphonium hexafluorophosphate (BOP), 1H-benzotriazol-1-yloxytripyrrolidinophosphonium hexafluorophosphate (PyBOP), 2-(7-azobenzotriazolyl-1-oxy)-N,N,N',N'-tetramethyluronium hexafluorophosphate (HATU), 2-(1H-benzotriazol-1-yl)-1,1,3,3-tetramethyluronium hexafluorphosphate (HBTU), or 1-(3-dimethylaminopyopyl)-3-ethylcarbodiimide hydrochloride (EDC) ($R^{30}$, $R^{40}$, $R^{50}$ and $R^{60}$ are, e.g., independently H, alkyl, a cyclic moiety, or substituted versions thereof).

Scheme 6

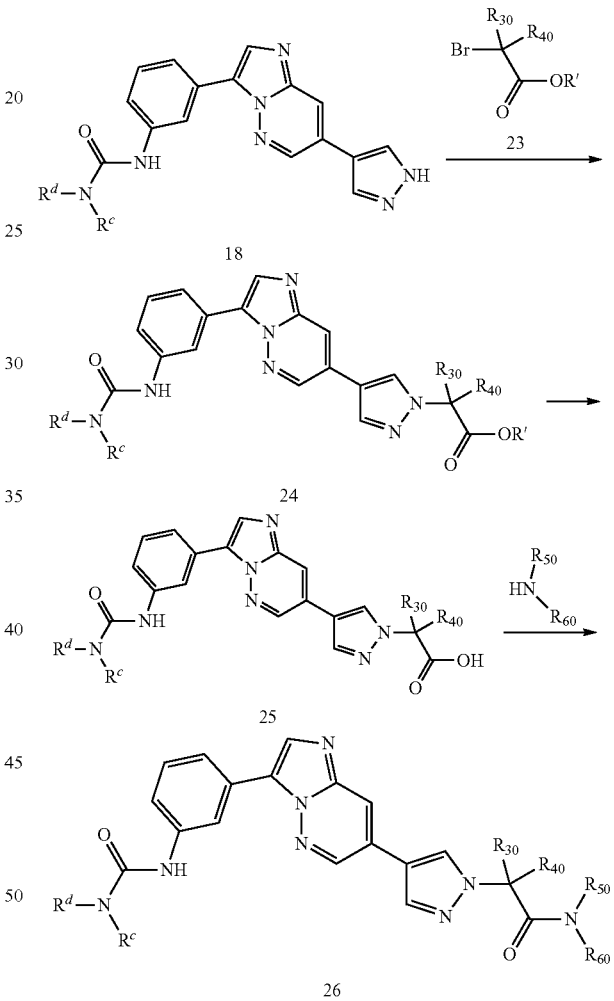

Alternatively, a series of urea ester derivatives 24 can be prepared according to the procedure outlined in Scheme 7. Pyrazole boronic ester 28 can be prepared by alkylation of the boronic ester 27 with bromide 23 in the presence of a suitable base such as, but not limited to, potassium carbonate, cesium carbonate, sodium carbonate, potassium tert-butoxide or sodium hydride (R' is, e.g., alkyl). Suzuki coupling of the ester 28 with imidazo[1,2-b]pyridazine derivatives 15 affords the urea ester 24 which can be transformed to the desired urea amide 26 as previously described.

Scheme 7

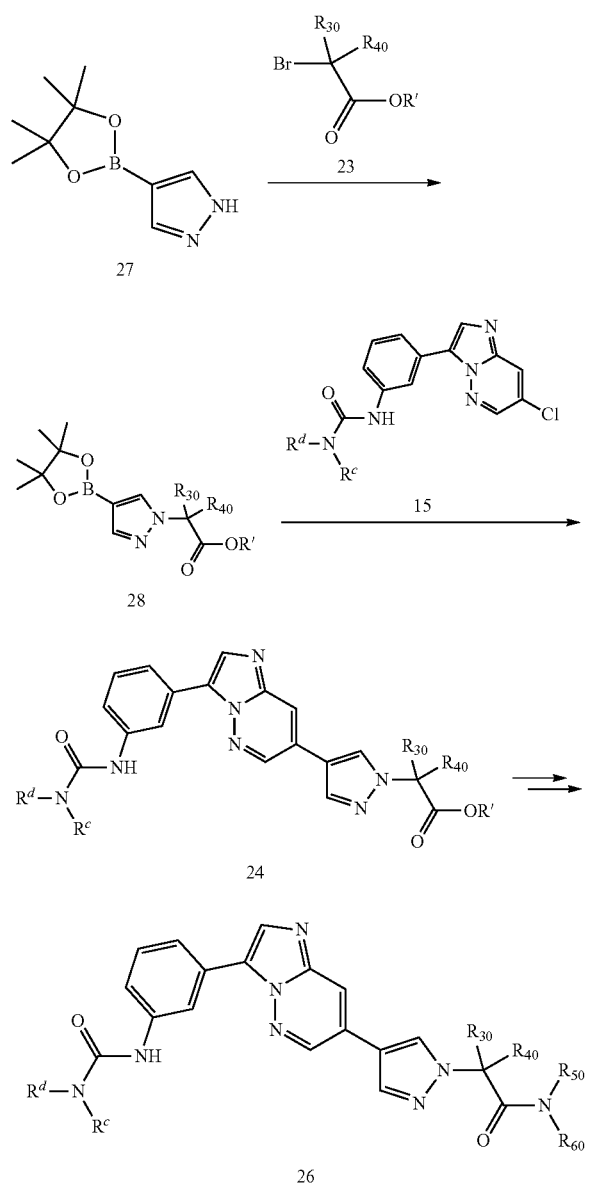

Scheme 8

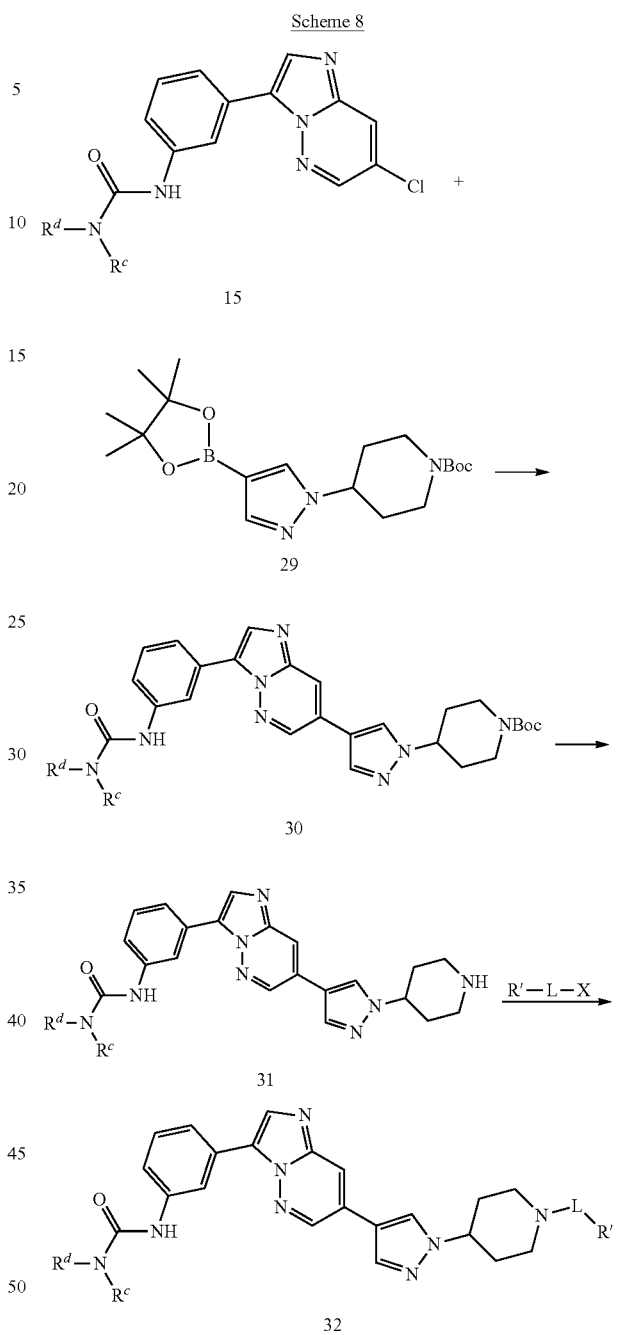

A series of urea derivatives 32 can be prepared according to the procedure outlined in Scheme 8. Suzuki coupling of imidazo[1,2-b]pyridazine derivatives 15 with boronic ester 29 produces compound 30. Removal of the Boc group of compound 30 provides compound 31 by treatment with an acid such as trifluoroacetic acid (TFA) or HCl. Compound 31 can converted to corresponding compound 32 by reaction with a suitable reagent R'LX (L is linker which can be, but is not limited to, CO, COO, CONR'', or SO$_2$; X is a leaving group such as Cl, Br, 4-nitrophenoxy, etc. . . . ): to amides by reaction with acyl chloride in the presence of a suitable base or with acid and in the presence of amide coupling reagents such BOP, PyBOP, HATU, HBTU, or EDC; to carbamates by reaction with chloroformates or 4-nitrophenyl carbonate; to sulfonamides by reaction with sulfonylchloride; or to ureas by reaction with isocyanate or carbamic chloride or an appropriate amine in the presence of phosgene or triphosgene.

A series of urea derivatives 33, 34 and 37 can be prepared according to the procedure outlined in Scheme 9. Compound 33 can be directly prepared by amination of aryl halides ArX (Ar=aryl or heteroaryl; X=F, Cl, Br, OTf, or OTs), or by copper- or palladium-catalyzed C—N bond formation with aryl halides. Compound 34 can be obtained by N-alkylation with R'R''CHX (X is a leaving group which can be, but not limit to, Cl, Br, OMs, or OTs), or by reductive amination with aldehydes or ketones R'COR'' (R' and R'' can be, e.g., independently H, alkyl, a cyclic moiety, or substituted versions thereof). Michael addition of 31 with α,β-unsaturated nitrile 19 afford the urea imidazo[1,2-b]pyridazine derivatives 35.

Scheme 9

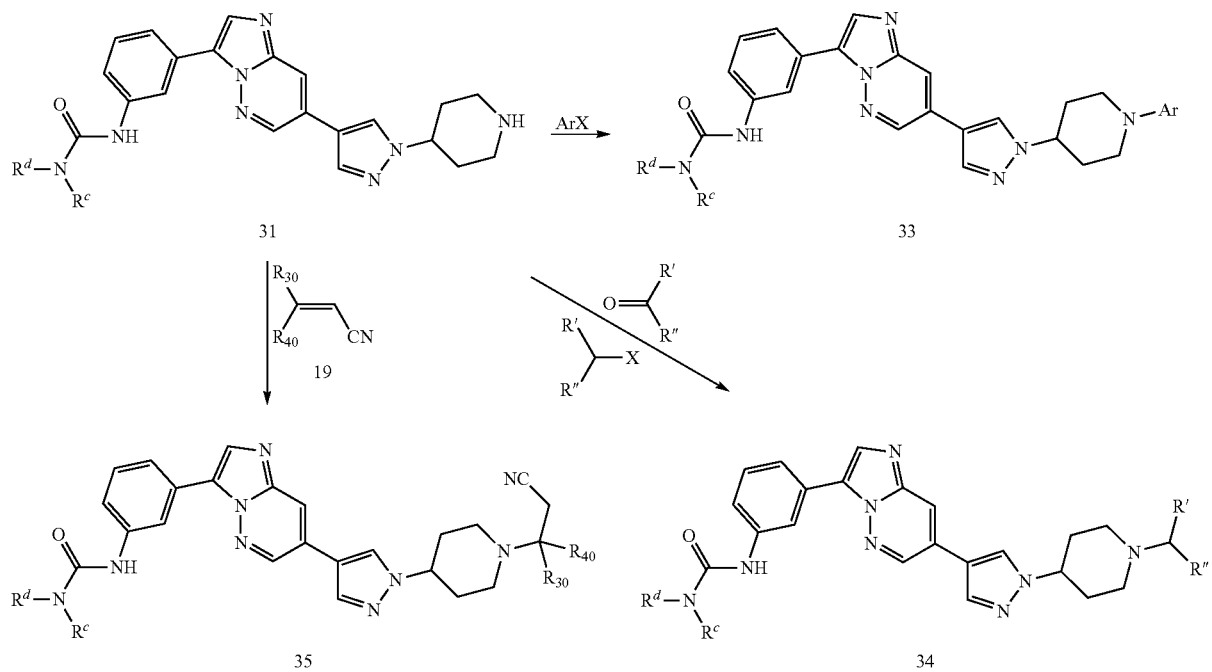

A series of urea derivatives 38 can be prepared according to the procedure outlined in Scheme 10. Alkylation of compound 31 with substituted 2-bromoacetic ester 23 provides the urea ester 36. The urea amide 38 can be prepared by amide coupling of the acid 37 (obtained by hydrolysis of 36) with an appropriate amine by using an amidation coupling reagent such as, but not limited to, BOP, PyBOP, HATU, HBTU, or EDC.

Scheme 10

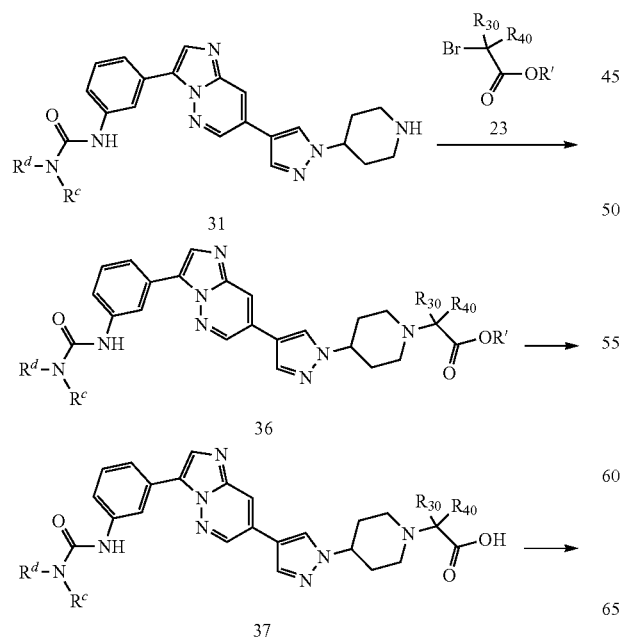

-continued

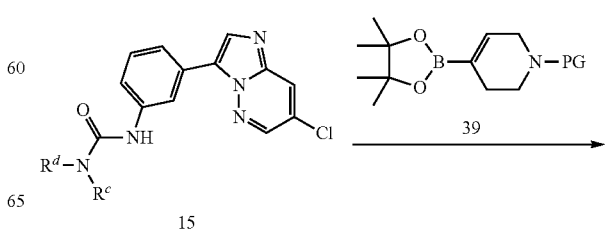

A series of urea derivatives 43 can be prepared according to the procedure outlined in Scheme 11. Suzuki coupling of imidazo[1,2-b]pyridazine derivatives 15 with boronic ester 39 (PG=protecting group) affords compound 40. The double bond in 40 can be reduced to give 41 by hydrogenation in the presence of a suitable catalyst such as palladium on carbon. Removal of the Boc group of 41 can be carried out to give compound 42 by treatment with acid such as TFA or HCl. Compound 42 can be converted to various compounds 43 similar to those previously described in Scheme 8-10.

Scheme 11

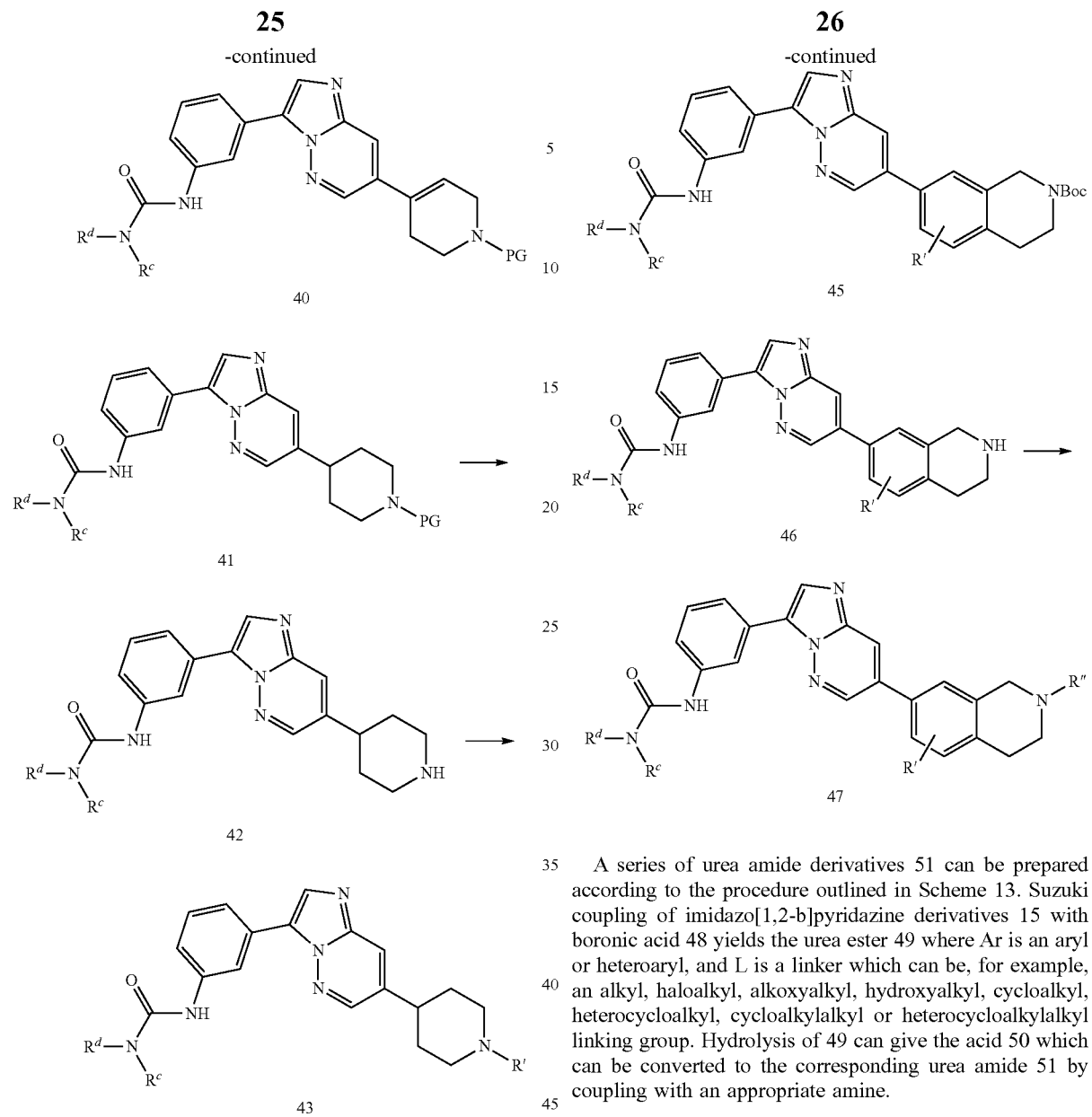

In a similar manner, a series of urea derivatives 47 can also be prepared according to the procedure outlined in Scheme 12. Suzuki coupling of imidazo[1,2-b]pyridazine derivatives 15 with boronic ester 44 can give compound 45. Compound 45 can be transformed to various compounds 47 similar to those previously described in Scheme 8-10.

A series of urea amide derivatives 51 can be prepared according to the procedure outlined in Scheme 13. Suzuki coupling of imidazo[1,2-b]pyridazine derivatives 15 with boronic acid 48 yields the urea ester 49 where Ar is an aryl or heteroaryl, and L is a linker which can be, for example, an alkyl, haloalkyl, alkoxyalkyl, hydroxyalkyl, cycloalkyl, heterocycloalkyl, cycloalkylalkyl or heterocycloalkylalkyl linking group. Hydrolysis of 49 can give the acid 50 which can be converted to the corresponding urea amide 51 by coupling with an appropriate amine.

Scheme 13

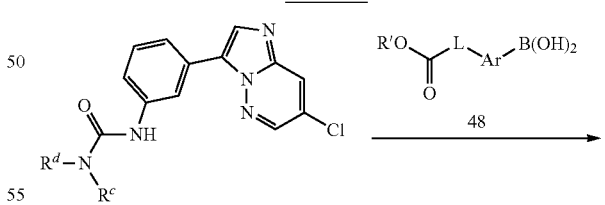

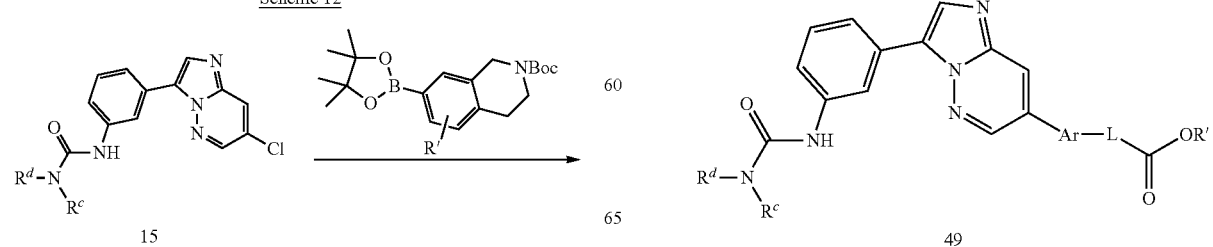

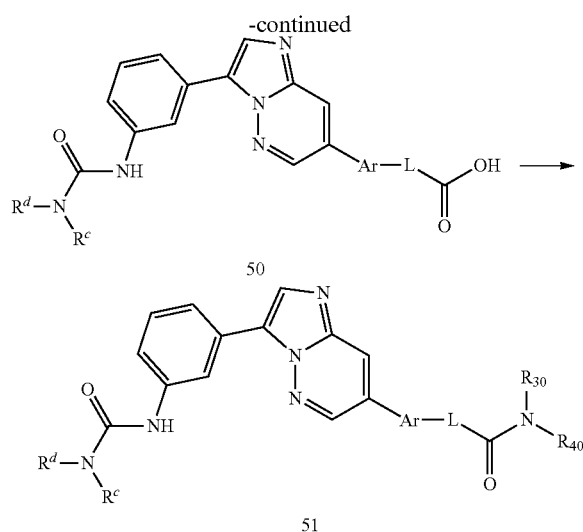

A series of urea benzimidazole derivatives 58 can be prepared according to the procedure outlined in Scheme 14. Amination of 4-bromo-1-fluoro-2-nitrobenzene 52 with 53 under thermal conditions produces compound 54 which can be transformed to compound 55 by reduction of the nitro group using $SnCl_2$ in ethanol followed by treatment with an acid such as HCl. Treatment of 55 with formic acid or with triethyl orthoformate in the presence of acid such as HCl or TsOH yields benzimidazole 56 which can be converted to the corresponding urea 57 by reaction with isocyanate, or with an appropriate amine and phosgene, or 1,1'-carbonyl diimidazole (CDI). Suzuki coupling of the benzimidazole 56 with various boronic acids $CyB(OH)_2$ can yield the urea benzimidazoles 58. The urea benzimidazoles 58 can also be obtained by Suzuki coupling of a suitable halide with the boronic acid 59 which can be prepared from compound 57 by general methods for preparing the boronic acid.

Methods of Use

Compounds of the invention can inhibit activity of one or more FGFR enzymes, including FGFR3. For example, the compounds of the invention can be used to inhibit activity of an FGFR enzyme in a cell or in an individual or patient in need of modulation of the enzyme by administering an inhibiting amount of a compound of the invention to the individual or patient.

In some embodiments, the compounds of the invention are selective inhibitors of FGFR3. A compound is selective if it inhibits FGFR3 with more potency than it does for other kinases, including one or more of FGFR1, FGFR2, and FGFR4. In some embodiments, the selectivity is greater than 2-fold, greater than 5-fold, greater than 10-fold, greater than 50-fold, greater than 100-fold, or greater than 500-fold over at least one of FGFR1, FGFR2, and FGFR4. In some embodiments, the compounds of the invention are selective for FGFR3 over all of FGFR1, FGFR2, and FGFR4.

As FGFR inhibitors, the compounds of the invention are useful in the treatment of various diseases associated with elevated expression or activity of FGFR enzymes, such as elevated expression or activity of FGFR3.

For example, the compounds of the invention are useful in the treatment of cancer. Example cancers include bladder cancer, breast cancer, cervical cancer, colorectal cancer, endometrial cancer, gastric cancer, head and neck cancer, kidney cancer, liver cancer, lung cancer (e.g., adenocarcinoma, small cell lung cancer and non-small cell lung carcinomas), ovarian cancer, prostate cancer, esophageal cancer, gall bladder cancer, ovarian cancer, pancreatic cancer (e.g. exocrine pancreatic carcinoma), stomach cancer, thyroid cancer, skin cancer (e.g., squamous cell carcinoma).

Further example cancers include hematopoietic malignancies such as leukemia, multiple myeloma, chronic lymphocytic lymphoma, adult T cell leukemia, B-cell lymphoma, acute myelogenous leukemia, Hodgkin's or non-Hodgkin's lymphoma, myeloproliferative neoplasms (e.g., poly- Scheme 14

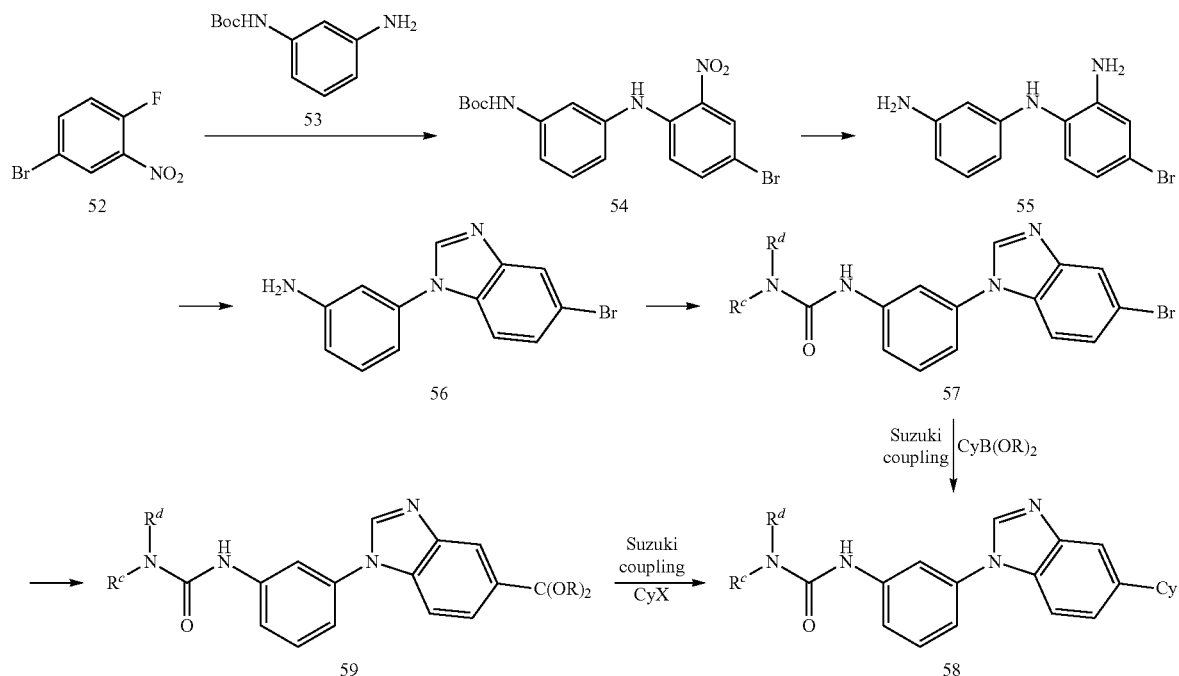

cythemia vera, essential thrombocythemia, and primary myelofibrosis), Waldenstrom's Macroglubulinemia, hairy cell lymphoma, and Burkett's lymphoma.

Other cancers treatable with the compounds of the invention include glioblastoma, melanoma, and rhabdosarcoma.

In addition to oncogenic neoplasms, the compounds of the invention can be useful in the treatment of skeletal and chondrocyte disorders including, but not limited to, achrondroplasia, hypochondroplasia, dwarfism, thanatophoric dysplasia (TD) (clinical forms TD I and TD II), and craniosynostosis syndromes.

As used herein, the term "cell" is meant to refer to a cell that is in vitro, ex vivo or in vivo.

In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the FGFR enzyme with a compound of the invention includes the administration of a compound of the present invention to an individual or patient, such as a human, having FGFR, as well as, for example, introducing a compound of the invention into a sample containing a cellular or purified preparation containing the FGFR enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) preventing the disease; for example, preventing a disease, condition or disorder in an individual who may be predisposed to the disease, condition or disorder but does not yet experience or display the pathology or symptomatology of the disease; 2) inhibiting the disease; for example, inhibiting a disease, condition or disorder in an individual who is experiencing or displaying the pathology or symptomatology of the disease, condition or disorder (i.e., arresting further development of the pathology and/or symptomatology), or 3) ameliorating the disease; for example, ameliorating a disease, condition or disorder in an individual who is experiencing or displaying the pathology or symptomatology of the disease, condition or disorder (i.e., reversing the pathology and/or symptomatology).

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with the compounds of the present invention for treatment of FGFR-associated diseases, disorders or conditions. The agents can be combined with the present compounds in a single dosage form, or the agents can be administered simultaneously or sequentially as separate dosage forms.

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2', 3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with the compounds of the present invention include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds according to the invention may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epipodophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions which refers to a combination of a compound of the invention and a pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, vaccines, antibodies, immune enhancers, immune suppressants, anti-inflammatory agents and the like.

Labeled Compounds and Assay Methods

Another aspect of the present invention relates to fluorescent dye, spin label, heavy metal or radio-labeled compounds of the invention that would be useful not only in imaging but also in assays, both in vitro and in vivo, for localizing and quantitating the FGFR enzyme in tissue samples, including human, and for identifying FGFR enzyme ligands by inhibition binding of a labeled compound. Accordingly, the present invention includes FGFR3 enzyme assays that contain such labeled compounds.

The present invention further includes isotopically-labeled compounds of Formula I. An "isotopically" or "radio-labeled" compound is a compound of the invention where one or more atoms are replaced or substituted by an atom having an atomic mass or mass number different from the atomic mass or mass number typically found in nature (i.e., naturally occurring).

Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro FGFR enzyme labeling and competition assays, compounds that incorporate $^3$H, $^{14}$C, $^{82}$Br, $^{125}$I, $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the FGFR enzyme. Accordingly, the ability of a test compound to compete with the radio-labeled compound for binding to the FGFR enzyme directly correlates to its binding affinity.

Kits

The present invention also includes pharmaceutical kits useful, for example, in the treatment or prevention of FGFR-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art.

Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of FGFR3 according to one or more of the assays provided herein.

EXAMPLES

Experimental procedures for compounds of the invention are provided below. Open Access Prep LC-MS Purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity under the following conditions: Instrument; Agilent 1100 series, LC/MSD, Column: Waters Sunfire™ $C_{18}$ 5 µm, 2.1×5.0 mm, Buffers: mobile phase A: 0.025% TFA in water and mobile phase B: 0.025% TFA in acetonitrile; gradient 2% to 80% of B in 3 minutes with flow rate 1.5 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm, 19×100 mm column, eluting with mobile phase A: 0.1% TFA (trifluoroacetic acid) in water and mobile phase B: 0.1% TFA in acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, J. Comb. Chem., 6, 874-883 (2004)]. Typically, the flow rate used with the with 30×100 mm column was 60 mL/minute.

pH=10 purifications: Waters XBridge $C_{18}$ 5 µm, 19×100 mm column, eluting with mobile phase A: 0.15% $NH_4OH$ in water and mobile phase B: 0.15% $NH_4OH$ in acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, J. Comb. Chem., 6, 874-883 (2004)]. Typically, the flow rate used with 30×100 mm column was 60 mL/minute.

Example 1

Cyclopropylmethyl 3-{1-[3-({[(2,2,2-trifluoroethyl) amino]carbonyl}amino)phenyl]-11H-benzimidazol-5-yl}benzoate

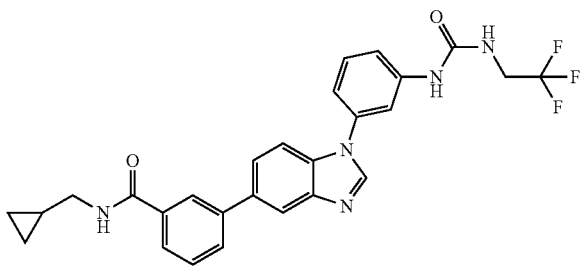 [SMILES: O=C(NCC(F)(F)F)Nc1cccc(-n2cnc3cc(-c4cccc(C(=O)NCC5CC5)c4)ccc32)c1]

Step 1: tert-butyl{3-[(4-bromo-2-nitrophenyl)amino] phenyl}carbamate

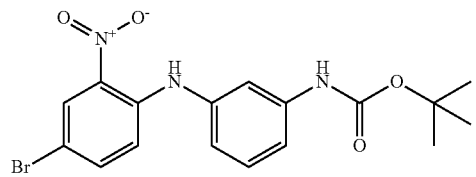 [SMILES: CC(C)(C)OC(=O)Nc1cccc(Nc2ccc(Br)cc2[N+](=O)[O-])c1]

A mixture of 4-bromo-1-fluoro-2-nitrobenzene (6.0 g, 27 mmol, Aldrich, Cat. No. 539112) and tert-butyl (3-aminophenyl)carbamate (6.7 g, 32 mmol, Aldrich, Cat. No. 53175) in N-methylpyrrolidinone (30 mL) was heated at 150° C. overnight. The solution was cooled to room temperature (r.t.) and quenched with $NaHCO_3$ aqueous solution, then extracted with ethyl acetate twice. The combined organic phases were washed with brine, and dried over $MgSO_4$. After filtration, the filtrate was concentrated under reduced pressure to afford the desired compound (10.1 g, 91%). LCMS $(M+H)^+$: m/z=408.0.

Step 2: N1-(3-aminophenyl)-4-bromobenzene-1,2-diamine

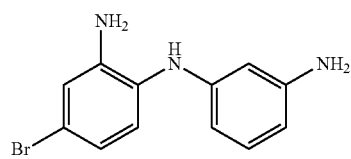 [SMILES: Nc1cccc(Nc2ccc(Br)cc2N)c1]

A mixture of tert-butyl {3-[(4-bromo-2-nitrophenyl) amino]phenyl}carbamate (10.1 g, 24.7 mmol) and tin dichloride (24 g, 120 mmol, Aldrich, Cat. No. 208256) in ethanol (100 mL) was heated at 100° C. overnight. The solution was quenched with 1N NaOH aqueous solution, and then extracted with ethyl acetate twice. The combined organic phases were washed with brine, and dried over $MgSO_4$. After filtration, the filtrate was concentrated under reduced pressure to afford the desired compound (6.8 g, 99%). LCMS $(M+H)^+$: m/z=278.0.

Step 3: 3-(5-bromo-1H-benzimidazol-1-yl)aniline

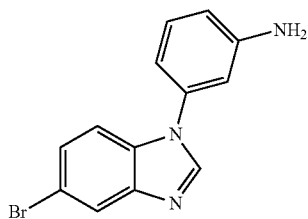 [SMILES: Nc1cccc(-n2cnc3cc(Br)ccc32)c1]

A mixture of N1-(3-aminophenyl)-4-bromobenzene-1,2-diamine (6.8 g, 24 mmol) and formic acid (50 mL, 1000 mmol, Fluka, Cat. No. 06440) with 1 mL concentrated HCl solution was heated at 150° C. overnight. The reaction solution was cooled to r.t. and concentrated under reduced pressure. The residue was dissolved in ethyl acetate, washed with saturated NaHCO$_3$ sol. and brine, dried over MgSO$_4$. After filtration, the filtrate was concentrated under reduced pressure The above residue was dissolved in 1.0 M hydrogen chloride in water (80 mL) and 1,4-dioxane (80 mL), then was heated at 100° C. for 2 h. The reaction solution was cooled to r.t., adjusted to pH of about 8 with Na$_2$CO$_3$ aqueous solution. The suspension was extracted with ethyl acetate twice. The combined organic phases were washed with brine, and dried over MgSO$_4$. After filtration, the filtrate was concentrated under reduced pressure to afford the desired compound (7 g, 100%). LCMS (M+H)$^+$: m/z=288.0.

Step 4: N-[3-(5-bromo-1H-benzimidazol-1-yl)phenyl]-N'-(2,2,2-trifluoroethyl)urea

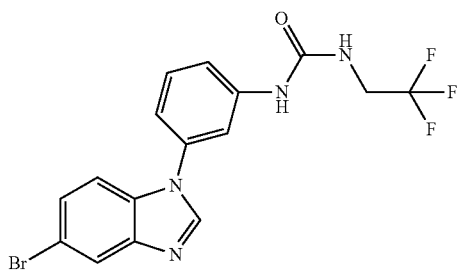 [SMILES: O=C(NCC(F)(F)F)Nc1cccc(-n2cnc3cc(Br)ccc32)c1]

To a solution of 3-(5-bromo-1H-benzimidazol-1-yl)aniline (1.0 g, 3.5 mmol) in tetrahydrofuran (20 mL) was added p-nitrophenyl chloroformate (980 mg, 4.8 mmol, Aldrich, Cat. 160210), triethylamine (1.4 mL, 10. mmol) and 4-dimethylaminopyridine (80 mg, 0.7 mmol, Aldrich, Cat. 107700). The solution was stirred at r.t. 1 h., then 2,2,2-trifluoroethanamine (520 mg, 5.2 mmol, Alfa Aesar, Cat. No. B20789) was added. The reaction mixture was stirred at r.t. overnight and quenched with NaHCO$_3$ aqueous solution, extracted with ethyl acetate. The combined organic phases were washed with brine, and dried over MgSO$_4$. After filtration, the filtrate was concentrated under reduced pressure. The residue was purified by flash chromatograph on a silica gel column using 85% ethyl acetate in methylene chloride as eluent to afford the desired compound (0.81 g, 56%). LCMS (M+H)$^+$: m/z=413.0.

$^1$H NMR (300 MHz, CDCl$_3$): 8.11 (s, 1H), 8.05 (s, 1H), 7.92 (s, 1H), 7.50 (s, 1H), 7.39 (m, 4H), 7.08 (m, 1H), 6.10 (m, 1H), 3.92 (m, 2H).

Step 5: 3-{1-[3-({[(2,2,2-trifluoroethyl)amino]carbonyl}amino)phenyl]-1H-benzimidazol-5-yl}benzoic acid

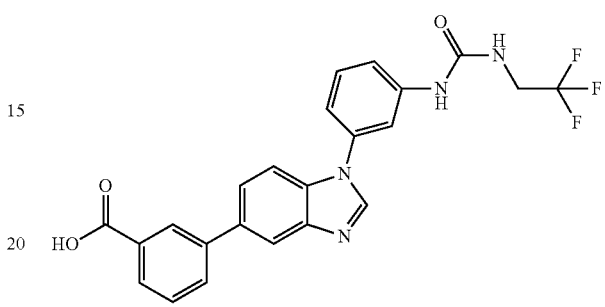

A mixture of N-[3-(5-bromo-1H-benzimidazol-1-yl)phenyl]-N'-(2,2,2-trifluoroethyl)urea (250.0 mg, 0.6050 mmol), [3-(methoxycarbonyl)phenyl]boronic acid (160 mg, 0.91 mmol Aldrich, Cat. No. 591130), tetrakis(triphenylphosphine)palladium(O) (40 mg, 0.04 mmol Aldrich, Cat. No. 216666) and sodium carbonate (130 mg, 1.2 mmol) in 1,4-dioxane (10 mL) and a few drops of water was heated at 120° C. overnight under nitrogen. After the reaction was cooled to r.t., 1.0 M sodium hydroxide in water (2.4 mL,) was added to the above mixture. The reaction mixture was heated at 100° C. 2 h., and then cooled to r.t. The reaction mixture was diluted with ethyl acetate, and extracted with 1N NaOH aqueous solution twice. The combined aqueous phases were acidified to pH-~-2 with 6 M HCl aqueous solution, and then extracted with ethyl acetate twice. The combined organic phases (only the extracted portion with acidic aqueous solution) were washed with brine, and dried over MgSO$_4$. After filtration, the filtrate was concentrated under reduced pressure to afford the desired product. LCMS (M+H)$^+$: m/z=455.1.

Step 6: cyclopropylmethyl 3-{1-[3-({[(2,2,2-trifluoroethyl)amino]carbonyl}amino) phenyl]-1H-benzimidazol-5-yl}benzoate

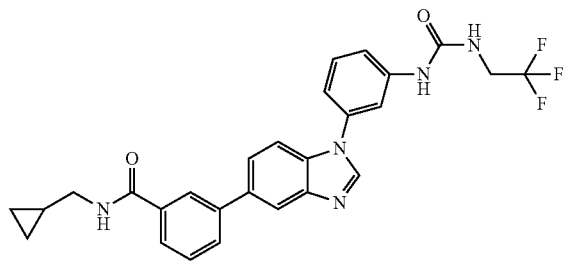 [SMILES: O=C(NCC(F)(F)F)Nc1cccc(-n2cnc3cc(-c4cccc(C(=O)NCC5CC5)c4)ccc32)c1]

To a solution of 3-{1-[3-({[(2,2,2-trifluoroethyl)amino]carbonyl}amino)phenyl]-1H-benzimidazol-5-yl}benzoic acid (20.0 mg, 0.0440 mmol) and cyclopropylmethylamine (6.3 mg, 0.088 mmol Aldrich, Cat. No. 359521) in N,N-dimethylformamide (DMF) (1 mL) was added benzotriazol-1-yloxytris(dimethylamino) phosphonium hexafluorophosphate (23 mg, 0.053 mmol, Adv. ChemTech. Cat. No. RC8105) and N,N-diisopropylethylamine (23 μL, 0.13 mmol). The reaction mixture was stirred at r.t. 2 h., then diluted with MeOH, and purified by RP-HPLC (pH=10) to afford the desired compound. LCMS (M+H)+: m/z=508.2.

Example 2

N-(Tetrahydrofuran-2-ylmethyl)-3-{1-[3-({[(2,2,2-trifluoroethyl)amino]carbonyl}amino)phenyl]-1H-benzimidazol-5-yl}benzamide

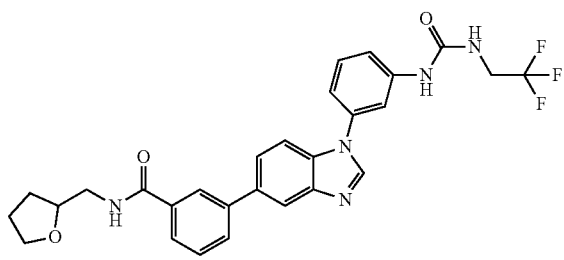 [SMILES: O=C(NCC(F)(F)F)Nc1cccc(-n2cnc3cc(-c4cccc(C(=O)NCC5CCCO5)c4)ccc32)c1]

This compound was prepared by using procedures analogous to those described for the synthesis of Example 1 starting from 3-{1-[3-({[(2,2,2-trifluoroethyl)amino]-carbonyl}amino)-phenyl]-1H-benzimidazol-5-yl}benzoic acid and 2-tetrahydrofuranmethanamine, (Aldrich, Cat. No. 131911). LCMS (M+H)+: m/z=538.3.

Example 3

N-[(1-Methylpiperidin-4-yl)methyl]-3-{1-[3-({[(2,2,2-trifluoroethyl)amino]carbonyl}amino)phenyl]-1H-benzimidazol-5-yl}benzamide

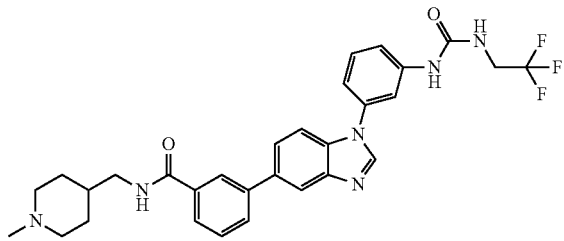 [SMILES: CN1CCC(CNC(=O)c2cccc(-c3ccc4c(c3)ncn4-c3cccc(NC(=O)NCC(F)(F)F)c3)c2)CC1]

This compound was prepared by using procedures analogous to those described for the synthesis of Example 1 starting from 3-{1-[3-({[(2,2,2-trifluoroethyl)amino]carbonyl}amino)-phenyl]-1H-benzimidazol-5-yl}benzoic acid and 1-(1-methylpiperidin-4-yl)methanamine (Matrix Sci., Cat. No. 016352). LCMS (M+H)+: m/z=565.3.

Example 4

N-(2-Morpholin-4-ylethyl)-3-{1-[3-({[(2,2,2-trifluoroethyl)amino]carbonyl}amino)phenyl]-1H-benzimidazol-5-yl}benzamide

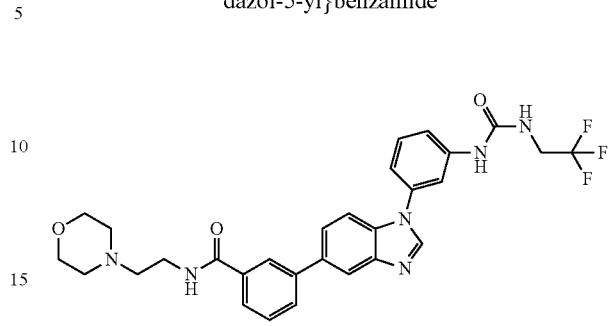

This compound was prepared by using procedures analogous to those described for the synthesis of Example 1 starting from 3-{1-[3-({[(2,2,2-trifluoroethyl)amino]carbonyl-amino)phenyl]-1H-benzimidazol-5-yl}benzoic acid and N-(2-aminoethyl)morpholine (Aldrich Cat. No. A55004). LCMS (M+H)+: m/z=567.3.

Example 5

N-(Pyridin-3-ylmethyl)-3-{1-[3-({[(2,2,2-trifluoroethyl)amino]carbonyl}amino)phenyl]-1H-benzimidazol-5-yl}benzamide

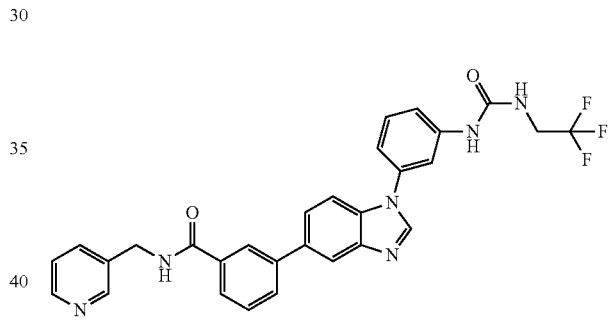

This compound was prepared by using procedures analogous to those described for the synthesis of Example 1 starting from 3-{1-[3-({[(2,2,2-trifluoroethyl)amino]-carbonyl}amino)phenyl]-1H-benzimidazol-5-yl}benzoic acid and picolamine (Aldrich Cat. No. A65409). LCMS (M+H)+: m/z=545.2.

Example 6

N-[(1-Methyl-1H-imidazol-2-yl)methyl]-3-{1-[3-({[(2,2,2-trifluoroethyl)amino]carbonyl}amino)phenyl]-1H-benzimidazol-5-yl}benzamide

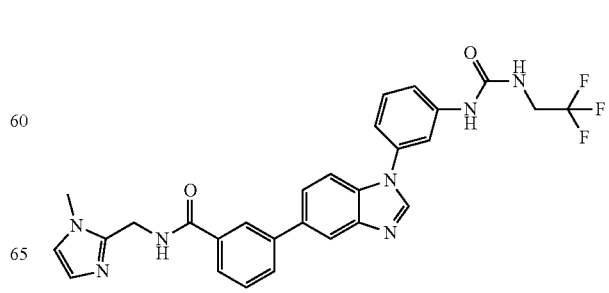

This compound was prepared by using procedures analogous to those described for the synthesis of Example 1 starting from 3-{1-[3-({[(2,2,2-trifluoroethyl)amino]carbonyl-amino)phenyl]-1H-benzimidazol-5-yl}benzoic acid and 1-(1-methyl-1H-imidazol-2-yl)methanamine (Matrix Sci., Cat. No. 020650). LCMS (M+H)+: m/z=548.2.

Example 7

N-(Cyclopropylmethyl)-4-{1-[3-({[(2,2,2-trifluoroethyl)amino]carbonyl}amino)phenyl]-1H-benzimidazol-5-yl}benzamide

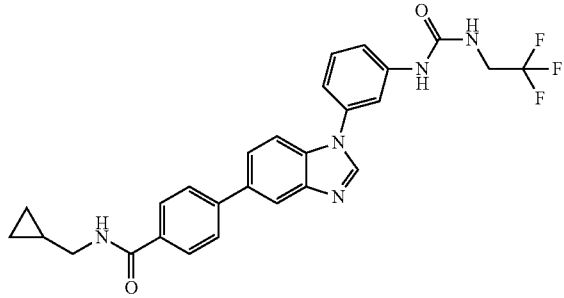 [SMILES: O=C(NCC(F)(F)F)Nc1cccc(-n2cnc3cc(-c4ccc(C(=O)NCC5CC5)cc4)ccc32)c1]

Step 1: 4-{1-[3-({[(2,2,2-trifluoroethyl)amino]carbonyl}amino)phenyl]-1H-benzimidazol-5-yl}benzoic acid

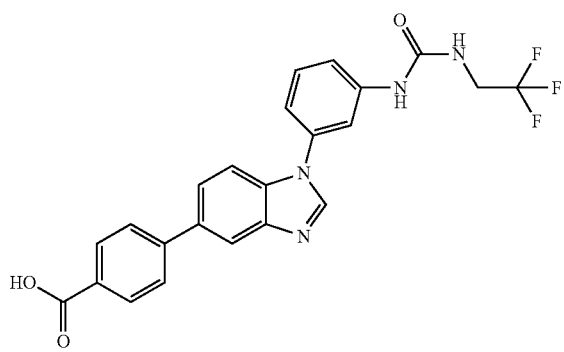 [SMILES: O=C(NCC(F)(F)F)Nc1cccc(-n2cnc3cc(-c4ccc(C(=O)O)cc4)ccc32)c1]

A mixture of N-[3-(5-bromo-1H-benzimidazol-1-yl)phenyl]-N'-(2,2,2-trifluoroethyl)urea (250.0 mg, 0.6050 mmol) (prepared by the procedure for Example 1, step 4), [4-(methoxycarbonyl)phenyl]boronic acid (160 mg, 0.91 mmol, Aldrich, Cat. No. 594539), [1,1'-bis(diphenylphosphino) ferrocene]dichloropalladium(II), complex with dichloromethane (1:1) (30 mg, 0.04 mmol, Aldrich, Cat. No. 379670) and sodium carbonate (130 mg, 1.2 mmol) in 1,4-dioxane (5 mL) and a few drops of water was heated at 120° C. overnight under nitrogen. After the reaction was cooled to r.t., 1.0 M sodium hydroxide in water (2.4 mL,) was added to the above mixture. The reaction mixture was heated at 100° C. for 2 h, then cooled to r.t. The reaction mixture was diluted with ethyl acetate, and extracted with 1N NaOH aqueous solution twice. The combined aqueous phases were acidified to pH~2 with 6 M HCl aqueous solution, and then extracted with ethyl acetate twice. The combined organic phases (only the extracted portion with acidic aqueous solution) were washed with brine, dried over MgSO4. After filtration, the filtrate was concentrated under reduced pressure to afford the desired product.
LCMS (M+H)+: m/z=455.1.

Step 2. N-(cyclopropylmethyl)-4-{1-[3-({[(2,2,2-trifluoroethyl)amino]carbonyl}amino) phenyl]-1H-benzimidazol-5-yl}benzamide

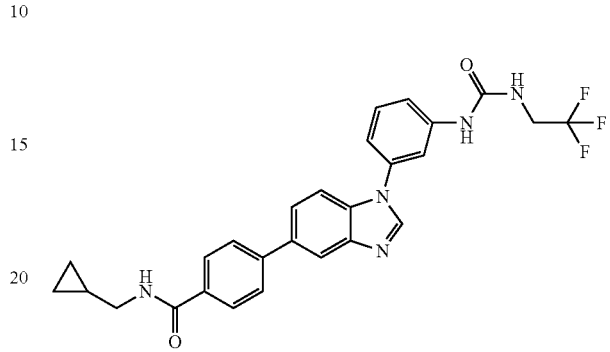

To a solution of 4-{1-[3-({[(2,2,2-trifluoroethyl)amino]carbonyl}amino)phenyl]-1H-benzimidazol-5-yl}benzoic acid (20.0 mg, 0.0440 mmol) and cyclopropylmethylamine (6.3 mg, 0.088 mmol, Aldrich, Cat. No. 359521) in N,N-dimethylformamide (1 mL) was added benzotriazol-1-yloxytris(dimethylamino) phosphonium hexafluorophosphate (23 mg, 0.053 mmol, Adv. ChemTech. Cat. No. RC8105) and N,N-diisopropylethylamine (23 µL, 0.13 mmol). The reaction mixture was stirred at r.t. for 2 h, then diluted with MeOH, and purified by RP-HPLC (pH=10) to afford the desired compound. LCMS (M+H)+: m/z=508.2.
1H NMR (300 MHz, CDCl3): 8.44 (s, 1H), 7.84 (dd, J=8.8, 2.5 Hz, 1H), 7.79 (s, 1H), 7.69 (d, J=8.8 Hz, 2H), 7.62 (s, 1H), 7.41 (d, J=8.6 Hz, 2H), 7.32 (m, 2H), 7.17 (m, 1H), 6.92 (m, 1H), 6.62 (s, 1H), 5.51 (m, 2H), 3.94 (m, 2H), 3.29 (m, 2H), 1.05 (m, 1H), 0.54 (m, 2H), 0.25 (m, 2H).

Example 8

N-(Tetrahydrofuran-2-ylmethyl)-4-{1-[3-({[(2,2,2-trifluoroethyl)amino]carbonyl}amino)phenyl]-1H-benzimidazol-5-yl}benzamide

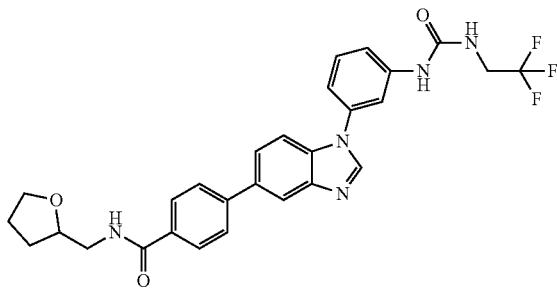 [SMILES: O=C(NCC(F)(F)F)Nc1cccc(-n2cnc3cc(-c4ccc(C(=O)NCC5CCCO5)cc4)ccc32)c1]

This compound was prepared by using procedures analogous to those described for the synthesis of Example 7 starting from 4-{1-[3-({[(2,2,2-trifluoroethyl)amino]carbonyl}amino)-phenyl]-1H-benzimidazol-5-yl}benzoic acid and 2-furanmethanamine, tetrahydro-(Aldrich, Cat. No. 131911). LCMS (M+H)+: m/z=538.3.

Example 9

N-[(2-Hydroxycyclohexyl)methyl]-4-{1-[3-({[(2,2,2-trifluoroethyl)amino]carbonyl}amino)phenyl]-1H-benzimidazol-5-yl}benzamide

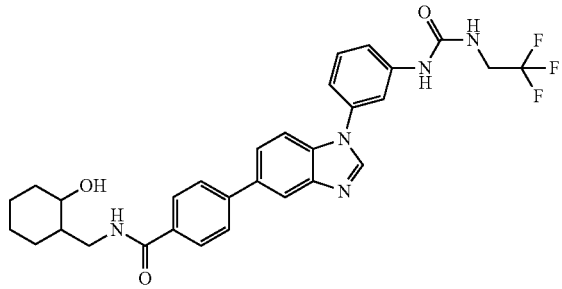 [SMILES: O=C(NCC(F)(F)F)Nc1cccc(-n2cnc3cc(-c4ccc(C(=O)NCC5CCCCC5O)cc4)ccc32)c1]

This compound was prepared by using procedures analogous to those described for the synthesis of Example 7 starting from 4-{1-[3-({[(2,2,2-trifluoroethyl)amino]carbonyl-amino)phenyl]-1H-benzimidazol-5-yl}benzoic acid and trans-2-(aminomethyl)cyclohexanol (Acros Organics, Cat. No. 26589). LCMS (M+H)$^+$: m/z=566.3.

Example 10

N-[(1-Methylpiperidin-4-yl)methyl]-4-{1-[3-({[(2,2,2-trifluoroethyl)amino]carbonyl}amino)phenyl]-1H-benzimidazol-5-yl}benzamide

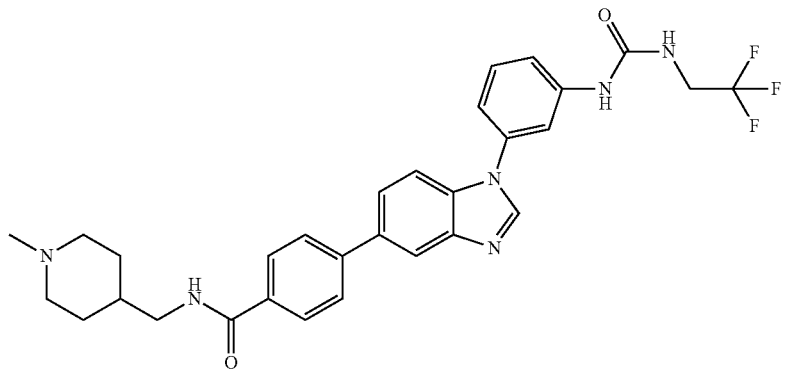 [SMILES: CN1CCC(CNC(=O)c2ccc(-c3ccc4c(c3)ncn4-c3cccc(NC(=O)NCC(F)(F)F)c3)cc2)CC1]

This compound was prepared by using procedures analogous to those described for the synthesis of Example 7 starting from 4-{1-[3-({[(2,2,2-trifluoroethyl)amino]carbonyl-amino)phenyl]-1H-benzimidazol-5-yl}benzoic acid and 1-(1-methylpiperidin-4-yl)methanamine (Matrix Sci., Cat. No. 016352). LCMS (M+H)$^+$: m/z=565.3.

Example 11

N-(2-Morpholin-4-ylethyl)-4-{1-[3-({[(2,2,2-trifluoroethyl)amino]carbonyl}amino)phenyl]-1H-benzimidazol-5-yl}benzamide

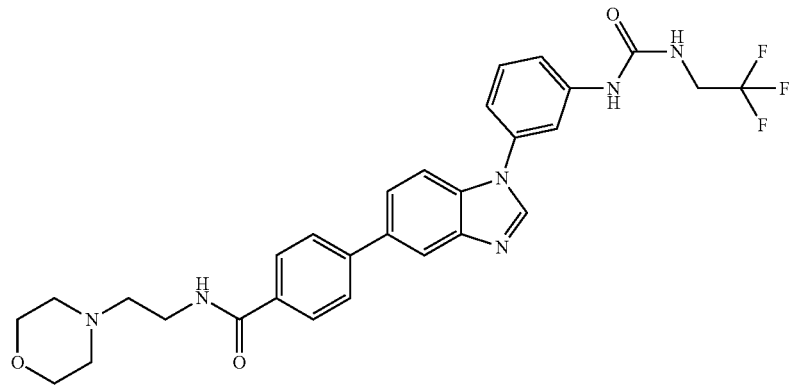 [SMILES: O=C(NCC(F)(F)F)Nc1cccc(-n2cnc3cc(-c4ccc(C(=O)NCCN5CCOCC5)cc4)ccc32)c1]

This compound was prepared by using procedures analogous to those described for the synthesis of Example 7 starting from 4-{1-[3-({[(2,2,2-trifluoroethyl)amino]carbonyl-amino)phenyl]-1H-benzimidazol-5-yl}benzoic acid and N-(2-aminoethyl)morpholine (Aldrich Cat. No. A55004). LCMS (M+H)+: m/z=567.3.

Example 12

N-(Pyridin-3-ylmethyl)-4-{1-[3-({[(2,2,2-trifluoroethyl)amino]carbonyl}amino)phenyl]-1H-benzimidazol-5-yl}benzamide

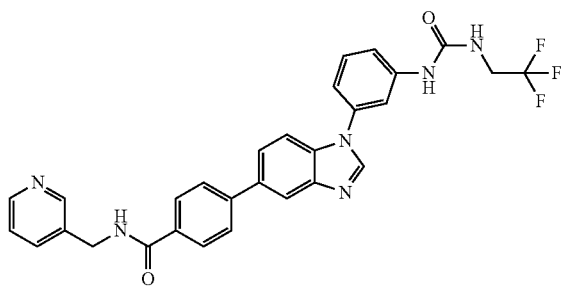 [SMILES: O=C(NCC(F)(F)F)Nc1cccc(-n2cnc3cc(-c4ccc(C(=O)NCc5cccnc5)cc4)ccc32)c1]

This compound was prepared by using procedures analogous to those described for the synthesis of Example 7 starting from 4-{1-[3-({[(2,2,2-trifluoroethyl)amino]carbonyl)-amino)phenyl]-1H-benzimidazol-5-yl}benzoic acid and picolamine (Aldrich Cat. No. A65409).
LCMS (M+H)+: m/z=545.2.

Example 13

N-[(1-Methyl-1H-imidazol-2-yl)methyl]-4-{1-[3-({[(2,2,2-trifluoroethyl)amino]carbonyl}amino)phenyl]-1H-benzimidazol-5-yl}benzamide

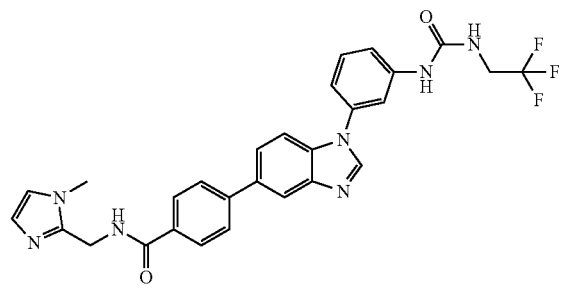 [SMILES: Cn1ccnc1CNC(=O)c1ccc(-c2ccc3c(c2)ncn3-c2cccc(NC(=O)NCC(F)(F)F)c2)cc1]

This compound was prepared by using procedures analogous to those described for the synthesis of Example 7 starting from 4-{1-[3-({[(2,2,2-trifluoroethyl)amino]carbonyl-amino)phenyl]-1H-benzimidazol-5-yl}benzoic acid and 1-(1-methyl-1H-imidazol-2-yl)methanamine (Matrix Sci., Cat. No. 020650). LCMS (M+H)+: m/z=548.2.

Example 14

N-Methyl-2-(4-{1-[3-({[(2,2,2-trifluoroethyl)amino]carbonyl}amino)phenyl]-1H-benzimidazol-5-yl}phenyl)propanamide

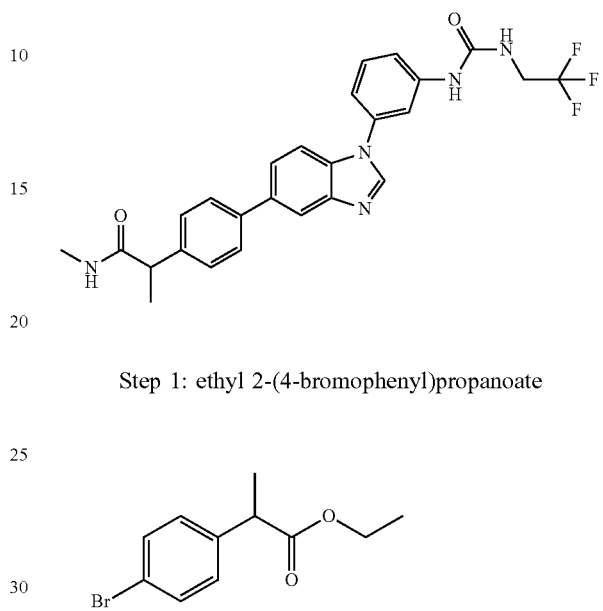

Step 1: ethyl 2-(4-bromophenyl)propanoate

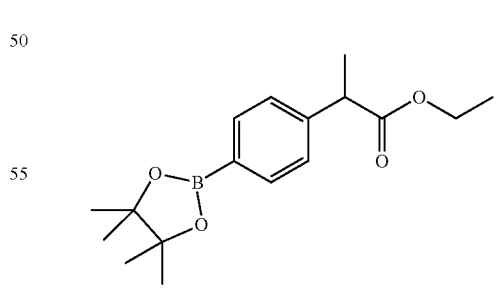

2.0 M LDA in heptane/THF/ethylbenzene (6.0 mL, 12 mmol) was slowly added to a solution of ethyl (4-bromophenyl)acetate (2.43 g, 10.0 mmol) in THF (20 mL) at −78° C. and then the mixture was stirred for 30 min. Methyl iodide (0.93 mL, 15 mmol) was added at −78° C. and then the reaction was stirred for an additional 30 min. Saturated NH4Cl aq. was added to quench the reaction. The mixture was extracted with ethyl acetate. The combined organic layers were washed with water and brine, dried over Na2SO4, filtered and concentrated under reduced pressure. The residue was purified by flash chromatography on a silica gel column with ethyl acetate in hexane (0-10%) to afford the desired product (2.0 g).

Step 2: ethyl 2-[4-(4,4,5,5-tetramethyl-1,3,2-dioxaborolan-2-yl)phenyl]propanoate 4,4,5,5-Tetramethyl-1,3,2-dioxaborolane (1.3 mL, 9.0 mmol) was added to a mixture of ethyl 2-(4-bromophenyl)propanoate (1.3 g, 5.0 mmol), bis(acetonitrile)palladium(II) chloride (26 mg, 0.10 mmol), 2-(dicyclohexylphosphino)-2',6'-dimethoxy-1,1'-biphenyl (160 mg, 0.40 mmol) and triethylamine (2.1 mL, 15 mmol) in 1,4-dioxane (3.0 mL) and then the mixture was evacuated under reduced pressure and then refilled with nitrogen thrice. The reaction was then heated at 110° C. for 4 h. The mixture was cooled to r.t. and filtered through a short pad of silical gel and then washed with ethyl acetate. The solvent was removed under reduced pressure. The residue was purified by flash chromatography on a silica gel column eluting with ethyl acetate in hexane (0-10%) to afford the desired product.

Step 3: 2-(4-{1-[3-({[(2,2,2-trifluoroethyl)amino]carbonyl}amino)phenyl]-1H-benzimidazol-5-yl}phenyl)propanoic acid

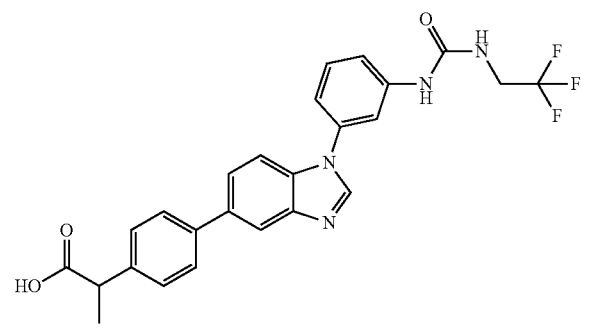 [SMILES: CC(C(=O)O)c1ccc(-c2ccc3c(c2)ncn3-c2cccc(NC(=O)NCC(F)(F)F)c2)cc1]

A mixture of N-[3-(5-bromo-1H-benzimidazol-1-yl)phenyl]-N'-(2,2,2-trifluoroethyl)urea (250.0 mg, 0.6050 mmol) (from Example 1, step 4), ethyl 2-[4-(4,4,5,5-tetramethyl-1,3,2-dioxaborolan-2-yl)phenyl]propanoate (280 mg, 0.91 mmol), [1,1'-bis(diphenylphosphino)ferrocene]-dichloropalladium(II) complex with dichloromethane (1:1) (30 mg, 0.04 mmol, Aldrich, Cat. No. 379670) and sodium carbonate (130 mg, 1.2 mmol) in 1,4-dioxane (5 mL) and a few drops water was heated at 120° C. overnight under nitrogen. After the reaction was cooled to r.t., 1.0 M sodium hydroxide in water (2.4 mL,) was added to the above mixture. The reaction mixture was heated at 100° C. 2 h., then cooled to r.t. The reaction mixture was diluted with ethyl acetate, and extracted with 1N NaOH aqueous solution twice. The combined aqueous phases were acidified to pH-2 with 6 M HCl aqueous solution, and then extracted with ethyl acetate twice. The combined organic phases (only the extracted portion with acidic aqueous solution) were washed with brine, dried over MgSO$_4$. After filtration, the filtrate was concentrated under reduced pressure to afford the desired product. LCMS (M+H)$^+$: m/z=483.1.

Step 4: N-methyl-2-(4-{1-[3-({[(2,2,2-trifluoroethyl)amino]carbonyl}amino)phenyl]-1H-benzimidazol-5-yl}phenyl)propanamide

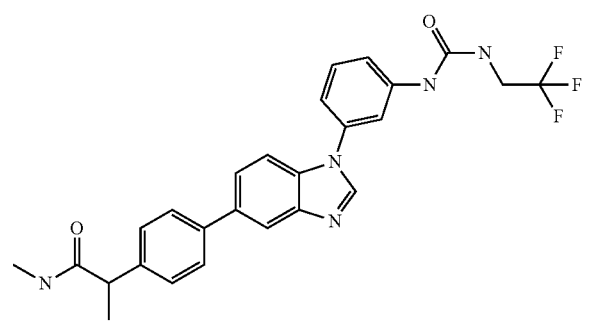 [SMILES: CNC(=O)C(C)c1ccc(-c2ccc3c(c2)ncn3-c2cccc(NC(=O)NCC(F)(F)F)c2)cc1]

To a solution of 2-(4-{1-[3-({[(2,2,2-trifluoroethyl)amino]carbonyl}amino) phenyl]-1H-benzimidazol-5-yl}phenyl)propanoic acid (20.0 mg, 0.0414 mmol) and 2.0 M methylamine in THF (41 µL, 0.083 mmol, Aldrich, Cat. No. 395056) in N,N-dimethylformamide (1 mL) was added benzotriazol-1-yloxytris(dimethylamino) phosphonium hexafluorophosphate (23 mg, 0.053 mmol, Adv. ChemTech. Cat. No. RC8105) and N,N-diisopropylethylamine (23 µL, 0.13 mmol). The reaction mixture was stirred at r.t. 2 h., then diluted with MeOH, and purified by RP-HPLC (pH=10) to afford the desired compound. LCMS (M+H)$^+$: m/z=496.2.

Example 15

N,N-Dimethyl-2-(4-{1-[3-({[(2,2,2-trifluoroethyl)amino]carbonyl}amino)phenyl]-1H-benzimidazol-5-yl}phenyl)propanamide

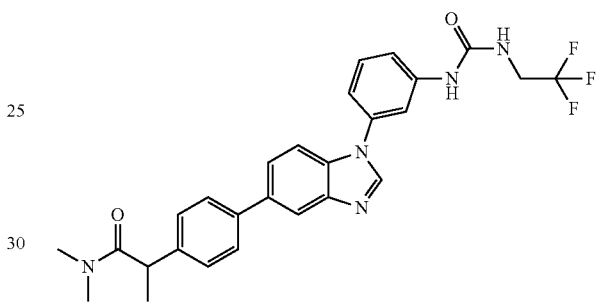

This compound was prepared by using procedures analogous to those described for the synthesis of Example 14 starting from 2-(4-{1-[3-({[(2,2,2-trifluoroethyl)amino]carbonyl-amino)phenyl]-1H-benzimidazol-5-yl}phenyl)propanoic acid (prepared by the procedure for Example 14, step 3) and dimethylamine in THF solution (2.0 M), LCMS (M+H)$^+$: m/z=510.2.

$^1$H NMR (300 MHz, CDCl$_3$): 8.34 (s, 1H), 7.97 (s, 1H), 7.78 (d, J=1.5 Hz, 1H), 7.39 (s, 1H), 7.32 (d, J=8.3 Hz, 2H), 7.30 (m, 2H), 7.21 (d, J=8.7 Hz, 2H), 7.17 (m, 2H), 6.97 (m, 1H), 6.42 (t, J=6.8 Hz, 1H), 3.97 (m, 1H), 3.87 (m, 2H), 3.00 (s, 3H), 2.95 (s, 3H), 1.44 (d, J=7.0 Hz, 3H).

Example 16

N-(Cyclopropylmethyl)-2-(4-{1-[3-({[(2,2,2-trifluoroethyl)amino]carbonyl)}amino)phenyl]-1H-benzimidazol-5-yl}phenyl)propanamide

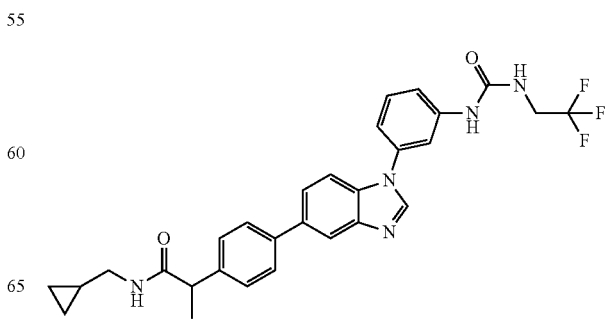

This compound was prepared by using procedures analogous to those described for the synthesis of Example 14 starting from 2-(4-{1-[3-({[(2,2,2-trifluoroethyl)amino]carbonyl}amino)phenyl]-1H-benzimidazol-5-yl}phenyl)propanoic acid (prepared by the procedure for Example 14, step 3) and cyclopropylmethylamine (Aldrich, Cat. No. 359521), LCMS (M+H)+: m/z=536.2.

Example 17

N-(3-{5-[4-(1-Methyl-2-oxo-2-pyrrolidin-1-ylethyl)phenyl]-1H-benzimidazol-1-yl}phenyl)-N'-(2,2,2-trifluoroethyl)urea

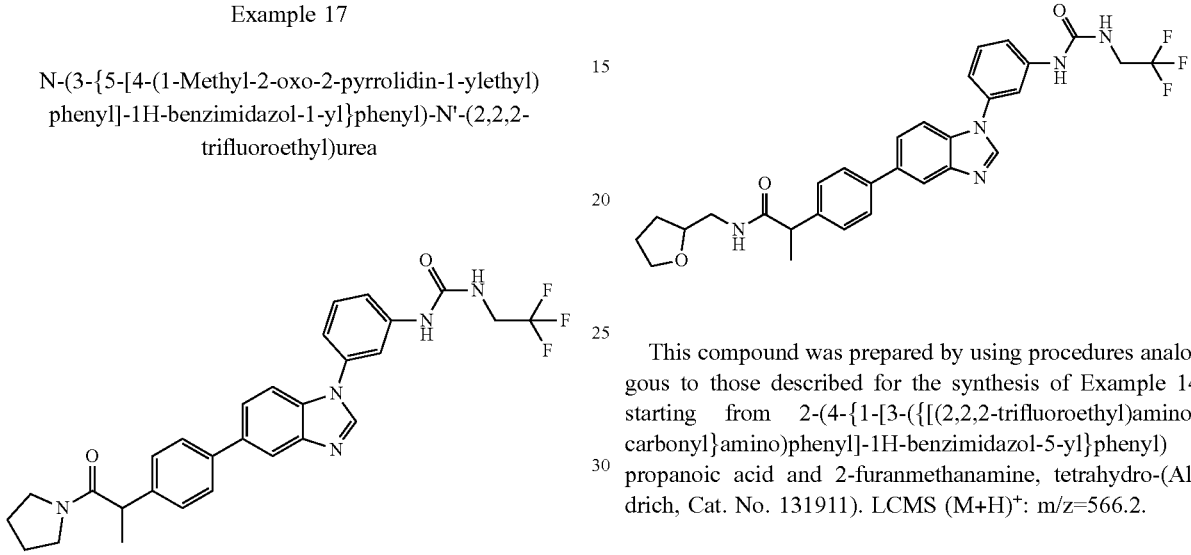

This compound was prepared by using procedures analogous to those described for the synthesis of Example 14 starting from 2-(4-{1-[3-({[(2,2,2-trifluoroethyl)amino]carbonyl-amino)phenyl]-1H-benzimidazol-5-yl}phenyl)propanoic acid (prepared by the procedure for Example 14, step 3) and pyrrolidine, LCMS (M+H)+: m/z=536.2.

Example 18

N-(Tetrahydrofuran-2-ylmethyl)-2-(4-{1-[3-({[(2,2,2-trifluoroethyl)amino]carbonyl}amino)phenyl]-1H-benzimidazol-5-yl}phenyl)propanamide This compound was prepared by using procedures analogous to those described for the synthesis of Example 14 starting from 2-(4-{1-[3-({[(2,2,2-trifluoroethyl)amino]carbonyl}amino)phenyl]-1H-benzimidazol-5-yl}phenyl)propanoic acid and 2-furanmethanamine, tetrahydro-(Aldrich, Cat. No. 131911). LCMS (M+H)+: m/z=566.2.

Example 19

N-[3-(5-{4-[2-(3-Cyanopyrrolidin-1-yl)-1-methyl-2-oxoethyl]phenyl}-1H-benzimidazol-1-yl)phenyl]-N'-(2,2,2-trifluoroethyl)urea

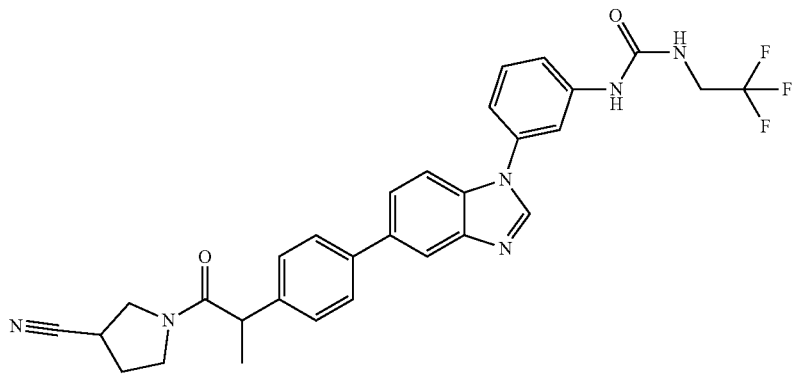 [SMILES: CC(C(=O)N1CCC(C#N)C1)c1ccc(-c2ccc3c(c2)ncn3-c2cccc(NC(=O)NCC(F)(F)F)c2)cc1]

This compound was prepared by using procedures analogous to those described for the synthesis of Example 14 starting from 2-(4-{1-[3-({[(2,2,2-trifluoroethyl)amino]carbonyl-amino)phenyl]-1H-benzimidazol-5-yl}phenyl)propanoic acid and pyrrolidine-3-carbonitrile hydrochloride (1-N-Boc-3-cyano-pyrrolidine, Alfa Aesar, Cat. No. H50082), LCMS (M+H)+: m/z=561.2.

Example 20

N-[(1-Methyl-1H-imidazol-2-yl)methyl]-2-(4-{1-[3-({[(2,2,2-trifluoroethyl)amino]carbonyl}amino)phenyl]-1H-benzimidazol-5-yl}phenyl)propanamide

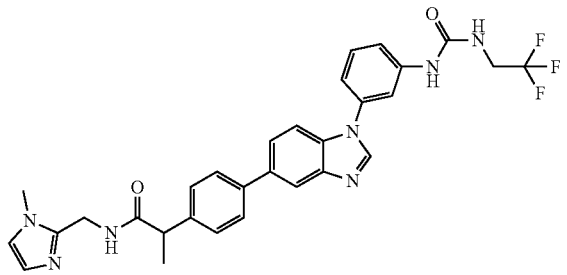 [SMILES: CC(C(=O)NCc1nccn1C)c1ccc(-c2ccc3c(c2)ncn3-c2cccc(NC(=O)NCC(F)(F)F)c2)cc1]

This compound was prepared by using procedures analogous to those described for the synthesis of Example 14 starting from 2-(4-{1-[3-({[(2,2,2-trifluoroethyl)amino]carbonyl-amino)phenyl]-1H-benzimidazol-5-yl}phenyl)propanoic acid and 1-(1-methyl-1H-imidazol-2-yl)methanamine (Matrix Sci., Cat. No. 020650), LCMS (M+H)+: m/z=576.2.

Example 21

N-[3-(5-{1-[1-(Cyclopropylmethyl)piperidin-4-yl]-1H-pyrazol-4-yl}-1H-benzimidazol-1-yl)phenyl]-N'-(2,2,2-trifluoroethyl)urea

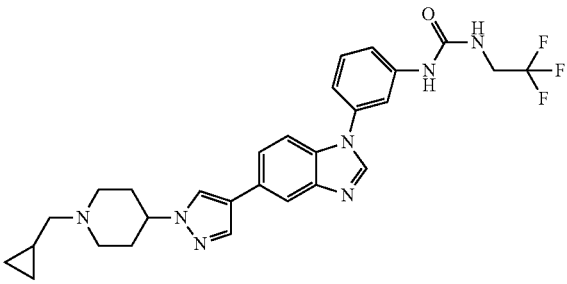 [SMILES: O=C(NCC(F)(F)F)Nc1cccc(-n2cnc3cc(-c4cnn(C5CCN(CC6CC6)CC5)c4)ccc32)c1]

Step 1: tert-butyl 4-[(methylsulfonyl)oxy]piperidine-1-carboxylate

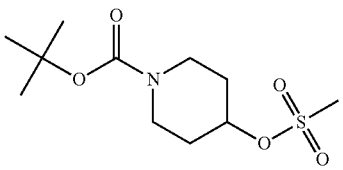 [SMILES: CC(C)(C)OC(=O)N1CCC(OS(C)(=O)=O)CC1]

To a solution of tert-butyl 4-hydroxypiperidine-1-carboxylate (5.03 g, 0.0250 mol, Aldrich Cat. No. 495484) in methylene chloride (50 mL) were added methanesulfonyl chloride (2.03 mL, 0.0262 mol, Aldrich, Cat. No. 471259) and triethylamine (3.66 mL, 0.0262 mol) at 0° C. The solution was stirred at r.t. overnight, then diluted with ethyl acetate, and washed with NaHCO$_3$ aqueous solution and brine successively. The organic layers were dried over MgSO$_4$ and then concentrated under reduced pressure to afford the desired product which was directly used in next step. LCMS (M+Na)+: m/z=302.3.

Step 2: tert-butyl 4-[4-(4,4,5,5-tetramethyl-1,3,2-dioxaborolan-2-yl)-1H-pyrazol-1-yl]piperidine-1-carboxylate

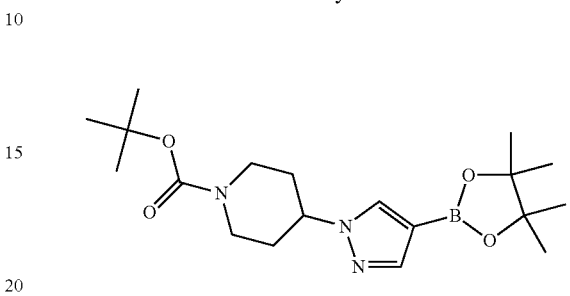

To a solution of 4-(4,4,5,5-tetramethyl-1,3,2-dioxaborolan-2-yl)-1H-pyrazole (4.12 g, 21.2 mmol, Aldrich, Cat. 525057) in N,N-dimethylformamide (20 mL) was added sodium hydride (1.78 g, 44.5 mmol) at 0° C. The resulting solution was stirred at r.t. for one hour, and then tert-butyl 4-[(methylsulfonyl)oxy]piperidine-1-carboxylate (6.3 g, 22 mmol) in DMF (2 mL) was added. The reaction mixture was heated at 90° C. overnight. Then the reaction mixture was cooled to r.t., quenched with water, and extracted with ethyl acetate. The organic layer was washed with NaHCO$_3$ aqueous solution and brine successively, dried over MgSO$_4$, and concentrated under reduced pressure. The residue was purified by flash column chromatography on a silica gel column using 30% ethyl acetate in hexane as eluent to afford the desired compound (2.30 g, 28.74%). LCMS (M+H)+: m/z=378.4.

Step 3: tert-butyl 4-(4-{1-[3-({[(2,2,2-trifluoroethyl)amino]carbonyl}amino)phenyl]-1H-benzimidazol-5-yl}-1H-pyrazol-1-yl)piperidine-1-carboxylate

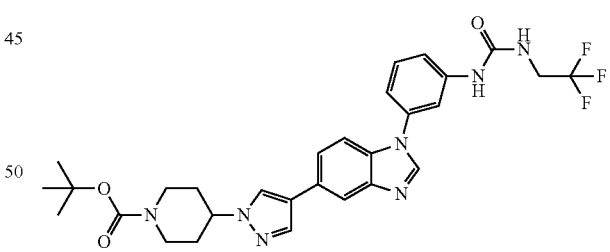

The mixture of N-[3-(5-bromo-1H-benzimidazol-1-yl)phenyl]-N'-(2,2,2-trifluoroethyl)urea (1.0000 g, 2.4202 mmol) (prepared from the procedure of Example 1, step 4), tert-butyl 4-[4-(4,4,5,5-tetramethyl-1,3,2-dioxaborolan-2-yl)-1H-pyrazol-1-yl]piperidine-1-carboxylate (1.1 g, 2.8 mmol), [1,1'-bis(diphenylphosphino)ferrocene]-dichloropalladium(II), complex with dichloromethane (1:1) (0.1 g, 0.1 mmol, Aldrich, Cat. No. 697360) and sodium carbonate (510 mg, 4.8 mmol) in 1,4-dioxane (10 mL) and a few drops of water was heated at 120° C. under nitrogen overnight. After the reaction mixture was cooled to r.t., it was filtered, and the solid was washed with ethyl acetate. The filtrate was concentrated under reduced pressure. The residue was purified by flash column chromatography on a silica gel column using 6% MeOH CH$_2$Cl$_2$ as eluent to afford the desired compound (0.48 g, 34%). LCMS (M+H)$^+$: m/z=584.2.

Step 4: N-{3-[5-(1-piperidin-4-yl-1H-pyrazol-4-yl)-1H-benzimidazol-1-yl]phenyl}-N'-(2,2,2-trifluoroethyl)urea

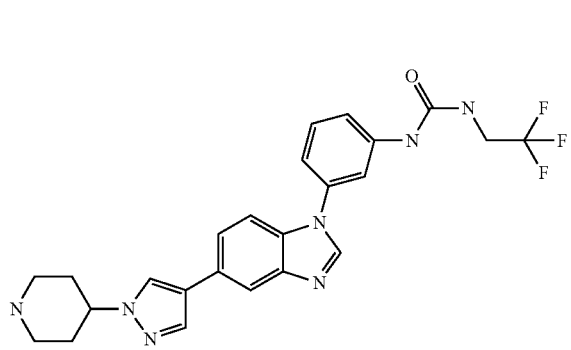 [SMILES: O=C(NCC(F)(F)F)Nc1cccc(-n2cnc3cc(-c4cnn(C5CCNCC5)c4)ccc32)c1]

To a solution of tert-buty 4-(4-{-[3-({[(2,2,2-trifluoroethyl)amino]carbonyl}amino)phenyl]-1H-benzimidazol-5-yl}-1H-pyrazol-1-yl)piperidine-1-carboxylate (130 mg, 0.22 mmol) in ethyl acetate (2 mL) was added 4.0 M hydrogen chloride in dioxane (0.22 mL, 0.89 mmol). The suspension was stirred at r.t. 2 h. and then concentrated under reduced pressure to afford the desired compound as HCl salt. LCMS (M+H)$^+$: m/z=484.2.

Step 5: N-[3-(5-{1-[1-(Cyclopropylmethyl)piperidin-4-yl]-1H-pyrazol-4-yl}-1H-benzimidazol-1-yl)phenyl]-N'-(2,2,2-trifluoroethyl)urea

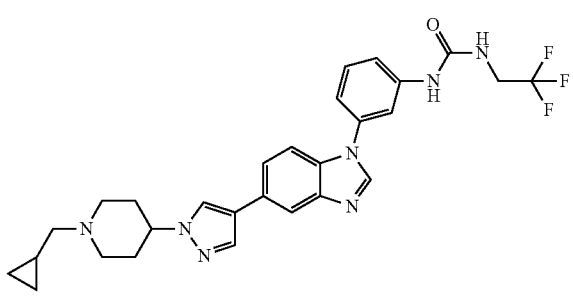 [SMILES: O=C(NCC(F)(F)F)Nc1cccc(-n2cnc3cc(-c4cnn(C5CCN(CC6CC6)CC5)c4)ccc32)c1]

To a solution of N-{3-[5-(1-piperidin-4-yl-1H-pyrazol-4-yl)-1H-benzimidazol-1-yl]phenyl}-N'-(2,2,2-trifluoroethyl)urea HCl salt (20.0 mg, 0.0414 mmol) in 1,2-dichloroethane (2 mL) and ethanol (0.5 mL) was added cyclopropanecarboxaldehyde (4.6 µL, 0.062 mmol) and triethylamine (17 µL, 0.12 mmol). The suspension was stirred at r.t. for 1 h then sodium triacetoxyborohydride (18 mg, 0.083 mmol) was added. The reaction solution was stirred at r.t. overnight. The reaction solution was concentrated under reduced pressure to dryness. The residue was dissolved in MeOH, and purified by RP-HPLC (pH=10) to afford the desired compound. LCMS (M+H)$^+$: m/z=538.2.

$^1$H NMR (300 MHz, CDCl$_3$): 8.70 (s, 1H), 7.94 (s, 1H), 7.73 (s, 1H), 7.66 (s, 1H), 7.57 (s, 1H), 7.41 (s, 1H), 7.30 (m, 4H), 6.96 (d, J=9.2 Hz, 1H), 6.58 (t, J=8.9 Hz, 1H), 4.05 (m, 1H), 3.88 (m, 2H), 3.13 (d, J=10.6 Hz, 2H), 2.33 (s, 1H), 2.22 (d, J=6.5 Hz, 1H), 2.05 (m, 6H), 0.80 (m, 1H), 0.45 (m, 2H), 0.04 (m, 2H).

Example 22

N-[3-(5-{1-[1-(Cyanomethyl)-2,2,2-trifluoroethyl]-1H-pyrazol-4-yl}-1H-benzimidazol-1-yl)phenyl]-N'-(2,2,2-trifluoroethyl)urea

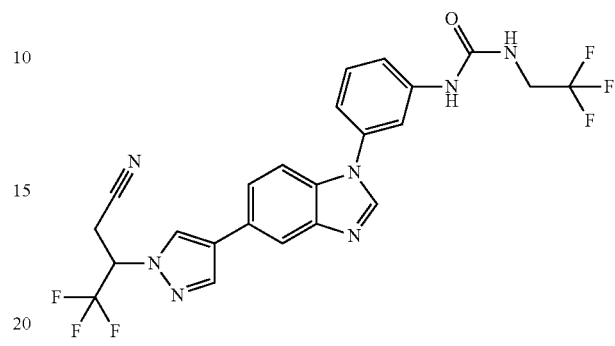

Step 1: N-(3-{5-[1-(1-ethoxyethyl)-1H-pyrazol-4-yl]-1H-benzimidazol-1-yl}phenyl)-N'-(2,2,2-trifluoroethyl)urea

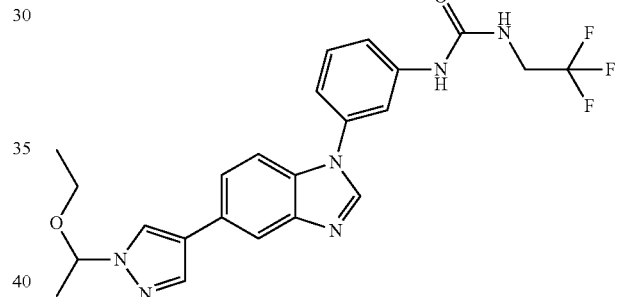

This compound was prepared by using procedures analogous to those described for the synthesis of Example 21 (step 3) starting from N-{3-[5-(1-piperidin-4-yl-1H-pyrazol-4-yl)-1H-benzimidazol-1-yl]phenyl}-N'-(2,2,2-trifluoroethyl)urea (prepared from the procedure for Example 21, step 4) and 1-(1-ethoxyethyl)-4-(4,4,5,5-tetramethyl-1,3,2-dioxaborolan-2-yl)-1H-pyrazole (Adesis, Cat. No. 9-243), LCMS (M+H)$^+$: m/z=473.1.

Step 2: N-{3-[5-(1H-pyrazol-4-yl)-1H-benzimidazol-1-yl]phenyl}-N'-(2,2,2-trifluoroethyl)urea

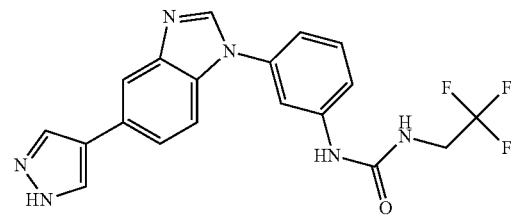 [SMILES: O=C(NCC(F)(F)F)Nc1cccc(-n2cnc3cc(-c4cn[nH]c4)ccc32)c1]

The mixture of N-(3-{5-[1-(1-ethoxyethyl)-1H-pyrazol-4-yl]-1H-benzimidazol-1-yl}phenyl)-N'-(2,2,2-trifluoroethyl)urea (190 mg, 0.40 mmol) and 1.0 M hydrogen chloride in water (3 mL, 3 mmol) in tetrahydrofuran (5 mL) was stirred at r.t. 2 hours. The reaction mixture was concentrated under reduced pressure to dryness to afford the desired compound as HCl salt which was directly used in next step reaction without further purification. LCMS (M+H)⁺: m/z=401.2.

Step 3: N-[3-(5-{1-[1-(cyanomethyl)-2,2,2-trifluoroethyl]-1H-pyrazol-4-yl}-1H-benzimidazol-1-yl)phenyl]-N'-(2,2,2-trifluoroethyl)urea

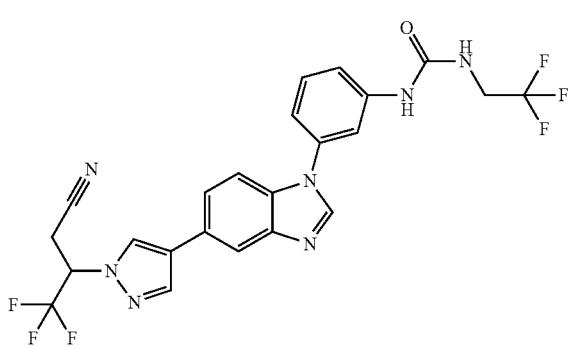 [SMILES: N#CCC(n1cc(-c2ccc3c(c2)ncn3-c2cccc(NC(=O)NCC(F)(F)F)c2)cn1)C(F)(F)F]

To a solution of N-{3-[5-(1H-pyrazol-4-yl)-1H-benzimidazol-1-yl]phenyl}-N'-(2,2,2-trifluoroethyl)urea HCl salt (20.0 mg, 0.0458 mmol) in acetonitrile (1 mL) was added (2E)-4,4,4-trifluorobut-2-enenitrile (8.3 mg, 0.069 mmol) and 1,8-diazabicyclo[5.4.0]undec-7-ene (14 μL, 0.092 mmol). The solution was stirred and heated at 80° C. for several hours. The reaction solution was concentrated under reduced pressure to dryness. The residue was dissolved in MeOH, and purified by RP-HPLC (pH=10) to afford the desired compound. LCMS(M+H)⁺: m/z=522.1.

Example 23

N-{3-[5-(1-{1-[(1-Methyl-1H-pyrazol-4-yl)carbonyl]piperidin-4-yl}-1H-pyrazol-4-yl)-1H-benzimidazol-1-yl]phenyl}-N'-(2,2,2-trifluoroethyl)urea

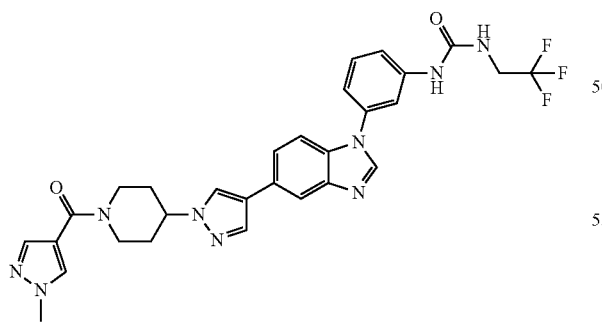

To a solution of N-{3-[5-(1-piperidin-4-yl-1H-pyrazol-4-yl)-1H-benzimidazol-1-yl]phenyl}-N'-(2,2,2-trifluoroethyl)urea HCl salt (20.0 mg, 0.0385 mmol) in acetonitrile (1 mL) was added 1-methyl-1H-pyrazole-4-carbonyl chloride (8.3 mg, 0.058 mmol, Matrix Sci., Cat. No. 019861) and pyridine (60 μL, 0.8 mmol), the solution was stirred at r.t. overnight. The reaction solution was diluted with MeOH and then purified by RP-HPLC (pH=10) to afford the desired compound. LCMS (M+H)⁺: m/z=592.3.

Example 24

N-{3-[5-(1-{1-[(1-Methyl-1H-pyrazol-3-yl)sulfonyl]piperidin-4-yl}-1H-pyrazol-4-yl)-1H-benzimidazol-1-yl]phenyl}-N'-(2,2,2-trifluoroethyl)urea

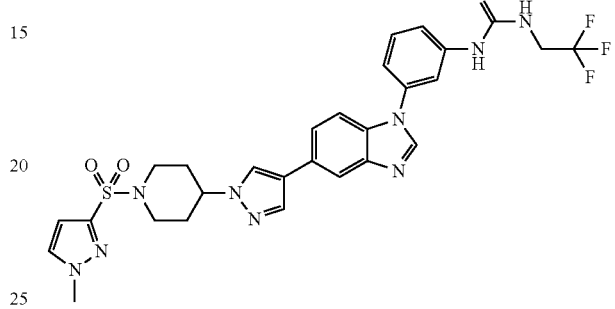

To a solution of N-{3-[5-(1-piperidin-4-yl-1H-pyrazol-4-yl)-1H-benzimidazol-1-yl]phenyl}-N'-(2,2,2-trifluoroethyl)urea HCl salt (20.0 mg, 0.0385 mmol) in acetonitrile (1 mL) was added 1-methyl-1H-pyrazole-3-sulfonyl chloride (10. mg, 0.058 mmol, Maybridge, Cat. No. CC48303) and triethylamine (16 μL, 0.12 mmol), the solution was stirred at r.t. overnight. The reaction solution was diluted with MeOH and then purified by RP-HPLC (pH=10) to afford the desired compound. LCMS(M+H)⁺: m/z=628.2.

Example 25

N-Pyridin-3-yl-4-(4-{1-[3-({[(2,2,2-trifluoroethyl)amino]carbonyl}amino)phenyl]-1H-benzimidazol-5-yl}-1H-pyrazol-1-yl)piperidine-1-carboxamide

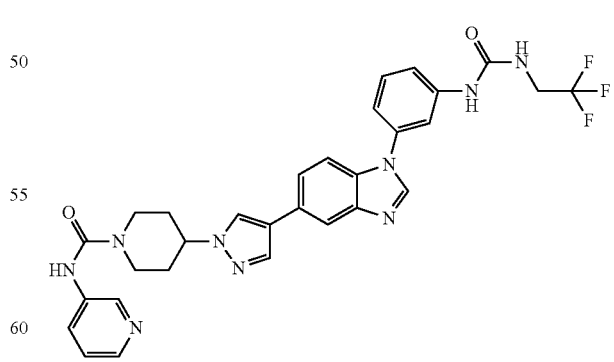

This compound was prepared by using procedures analogous to those described for the synthesis of Example 24 starting from N-{3-[5-(1-piperidin-4-yl-1H-pyrazol-4-yl)-1H-benzimidazol-1-yl]phenyl}-N'-(2,2,2-trifluoroethyl)urea HCl salt (prepared from the procedure for Example 21, step 4) and 3-isocyanatopyridine (Oakwood, Cat. No. 022077), LCMS (M+H)⁺: m/z=604.3.

Example 26

N-[3-(5-{t-[1-(Pyrrolidin-1-ylcarbonyl)piperidin-4-yl]-1H-pyrazol-4-yl}-1H-benzimidazol-1-yl)phenyl]-N'-(2,2,2-trifluoroethyl)urea

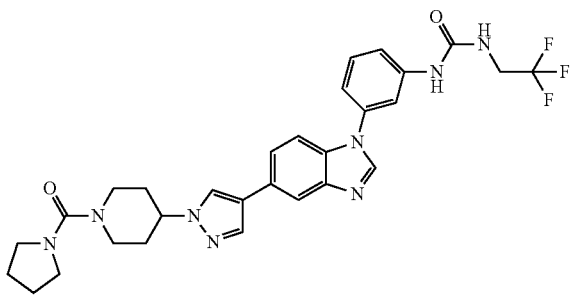 [SMILES: O=C(NCC(F)(F)F)Nc1cccc(-n2cnc3cc(-c4cnn(C5CCN(C(=O)N6CCCC6)CC5)c4)ccc32)c1]

To a solution of N-{3-[5-(1-piperidin-4-yl-1H-pyrazol-4-yl)-1H-benzimidazol-1-yl]phenyl}-N'-(2,2,2-trifluoroethyl) urea HCl salt (20.0 mg, 0.0385 mmol) in tetrahydrofuran (1 mL) was added p-nitrophenyl chloroformate (12 mg, 0.058 mmol), triethylamine (16 μL, 0.12 mmol). The solution was stirred at r.t. for 1 h, then pyrrolidine (6.4 μL, 0.077 mmol) was added. The reaction solution was stirred at r.t. overnight, and then heated at 100° C. 2 h. LC/MS analysis showed reaction was finished. The reaction solution was concentrated under reduced pressure to dryness. The residue was dissolved in MeOH, and purified by RP-HPLC (pH=10) to afford the desired compound. LCMS (M+H)⁺: m/z=581.3

Example 27

N-[3-(5-{1-[1-(Cyclopropylacetyl)piperidin-4-yl]-1H-pyrazol-4-yl}-1H-benzimidazol-1-yl)phenyl]-N'-(2,2,2-trifluoroethyl)urea

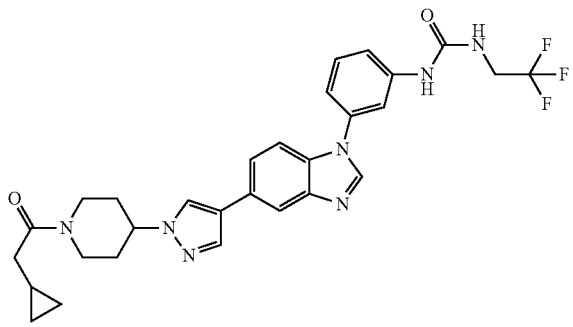 [SMILES: O=C(NCC(F)(F)F)Nc1cccc(-n2cnc3cc(-c4cnn(C5CCN(C(=O)CC6CC6)CC5)c4)ccc32)c1]

This compound was prepared by using procedures analogous to those described for the synthesis of Example 1 (Step 6) starting from N-{3-[5-(1-piperidin-4-yl-1H-pyrazol-4-yl)-1H-benzimidazol-1-yl]phenyl}-N'-(2,2,2-trifluoroethyl) urea HCl salt and cyclopropylacetic acid, (Alfa aesar, Cat. No. L09416), LCMS (M+H)⁺: m/z=566.2.

Example 28

N-[3-(5-{1-[1-(Cyanoacetyl)piperidin-4-yl]-1H-pyrazol-4-yl}-1H-benzimidazol-1-yl)phenyl]-N'-(2,2,2-trifluoroethyl)urea

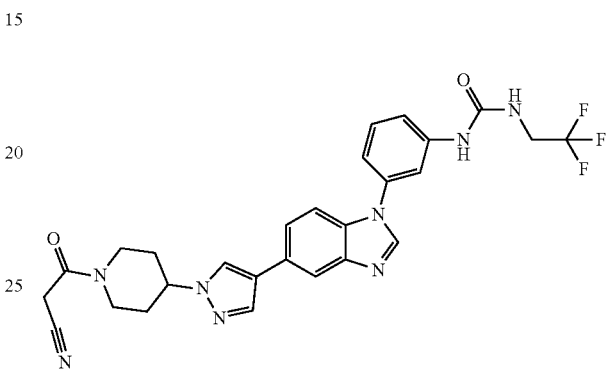

This compound was prepared by using procedures analogous to those described for the synthesis of Example 1 (Step 6) starting from N-{3-[5-(1-piperidin-4-yl-1H-pyrazol-4-yl)-1H-benzimidazol-1-yl]phenyl}-N'-(2,2,2-trifluoroethyl) urea HCl salt and cyanoacetic acid, (Aldrich, Cat. No. C88505), LCMS (M+H)⁺: m/z=551.2.

Example 29

N-[3-(5-{1-[1-(Tetrahydrofuran-2-ylcarbonyl)piperidin-4-yl]-1H-pyrazol-4-yl}-1H-benzimidazol-1-yl)phenyl]-N'-(2,2,2-trifluoroethyl)urea

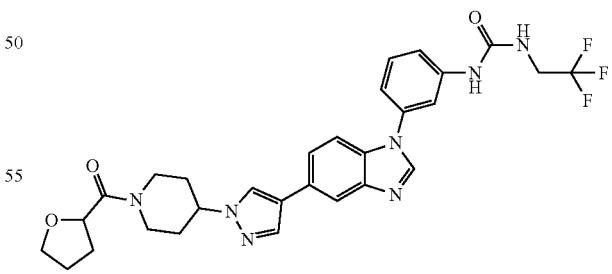

This compound was prepared by using procedures analogous to those described for the synthesis of Example 1 (Step 6) starting from N-{3-[5-(1-piperidin-4-yl-1H-pyrazol-4-yl)-1H-benzimidazol-1-yl]phenyl}-N'-(2,2,2-trifluoroethyl) urea HCl salt and 2-tetrahydro-furancarboxylic acid, (Aldrich, Cat. No. 341517), LCMS (M+H)⁺: m/z=582.2.

Example 30

N-[3-(7-{1-[1-(Methoxyacetyl)piperidin-4-yl]-1H-pyrazol-4-yl}imidazo[1,2-b]pyridazin-3-yl)phenyl]-N'-(2,2,2-trifluoroethyl)urea

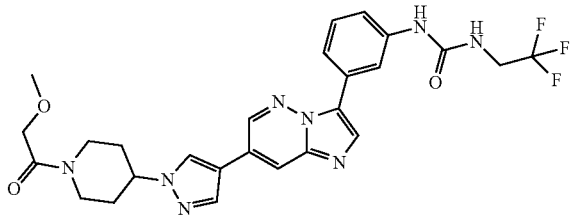 [SMILES: COCC(=O)N1CCC(n2cc(-c3cnn4c(-c5cccc(NC(=O)NCC(F)(F)F)c5)cnc4c3)cn2)CC1]

Step 1: 7-chloroimidazo[1,2-b]pyridazine

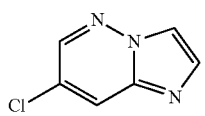

A mixture of 3,5-dichloropyridazine (1.49 g, 10.0 mmol, Maybridge, MO08501), benzophenone imine (2.01 g, 11.1 mmol, Aldrich, Cat. No. 293733), (9,9-dimethyl-9H-xanthene-4,5-diyl)bis(diphenylphosphine) (208 mg, 0.360 mmol), tris(dibenzylideneacetone)dipalladium(O) (165 mg, 0.180 mmol) and 1,4-dioxane (30 mL) was degassed and recharged with nitrogen for three times, and was heated and stirred at 90° C. overnight. After cooling, the mixture was filtered through a pad of silica gel, and washed with THF. [LCMS (M+H)$^+$: m/z=294.1/296.0 corresponds to 5-chloro-N-(diphenylmethylene)pyridazin-3-amine]. The filtrate was treated with 3 N HCl aq. (6 ml) at RT and stirred for 30 min. The mixture was adjusted with NaOH (2 N) to pH=7. The resulting mixture was concentrated under reduced pressure to about the volume of 30 mL. [LCMS (M+H)$^+$: m/z=130.1/132.0 corresponds to 5-chloropyridazin-3-amine]. Isopropanol (50 mL) and chloroacetaldehyde (10.0 mL, 78.7 mmol) was added to the solution. The mixture was heated and stirred at 90° C. for 5 h. After cooling, the mixture was concentrated under reduced pressure. The residue was diluted with ethyl acetate, and extracted with water. The combined aqueous layers were adjusted to about pH=9 with 1 N NaOH aq. Solution. The resulting solution was extracted with ethyl acetate (3×30 mL). The combined organic layers were washed with brine, dried over MgSO$_4$, filtered and concentrated under reduced pressure to afford the desired product (0.988 g, 64.3%) which was directly used in next step reaction without further purification.

LCMS (M+H)$^+$: m/z=153.9/155.9.

Step 2: 7-chloro-3-iodoimidazo[1,2-b]pyridazine

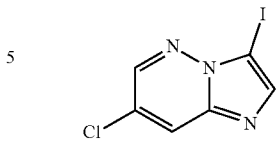

N-Iodosuccinimide (2.17 g, 9.65 mmol) was added to a solution of 7-chloroimidazo[1,2-b]pyridazine (0.988 g, 6.43 mmol) in N,N-dimethylformamide (25 mL). The reaction mixture was stirred at r.t. overnight. The mixture was diluted with ethyl acetate, washed with water and brine. The organic layer was dried over MgSO$_4$, filtered, and concentrated under reduced pressure. The residue was purified by flash chromatography on a silica gel column with ethyl acetate in hexane (gradient: 0-50%) to afford the desired product (1.40 g, 77.9%). LCMS (M+H)$^+$: m/z=279.9/281.9.

Step 3: N-[3-(7-chloroimidazo[1,2-b]pyridazin-3-yl)phenyl]-N'-(2,2,2-trifluoroethyl)urea

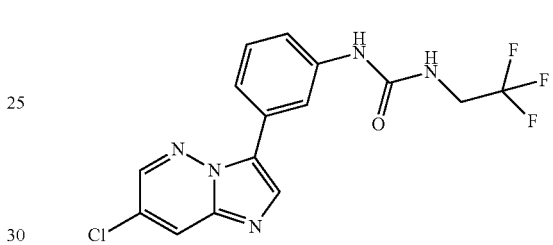

A mixture of 7-chloro-3-iodoimidazo[1,2-b]pyridazine (1.40 g, 5.01 mmol), N-[3-(4,4,5,5-tetramethyl-1,3,2-dioxaborolan-2-yl)phenyl]-N'-(2,2,2-trifluoroethyl)urea (1.76 g, 5.11 mmol), [1,1'-bis(diphenylphosphino)ferrocene]dichloropalladium(II), complex with dichloromethane (DCM) (1:1) (164 mg, 0.200 mmol), and potassium carbonate (2.08 g, 15.0 mmol) in 1,4-dioxane (15 mL) and water (5 mL) was degassed and recharged with nitrogen three times. The mixture was then heated and stirred at 60° C. overnight. After cooling, the mixture was diluted with ethyl acetate, washed with water and brine, dried over Na$_2$SO$_4$, filtered, and concentrated under reduced pressure. The residue was treated with DCM (3 mL) and acetonitrile (3 mL). The precipitate was collected by filtration and washed with acetonitrile, dried under vacuum to afford the desired product (0.988 g). The filtrate (mother liquid) was concentrated. The residue was purified by flash chromatography on a silica gel column with methanol in DCM (0-10%) to afford the additional product 0.17 g. The total product is 1.158 g (62.5%). LCMS (M+H)$^+$: m/z=370.0/372.0.

Step 4: tert-butyl 4-(4-{3-[3-({[(2,2,2-trifluoroethyl)amino]carbonyl}amino)phenyl]imidazo[1,2-b]pyridazin-7-yl}-1H-pyrazol-1-yl)piperidine-1-carboxylate

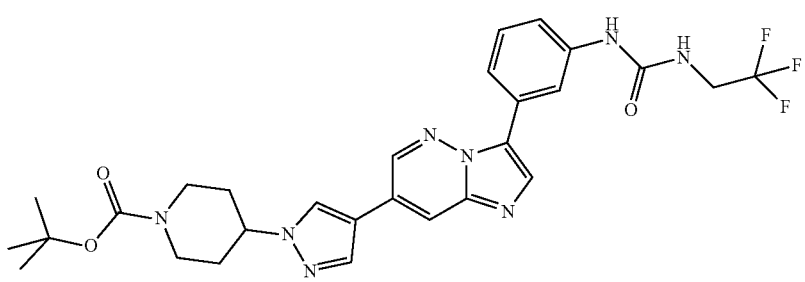 [SMILES: CC(C)(C)OC(=O)N1CCC(n2cc(-c3cnn4c(-c5cccc(NC(=O)NCC(F)(F)F)c5)cnc4c3)cn2)CC1]

A mixture of tert-butyl 4-[4-(4,4,5,5-tetramethyl-1,3,2-dioxaborolan-2-yl)-1H-pyrazol-1-yl]piperidine-1-carboxylate (0.830 g, 2.20 mmol, Combi-Block, Cat. No. FM-2957), N-[3-(7-chloroimidazo[1,2-b]pyridazin-3-yl)phenyl]-N'-(2,2,2-trifluoroethyl)urea (0.739 g, 2.00 mmol), tetrakis(triphenylphosphine)palladium(0) (116 mg, 0.100 mmol) and sodium carbonate (0.636 g, 6.00 mmol) in dioxane (15 mL) and water (5 mL) was degassed and recharged with nitrogen three times, and heated and stirred at 100° C. overnight. After cooling, the mixture was diluted with ethyl acetate, washed with water and brine. The organic layer was dried over MgSO$_4$, filtered and concentrated under reduced pressure. The residue was purified by flash chromatography on a silica gel column with ethyl acetate in hexane (gradient: 0-50%) to afford the desired product (0.965 g, 82.5%). LCMS (M+H)$^+$: m/z=585.2.

Step 5: N-{3-[7-(1-piperidin-4-yl-1H-pyrazol-4-yl)imidazo[1,2-b]pyridazin-3-yl]phenyl}-N'-(2,2,2-trifluoroethyl) urea

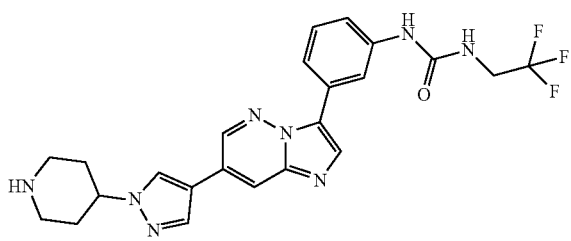 [SMILES: O=C(NCC(F)(F)F)Nc1cccc(-c2cnc3cc(-c4cnn(C5CCNCC5)c4)cnn23)c1]

tert-Butyl 4-(4-{3-[3-({[(2,2,2-trifluoroethyl)amino]carbonyl}amino)phenyl]-imidazo[1,2-b]pyridazin-7-yl}-1H-pyrazol-1-yl)piperidine-1-carboxylate (0.965 g, 1.65 mmol) was dissolved in methanol (1.0 mL). To the solution was added 4 N HCl in dioxane (1.5 mL). The mixture was stirred at r.t. for 2 h. The mixture was cooled with ice-water, and was carefully neutralized with sodium methoxide in methanol solution (25% w/w, about 4.375 M, 1.38 mL) to pH about 8. The volatiles were removed under reduced pressure. The residue was dried in vacuo to afford the desired product which contained residual NaCl, and was directly used in next step reaction without further purification. LCMS (M+H)$^+$: m/z=485.2.

Step 6. N-[3-(7-{1-[1-(methoxyacetyl)piperidin-4-yl]-1H-pyrazol-4-yl}imidazo[1,2-b]pyridazin-3-yl)phenyl]-N'-(2,2,2-trifluoroethyl)urea A mixture of N-{3-[7-(1-piperidin-4-yl-1H-pyrazol-4-yl)imidazo[1,2-b]pyridazin-3-yl]phenyl}-N'-(2,2,2-trifluoroethyl)urea (20.0 mg, 0.0413 mmol), methoxyacetyl chloride (5.66 μL, 0.0619 mmol) and N,N-diisopropylethylamine (40.0 μL, 0.230 mmol, Aldrich, Cat. No. M9653) in dimethylsulfoxide (DMSO) (0.5 mL) was stirred at r.t. for 4 h. The mixture was purified by RP-HPLC (pH=10) to afford the desired product. LCMS (M+H)$^+$: m/z=557.2.

Example 31

N-{3-[7-(1-{1-[(1-methyl-1H-pyrazol-3-yl)sulfonyl]piperidin-4-yl}-1H-pyrazol-4-yl)imidazo[1,2-b]pyridazin-3-yl]phenyl}-N'-(2,2,2-trifluoroethyl)urea

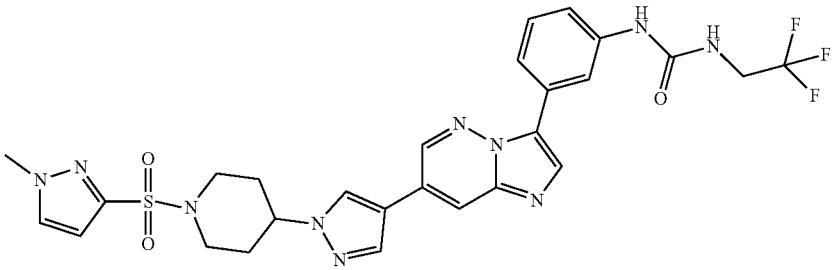 [SMILES: Cn1ccc(S(=O)(=O)N2CCC(n3cc(-c4cnn5c(-c6cccc(NC(=O)NCC(F)(F)F)c6)cnc5c4)cn3)CC2)n1]

This compound was prepared by using procedures analogous to those described for the synthesis of Example 30 (Step 6) starting from N-{3-[7-(1-piperidin-4-yl-1H-pyrazol-4-yl)imidazo[1,2-b]pyridazin-3-yl]phenyl}-N'-(2,2,2-trifluoroethyl)urea and 1-methyl-1H-pyrazole-3-sulfonyl chloride (Maybridge, Cat. No. CC48303). LCMS (M+H)$^+$: m/z=629.2.

$^1$H NMR (400 MHz, CDCl$_3$): 8.38 (d, J=2.5 Hz, 1H), 8.06 (s, 1H), 7.95 (s, 1H), 7.84 (d, J=2.5 Hz, 1H), 7.75 (s, 1H), 7.58-7.64 (m, 2H), 7.41 (d, J=2.2 Hz, 1H), 7.38 (s, 1H), 7.36 (s, 1H), 7.23 (s, 1H), 6.63 (d, J=2.5 Hz, 1H), 5.52 (t, J=6.5 Hz, 1H), 4.10-4.19 (m, 1H), 3.85-4.00 (m, 7H), 2.71 (td, J=12.3, 3.0 Hz, 2H), 2.15-2.23 (m, 2H), 2.00-2.13 (m, 2H).

Example 32

N-{3-[7-(1-{1-[(1-Methyl-1H-pyrazol-4-yl)carbonyl]piperidin-4-yl}-1H-pyrazol-4-yl)imidazo[1,2-b]pyridazin-3-yl]phenyl}-N'-(2,2,2-trifluoroethyl)urea

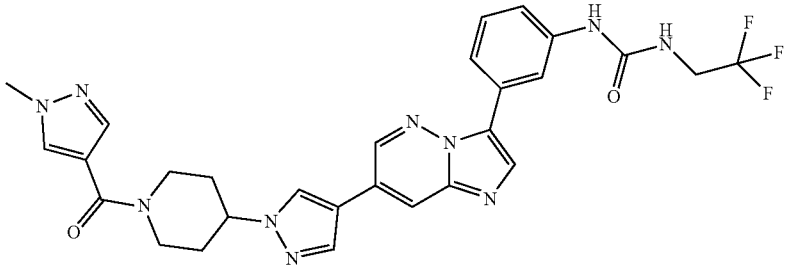 [SMILES: Cn1cc(C(=O)N2CCC(n3cc(-c4cnn5c(-c6cccc(NC(=O)NCC(F)(F)F)c6)cnc5c4)cn3)CC2)cn1]

This compound was prepared by using procedures analogous to those described for the synthesis of Example 30 (Step 6) starting from N-{3-[7-(1-piperidin-4-yl-1H-pyrazol-4-yl)imidazo[1,2-b]pyridazin-3-yl]phenyl}-N'-(2,2,2-trifluoroethyl)urea and 1-methyl-1H-pyrazole-4-carbonyl chloride (Maybridge, Cat. No. CC77402). LCMS (M+H)$^+$: m/z=593.2.

Example 33

N-{3-[7-(1-{1-[(Dimethylamino)acetyl]piperidin-4-yl}-1H-pyrazol-4-yl)imidazo[1,2-b]pyridazin-3-yl]phenyl}-N'-(2,2,2-trifluoroethyl)urea

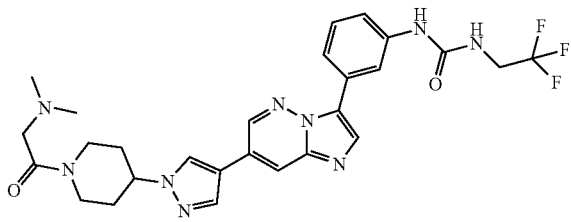 [SMILES: CN(C)CC(=O)N1CCC(n2cc(-c3cnn4c(-c5cccc(NC(=O)NCC(F)(F)F)c5)cnc4c3)cn2)CC1]

This compound was prepared by using procedures analogous to those described for the synthesis of Example 30 (Step 6) starting from N-{3-[7-(1-piperidin-4-yl-1H-pyrazol-4-yl)imidazo[1,2-b]pyridazin-3-yl]phenyl}-N'-(2,2,2-trifluoroethyl)urea and dimethylaminoacetyl chloride hydrochloride (Lancaster, Cat. No. L18475). LCMS (M+H)$^+$: m/z=570.2.

$^1$H NMR (400 MHz, CDCl$_3$): 8.49 (d, J=2.5 Hz, 1H), 8.06 (s, 1H), 8.00 (s, 1H), 7.98 (d, J=2.5 Hz, 1H), 7.84 (s, 1H), 7.76 (s, 1H), 7.70 (d, J=7.8 Hz, 1H), 7.65 (s, 1H), 7.50 (m, 1H), 7.43 (d, J=7.8 Hz, 1H), 5.01 (t, J=6.5 Hz, 1H), 4.78 (dm, 1H), 4.40 (m, 1H), 4.30 (dm, 1H), 3.92-4.02 (m, 2H), 3.10-3.27 (m, 2H), 2.78-2.87 (m, 1H), 2.18-2.36 (m, 9H), 1.93-2.06 (m, 2H).

Example 34

N-[3-(7-{1-[1-(Benzylsulfonyl)piperidin-4-yl]-1H-pyrazol-4-yl}imidazo[1,2-b]pyridazin-3-yl)phenyl]-N'-(2,2,2-trifluoroethyl)urea

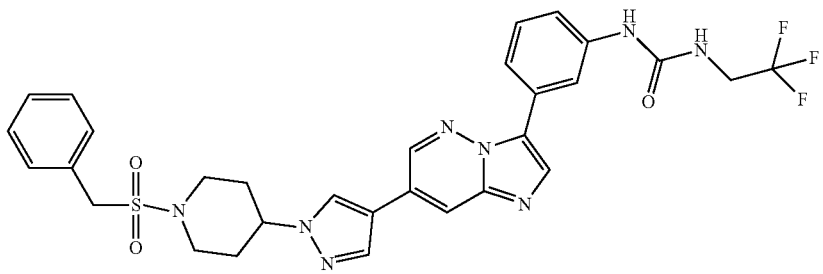 [SMILES: O=C(NCC(F)(F)F)Nc1cccc(-c2cnc3cc(-c4cnn(C5CCN(S(=O)(=O)Cc6ccccc6)CC5)c4)cnn23)c1]

This compound was prepared by using procedures analogous to those described for the synthesis of Example 30 (Step 6) starting from N-{3-[7-(1-piperidin-4-yl-1H-pyrazol-4-yl)imidazo[1,2-b]pyridazin-3-yl]phenyl}-N'-(2,2,2-trifluoroethyl)urea and phenylmethanesulfonyl chloride. LCMS (M+H)$^+$: m/z=639.2.

Example 35

N-[3-(7-{1-[1-(cyclopentylacetyl)piperidin-4-yl]-1H-pyrazol-4-yl}imidazo[1,2-b]pyridazin-3-yl)phenyl]-N'-(2,2,2-trifluoroethyl)urea

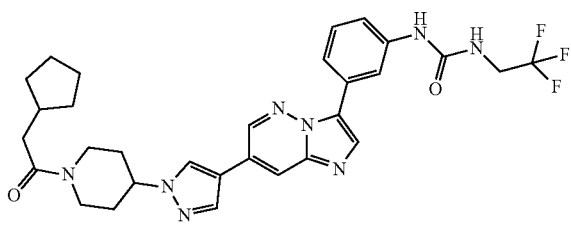 [SMILES: O=C(NCC(F)(F)F)Nc1cccc(-c2cnc3cc(-c4cnn(C5CCN(C(=O)CC6CCCC6)CC5)c4)cnn23)c1]

This compound was prepared by using procedures analogous to those described for the synthesis of Example 30 (Step 6) starting from N-{3-[7-(1-piperidin-4-yl-1H-pyrazol-4-yl)imidazo[1,2-b]pyridazin-3-yl]phenyl}-N'-(2,2,2-trifluoroethyl)urea and cyclopentylacetyl chloride (Lancaster, Cat. No. L14562). LCMS (M+H)$^+$: m/z=595.2.

Example 36

N-[3-(7-{1-[1-(Pyrrolidin-1-ylcarbonyl)piperidin-4-yl]-1H-pyrazol-4-yl}imidazo[1,2-b]pyridazin-3-yl)phenyl]-N'-(2,2,2-trifluoroethyl)urea

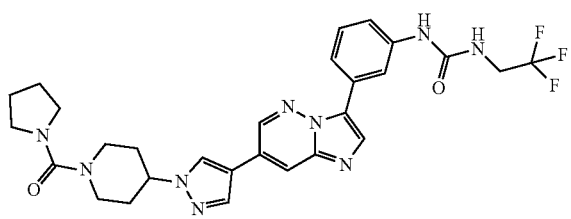 [SMILES: O=C(NCC(F)(F)F)Nc1cccc(-c2cnc3cc(-c4cnn(C5CCN(C(=O)N6CCCC6)CC5)c4)cnn23)c1]

This compound was prepared by using procedures analogous to those described for the synthesis of Example 30 (Step 6) starting from N-{3-[7-(1-piperidin-4-yl-1H-pyrazol-4-yl)imidazo[1,2-b]pyridazin-3-yl]phenyl}-N'-(2,2,2-trifluoroethyl)urea and 1-pyrrolidinecarbonyl chloride (Aldrich, Cat. No. 206350). LCMS (M+H)$^+$: m/z=582.3.

Example 37

N-[3-(7-{1-[1-(morpholin-4-ylcarbonyl)piperidin-4-yl]-1H-pyrazol-4-yl}imidazo[1,2-b]pyridazin-3-yl)phenyl]-N'-(2,2,2-trifluoroethyl)urea

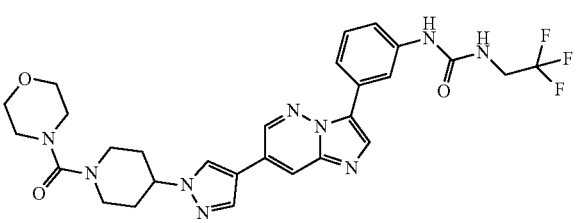 [SMILES: O=C(NCC(F)(F)F)Nc1cccc(-c2cnc3cc(-c4cnn(C5CCN(C(=O)N6CCOCC6)CC5)c4)cnn23)c1]

This compound was prepared by using procedures analogous to those described for the synthesis of Example 30 (Step 6) starting from N-{3-[7-(1-piperidin-4-yl-1H-pyrazol-4-yl)imidazo[1,2-b]pyridazin-3-yl]phenyl}-N'-(2,2,2-trifluoroethyl)urea and morpholine-4-carbonyl chloride (Aldrich, Cat. No. 348295). LCMS (M+H)$^+$: m/z=598.2.

$^1$H NMR (400 MHz, CDCl$_3$): 8.40 (d, J=2.5 Hz, 1H), 8.03 (s, 1H), 7.94 (s, 1H), 7.85 (d, J=2.5 Hz, 1H), 7.77 (s, 1H), 7.65 (s, 1H), 7.62 (dt, J=7.2, 1.5, 2H), 7.28-7.38 (m, 2H), 5.59 (t, J=6.5 Hz, 1H), 4.24-4.43 (m, 1H), 3.85-3.96 (m, 2H), 3.81 (dm, 2H), 3.62-3.66 (m, 4H), 3.23-3.28 (m, 4H), 2.93 (td, J=12.7, 2.6 Hz, 2H), 2.10-2.17 (m, 2H), 1.91-2.02 (m, 2H).

Example 38

N-Pyridin-3-yl-4-(4-{3-[3-({[(2,2,2-trifluoroethyl)amino]carbonyl}amino)phenyl]imidazo[1,2-b]pyridazin-7-yl}-1H-pyrazol-1-yl)piperidine-1-carboxamide

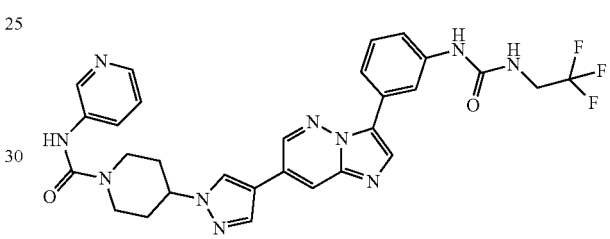

This compound was prepared by using procedures analogous to those described for the synthesis of Example 30 (Step 6) starting from N-{3-[7-(1-piperidin-4-yl-1H-pyrazol-4-yl)imidazo[1,2-b]pyridazin-3-yl]phenyl}-N'-(2,2,2-trifluoroethyl)urea and 3-isocyanatopyridine (Oakwood, Cat. No. 022077). LCMS (M+H)$^+$: m/z=605.3.

Example 39

N-Benzyl-4-(4-{3-[3-({[(2,2,2-trifluoroethyl)amino]carbonyl}amino)phenyl]imidazo[1,2-b]pyridazin-7-yl}-1H-pyrazol-1-yl)piperidine-1-carboxamide

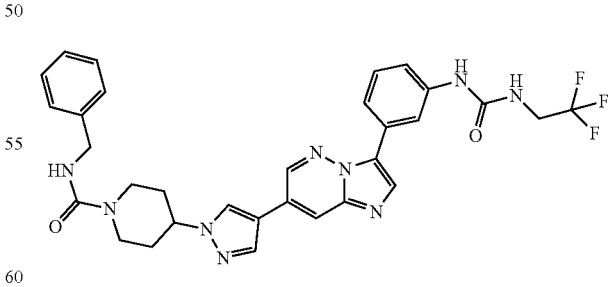

This compound was prepared by using procedures analogous to those described for the synthesis of Example 30 (Step 6) starting from N-{3-[7-(1-piperidin-4-yl-1H-pyrazol-4-yl)imidazo[1,2-b]pyridazin-3-yl]phenyl}-N'-(2,2,2-trifluoroethyl)urea and benzyl isocyanate (Aldrich, Cat. No. 227269). LCMS (M+H)$^+$: m/z=618.2.

Example 40

N-(tetrahydrofuran-2-ylmethyl)-4-(4-{3-[3-({[(2,2,2-trifluoroethyl)amino]carbonyl}amino)phenyl]imidazo[1,2-b]pyridazin-7-yl}-1H-pyrazol-1-yl)piperidine-1-carboxamide

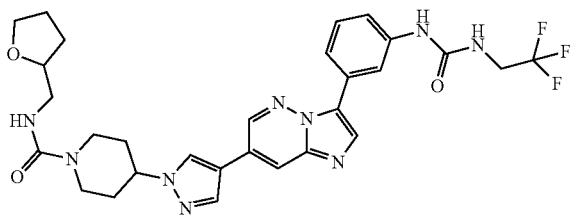 [SMILES: O=C(NCC(F)(F)F)Nc1cccc(-c2cnc3cc(-c4cnn(C5CCN(C(=O)NCC6CCCO6)CC5)c4)cnn23)c1]

This compound was prepared by using procedures analogous to those described for the synthesis of Example 30 (Step 6) starting from N-{3-[7-(1-piperidin-4-yl-1H-pyrazol-4-yl)imidazo[1,2-b]pyridazin-3-yl]phenyl}-N'-(2,2,2-trifluoroethyl)urea and 2-(isocyanatomethyl)tetrahydrofuran (Matrix Scientific, Cat. No. 030196). LCMS (M+H)+: m/z=612.3.

Example 41

N-[3-(7-{1-[1-(Cyclopropylacetyl)piperidin-4-yl]-1H-pyrazol-4-yl}imidazo[1,2-b]pyridazin-3-yl)phenyl]-N'-(2,2,2-trifluoroethyl)urea

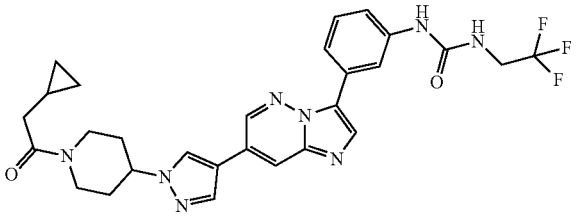 [SMILES: O=C(NCC(F)(F)F)Nc1cccc(-c2cnc3cc(-c4cnn(C5CCN(C(=O)CC6CC6)CC5)c4)cnn23)c1]

A mixture of N-{3-[7-(1-piperidin-4-yl-1H-pyrazol-4-yl)imidazo[1,2-b]pyridazin-3-yl]phenyl}-N'-(2,2,2-trifluoroethyl)urea (15.0 mg, 0.0310 mmol) (prepared by the procedure for Example 30, step 5), benzotriazol-1-yloxytris(dimethylamino)phosphonium hexafluorophosphate (15.1 mg, 0.0340 mmol), cyclopropylacetic acid (4.65 mg, 0.0464 mmol, Lancaster, Cat. No. L09616) and N,N-diisopropylethylamine (30.0 μL, 0.172 mmol) in DMSO (0.5 mL) was stirred at for 3 h. The mixture was purified by RP-HPLC (pH=10) to afford the desired product. LCMS (M+H)+: m/z=567.3.

Example 42

N-{3-[7-(1-{1-[(1-Methylcyclopropyl)carbonyl]piperidin-4-yl}-1H-pyrazol-4-yl)imidazo[1,2-b]pyridazin-3-yl]phenyl}-N'-(2,2,2-trifluoroethyl)urea

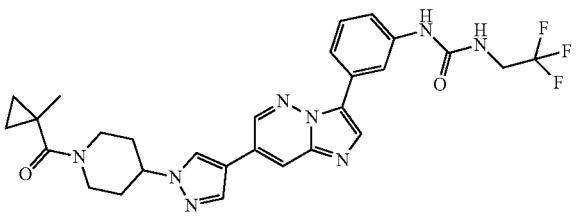 [SMILES: CC1(C(=O)N2CCC(n3cc(-c4cnn5c(-c6cccc(NC(=O)NCC(F)(F)F)c6)cnc5c4)cn3)CC2)CC1]

This compound was prepared by using procedures analogous to those described for the synthesis of Example 41 starting from N-{3-[7-(1-piperidin-4-yl-1H-pyrazol-4-yl)imidazo[1,2-b]pyridazin-3-yl]phenyl}-N'-(2,2,2-trifluoroethyl)urea and 1-methylcyclopropanecarboxylic acid (Aldrich, Cat. No. 205605). LCMS (M+H)+: m/z=567.3.

Example 43

N-{3-[7-(1-{1-[(1-hydroxycyclopropyl)carbonyl]piperidin-4-yl}-1H-pyrazol-4-yl)imidazo[1,2-b]pyridazin-3-yl]phenyl}-N'-(2,2,2-trifluoroethyl)urea

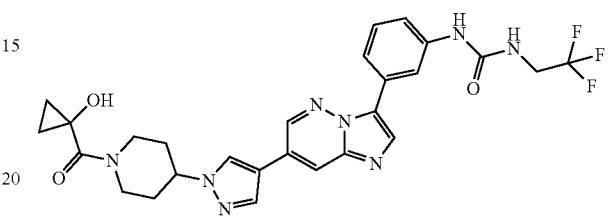

This compound was prepared by using procedures analogous to those described for the synthesis of Example 41 starting from N-{3-[7-(1-piperidin-4-yl-1H-pyrazol-4-yl)imidazo[1,2-b]pyridazin-3-yl]phenyl}-N'-(2,2,2-trifluoroethyl)urea and 1-hydroxycyclopropanecarboxylic acid (Aldrich, Cat. No. 293881). LCMS (M+H)+: m/z=569.3.

Example 44

N-[3-(7-{1-[1-(Cyanoacetyl)piperidin-4-yl]-1H-pyrazol-4-yl}imidazo[1,2-b]pyridazin-3-yl)phenyl]-N'-(2,2,2-trifluoroethyl)urea

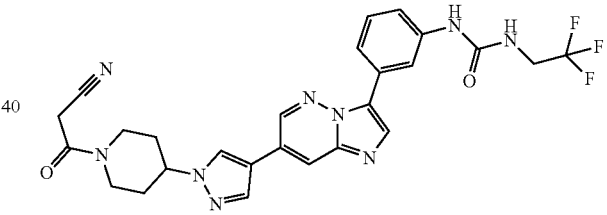

This compound was prepared by using procedures analogous to those described for the synthesis of Example 41 starting from N-{3-[7-(1-piperidin-4-yl-1H-pyrazol-4-yl)imidazo[1,2-b]pyridazin-3-yl]phenyl}-N'-(2,2,2-trifluoroethyl)urea and Cyanoacetic acid (Aldrich, Cat. No. C88505). LCMS (M+H)+: m/z=552.2.

Example 45

N-{3-[7-(1-{1-[(1-Cyanocyclopropyl)carbonyl]piperidin-4-yl}-1H-pyrazol-4-yl)imidazo[1,2-b]pyridazin-3-yl]phenyl}-N'-(2,2,2-trifluoroethyl)urea

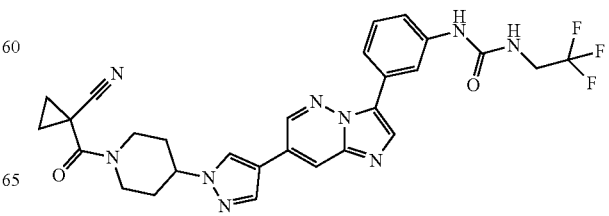

This compound was prepared by using procedures analogous to those described for the synthesis of Example 41 starting from N-{3-[7-(1-piperidin-4-yl-1H-pyrazol-4-yl)imidazo[1,2-b]pyridazin-3-yl]phenyl}-N'-(2,2,2-trifluoroethyl)urea and 1-cyanocyclopropanecarboxylic acid (Aldrich, Cat. No. 343390). LCMS (M+H)+: m/z=578.2.

Example 46

N-[3-(7-{1-[1-(3-Cyclopropylpropanoyl)piperidin-4-yl]-1H-pyrazol-4-yl}imidazo[1,2-b]pyridazin-3-yl)phenyl]-N'-(2,2,2-trifluoroethyl)urea

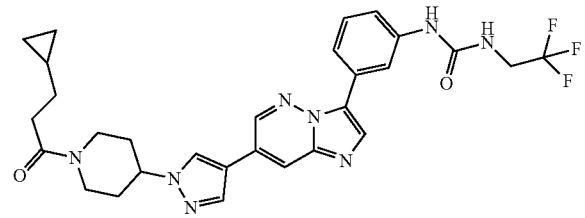 [SMILES: O=C(NCC(F)(F)F)Nc1cccc(-c2cnc3cc(-c4cnn(C5CCN(C(=O)CCC6CC6)CC5)c4)cnn23)c1]

This compound was prepared by using procedures analogous to those described for the synthesis of Example 41 starting from N-{3-[7-(1-piperidin-4-yl-1H-pyrazol-4-yl)imidazo[1,2-b]pyridazin-3-yl]phenyl}-N'-(2,2,2-trifluoroethyl)urea and 3-cyclopropylpropanoic acid (Oakwood, Cat. No. 011665). LCMS (M+H)+: m/z=581.3.

Example 47

N-{3-[7-(1-{1-[(3-hydroxycyclobutyl)carbonyl]piperidin-4-yl}-1H-pyrazol-4-yl)imidazo[1,2-b]pyridazin-3-yl]phenyl}-N'-(2,2,2-trifluoroethyl)urea

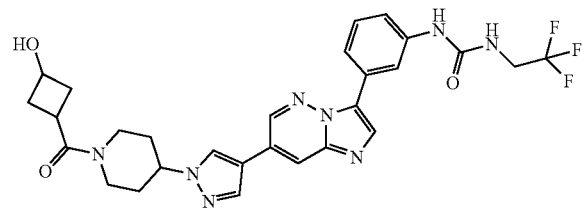 [SMILES: O=C(NCC(F)(F)F)Nc1cccc(-c2cnc3cc(-c4cnn(C5CCN(C(=O)C6CC(O)C6)CC5)c4)cnn23)c1]

This compound was prepared by using procedures analogous to those described for the synthesis of Example 41 starting from N-{3-[7-(1-piperidin-4-yl-1H-pyrazol-4-yl)imidazo[1,2-b]pyridazin-3-yl]phenyl}-N'-(2,2,2-trifluoroethyl)urea and 3-hydroxycyclobutanecarboxylic acid (Parkway, Cat. No. BX-111). LCMS (M+H)+: m/z=583.3.

Example 48

N-[3-(7-{1-[1-(tetrahydrofuran-3-ylcarbonyl)piperidin-4-yl]-1H-pyrazol-4-yl}imidazo[1,2-b]pyridazin-3-yl)phenyl]-N'-(2,2,2-trifluoroethyl)urea

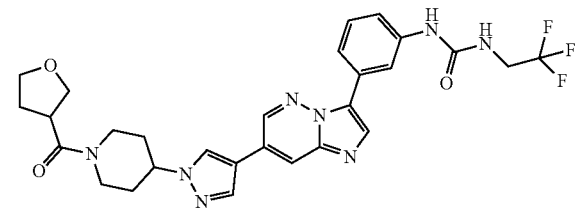 [SMILES: O=C(NCC(F)(F)F)Nc1cccc(-c2cnc3cc(-c4cnn(C5CCN(C(=O)C6CCOC6)CC5)c4)cnn23)c1]

This compound was prepared by using procedures analogous to those described for the synthesis of Example 41 starting from N-{3-[7-(1-piperidin-4-yl-1H-pyrazol-4-yl)imidazo[1,2-b]pyridazin-3-yl]phenyl}-N'-(2,2,2-trifluoroethyl)urea and tetrahydrofuran-3-carboxylic acid (Aldrich, Cat. No. 339954). LCMS (M+H)+: m/z=583.2.

Example 49

N-(2,2,2-trifluoroethyl)-N'-[3-(7-{1-[1-(3,3,3-trifluoro-2-hydroxypropanoyl)piperidin-4-yl]-1H-pyrazol-4-yl}imidazo[1,2-b]pyridazin-3-yl)phenyl]urea

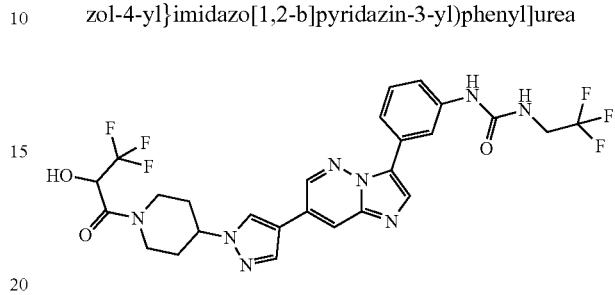

This compound was prepared by using procedures analogous to those described for the synthesis of Example 41 starting from N-{3-[7-(1-piperidin-4-yl-1H-pyrazol-4-yl)imidazo[1,2-b]pyridazin-3-yl]phenyl}-N'-(2,2,2-trifluoroethyl)urea and 3,3,3-trifluoro-2-hydroxypropanoic acid (Lancaster, Cat. No. L07742). LCMS (M+H)+: m/z=611.2.

Example 50

N-[3-(7-{1-[1-(tetrahydrofuran-2-ylacetyl)piperidin-4-yl]-1H-pyrazol-4-yl}imidazo[1,2-b]pyridazin-3-yl)phenyl]-N'-(2,2,2-trifluoroethyl)urea

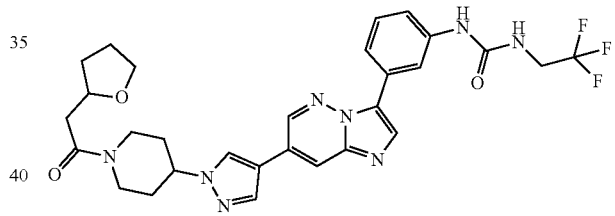

This compound was prepared by using procedures analogous to those described for the synthesis of Example 41 starting from N-{3-[7-(1-piperidin-4-yl-1H-pyrazol-4-yl)imidazo[1,2-b]pyridazin-3-yl]phenyl}-N'-(2,2,2-trifluoroethyl)urea and tetrahydrofuran-2-ylacetic acid (Matrix Scientific, Cat. No. 020454). LCMS (M+H)+: m/z=597.2.

Example 51

N-[3-(7-{6-[4-(methoxyacetyl)piperazin-1-yl]pyridin-3-yl}imidazo[1,2-b]pyridazin-3-yl)phenyl]-N'-(2,2,2-trifluoroethyl)urea

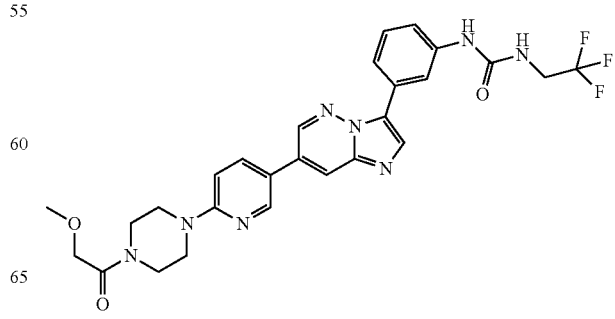

Step 1: tert-butyl 4-(5-{3-[3-({[(2,2,2-trifluoroethyl)amino]carbonyl}amino)phenyl]imidazo[1,2-b]pyridazin-7-yl}pyridin-2-yl)piperazine-1-carboxylate

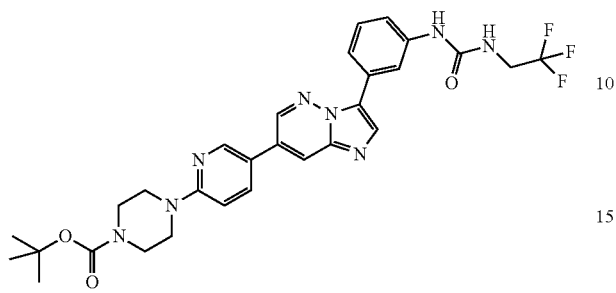

A mixture of tert-butyl 4-[5-(4,4,5,5-tetramethyl-1,3,2-dioxaborolan-2-yl)pyridin-2-yl]piperazine-1-carboxylate (46.3 mg, 0.119 mmol, Aldrich, Cat. No. 654337), N-[3-(7-chloroimidazo[1,2-b]pyridazin-3-yl)phenyl]-N'-(2,2,2-trifluoroethyl)urea (40.0 mg, 0.108 mmol, Example 30, Step 3), tetrakis(triphenylphosphine)palladium(0) (6.25 mg, 0.00541 mmol) and sodium carbonate (34.4 mg, 0.324 mmol) in dioxane (1 mL) and water (0.3 mL) was degassed and recharged with nitrogen three times, and heated and stirred at 110° C. for 3 h. After cooling, the mixture was diluted with ethyl acetate, washed with water and brine. The organic layer was dried over MgSO₄, filtered and concentrated under reduced pressure. The residue was the desired product which was directly used in next step without further purification. LCMS (M+H)⁺: m/z=597.2.

Step 2: N-{3-[7-(6-piperazin-1-ylpyridin-3-yl) imidazo[1,2-b]pyridazin-3-yl]phenyl}-N'-(2,2,2-trifluoroethyl) urea

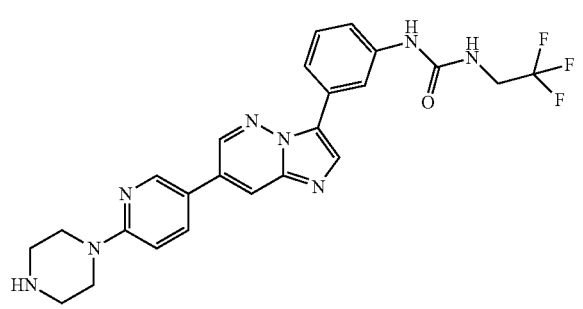 [SMILES: O=C(NCC(F)(F)F)Nc1cccc(-c2cnc3cc(-c4ccc(N5CCNCC5)nc4)cnn23)c1]

tert-Butyl 4-(5-{3-[3-({[(2,2,2-trifluoroethyl)amino]carbonyl}amino)phenyl]-imidazo[1,2-b]pyridazin-7-yl}pyridin-2-yl)piperazine-1-carboxylate (64 mg, 0.11 mmol) in methanol (0.5 mL) was treated with 4 N HCl in dioxane (0.4 mL) at r.t. for 1 h. The volatiles were removed under reduced pressure. The residue was dried in vacuum to afford the desired crude product which was used directly in next step without further purification. LCMS (M+H)⁺: m/z=497.1.

Step 3: N-[3-(7-{6-[4-(methoxyacetyl)piperazin-1-yl]pyridin-3-yl}imidazo[1,2-b]pyridazin-3-yl)phenyl]-N'-(2,2,2-trifluoroethyl)urea A mixture of N-{3-[7-(6-piperazin-1-ylpyridin-3-yl)imidazo[1,2-b]pyridazin-3-yl]phenyl}-N'-(2,2,2-trifluoroethyl) urea (20.5 mg, 0.0413 mmol) HCl salt, methoxyacetyl chloride (5.66 μL, 0.0619 mmol) and N,N-diisopropylethylamine (40.0 μL, 0.230 mmol) in DMSO (0.5 mL) was stirred at RT for 1 h. The mixture was diluted with DMSO, and purified by RP-HPLC (pH=10) to afford the desired product. LCMS (M+H)⁺: m/z=569.2.

Example 52

N-[3-(7-{6-[4-(Cyclopentylacetyl)piperazin-1-yl]pyridin-3-yl}imidazo[1,2-b]pyridazin-3-yl)phenyl]-N'-(2,2,2-trifluoroethyl)urea

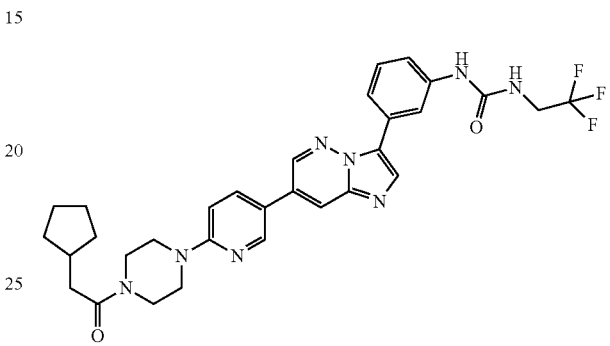

A mixture of N-{3-[7-(6-piperazin-1-ylpyridin-3-yl)imidazo[1,2-b]pyridazin-3-yl]phenyl}-N'-(2,2,2-trifluoroethyl) urea (20.5 mg, 0.0413 mmol) HCl salt, cyclopentylacetyl chloride (9.08 mg, 0.0619 mmol) and N,N-diisopropylethylamine (40.0 μL, 0.230 mmol) in DMSO (0.5 mL) was stirred at r.t. for 1 h. The mixture was diluted with DMSO, and purified by RP-HPLC (pH=10) to afford the desired product. LCMS (M+H)⁺: m/z=607.2.

Example 53

N-[3-(7-{6-[4-(pyrrolidin-1-ylcarbonyl)piperazin-1-yl]pyridin-3-yl}imidazo[1,2-b]pyridazin-3-yl)phenyl]-N'-(2,2,2-trifluoroethyl)urea

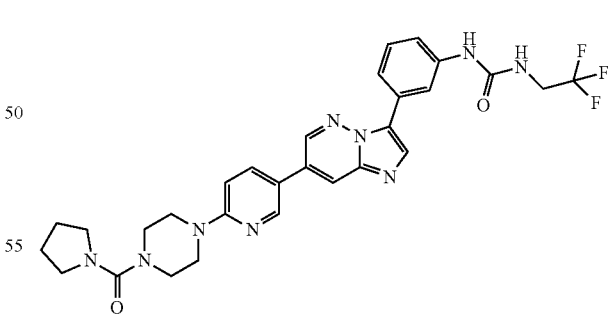

A mixture of N-{3-[7-(6-piperazin-1-ylpyridin-3-yl)imidazo[1,2-b]pyridazin-3-yl]phenyl}-N'-(2,2,2-trifluoroethyl) urea (20.5 mg, 0.0413 mmol) HCl salt, 1-pyrrolidinecarbonyl chloride (6.84 μL, 0.0619 mmol) and N,N-diisopropylethylamine (40.0 μL, 0.230 mmol) in DMSO (0.5 mL) was stirred at r.t. for 1 h. The mixture was diluted with DMSO, and purified by RP-HPLC (pH=10) to afford the desired product. LCMS (M+H)⁺: m/z=594.2.

Example 54

N-Cyclopropyl-2-(4-{3-[3-({[(2,2,2-trifluoroethyl)amino]carbonyl}amino)phenyl]imidazo[1,2-b]pyridazin-7-yl}-1H-pyrazol-1-yl)propanamide

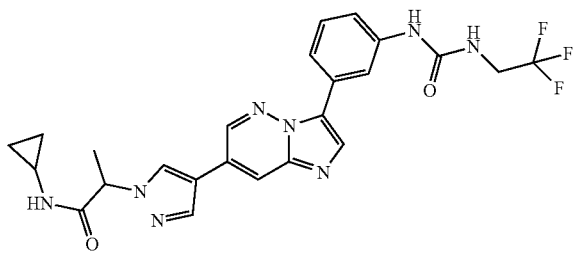 [SMILES: CC(N/C=C(\C=N)c1cnn2c(-c3cccc(NC(=O)NCC(F)(F)F)c3)cnc2c1)C(=O)NC1CC1]

Step 1: ethyl 2-[4-(4,4,5,5-tetramethyl-1,3,2-dioxaborolan-2-yl)-1H-pyrazol-1-yl]propanoate

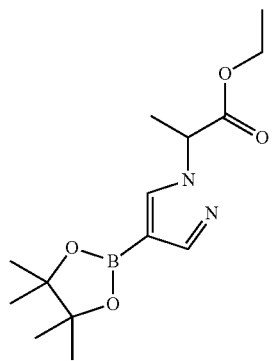 [SMILES: CCOC(=O)C(C)N/C=C(\C=N)B1OC(C)(C)C(C)(C)O1]

A mixture of 4-(4,4,5,5-tetramethyl-1,3,2-dioxaborolan-2-yl)-1H-pyrazole (0.40 g, 2.1 mmol, Aldrich, Cat. 525057), ethyl 2-bromopropanoate (290 µL, 2.3 mmol), and cesium carbonate (1.5 g, 4.6 mmol) in acetonitrile (8 mL) was stirred at 90° C. for 4 h. After cooling, the reaction mixture was worked up with aqueous Na₂CO₃, extracted with ethyl acetate (3×20 mL), and washed with brine. The combined organic layers were dried over MgSO₄, filtered and concentrated under reduced pressure. The residue was purified by flash chromatography on a silica gel column with ethyl acetate in hexanes (0-50%) to afford the desired product (0.42 g, 61%). LCMS (M+H)⁺: m/z=295.1.

Step 2: 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid

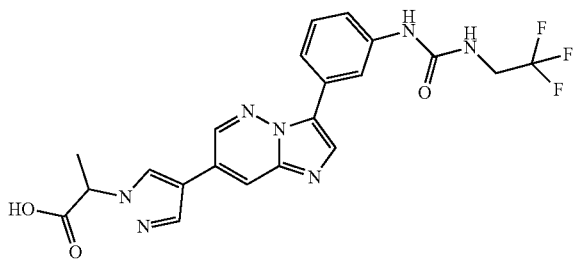 [SMILES: CC(N/C=C(\C=N)c1cnn2c(-c3cccc(NC(=O)NCC(F)(F)F)c3)cnc2c1)C(=O)O]

A mixture of N-[3-(7-chloroimidazo[1,2-b]pyridazin-3-yl)phenyl]-N'-(2,2,2-trifluoroethyl)urea (0.206 g, 0.556 mmol, Example 30, Step 3), ethyl 2-[4-(4,4,5,5-tetramethyl-1,3,2-dioxaborolan-2-yl)-1H-pyrazol-1-yl]propanoate (0.18 g, 0.61 mmol), tetrakis(triphenylphosphine)palladium(O) (32.1 mg, 0.00278 mmol) and K₃PO₄ (0.30 g, 1.4 mmol) in 1,4-dioxane (3.0 mL) and water (2.0 mL) was heated at 100° C. under an atmosphere of nitrogen for 3 h. After cooling, the reaction mixture was adjusted to pH=4, extracted with ethyl acetate (3×30 mL), and washed with brine. The combined organic layers were dried over MgSO₄, filtered and concentrated under reduced pressure to afford the crude product without further purification. LCMS (M+H)⁺: m/z=474.1.

Step 3: N-cyclopropyl-2-(4-{3-[3-({[(2,2,2-trifluoroethyl)amino]carbonyl}amino)phenyl]imidazo[1,2-b]pyridazin-7-yl}-1H-pyrazol-1-yl)propanamide

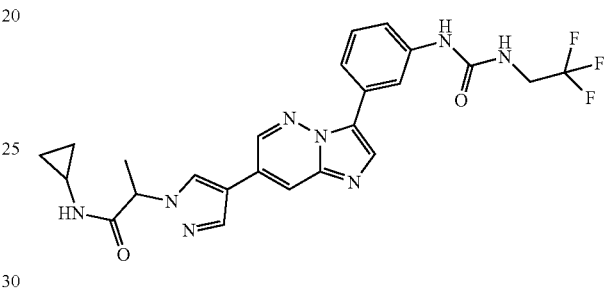

Cyclopropylamine (17 µL, 0.24 mmol) was added to a mixture of 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid (0.16 mmol) and benzotriazol-1-yloxytris(dimethylamino)phosphonium hexafluorophosphate (110 mg, 0.24 mmol) in DMF (2.0 mL), followed by triethylamine (45 µL, 0.32 mmol). The reaction mixture was stirred at r.t. for 30 min. The mixture was purified by RP-HPLC (pH=10) to afford the desired product. LCMS (M+H)⁺: m/z=513.2.

Example 55

N-Methyl-2-(4-{3-[3-({[(2,2,2-trifluoroethyl)amino]carbonyl}amino)phenyl]imidazo[1,2-b]pyridazin-7-yl}-1H-pyrazol-1-yl)propanamide

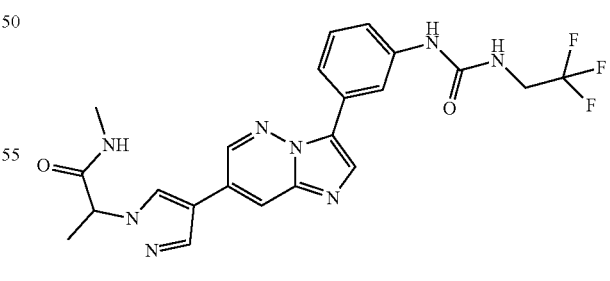

This compound was prepared by using procedures analogous to those described for the synthesis of Example 54, Step 3 starting from 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid (prepared from the procedure for Example 54, step 2) and methylamine (2.0N in THF). LCMS (M+H)⁺: m/z=487.2.

Example 56

N,N-Dimethyl-2-(4-{3-[3-({[(2,2,2-trifluoroethyl)amino]carbonyl}amino)phenyl]imidazo[1,2-b]pyridazin-7-yl}-1H-pyrazol-1-yl)propanamide

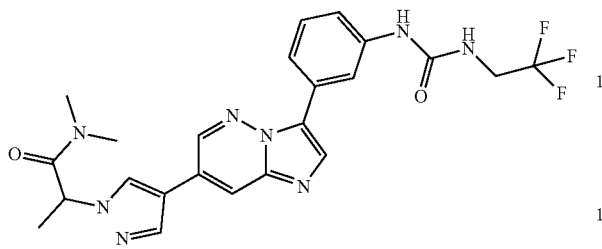

This compound was prepared by using procedures analogous to those described for the synthesis of Example 54, Step 3 starting from 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid and dimethylamine (2.0N in THF). LCMS (M+H)$^+$: m/z=501.2.

Example 57

N-(Tetrahydro-2H-pyran-4-yl)-2-(4-{3-[3-({[(2,2,2-trifluoroethyl)amino]carbonyl}amino)phenyl]imidazo[1,2-b]pyridazin-7-yl}-1H-pyrazol-1-yl)propanamide

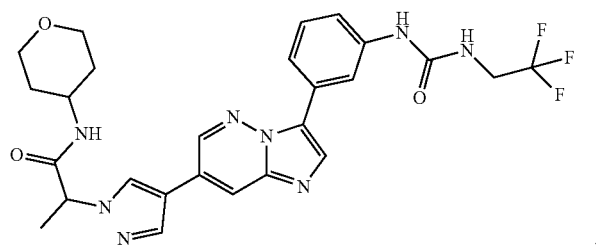

This compound was prepared by using procedures analogous to those described for the synthesis of Example 54, Step 3 starting from 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid and 4-aminotetrahydropyran hydrochloride (Combi-Blocks and Cat. No. AM-1014). LCMS (M+H)$^+$: m/z=557.3.

Example 58

N-(3-{7-[1-(1-Methyl-2-morpholin-4-yl-2-oxoethyl)-1H-pyrazol-4-yl]imidazo[1,2-b]pyridazin-3-yl}phenyl)-N'-(2,2,2-trifluoroethyl)urea

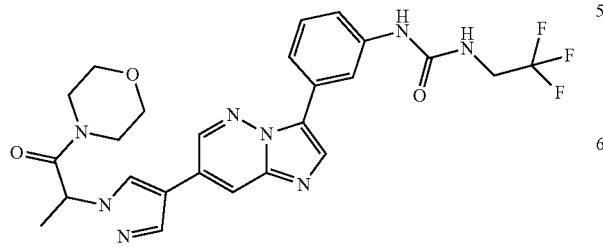

This compound was prepared by using procedures analogous to those described for the synthesis of Example 54, Step 3 starting from 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid and morpholine. LCMS (M+H)$^+$: m/z=543.2.

Example 59

N-Methyl-N-(tetrahydro-2H-pyran-4-yl)-2-(4-{3-[3-({[(2,2,2-trifluoroethyl)amino]carbonyl}amino)phenyl]imidazo[1,2-b]pyridazin-7-yl}-1H-pyrazol-1-yl)propanamide

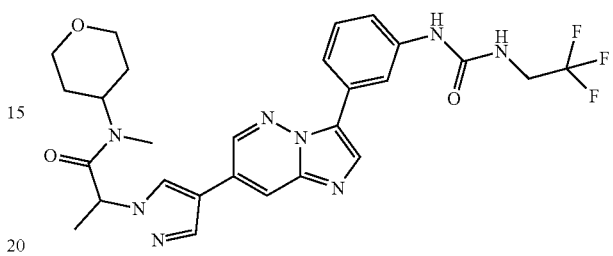

This compound was prepared by using procedures analogous to those described for the synthesis of Example 54, Step 3 starting from 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid and N-methyltetrahydro-2H-pyran-4-amine (Peakdale and Cat. No. 2006971). LCMS (M+H)$^+$: m/z=571.3.

Example 60

N-[3-(7-{1-[1-Methyl-2-(4-methylpiperazin-1-yl)-2-oxoethyl]-1H-pyrazol-4-yl}imidazo[1,2-b]pyridazin-3-yl)phenyl]-N'-(2,2,2-trifluoroethyl)urea

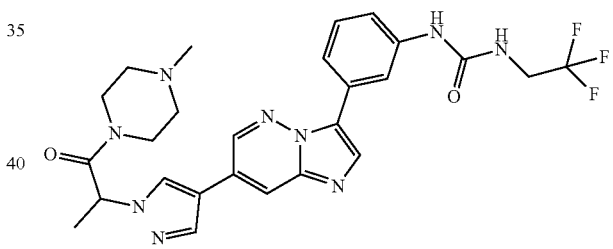

This compound was prepared by using procedures analogous to those described for the synthesis of Example 54, Step 3 starting from 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid and 1-methylpiperazine. LCMS (M+H)$^+$: m/z=556.3.

Example 61

N-(Pyridin-2-ylmethyl)-2-(4-{3-[3-({[(2,2,2-trifluoroethyl)amino]carbonyl}amino)phenyl]imidazo[1,2-b]pyridazin-7-yl}-1H-pyrazol-1-yl)propanamide

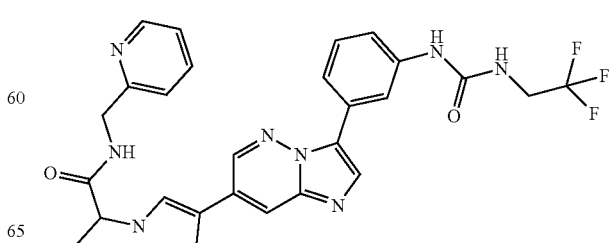

This compound was prepared by using procedures analogous to those described for the synthesis of Example 54, Step 3 starting from 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid and 2-pyridinemethanamine (Aldrich and Cat. No. A65204). LCMS (M+H)+: m/z=564.2.

Example 62

N-[2-(2-Oxopyrrolidin-1-yl)ethyl]-2-(4-{3-[3-({[(2,2,2-trifluoroethyl)amino]carbonyl}amino)phenyl]imidazo[1,2-b]pyridazin-7-yl}-1H-pyrazol-1-yl)propanamide

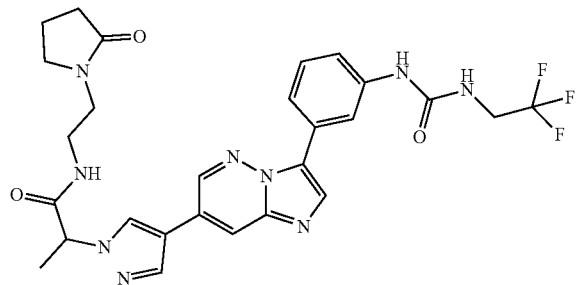 [SMILES: CC(N/C=C(\C=N)c1cnn2c(-c3cccc(NC(=O)NCC(F)(F)F)c3)cnc2c1)C(=O)NCCN1CCCC1=O]

This compound was prepared by using procedures analogous to those described for the synthesis of Example 54, Step 3 starting from 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid and 1-(2-aminoethyl)pyrrolidin-2-one (Matrix and Cat. No. 016683). LCMS (M+H)+: m/z=584.2.

Example 63

N-(2-Hydroxypropyl)-2-(4-{3-[3-({[(2,2,2-trifluoroethyl)amino]carbonyl}amino)phenyl]imidazo[1,2-b]pyridazin-7-yl}-1H-pyrazol-1-yl)propanamide

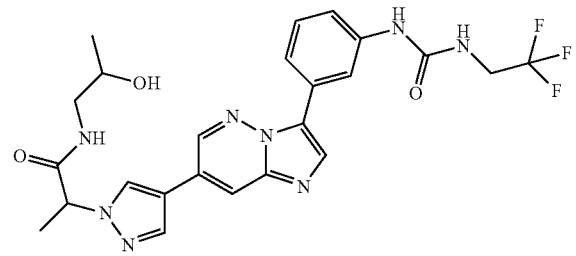 [SMILES: CC(O)CNC(=O)C(C)n1cc(-c2cnn3c(-c4cccc(NC(=O)NCC(F)(F)F)c4)cnc3c2)cn1]

This compound was prepared by using procedures analogous to those described for the synthesis of Example 54, Step 3 starting from 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid and 1-amino-2-propanol. LCMS (M+H)+: m/z=531.2.

Example 64

N-[3-(7-{1-[2-(3-Hydroxyazetidin-1-yl)-1-methyl-2-oxoethyl]-1H-pyrazol-4-yl}imidazo[1,2-b]pyridazin-3-yl)phenyl]-N'-(2,2,2-trifluoroethyl)urea

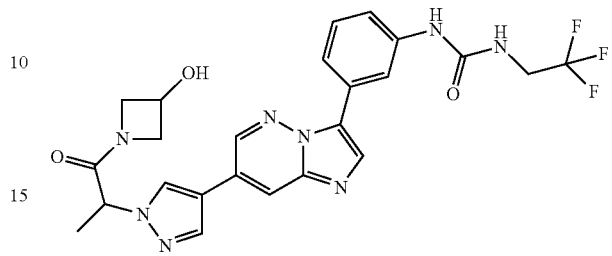

This compound was prepared by using procedures analogous to those described for the synthesis of Example 54, Step 3 starting from 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid and azetidin-3-ol hydrochloride (Oakwood and Cat. No. 013898). LCMS (M+H)+: m/z=529.2.

Example 65

N-[3-(7-{1-[2-(3,3-Difluoropyrrolidin-1-yl)-1-methyl-2-oxoethyl]-1H-pyrazol-4-yl}imidazo[1,2-b]pyridazin-3-yl)phenyl]-N'-(2,2,2-trifluoroethyl)urea

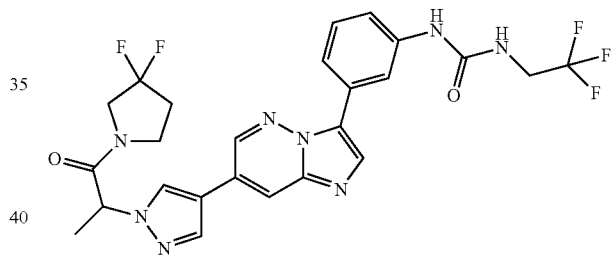

This compound was prepared by using procedures analogous to those described for the synthesis of Example 54, Step 3 starting from 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid and 3,3-difluoropyrrolidine hydrochloride (Matrix and Cat. No. 008716). LCMS (M+H)+: m/z=563.3.

Example 66

N-(Cyanomethyl)-2-(4-{3-[3-({[(2,2,2-trifluoroethyl)amino]carbonyl}amino)phenyl]imidazo[1,2-b]pyridazin-7-yl}-1H-pyrazol-1-yl)propanamide

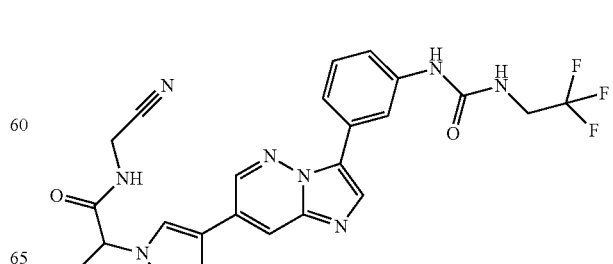

This compound was prepared by using procedures analogous to those described for the synthesis of Example 54, Step 3 starting from 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid and aminoacetonitrile (Aldrich and Cat. No. A5802). LCMS (M+H)+: m/z=512.2.

Example 67

N-[3-(7-{1-[2-(3-Cyanopyrrolidin-1-yl)-1-methyl-2-oxoethyl]-1H-pyrazol-4-yl}imidazo[1,2-b]pyridazin-3-yl)phenyl]-N'-(2,2,2-trifluoroethyl)urea

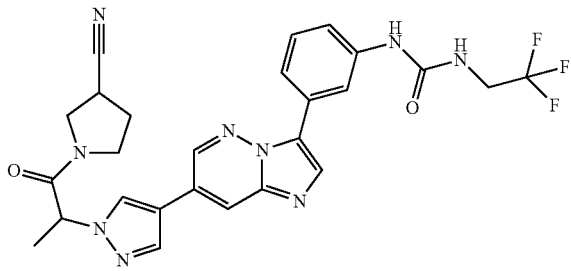 [SMILES: CC(C(=O)N1CCC(C#N)C1)n1cc(-c2cnn3c(-c4cccc(NC(=O)NCC(F)(F)F)c4)cnc3c2)cn1]

This compound was prepared by using procedures analogous to those described for the synthesis of Example 54, Step 3 starting from 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid and pyrrolidine-3-carbonitrile hydrochloride (Tyger and Cat. No. P76159).

LCMS (M+H)+: m/z=552.2.

$^1$H NMR (400 MHz, CD$_3$OD): 8.91 (s, 1H), 8.71 (s, 1H), 8.49 (s, 1H), 8.23-8.10 (m, 3H), 8.05 (s, 1H), 7.79 (m, 1H), 7.41 (m, 2H), 5.48 (m, 1H), 4.0-3.4 (m, 7H), 2.5-2.1 (m, 3H), 1.77 (t, J=6.8 Hz, 3H).

Example 68

N-[3-(7-{1-[2-(3-Methoxypyrrolidin-1-yl)-1-methyl-2-oxoethyl]-1H-pyrazol-4-yl}imidazo[1,2-b]pyridazin-3-yl)phenyl]-N'-(2,2,2-trifluoroethyl)urea

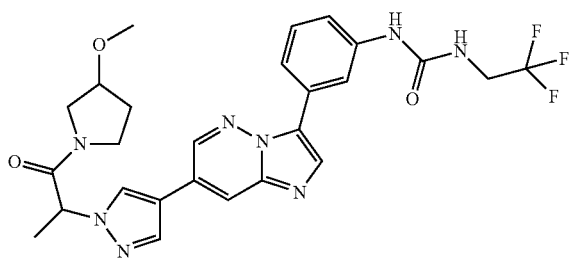 [SMILES: COC1CCN(C(=O)C(C)n2cc(-c3cnn4c(-c5cccc(NC(=O)NCC(F)(F)F)c5)cnc4c3)cn2)C1]

This compound was prepared by using procedures analogous to those described for the synthesis of Example 54, Step 3 starting from 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid and 3-methoxypyrrolidine hydrochloride (Matrix and Cat. No. 023344).

LCMS (M+H)+: m/z=557.2.

Example 69

N-[3-(7-{1-[2-(4-Methoxypiperidin-1-yl)-1-methyl-2-oxoethyl]-1H-pyrazol-4-yl}imidazo[1,2-b]pyridazin-3-yl)phenyl]-N'-(2,2,2-trifluoroethyl)urea

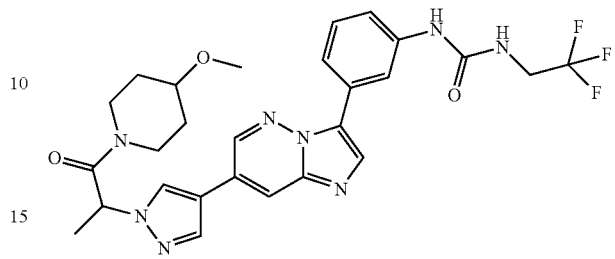

This compound was prepared by using procedures analogous to those described for the synthesis of Example 54, Step 3 starting from 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid and 4-methoxypiperidine hydrochloride (Matrix and Cat. No. 015567). LCMS (M+H)+: m/z=571.3.

Example 70

N-[3-(7-{1-[2-(4-Cyanopiperidin-1-yl)-1-methyl-2-oxoethyl]-1H-pyrazol-4-yl}imidazo[1,2-b]pyridazin-3-yl)phenyl]-N'-(2,2,2-trifluoroethyl)urea

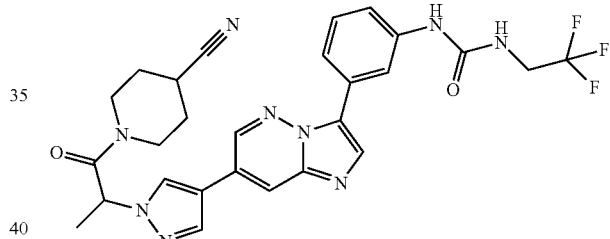

This compound was prepared by using procedures analogous to those described for the synthesis of Example 54, Step 3 starting from 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid and piperidine-4-carbonitrile hydrochloride (and Cat. No.). LCMS (M+H)+: m/z=566.2.

Example 71

N-(1-Methylpiperidin-4-yl)-2-(4-{3-[3-({[(2,2,2-trifluoroethyl)amino]carbonyl}amino)phenyl]imidazo[1,2-b]pyridazin-7-yl}-1H-pyrazol-1-yl)propanamide

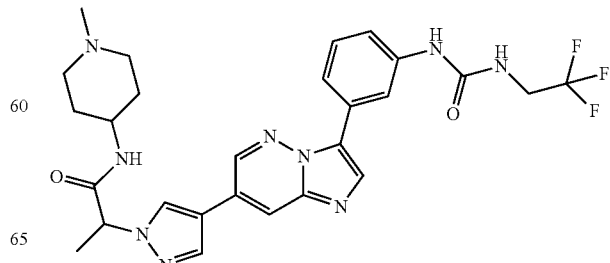

This compound was prepared by using procedures analogous to those described for the synthesis of Example 54, Step 3 starting from 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid and 1-methylpiperidin-4-amine (ABCR and Cat. No. MK534). LCMS (M+H)+: m/z=570.2.

Example 72

N-[3-(7-{1-[2-(3-Cyanoazetidin-1-yl)-1-methyl-2-oxoethyl]-1H-pyrazol-4-yl}imidazo[1,2-b]pyridazin-3-yl)phenyl]-N'-(2,2,2-trifluoroethyl)urea

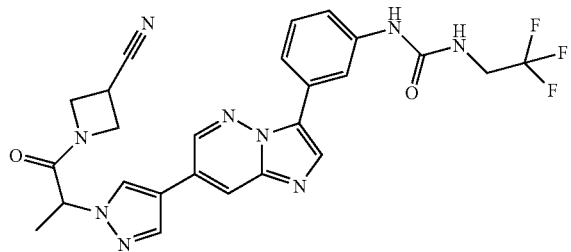 [SMILES: CC(C(=O)N1CC(C#N)C1)n1cc(-c2cnn3c(-c4cccc(NC(=O)NCC(F)(F)F)c4)cnc3c2)cn1]

This compound was prepared by using procedures analogous to those described for the synthesis of Example 54, Step 3 starting from 2-(4-{3-[3-({[(2,2,2-trifluoroethyl)amino]carbonyl}amino)phenyl]imidazo[1,2-b]pyridazin-7-yl}-1H-pyrazol-1-yl)propanoic acid and azetidine-3-carbonitrile hydrochloride (Asta Tech, Inc. and Cat. No. 52028). LCMS (M+H)+: m/z=538.2.

Example 73

N-{3-[7-(1-{3-(Cyanomethyl)-1-[(1-methyl-1H-pyrazol-3-yl)sulfonyl]azetidin-3-yl}-1H-pyrazol-4-yl)imidazo[1,2-b]pyridazin-3-yl]phenyl}-N'-(2,2,2-trifluoroethyl)urea

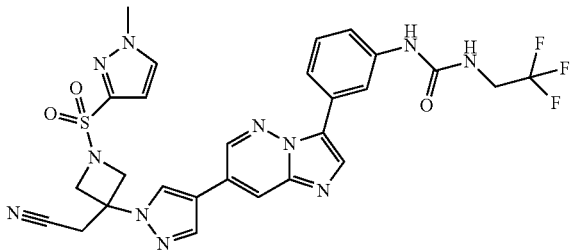 [SMILES: Cn1ccc(S(=O)(=O)N2CC(CC#N)(n3cc(-c4cnn5c(-c6cccc(NC(=O)NCC(F)(F)F)c6)cnc5c4)cn3)C2)n1]

Step 1: tert-butyl 3-(cyanomethyl)-3-[4-(4,4,5,5-tetramethyl-1,3,2-dioxaborolan-2-yl)-1H-pyrazol-1-yl]azetidine-1-carboxylate

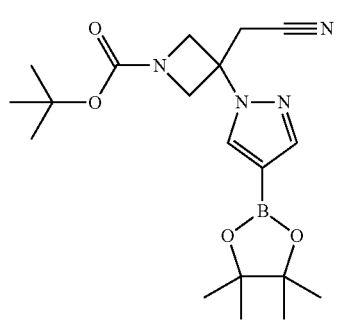 [SMILES: CC(C)(C)OC(=O)N1CC(CC#N)(n2cc(B3OC(C)(C)C(C)(C)O3)cn2)C1]

To a solution of 4-(4,4,5,5-tetramethyl-1,3,2-dioxaborolan-2-yl)-1H-pyrazole (0.40 g, 2.0 mmol, Aldrich, Cat. 525057) and tert-butyl 3-(cyanomethylene)azetidine-1-carboxylate (0.40 g, 2.0 mmol) in acetonitrile (7 mL) was added 1,8-diazabicyclo[5.4.0]undec-7-ene (0.37 mL, 2.5 mmol). The mixture was stirred at 70° C. overnight. The mixture was concentrated. The residue was purified by flash chromatography on a silica gel column with ethyl acetate in hexanes (0-90%) to afford the desired product. LCMS (M+Na)+: m/z=411.2.

Step 2: tert-butyl 3-(cyanomethyl)-3-(4-{3-[3-({[(2,2,2-trifluoroethyl)amino]carbonyl}amino)phenyl]imidazo[1,2-b]pyridazin-7-yl}-1H-pyrazol-1-yl)azetidine-1-carboxylate

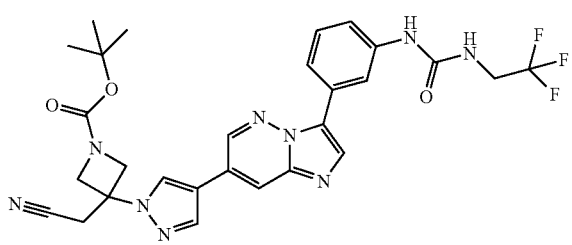 [SMILES: CC(C)(C)OC(=O)N1CC(CC#N)(n2cc(-c3cnn4c(-c5cccc(NC(=O)NCC(F)(F)F)c5)cnc4c3)cn2)C1]

A mixture of N-[3-(7-chloroimidazo[1,2-b]pyridazin-3-yl)phenyl]-N'-(2,2,2-trifluoroethyl)urea (600 mg, 2 mmol), tert-butyl 3-(cyanomethyl)-3-[4-(4,4,5,5-tetramethyl-1,3,2-dioxaborolan-2-yl)-1H-pyrazol-1-yl]azetidine-1-carboxylate (760 mg, 1.9 mmol), tetrakis(triphenylphosphine)palladium(0) (94.9 mg, 0.0822 mmol) and potassium carbonate (570 mg, 4.1 mmol) in 1,4-dioxane (9.0 mL) and water (4 mL) was heated at 100° C. under an atmosphere of nitrogen for 4 h. After cooling, the reaction mixture was extracted with ethyl acetate (3×20 mL), and washed with brine. The combined organic layers were dried over MgSO4, filtered and concentrated under reduced pressure. The residue was purified by flash chromatography on a silica gel column with methanol in dichloromethane (0-10%) to afford the desired product. LCMS (M+H)+: m/z=596.2.

Step 3: N-[3-(7-{1-[3-(cyanomethyl)azetidin-3-yl]-1H-pyrazol-4-yl}imidazo[1,2-b]pyridazin-3-yl)phenyl]-N'-(2,2,2-trifluoroethyl)urea

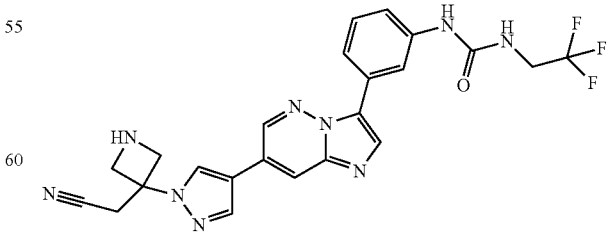

HCl in 1,4-dioxane (4.0 N, 2 mL) was added to a mixture of tert-butyl 3-(cyanomethyl)-3-(4-{3-[3-({[(2,2,2-trifluoroethyl)amino]carbonyl}amino)phenyl]imidazo[1,2-b]

pyridazin-7-yl}-1H-pyrazol-1-yl)azetidine-1-carboxylate (0.55 g, 0.92 mmol) in methylene chloride (10.0 mL). The reaction mixture was stirred at r.t. for 1 h. The mixture was adjusted to pH=8 with aqueous Na₂CO₃, and extracted with ethyl acetate (3×40 mL). The combined organic layers were dried over MgSO₄, filtered and concentrated under reduced pressure. The residue was purified by flash chromatography on a silica gel column with MeOH (with 5% NH₃.H₂O) in DCM (0-15%) to afford the desired product. LCMS (M+H)⁺: m/z=496.1.

Step 4: N-{3-[7-(1-{3-(cyanomethyl)-1-[(1-methyl-1H-pyrazol-3-yl)sulfonyl]azetidin-3-yl}-1H-pyrazol-4-yl)imidazo[1,2-b]pyridazin-3-yl]phenyl}-N'-(2,2,2-trifluoroethyl) urea

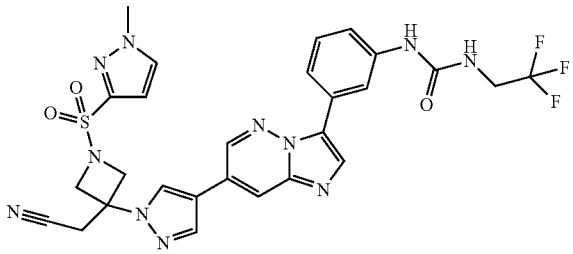 [SMILES: Cn1ccc(S(=O)(=O)N2CC(CC#N)(n3cc(-c4cnn5c(-c6cccc(NC(=O)NCC(F)(F)F)c6)cnc5c4)cn3)C2)n1]

1-Methyl-1H-pyrazole-3-sulfonyl chloride (5.5 mg, 0.030 mmol) (Maybridge and Cat. No. CC 48303) was added to a mixture of N-[3-(7-{1-[3-(cyanomethyl)azetidin-3-yl]-1H-pyrazol-4-yl}imidazo[1,2-b]pyridazin-3-yl)phenyl]-N'-(2,2,2-trifluoroethyl)urea (10.0 mg, 0.0202 mmol) and triethylamine (8.4 µL, 0.060 mmol) in acetonitrile (1.0 mL) and MeOH (0.2 mL). The reaction mixture was stirred at r.t. for 30 min. The mixture was purified by RP-HPLC (pH=10) to afford the desired product. LCMS (M+H)⁺: m/z=640.2.

¹H NMR (400 MHz, CD₃OD): 8.89 (d, J=2.2 Hz, 1H), 8.53 (s, 1H), 8.24 (m, 1H), 8.19 (br, 1H), 8.08 (s, 1H), 7.89 (dt, J=6.8, 1.72 Hz, 1H), 7.76 (d, J=7.6 Hz, 1H), 7.50-7.39 (m, 3H), 6.79 (d, J=2.3 Hz, 1H), 4.56 (d, J=10.4 Hz, 2H), 4.34 (d, J=10.4 Hz, 2H), 3.94 (q, J=9.6 Hz, 2H), 3.88 (s, 3H), 3.38 (s, 2H).

Example 74

N-{3-[7-(1-{3-(Cyanomethyl)-1-[(5-methylisoxazol-4-yl)sulfonyl]azetidin-3-yl}-1H-pyrazol-4-yl)imidazo[1,2-b]pyridazin-3-yl]phenyl}-N'-(2,2,2-trifluoroethyl)urea

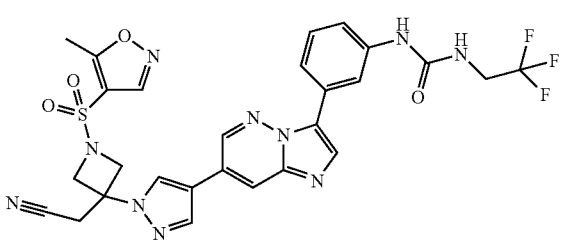 [SMILES: Cc1oncc1S(=O)(=O)N1CC(CC#N)(n2cc(-c3cnn4c(-c5cccc(NC(=O)NCC(F)(F)F)c5)cnc4c3)cn2)C1]

This compound was prepared by using procedures analogous to those described for the synthesis of Example 73, Step 4 starting from N-[3-(7-{1-[3-(cyanomethyl)azetidin-3-yl]-1H-pyrazol-4-yl}imidazo[1,2-b]pyridazin-3-yl)phenyl]-N'-(2,2,2-trifluoroethyl)urea and 5-methylisoxazole-4-sulfonyl chloride. LCMS (M+H)⁺: m/z=641.2.

Example 75

N-[3-(7-{1-[3-(Cyanomethyl)-1-(methoxyacetyl)azetidin-3-yl]-1H-pyrazol-4-yl}imidazo[1,2-b]pyridazin-3-yl)phenyl]-N'-(2,2,2-trifluoroethyl)urea

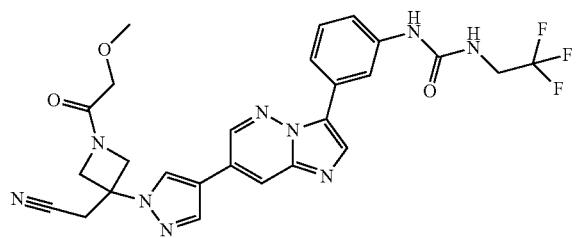 [SMILES: COCC(=O)N1CC(CC#N)(n2cc(-c3cnn4c(-c5cccc(NC(=O)NCC(F)(F)F)c5)cnc4c3)cn2)C1]

This compound was prepared by using procedures analogous to those described for the synthesis of Example 73, Step 4 starting from N-[3-(7-{1-[3-(cyanomethyl)azetidin-3-yl]-1H-pyrazol-4-yl}imidazo[1,2-b]pyridazin-3-yl)phenyl]-N'-(2,2,2-trifluoroethyl)urea and methoxyacetyl chloride. LCMS (M+H)⁺: m/z=568.2.

¹H NMR (400 MHz, CD₃OD): 8.92 (d, J=1.9 Hz, 1H), 8.71 (s, 1H), 8.26 (s, 1H), 8.22 (dd, J=6.8, 1.7 Hz, 2H), 8.07 (s, 1H), 7.79 (m, 1H), 7.5-7.39 (m, 2H), 4.95 (m, 1H), 4.64 (d, J=11.6 Hz, 2H), 4.43 (d, J=11.6 Hz, 1H), 4.09 (s, 2H), 3.94 (q, J=8.4 Hz, 2H), 3.57 (s, 2H), 3.41 (s, 3H).

Example 76

N-{3-[7-(1-{3-(Cyanomethyl)-1-[(dimethylamino)acetyl]azetidin-3-yl}-1H-pyrazol-4-yl)imidazo[1,2-b]pyridazin-3-yl]phenyl}-N'-(2,2,2-trifluoroethyl)urea

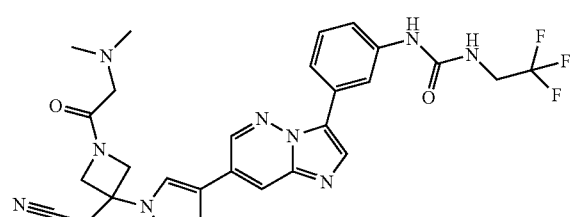

This compound was prepared by using procedures analogous to those described for the synthesis of Example 73, Step 4 starting from N-[3-(7-{1-[3-(cyanomethyl)azetidin-3-yl]-1H-pyrazol-4-yl}imidazo[1,2-b]pyridazin-3-yl)phenyl]-N'-(2,2,2-trifluoroethyl)urea and dimethylaminoacetyl chloride hydrochloride (Lancaster and Cat. No. L18475). LCMS (M+H)⁺: m/z=581.3.

Example 77

N-[3-(7-{1-[1-(Cyanoacetyl)-3-(cyanomethyl)azetidin-3-yl]-1H-pyrazol-4-yl}imidazo[1,2-b]pyridazin-3-yl)phenyl]-N'-(2,2,2-trifluoroethyl)urea

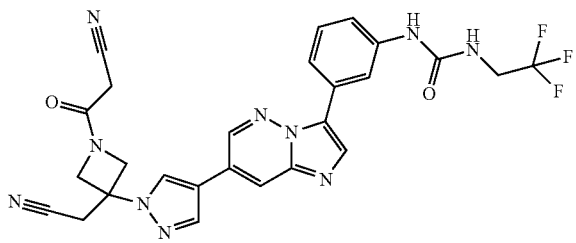 [SMILES: N#CCC(=O)N1CC(CC#N)(n2cc(-c3cnn4c(-c5cccc(NC(=O)NCC(F)(F)F)c5)cnc4c3)cn2)C1]

Cyanoacetic acid (3.1 mg, 0.036 mmol) was added to a mixture of N-[3-(7-{1-[3-(cyanomethyl)azetidin-3-yl]-1H-pyrazol-4-yl}imidazo[1,2-b]pyridazin-3-yl)phenyl]-N'-(2,2,2-trifluoroethyl)urea (11.9 mg, 0.0241 mmol) and benzotriazol-1-yloxytris(dimethylamino)phosphonium hexafluorophosphate (16 mg, 0.036 mmol) in N,N-dimethylformamide (0.6 mL), followed by triethylamine (10. µL, 0.072 mmol). The reaction mixture was stirred at r.t. for 1 h. The mixture was purified by RP-HPLC (pH=10) to afford the desired product. LCMS (M+H)$^+$: m/z=563.2.

Example 78

N-[3-(7-{1-[3-(Cyanomethyl)-1-(cyclopropylacetyl)azetidin-3-yl]-1H-pyrazol-4-yl}imidazo[1,2-b]pyridazin-3-yl)phenyl]-N'-(2,2,2-trifluoroethyl)urea

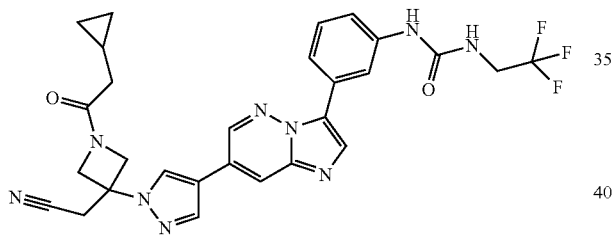

This compound was prepared by using procedures analogous to those described for the synthesis of Example 77 starting from N-[3-(7-{1-[3-(cyanomethyl)azetidin-3-yl]-1H-pyrazol-4-yl}imidazo[1,2-b]pyridazin-3-yl)phenyl]-N'-(2,2,2-trifluoroethyl)urea and cyclopropylacetic acid. LCMS (M+H)$^+$: m/z=578.2.

Example 79

N-{3-[7-(1-{3-(Cyanomethyl)-1-[(1-methylcyclopropyl)carbonyl]azetidin-3-yl}-1H-pyrazol-4-yl)imidazo[1,2-b]pyridazin-3-yl]phenyl}-N'-(2,2,2-trifluoroethyl)urea

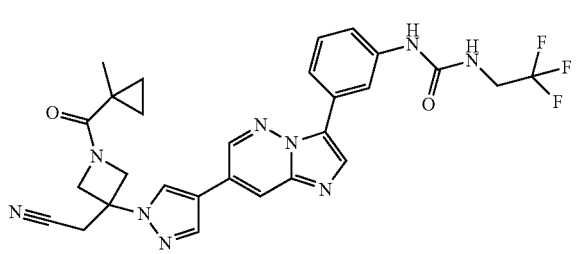 [SMILES: CC1(C(=O)N2CC(CC#N)(n3cc(-c4cnn5c(-c6cccc(NC(=O)NCC(F)(F)F)c6)cnc5c4)cn3)C2)CC1]

This compound was prepared by using procedures analogous to those described for the synthesis of Example 77 starting from N-[3-(7-{1-[3-(cyanomethyl)azetidin-3-yl]-1H-pyrazol-4-yl}imidazo[1,2-b]pyridazin-3-yl)phenyl]-N'-(2,2,2-trifluoroethyl)urea and 1-methylcyclopropanecarboxylic acid. LCMS (M+H)$^+$: m/z=578.2

Example 80

N-[3-(7-{1-[1-[(1-Cyanocyclopropyl)carbonyl]-3-(cyanomethyl)azetidin-3-yl]-1H-pyrazol-4-yl}imidazo[1,2-b]pyridazin-3-yl)phenyl]-N'-(2,2,2-trifluoroethyl)urea

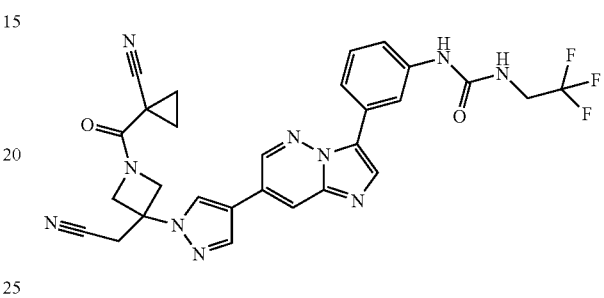

This compound was prepared by using procedures analogous to those described for the synthesis of Example 77 starting from N-[3-(7-{1-[3-(cyanomethyl)azetidin-3-yl]-1H-pyrazol-4-yl}imidazo[1,2-b]pyridazin-3-yl)phenyl]-N'-(2,2,2-trifluoroethyl)urea and 1-cyanocyclopropanecarboxylic acid. LCMS (M+H)$^+$: m/z=589.2.

Example 81

N-[3-(7-{1-[3-(Cyanomethyl)-1-(tetrahydrofuran-2-ylacetyl)azetidin-3-yl]-1H-pyrazol-4-yl}imidazo[1,2-b]pyridazin-3-yl)phenyl]-N'-(2,2,2-trifluoroethyl)urea

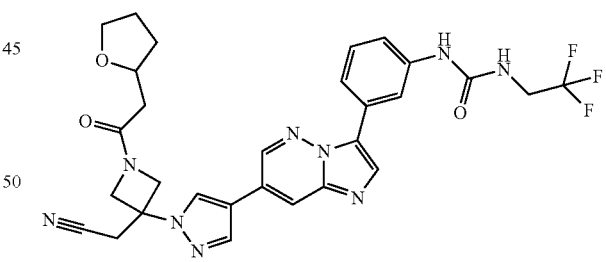

This compound was prepared by using procedures analogous to those described for the synthesis of Example 77 starting from N-[3-(7-{1-[3-(cyanomethyl)azetidin-3-yl]-1H-pyrazol-4-yl}imidazo[1,2-b]pyridazin-3-yl)phenyl]-N'-(2,2,2-trifluoroethyl)urea and tetrahydrofuran-2-ylacetic acid (Matrix Scitific, cat. No. 020454). LCMS (M+H)$^+$: m/z=608.2.

$^1$H NMR (400 MHz, CD$_3$OD): 8.91 (s, 1H), 8.70 (s, 1H), 8.28-8.20 (m, 3H), 8.07 (s, 1H), 7.79 (m, 1H), 7.5-7.4 (m, 2H), 4.9 (m, 1H), 4.7-4.5 (m, 2H), 4.39 (m, 1H), 4.25 (m, 1H), 4.0-3.8 (m, 3H), 3.75 (m, 1H), 3.55 (m, 2H), 2.3-2.6 (m, 2H), 2.15 (m, 1H), 1.95 (m, 2H), 1.65 (m, 1H).

Example 82

N-[3-(7-{1-[3-(Cyanomethyl)-1-(tetrahydrofuran-3-ylcarbonyl)azetidin-3-yl]-1H-pyrazol-4-yl}imidazo[1,2-b]pyridazin-3-yl)phenyl]-N'-(2,2,2-trifluoroethyl)urea

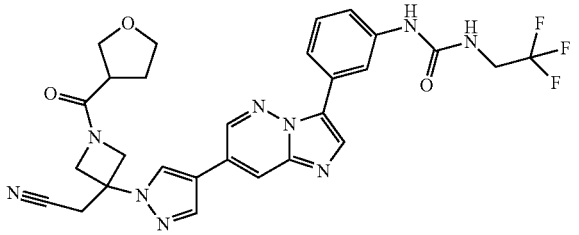

This compound was prepared by using procedures analogous to those described for the synthesis of Example 77 starting from N-[3-(7-{1-[3-(cyanomethyl)azetidin-3-yl]-1H-pyrazol-4-yl}imidazo[1,2-b]pyridazin-3-yl)phenyl]-N'-(2,2,2-trifluoroethyl)urea and tetrahydrofuran-3-carboxylic acid. LCMS (M+H)$^+$: m/z=594.2.

Example 83

N-[3-(7-{1-[3-(Cyanomethyl)-1-(cyclopropylmethyl)azetidin-3-yl]-1H-pyrazol-4-yl}imidazo[1,2-b]pyridazin-3-yl)phenyl]-N'-(2,2,2-trifluoroethyl)urea

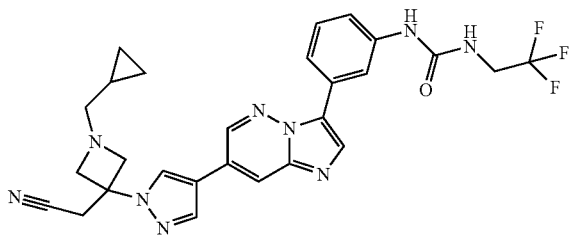 [SMILES: N#CCC1(n2cc(-c3cnn4c(-c5cccc(NC(=O)NCC(F)(F)F)c5)cnc4c3)cn2)CN(CC2CC2)C1]

Cyclopropanecarboxaldehyde (4.2 mg, 0.060 mmol) was added to a mixture of N-[3-(7-{1-[3-(cyanomethyl)azetidin-3-yl]-1H-pyrazol-4-yl}imidazo[1,2-b]pyridazin-3-yl)phenyl]-N'-(2,2,2-trifluoroethyl)urea (15 mg, 0.030 mmol) in methanol (1.0 mL). After stirring at r.t. for 20 min, sodium triacetoxyborohydride (13 mg, 0.060 mmol) was added. The reaction mixture was stirred at r.t. for 4 h. The mixture was purified by RP-HPLC (pH=10) to afford the desired product. LCMS (M+H)$^+$: m/z=550.2.

Example 84

3-(Cyanomethyl)-N-phenyl-3-(4-{3-[3-({[(2,2,2-trifluoroethyl)amino]carbonyl}amino)phenyl]imidazo[1,2-b]pyridazin-7-yl}-1H-pyrazol-1-yl)azetidine-1-carboxamide

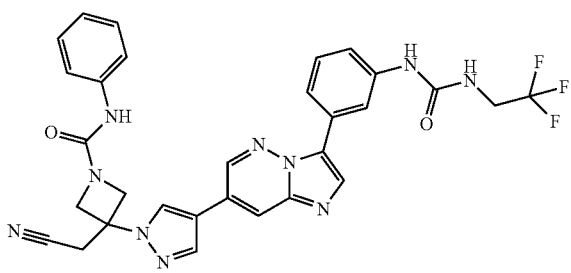 [SMILES: N#CCC1(n2cc(-c3cnn4c(-c5cccc(NC(=O)NCC(F)(F)F)c5)cnc4c3)cn2)CN(C(=O)Nc2ccccc2)C1]

Phenyl isocyanate (5.4 mg, 0.045 mmol) was added to a mixture of N-[3-(7-{1-[3-(cyanomethyl)azetidin-3-yl]-1H-pyrazol-4-yl}imidazo[1,2-b]pyridazin-3-yl)phenyl]-N'-(2,2,2-trifluoroethyl)urea (15.0 mg, 0.0303 mmol) and triethylamine (13 μL, 0.093 mmol) in N,N-dimethylformamide (0.5 mL) and methanol (0.1 mL). The reaction mixture was stirred at r.t. for 2 h. The mixture was purified by RP-HPLC (pH=10) to afford the desired product. LCMS (M+H)$^+$: m/z=615.2.

Example 85

N-[3-(7-{1-[3-(Cyanomethyl)-1-(morpholin-4-ylcarbonyl)azetidin-3-yl]-1H-pyrazol-4-yl}imidazo[1,2-b]pyridazin-3-yl)phenyl]-N'-(2,2,2-trifluoroethyl)urea

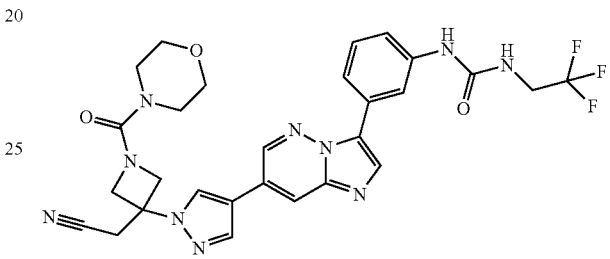

Morpholine-4-carbonyl chloride (6.8 mg, 0.045 mmol) was added to a mixture of N-[3-(7-{1-[3-(cyanomethyl)azetidin-3-yl]-1H-pyrazol-4-yl})imidazo[1,2-b]pyridazin-3-yl)phenyl]-N'-(2,2,2-trifluoroethyl)urea (15.0 mg, 0.0303 mmol) and triethylamine (13 μL, 0.093 mmol) in N,N-dimethylformamide (0.5 mL) and methanol (0.1 mL). The reaction mixture was stirred at r.t. for 2 h. The mixture was purified by RP-HPLC (pH=10) to afford the desired product. LCMS (M+H)$^+$: m/z=609.2.

Example 86

N-[3-(7-{1-[3-(Cyanomethyl)-1-(pyrrolidin-1-ylcarbonyl)azetidin-3-yl]-1H-pyrazol-4-yl}imidazo[1,2-b]pyridazin-3-yl)phenyl]-N'-(2,2,2-trifluoroethyl)urea

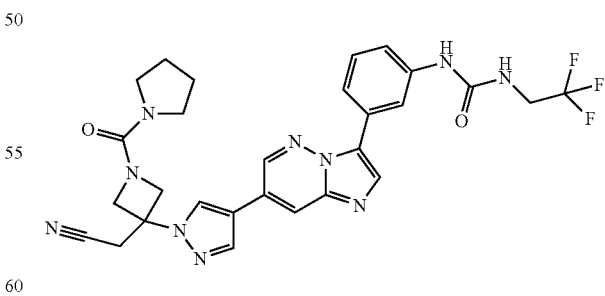

This compound was prepared by using procedures analogous to those described for the synthesis of Example 85 starting from N-[3-(7-{1-[3-(cyanomethyl)azetidin-3-yl]-1H-pyrazol-4-yl}imidazo[1,2-b]pyridazin-3-yl)phenyl]-N'-(2,2,2-trifluoroethyl)urea and 1-pyrrolidinecarbonyl chloride. LCMS (M+H)$^+$: m/z=593.2.

Example 87

3-(Cyanomethyl)-N-(cyclopropylmethyl)-3-(4-{3-[3-({[(2,2,2-trifluoroethyl)amino]carbonyl}amino)phenyl]imidazo[1,2-b]pyridazin-7-yl}-1H-pyrazol-1-yl)azetidine-1-carboxamide

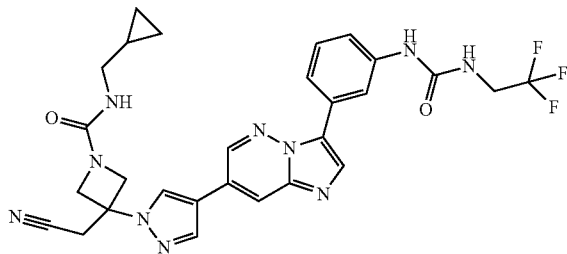 [SMILES: N#CCC1(n2cc(-c3cnn4c(-c5cccc(NC(=O)NCC(F)(F)F)c5)cnc4c3)cn2)CN(C(=O)NCC2CC2)C1]

Triphosgene (22 mg, 0.074 mmol) was dissolved in DCM (1.0 mL). To the solution was added a solution of triethylamine (12.6 µL, 0.0908 mmol) and cyclopropylmethylamine (6.2 µL, 0.073 mmol) in DCM (1 mL). The mixture was stirred at r.t. for 1 h., the volatiles were removed. To the residue was added a solution of triethylamine (22.9 µL, 0.164 mmol) and N-[3-(7-{1-[3-(cyanomethyl)azetidin-3-yl]-1H-pyrazol-4-yl}imidazo[1,2-b]pyridazin-3-yl)phenyl]-N'-(2,2,2-trifluoroethyl)urea (15 mg, 0.030 mmol) in N,N-dimethylformamide (0.5 mL) and methanol (0.1 mL). The mixture was stirred at r.t. for 1h., the mixture was purified by RP-LCMS (pH=10) to afford the desired product. LCMS (M+H)+: m/z=593.2.

Example 88

Cyclopropylmethyl 3-(cyanomethyl)-3-(4-{3-[3-({[(2,2,2-trifluoroethyl)amino]carbonyl}amino)phenyl]imidazo[1,2-b]pyridazin-7-yl}-1H-pyrazol-1-yl)azetidine-1-carboxylate

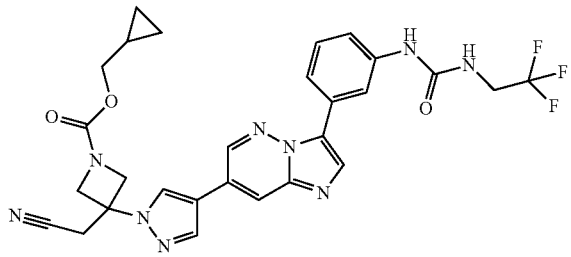 [SMILES: N#CCC1(n2cc(-c3cnn4c(-c5cccc(NC(=O)NCC(F)(F)F)c5)cnc4c3)cn2)CN(C(=O)OCC2CC2)C1]

Step 1: cyclopropylmethyl 4-nitrophenyl carbonate

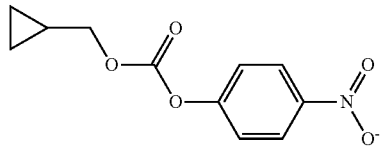

p-Nitrophenyl chloroformate (0.56 g, 2.8 mmol) was added to a mixture of cyclopropyl carbinol (0.20 g, 2.8 mmol) and triethylamine (0.58 mL, 4.2 mmol) in methylene chloride (5 mL). The mixture was stirred at r.t. for 2 h. After removal of solvent, the residue was purified by flash chromatography on a silica gel column with ethyl acetate in hexanes (0-40%) to afford the desired product.

Step 2: cyclopropylmethyl 3-(cyanomethyl)-3-(4-{3-[3-({[(2,2,2-trifluoroethyl)amino]carbonyl}amino)phenyl]imidazo[1,2-b]pyridazin-7-yl}-1H-pyrazol-1-yl)azetidine-1-carboxylate

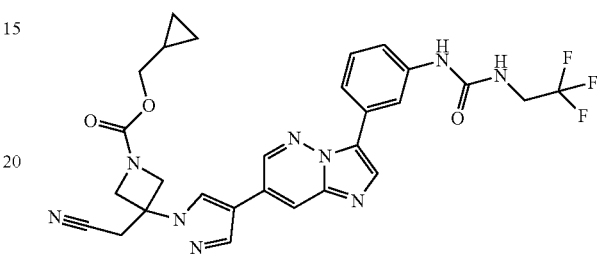

Cyclopropylmethyl 4-nitrophenyl carbonate (11 mg, 0.045 mmol) was added to a mixture of N-[3-(7-{1-[3-(cyanomethyl)azetidin-3-yl]-1H-pyrazol-4-yl}imidazo[1,2-b]pyridazin-3-yl)phenyl]-N'-(2,2,2-trifluoroethyl)urea (15.0 mg, 0.0303 mmol) and triethylamine (13 µL, 0.093 mmol) in N,N-dimethylformamide (0.5 mL) and methanol (0.1 mL). The reaction mixture was stirred at r.t. for 2 h. The mixture was purified by RP-HPLC (pH=10) to afford the desired product. LCMS (M+H)+: m/z=594.2.

Example 89

N-(3-{7-[1-(2-Cyano-1-methylethyl)-1H-pyrazol-4-yl]imidazo[1,2-b]pyridazin-3-yl}phenyl)-N'-(2,2,2-trifluoroethyl)urea

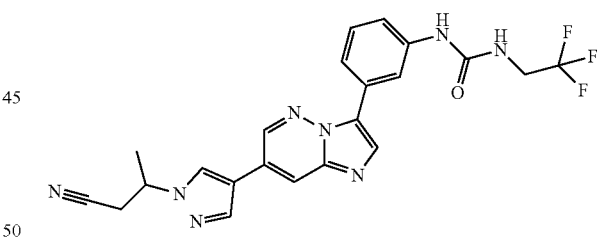

Step 1: N-{3-[7-(1H-pyrazol-4-yl)imidazo[1,2-b]pyridazin-3-yl]phenyl}-N'-(2,2,2-trifluoroethyl)urea

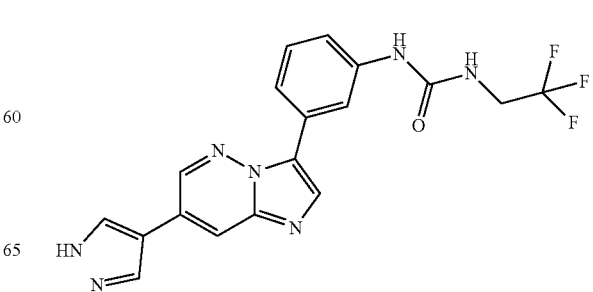

A mixture of N-[3-(7-chloroimidazo[1,2-b]pyridazin-3-yl)phenyl]-N'-(2,2,2-trifluoroethyl)urea (0.30 g, 0.81 mmol), tert-butyl 4-(4,4,5,5-tetramethyl-1,3,2-dioxaborolan-2-yl)-1H-pyrazole-1-carboxylate(0.29 g, 0.97 mmol), tetrakis(triphenylphosphine)palladium(O) (46.9 mg, 0.0406 mmol) and K$_3$PO$_4$ (0.43 g, 2.0 mmol) in 1,4-dioxane (4.0 mL) and water (2 mL) was heated at 100° C. under an atmosphere of nitrogen for 3 h. After cooling, the reaction mixture was extracted with ethyl acetate (3×30 mL), and washed with brine. The combined organic layers were dried over MgSO$_4$, filtered and concentrated under reduced pressure. The residue was purified by flash chromatography on a silica gel column with methanol in dichloromethane (0-15%) to afford the desired product. LCMS (M+H)$^+$: m/z=402.1.

Step 2: N-(3-{7-[1-(2-cyano-1-methylethyl)-1H-pyrazol-4-yl]imidazo[1,2-b]pyridazin-3-yl}phenyl)-N'-(2,2,2-trifluoroethyl)urea

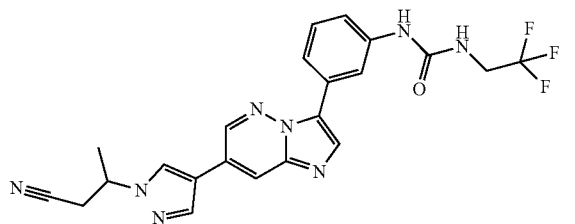 [SMILES: CC(CC#N)N/C=C(\C=N)c1cnn2c(-c3cccc(NC(=O)NCC(F)(F)F)c3)cnc2c1]

To a solution of N-{3-[7-(1H-pyrazol-4-yl)imidazo[1,2-b]pyridazin-3-yl]phenyl}-N'-(2,2,2-trifluoroethyl)urea (15 mg, 0.037 mmol) and 2-butenenitrile (3.8 mg, 0.056 mmol) in acetonitrile (0.5 mL) and methanol (0.2 mL) was added 1,8-diazabicyclo[5.4.0]undec-7-ene (5.6 μL, 0.037 mmol). The mixture was stirred at 60° C. overnight. The reaction mixture was stirred at 60° C. overnight. The mixture was purified by RP-HPLC (pH=10) to afford the desired product. LCMS (M+H)$^+$: m/z=469.1.

Example 90

N-[3-(7-{1-[1-(Cyanomethyl)-2,2,2-trifluoroethyl]-1H-pyrazol-4-yl}imidazo[1,2-b]pyridazin-3-yl)phenyl]-N'-(2,2,2-trifluoroethyl)urea

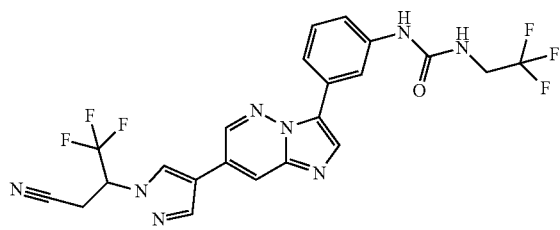 [SMILES: N#CCC(N/C=C(\C=N)c1cnn2c(-c3cccc(NC(=O)NCC(F)(F)F)c3)cnc2c1)C(F)(F)F]

This compound was prepared by using procedures analogous to those described for the synthesis of Example 89, Step 2 starting from N-{3-[7-(1H-pyrazol-4-yl)imidazo[1,2-b]pyridazin-3-yl]phenyl}-N'-(2,2,2-trifluoroethyl)urea and 4,4,4-trifluorobut-2-enenitrile. LCMS (M+H)$^+$: m/z=523.1.

Example 91

N-[3-(7-{1-[2-Cyano-1-(2-furyl)ethyl]-1H-pyrazol-4-yl}imidazo[1,2-b]pyridazin-3-yl)phenyl]-N'-(2,2,2-trifluoroethyl)urea

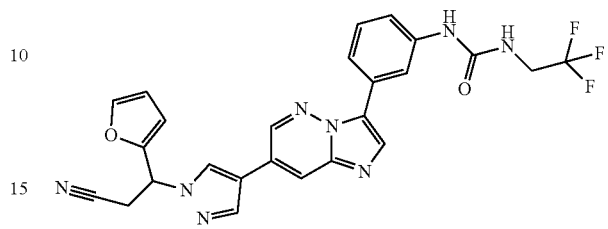

This compound was prepared by using procedures analogous to those described for the synthesis of Example 89, Step 2 starting from N-{3-[7-(1H-pyrazol-4-yl)imidazo[1,2-b]pyridazin-3-yl]phenyl}-N'-(2,2,2-trifluoroethyl)urea and 3-(2-furyl)acrylonitrile. LCMS (M+H)$^+$: m/z=521.0.

Example 92

N-(3-{7-[1-(2-Cyano-1-cyclopropylethyl)-1H-pyrazol-4-yl]imidazo[1,2-b]pyridazin-3-yl}phenyl)-N'-(2,2,2-trifluoroethyl)urea

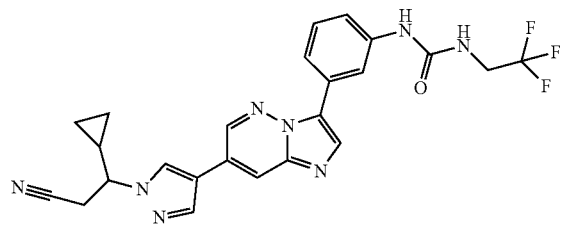 [SMILES: N#CCC(N/C=C(\C=N)c1cnn2c(-c3cccc(NC(=O)NCC(F)(F)F)c3)cnc2c1)C1CC1]

Step 1: (2E)-3-cyclopropylacrylonitrile

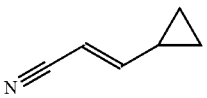

To a solution of potassium tert-butoxide in tetrahydrofuran (1.0 M, 14.0 mL, 14.0 mmol) at 0° C. was added a solution of diethyl cyanomethylphosphonate (2.61 g, 14.7 mmol) in tetrahydrofuran (10 mL) dropwise. The reaction was warmed to room temperature, and then recooled to 0° C. A solution of cyclopropanecarboxaldehyde (1.00 mL, 13.4 mmol) in Tetrahydrofuran (2 mL) was added dropwise. The bath was removed and the mixture was allowed to warm to r.t. for 20 h. Water was added; the product was extracted with diethyl ether 3×. The combined extracts were washed with brine, dried over sodium sulfate and concentrated. The product was used without further purification.

Step 2. N-(3-{7-[1-(2-Cyano-1-cyclopropylethyl)-1H-pyrazol-4-yl]imidazo[1,2-b]pyridazin-3-yl}phenyl)-N'-(2,2,2-trifluoroethyl)urea This compound was prepared by using procedures analogous to those described for the synthesis of Example 89, Step 2 starting from N-{3-[7-(1H-pyrazol-4-yl)imidazo[1,2-b]pyridazin-3-yl]phenyl}-N'-(2,2,2-trifluoroethyl)urea and (2E)-3-cyclopropylacrylonitrile. LCMS (M+H)+: m/z=495.2.

Example 93

N-(3-{7-[1-(2-Cyano-1-phenylethyl)-1H-pyrazol-4-yl]imidazo[1,2-b]pyridazin-3-yl}phenyl)-N'-(2,2,2-trifluoroethyl)urea

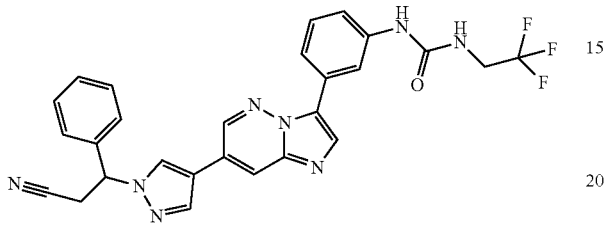

This compound was prepared by using procedures analogous to those described for the synthesis of Example 89, Step 2 starting from N-{3-[7-(1H-pyrazol-4-yl)imidazo[1,2-b]pyridazin-3-yl]phenyl}-N'-(2,2,2-trifluoroethyl)urea and cinnamonitrile. LCMS (M+H)+: m/z=531.2.

Example 94

Trans-N-{[(2-hydroxycyclohexyl]methyl}-3-{3-[3-({[(2,2,2-trifluoroethyl)amino]carbonyl}amino)phenyl]imidazo[1,2-b]pyridazin-7-yl}benzamide

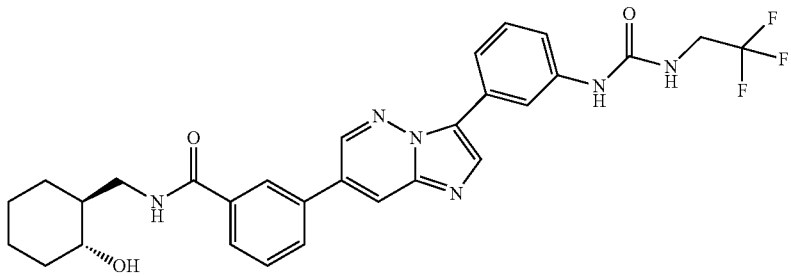 [SMILES: O=C(NCC(F)(F)F)Nc1cccc(-c2cnc3cc(-c4cccc(C(=O)NC[C@@H]5CCCC[C@H]5O)c4)cnn23)c1]

Step 1: methyl 3-(6-oxo-1,6-dihydropyridazin-4-yl)benzoate

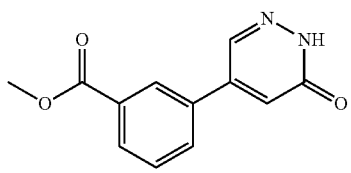 [SMILES: COC(=O)c1cccc(-c2cn[nH]c(=O)c2)c1]

Dichloro(bis{di-tert-butyl[4-(dimethylamino)phenyl]phosphoranyl})palladium (85 mg, 0.12 mmol) was added to a mixture of 5-chloropyridazin-3(4H)-one (0.52 g, 4.0 mmol, Maybridge, Cat. No. M008305), [3-(methoxycarbonyl)phenyl]boronic acid (0.864 g, 4.80 mmol, Aldrich, Cat. No. 591130) and sodium carbonate (0.85 g, 8.0 mmol) in 1,4-dioxane (9 mL) and water (1 mL). The reaction mixture was vacuumed and refilled with nitrogen 3 times. The reaction was stirred at 95° C. overnight. To this reaction mixture was added dioxane (3.0 ml) and water (10 ml) and then filtered, washed with acetonitrile/water, dried to provide the pure product (0.86 g). LCMS (M+H)+: m/z=231.1

Step 2: methyl 3-(6-chloropyridazin-4-yl)benzoate

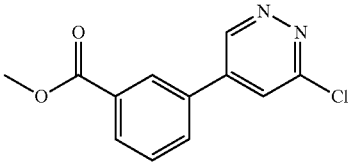 [SMILES: COC(=O)c1cccc(-c2cnnc(Cl)c2)c1]

A mixture of methyl 3-(2-oxo-1,2-dihydropyridin-4-yl)benzoate (0.40 g, 1.7 mmol) in phosphoryl chloride (5.0 mL) and DMF (50 µL) was stirred at 100° C. for 3 h. LCMS showed the reaction was complete. The solvent was removed under reduced pressure. The residue was diluted with methylene chloride, washed with saturated NaHCO₃, water and brine, dried over Na₂SO₄, filtered and concentrated under reduced pressure to provide the desired product which was directly used in next step reaction without further purification (0.40 g). LCMS (M+H)+: m/z=249.1

Step 3: methyl 3-{6-[(diphenylmethylene)amino]pyridazin-4-yl}benzoate

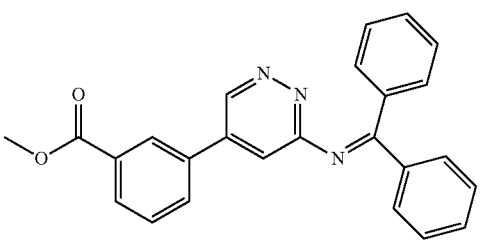 [SMILES: COC(=O)c1cccc(-c2cnnc(N=C(c3ccccc3)c3ccccc3)c2)c1]

A mixture of methyl 3-(6-chloropyridazin-4-yl)benzoate (0.21 g, 0.84 mmol), benzophenone imine (260 µL, 1.5 mmol), (R)-(+)-2,2'-bis(diphenylphosphino)-1,1'-binaphthyl (26 mg, 0.042 mmol), cesium carbonate (0.55 g, 1.7 mmol)

and palladium acetate (9.5 mg, 0.042 mmol) in 1,4-dioxane (3 mL) was vacuum and refilled with nitrogen for 3 times. The reaction was stirred at 110° C. overnight. After cooling it was diluted with ethyl acetate. The organic solution was washed with water and brine, dried over Na$_2$SO$_4$. After filtration the filtrate was concentrated under reduced pressure. The residue was purified by flash chromatography on a silica gel column with ethyl acetate in methylene chloride (0-20%) to afford the desired product (0.23 g). LCMS (M+H)$^+$: m/z=394.2

Step 4: methyl 3-(6-aminopyridazin-4-yl)benzoate

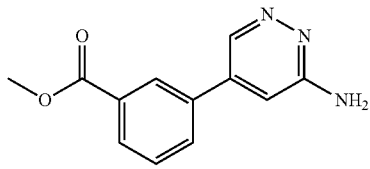 [SMILES: COC(=O)c1cccc(-c2cnnc(N)c2)c1]

1.0 M HCl (2.0 mL) was added to a solution of methyl 3-{6-[(diphenylmethylene)amino]pyridazin-4-yl}benzoate (0.16 g, 0.40 mmol) in THF (4.0 mL) and then the reaction was stirred at r.t. for 1.5 h. The mixture was carefully neutralized with Na$_2$CO$_3$ (2.0 eq) and then concentrated under reduced pressure to give the crude product (0.20 g) which was directly used in the next reaction without further purification. LCMS (M+H)$^+$: m/z=230.1

Step 5: methyl 3-imidazo[1,2-b]pyridazin-7-ylbenzoate

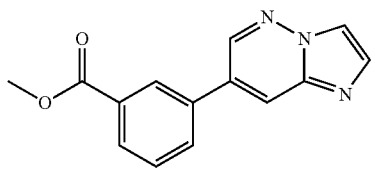 [SMILES: COC(=O)c1cccc(-c2cnn3ccnc3c2)c1]

A mixture of methyl 3-(6-aminopyridazin-4-yl)benzoate (0.20 g, 0.87 mmol) and chloroacetaldehyde in water (0.3 mL, 50%) in isopropyl alcohol (3.0 mL) was stirred at 100° C. for 4 h. The solvent was removed and the residue was dissolved in ethyl acetate, washed with saturated NaHCO$_3$, water and brine, dried over Na$_2$SO$_4$, filtered and concentrated under reduced pressure. The residue was purified by flash chromatography on a silica gel column with ethyl acetate in methylene chloride (0-30%) to afford the desired product (0.18 g). LCMS (M+H)$^+$: m/z=254.1

Step 6: methyl 3-(3-iodoimidazo[1,2-b]pyridazin-7-yl)benzoate

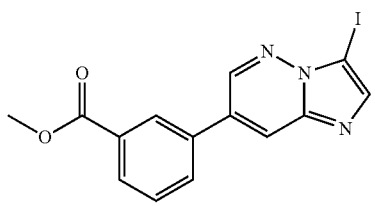 [SMILES: COC(=O)c1cccc(-c2cnn3c(I)cnc3c2)c1]

N-Iodosuccinimide (280 mg, 1.3 mmol) was added to a mixture of methyl 3-imidazo[1,2-b]pyridazin-7-ylbenzoate (160.0 mg, 0.6318 mmol) in DMF (2 mL) and then the reaction was stirred at r.t. for 6 h. The precipitate formed was filtered and washed with ether to provide the desired product (0.12 g). LCMS (M+H)$^+$: m/z=380.0

Step 7: methyl 3-{3-[3-({[(2,2,2-trifluoroethyl)amino]carbonyl}amino)phenyl]imidazo[1,2-b]pyridazin-7-yl}benzoate

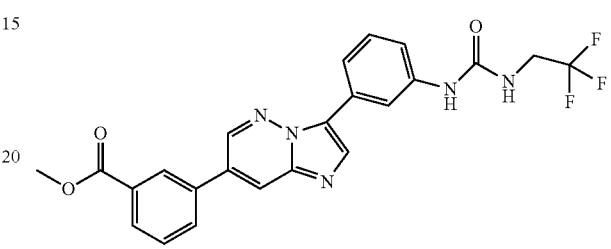

Dichloro(bis {di-tert-butyl[4-(dimethylamino)phenyl]phosphoranyl})palladium (6.7 mg, 0.0095 mmol) was added to a mixture of methyl 3-(3-iodoimidazo[1,2-b]pyridazin-7-yl)benzoate (0.12 g, 0.32 mmol), N-[3-(4,4,5,5-tetramethyl-1,3,2-dioxaborolan-2-yl)phenyl]-N'-(2,2,2-trifluoroethyl)urea (140 mg, 0.41 mmol) and sodium carbonate (67 mg, 0.63 mmol) in 1,4-dioxane (3 mL) and water (0.3 mL) and then the reaction vessel was evacuated under reduced pressure and refilled with nitrogen 3 times. The reaction was stirred at 100° C. overnight. To this mixture was added aqueous AcCN and then filtered, washed with aqueous AcCN, dried to provide the product (0.09 g). LCMS (M+H)$^+$: m/z=470.1

Step 8: 3-{3-[3-({[(2,2,2-trifluoroethyl)amino]carbonyl}amino)phenyl]imidazo[1,2-b]pyridazin-7-yl}benzoic acid

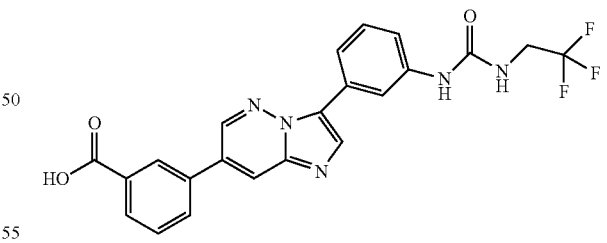

Lithium hydroxide monohydrate (40. mg, 0.96 mmol) was added to a mixture of methyl 3-{3-[3-({[(2,2,2-trifluoroethyl)amino]carbonyl}amino)phenyl]imidazo[1,2-b]pyridazin-7-yl}benzoate (0.090 g, 0.19 mmol) in methanol (2.0 mL)/THF (1.0 mL)/water (0.5 mL) and then the reaction was stirred at r.t. for 4 h. The mixture was adjusted with conc. HCl to PH~3, and then concentrated under reduced pressure to give the crude product which was directly used in the next reaction without further purification. LCMS (M+H)$^+$: m/z=456.1

Step 9: trans-N-{[(2-hydroxycyclohexyl)methyl]-3-{3-[3-({[(2,2,2-trifluoroethyl)amino]carbonyl}amino)phenyl]imidazo[1,2-b]pyridazin-7-yl}benzamide trans-2-(Aminomethyl)cyclohexanol (0.2 mmol) was added to a solution of 3-{3-[3-({[(2,2,2-trifluoroethyl)amino]carbonyl}amino)phenyl]imidazo[1,2-b]pyridazin-7-yl}benzoic acid (10.0 mg, 0.0220 mmol) and benzotriazol-1-yloxytris(dimethylamino)phosphonium hexafluorophosphate (14 mg, 0.033 mmol) in DMF (0.5 mL, 6 mmol) at r.t., followed by adding triethylamine (20.0 µL, 0.143 mmol). The reaction was stirred for 2 h., and then the mixture was purified by RP-HPLC (pH=2) to afford the desired product as TFA salt. LCMS (M+H)+: m/z=567.3

Example 95 cis-N-{[(2-Hydroxycyclohexyl)methyl]-3-{3-[3-({[(2,2,2-trifluoroethyl)amino]carbonyl}amino)phenyl]imidazo[1,2-b]pyridazin-7-yl}benzamide

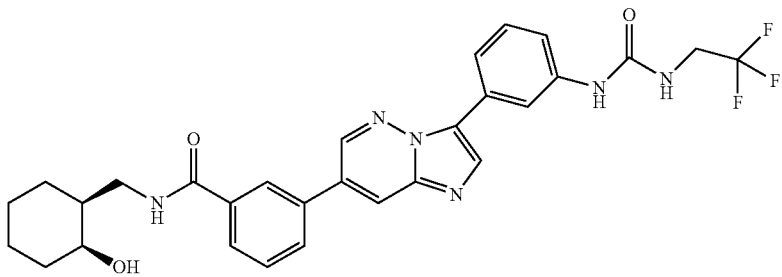 [SMILES: O=C(NCC(F)(F)F)Nc1cccc(-c2cnc3cc(-c4cccc(C(=O)NC[C@@H]5CCCC[C@@H]5O)c4)cnn23)c1]

This compound was prepared by using procedure analogous to those described for the synthesis of Example 94, Step 9 starting from 3-{3-[3-({[(2,2,2-trifluoroethyl)amino]carbonyl}amino)phenyl]imidazo[1,2-b]pyridazin-7-yl}benzoic acid and cis-2-(aminomethyl)cyclohexanol. LCMS (M+H)+: m/z=567.3

Example 96

N-(2-Fluorobenzyl)-3-[3-(3-{[(methylamino)carbonyl]amino}phenyl)imidazo[1,2-b]pyridazin-7-yl]benzamide

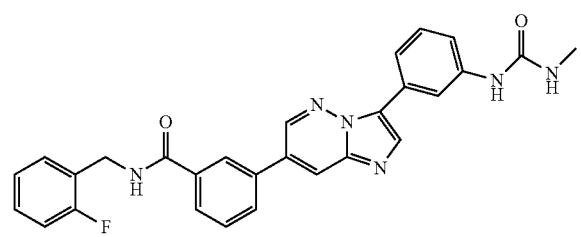 [SMILES: CNC(=O)Nc1cccc(-c2cnc3cc(-c4cccc(C(=O)NCc5ccccc5F)c4)cnn23)c1]

Step 1: N-methyl-N'-[3-(4,4,5,5-tetramethyl-1,3,2-dioxaborolan-2-yl)phenyl]urea

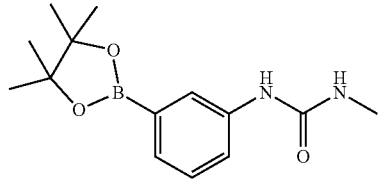

Methyl amine (2.0 M in THF) was added to a solution of 2-(3-isocyanatophenyl)-4,4,5,5-tetramethyl-1,3,2-dioxaborolane (0.49 g, 2.0 mmol) and in tetrahydrofuran (6.0 mL) at 0° C. The mixture was stirred at this temperature for 5 min, then at r.t. for 2 h. The mixture was diluted with ethyl acetate, washed with water, 1N HCl aq. and brine, dried over Na2SO4, filtered and concentrated under reduced pressure to provide the desired product which was directly used in next step without further purification. LCMS (M+H)+: m/z=277.1

Step 2: methyl 3-[3-(3-{[(methylamino)carbonyl]amino}phenyl)imidazo[1,2-b]pyridazin-7-yl]benzoate

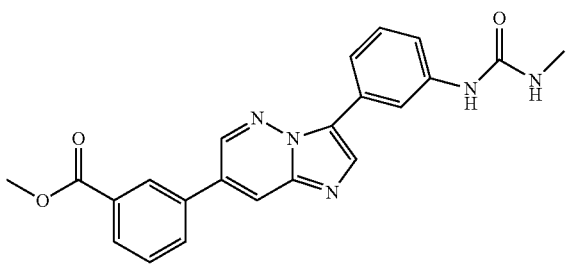

Dichloro(bis{di-tert-butyl[4-(dimethylamino)phenyl]phosphoranyl})palladium (2.8 mg, 0.0040 mmol) was added to a mixture of methyl 3-(3-iodoimidazo[1,2-b]pyridazin-7-yl)benzoate (0.050 g, 0.13 mmol), N-methyl-N'-[3-(4,4,5,5-tetramethyl-1,3,2-dioxaborolan-2-yl)phenyl]urea (44 mg, 0.16 mmol) and sodium carbonate (28 mg, 0.26 mmol) in 1,4-dioxane (1 mL) and water (0.1 mL) and then the reaction vessel containing the mixture was evacuated and refilled with nitrogen 3 times. The reaction was stirred at 100° C. overnight. To this mixture was added aqueous acetonitrile and then filtered, washed with aqueous AcCN, and dried to provide the product. LCMS (M+H)+: m/z=402.1

Step 3: 3-[3-(3-{[(methylamino)carbonyl]amino}phenyl)imidazo[1,2-b]pyridazin-7-yl]benzoic acid

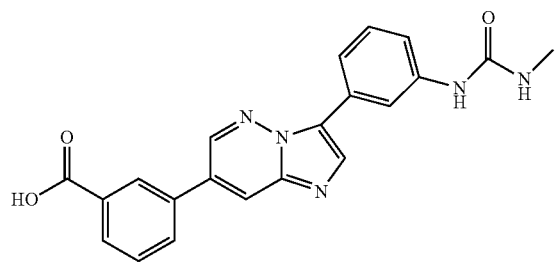 [SMILES: CNC(=O)Nc1cccc(-c2cnc3cc(-c4cccc(C(=O)O)c4)cnn23)c1]

Lithium hydroxide, monohydrate (89 mg, 2.1 mmol) was added to a mixture of methyl 3-[3-(3-{[(methylamino)carbonyl]amino}phenyl)imidazo[1,2-b]pyridazin-7-yl]benzoate (0.17 g, 0.43 mmol) in methanol (4.0 mL)/THF(2.0 mL)/water (1 mL) and then the reaction was stirred at r.t. for 4 h. The mixture was adjusted with conc. HCl to PH~3. The volatiles were removed under reduced pressure to provide the crude product which was directly used in the next step without further purification. LCMS (M+H)+: m/z=388.1

Step 4: N-(2-Fluorobenzyl)-3-[3-(3-{[(methylamino)carbonyl]amino}phenyl)imidazo[1,2-b]pyridazin-7-yl]benzamide 2-Fluoro-benzenemethanamine (0.06 mmol) was added to a solution of 3-[3-(3-{[(methylamino)carbonyl]amino}phenyl)imidazo[1,2-b]pyridazin-7-yl]benzoic acid (8.51 mg, 0.0220 mmol) and benzotriazol-1-yloxytris(dimethylamino)phosphonium hexafluorophosphate (14 mg, 0.033 mmol) in DMF (0.5 mL) at r.t. followed by adding triethylamine (20.0 µL, 0.143 mmol) and then the reaction was stirred for 2 h. The mixture was purified by RP-HPLC (pH=2) to afford the desired product as TFA salt. LCMS (M+H)+: m/z=495.2

Example 97

N-[1-(2-Fluorophenyl)ethyl]-3-[3-(3-{[(methylamino)carbonyl]amino}phenyl)imidazo[1,2-b]pyridazin-7-yl]benzamide

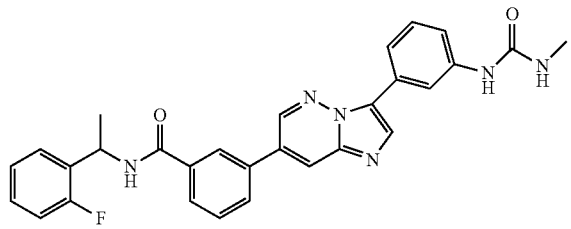 [SMILES: CNC(=O)Nc1cccc(-c2cnc3cc(-c4cccc(C(=O)NC(C)c5ccccc5F)c4)cnn23)c1]

This compound was prepared by using procedure analogous to those described for the synthesis of Example 96, Step 4 starting from 3-[3-(3-{[(methylamino)carbonyl]amino}phenyl)imidazo[1,2-b]pyridazin-7-yl]benzoic acid and 1-(2-fluorophenyl)ethanamine. LCMS (M+H)+: m/z=509.2

Example 98

N-Methyl-2-(4-{3-[3-({[(2,2,2-trifluoroethyl)amino]carbonyl}amino)phenyl]imidazo[1,2-b]pyridazin-7-yl}phenyl)propanamide

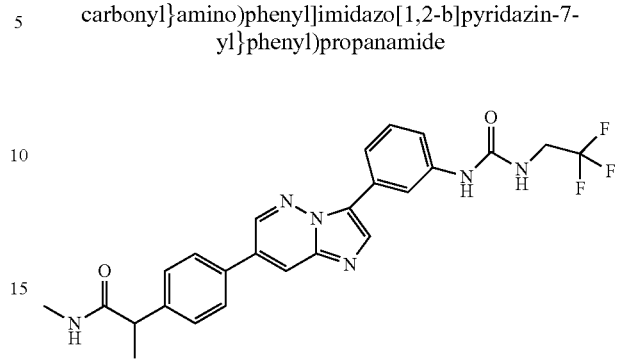

Step 1: ethyl 2-[4-(6-oxo-1,6-dihydropyridazin-4-yl)phenyl]propanoate

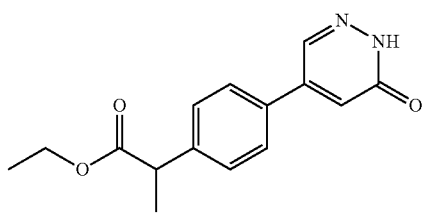 [SMILES: CCOC(=O)C(C)c1ccc(-c2cn[nH]c(=O)c2)cc1]

This compound was prepared by using procedure analogous to those described for the synthesis of Example 94, Step 1 starting from 5-chloropyridazin-3(4H)-one and ethyl 2-[4-(4,4,5,5-tetramethyl-1,3,2-dioxaborolan-2-yl)phenyl]propanoate (Example 14, Step 2). LCMS (M+H)+: m/z=273.1

Step 2: ethyl 2-[4-(6-chloropyridazin-4-yl)phenyl]propanoate

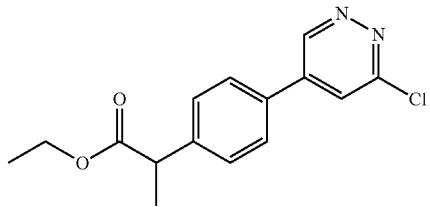 [SMILES: CCOC(=O)C(C)c1ccc(-c2cnnc(Cl)c2)cc1]

A mixture of ethyl 2-[4-(6-oxo-1,6-dihydropyridazin-4-yl)phenyl]propanoate (0.48 g, 1.7 mmol) in phosphoryl chloride (5.0 mL) and DMF (50 µL) was stirred at 100° C. for 3 h. The solvent was removed and the residue was diluted with methylene chloride, washed with saturated NaHCO3, water and brine, dried over Na2SO4, filtered and concentrated under reduced pressure. The residue was purified by flash chromatography on a silica gel column with ethyl acetate in methylene chloride (0-20%) to afford the desired product. LCMS (M+H)+: m/z=299.1

Step 3: ethyl 2-(4-{6-[(diphenylmethylene)amino]pyridazin-4-yl}phenyl)propanoate

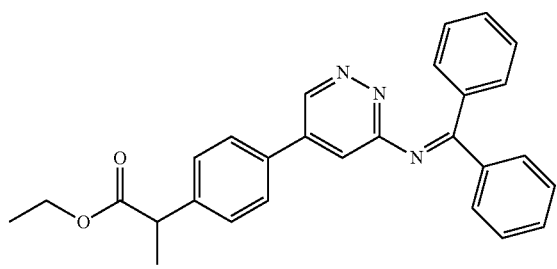 [SMILES: CCOC(=O)C(C)c1ccc(-c2cnnc(N=C(c3ccccc3)c3ccccc3)c2)cc1]

This compound was prepared by using procedure analogous to those described for the synthesis of Example 94, Step 3 starting from ethyl 2-[4-(6-chloropyridazin-4-yl)phenyl]propanoate. LCMS (M+H)+: m/z=436.2

Step 4: ethyl 2-[4-(6-aminopyridazin-4-yl)phenyl]propanoate

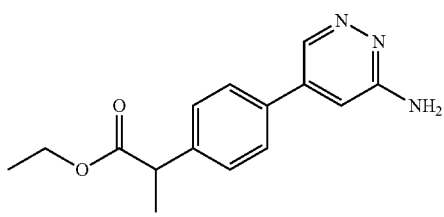 [SMILES: CCOC(=O)C(C)c1ccc(-c2cnnc(N)c2)cc1]

This compound was prepared by using procedure analogous to those described for the synthesis of Example 94, Step 4 starting from ethyl 2-(4-{6-[(diphenylmethylene)amino]pyridazin-4-yl}phenyl)propanoate. LCMS (M+H)+: m/z=272.1

Step 5: ethyl 2-(4-imidazo[1,2-b]pyridazin-7-ylphenyl)propanoate

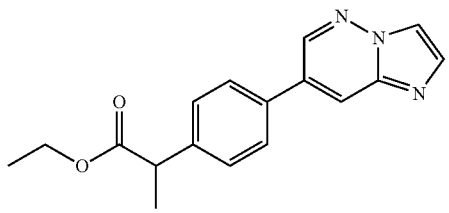 [SMILES: CCOC(=O)C(C)c1ccc(-c2cnn3ccnc3c2)cc1]

This compound was prepared by using procedure analogous to those described for the synthesis of Example 94, Step 5 starting from ethyl 2-[4-(6-aminopyridazin-4-yl)phenyl]propanoate. LCMS (M+H)+: m/z=296.0

Step 6: ethyl 2-[4-(3-iodoimidazo[1,2-b]pyridazin-7-yl)phenyl]propanoate

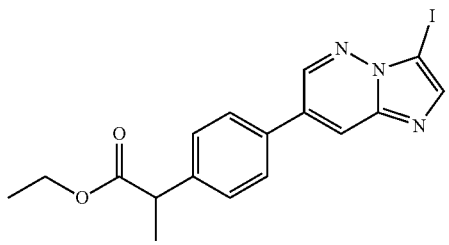 [SMILES: CCOC(=O)C(C)c1ccc(-c2cnn3c(I)cnc3c2)cc1]

NIS (200 mg, 0.88 mmol) was added to a mixture of methyl 4-imidazo[1,2-b]pyridazin-7-ylbenzoate (200.0 mg, 0.67 mmol) in DMF (1 mL) and then the reaction was stirred at r.t. for 20 h. The mixture was diluted with ethyl acetate and then was washed with saturated NaHCO₃, water and brine; dried over Na₂SO₄. After filtration the filtrate was concentrated under reduced pressure. The residue was purified by flash chromatography on a silica gel column with ethyl acetate in methylene chloride (0-20%) to afford the desired product (0.20 g). LCMS (M+H)+: m/z=421.9

Step 7: ethyl 2-(4-{3-[3-({[(2,2,2-trifluoroethyl)amino]carbonyl}amino)phenyl]imidazo[1,2-b]pyridazin-7-yl}phenyl)propanoate

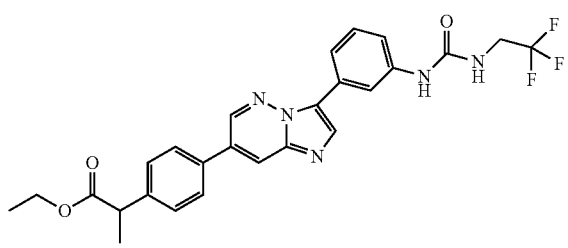 [SMILES: CCOC(=O)C(C)c1ccc(-c2cnn3c(-c4cccc(NC(=O)NCC(F)(F)F)c4)cnc3c2)cc1]

Dichloro(bis{di-tert-butyl[4-(dimethylamino)phenyl]phosphoranyl})palladium (12 mg, 0.017 mmol) was added to a mixture of ethyl 2-[4-(3-iodoimidazo[1,2-b]pyridazin-7-yl)phenyl]propanoate (0.24 g, 0.58 mmol), N-[3-(4,4,5,5-tetramethyl-1,3,2-dioxaborolan-2-yl)phenyl]-N'-(2,2,2-trifluoroethyl)urea (240 mg, 0.70 mmol), sodium carbonate (130 mg, 1.2 mmol) in 1,4-dioxane (5 mL) and water (0.5 mL) and then the reaction was vacuumed and refilled with nitrogen for 3 times. The reaction was stirred at 95° C. overnight. The mixture was diluted with ethyl acetate, washed with water and brine, dried over Na₂SO₄, filtered and concentrated under reduced pressure. The residue was purified by flash chromatography on a silica gel column with methanol in methylene chloride (0-10%) to afford the desired product. LCMS (M+H)+: m/z=512.1

Step 8: 2-(4-{3-[3-({[(2,2,2-trifluoroethyl)amino]carbonyl}amino)phenyl]imidazo[1,2-b]pyridazin-7-yl}phenyl)propanoic acid

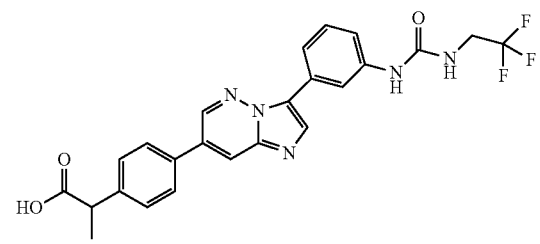 [SMILES: CC(C(=O)O)c1ccc(-c2cnn3c(-c4cccc(NC(=O)NCC(F)(F)F)c4)cnc3c2)cc1]

This compound was prepared by using procedure analogous to those described for the synthesis of Example 94, Step 8 starting from ethyl 2-(4-{3-[3-({[(2,2,2-trifluoroethyl)amino]carbonyl}amino)phenyl]imidazo[1,2-b]pyridazin-7-yl}phenyl)propanoate. LCMS (M+H)+: m/z=484.2

Step 9: N-methyl-2-(4-{3-[3-({[(2,2,2-trifluoroethyl)amino]carbonyl}amino)phenyl]imidazo[1,2-b]pyridazin-7-yl}phenyl)propanamide 2.0 M Methylamine in THF (0.2 mL, 0.4 mmol) was added to a solution of 2-(4-{3-[3-({[(2,2,2-trifluoroethyl)amino]carbonyl}amino)phenyl]imidazo[1,2-b]pyridazin-7-yl}phenyl)propanoic acid (10.0 mg, 0.0207 mmol) and benzotriazol-1-yloxytris(dimethylamino)phosphonium hexafluorophosphate (14 mg, 0.033 mmol) in DMF (0.5 mL) at r.t. followed by adding triethylamine (20.0 µL, 0.143 mmol) and then the reaction was stirred for 2 h. The mixture was purified by RP-HPLC (pH=2) to afford the desired product as TFA salt. (M+H)+: m/z=497.0

Example 99

N,N-Dimethyl-2-(4-{3-[3-({[(2,2,2-trifluoroethyl)amino]carbonyl}amino)phenyl]imidazo[1,2-b]pyridazin-7-yl}phenyl)propanamide

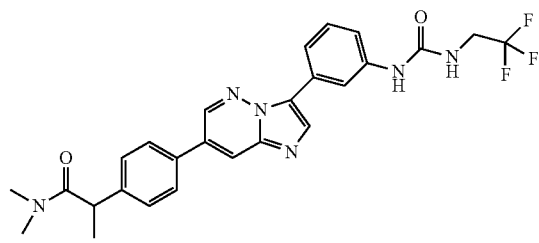 [SMILES: CC(C(=O)N(C)C)c1ccc(-c2cnn3c(-c4cccc(NC(=O)NCC(F)(F)F)c4)cnc3c2)cc1]

This compound was prepared by using procedure analogous to those described for the synthesis of Example 98, Step 9 starting from 2-(4-{3-[3-({[(2,2,2-trifluoroethyl)amino]-carbonyl}amino)phenyl]imidazo[1,2-b]pyridazin-7-yl}phenyl)propanoic acid and N,N-dimethylamine. LCMS (M+H)$^+$: m/z=511.2

Example 100

N-[(2S)-Tetrahydrofuran-2-ylmethyl]-2-(4-{3-[3-({[(2,2,2-trifluoroethyl)amino]carbonyl}amino)phenyl]imidazo[1,2-b]pyridazin-7-yl}phenyl)propanamide

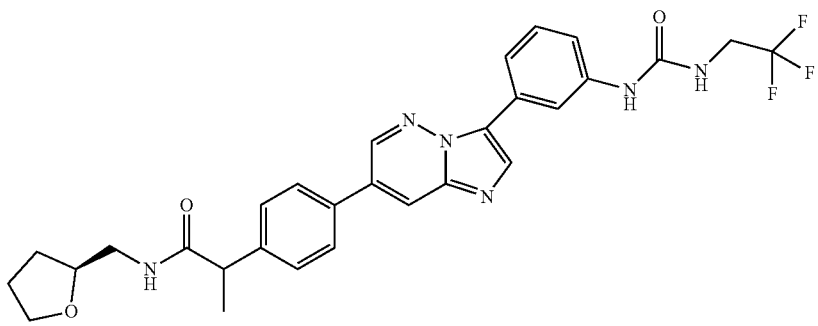 [SMILES: CC(C(=O)NC[C@@H]1CCCO1)c1ccc(-c2cnn3c(-c4cccc(NC(=O)NCC(F)(F)F)c4)cnc3c2)cc1]

This compound was prepared by using procedure analogous to those described for the synthesis of Example 98, Step 9 starting from 2-(4-{3-[3-({[(2,2,2-trifluoroethyl)amino]carbonyl}amino)phenyl]imidazo[1,2-b]pyridazin-7-yl}phenyl)propanoic acid and 1-[(2S)-tetrahydrofuran-2-yl]methanamine. LCMS (M+H)$^+$: m/z=567.3

Example 101

N-{3-[7-(4-{2-[(3S)-3-Hydroxypyrrolidin-1-yl]-1-methyl-2-oxoethyl}phenyl)imidazo[1,2-b]pyridazin-3-yl]phenyl}-N'-(2,2,2-trifluoroethyl)urea

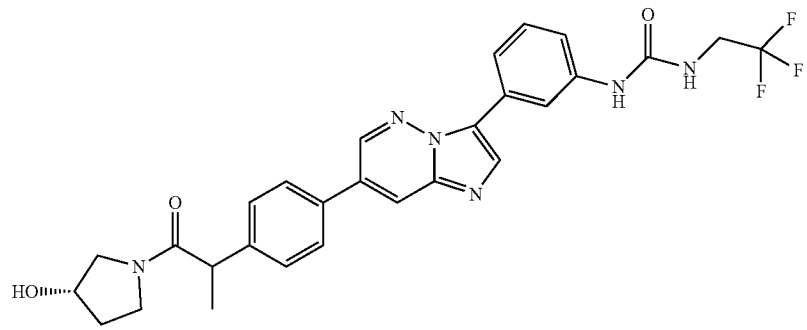 [SMILES: CC(C(=O)N1CC[C@H](O)C1)c1ccc(-c2cnn3c(-c4cccc(NC(=O)NCC(F)(F)F)c4)cnc3c2)cc1]

This compound was prepared by using procedure analogous to those described for the synthesis of Example 98, Step 9 starting from 2-(4-{3-[3-({[(2,2,2-trifluoroethyl)amino]carbonyl}amino)phenyl]imidazo[1,2-b]pyridazin-7-yl}phenyl)propanoic acid and (S)-3-hydroxypyrrolidine. LCMS (M+H)$^+$: m/z=553.3

Example 102

N-[3-(7-{4-[2-(4-Hydroxypiperidin-1-yl)-1-methyl-2-oxoethyl]phenyl}imidazo[1,2-b]pyridazin-3-yl)phenyl]-N'-(2,2,2-trifluoroethyl)urea

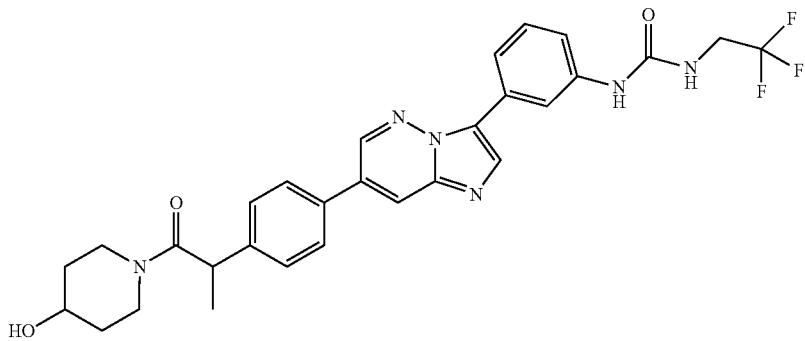 [SMILES: CC(C(=O)N1CCC(O)CC1)c1ccc(-c2cnn3c(-c4cccc(NC(=O)NCC(F)(F)F)c4)cnc3c2)cc1]

This compound was prepared by using procedure analogous to those described for the synthesis of Example 98, Step 9 starting from 2-(4-{3-[3-({[(2,2,2-trifluoroethyl)amino]carbonyl}amino)phenyl]imidazo[1,2-b]pyridazin-7-yl}phenyl)propanoic acid and 4-hydroxypiperidine. LCMS (M+H)$^+$: m/z=567.3

Example 103

N-[(3R)-Tetrahydrofuran-3-yl]-2-(4-{3-[3-({[(2,2,2-trifluoroethyl)amino]carbonyl}amino)phenyl]imidazo[1,2-b]pyridazin-7-yl}phenyl)propanamide

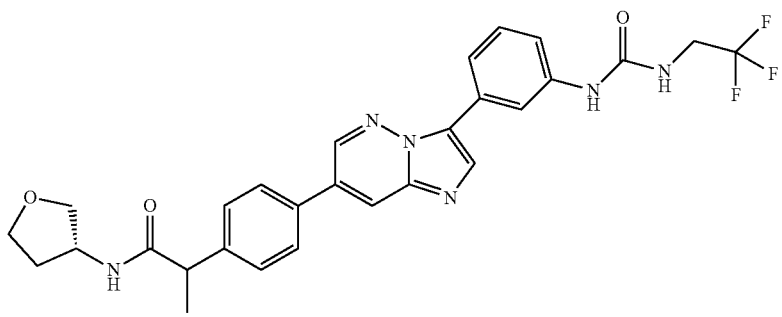 [SMILES: CC(C(=O)N[C@@H]1CCOC1)c1ccc(-c2cnn3c(-c4cccc(NC(=O)NCC(F)(F)F)c4)cnc3c2)cc1]

This compound was prepared by using procedure analogous to those described for the synthesis of Example 98, Step 9 starting from 2-(4-{3-[3-({[(2,2,2-trifluoroethyl)amino]carbonyl}amino)phenyl]imidazo[1,2-b]pyridazin-7-yl}phenyl)propanoic acid and (3R)-tetrahydrofuran-3-amine 4-methylbenzenesulfonate (Fluka, Cat. No. 09440). LCMS (M+H)$^+$: m/z=553.2.

Example 104

N-[3-(7-{4-[2-(3-Hydroxyazetidin-1-yl)-1-methyl-2-oxoethyl)]phenyl}imidazo[1,2-b]pyridazin-3-yl)phenyl]-N'-(2,2,2-trifluoroethyl)urea

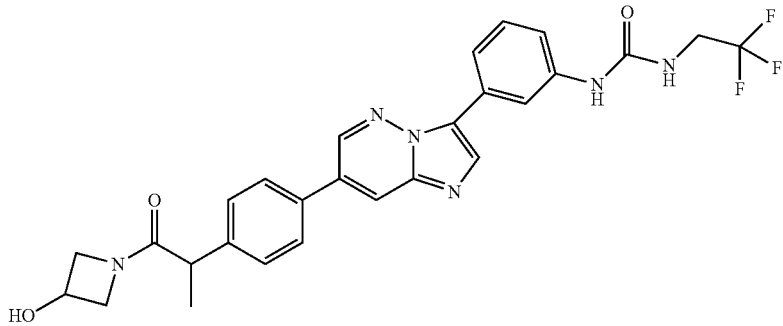 [SMILES: CC(C(=O)N1CC(O)C1)c1ccc(-c2cnn3c(-c4cccc(NC(=O)NCC(F)(F)F)c4)cnc3c2)cc1]

This compound was prepared by using procedure analogous to those described for the synthesis of Example 98, Step 9 starting from 2-(4-{3-[3-({[(2,2,2-trifluoroethyl)amino]carbonyl}amino)phenyl]imidazo[1,2-b]pyridazin-7-yl}phenyl)propanoic acid and azetidin-3-ol hydrochloride (Oakwood, Cat. No. 013898). LCMS (M+H)$^+$: m/z=539.3

Example 105

N-(3-{7-[4-(1-Methyl-2-morpholin-4-yl-2-oxoethyl)phenyl]imidazo[1,2-b]pyridazin-3-yl}phenyl)-N'-(2,2,2-trifluoroethyl)urea

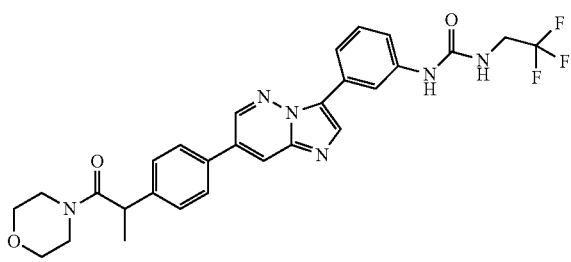 [SMILES: CC(C(=O)N1CCOCC1)c1ccc(-c2cnn3c(-c4cccc(NC(=O)NCC(F)(F)F)c4)cnc3c2)cc1]

This compound was prepared by using procedure analogous to those described for the synthesis of Example 98, Step 9 starting from 2-(4-{3-[3-({[(2,2,2-trifluoroethyl)amino]carbonyl}amino)phenyl]imidazo[1,2-b]pyridazin-7-yl}phenyl)propanoic acid and morpholine. LCMS (M+H)$^+$: m/z=553.3

Example 106

N-{3-[7-(4-{2-[(2S)-2-(Hydroxymethyl)pyrrolidin-1-yl]-1-methyl-2-oxoethyl}phenyl)imidazo[1,2-b]pyridazin-3-yl]phenyl}-N'-(2,2,2-trifluoroethyl)urea

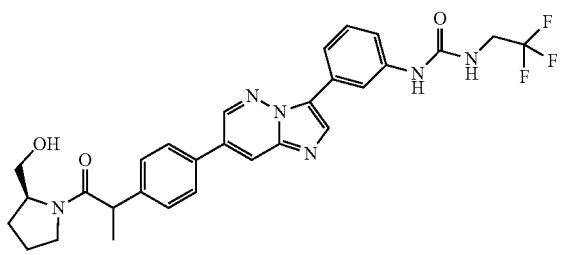 [SMILES: CC(C(=O)N1CCC[C@H]1CO)c1ccc(-c2cnn3c(-c4cccc(NC(=O)NCC(F)(F)F)c4)cnc3c2)cc1]

This compound was prepared by using procedure analogous to those described for the synthesis of Example 98, Step 9 starting from 2-(4-{3-[3-({[(2,2,2-trifluoroethyl)amino]carbonyl}amino)phenyl]imidazo[1,2-b]pyridazin-7-yl}phenyl)propanoic acid and (2S)-pyrrolidin-2-ylmethanol. LCMS (M+H)$^+$: m/z=567.3

Example 107

N-(2-Morpholin-4-ylethyl)-2-(4-{3-[3-({[(2,2,2-trifluoroethyl)amino]carbonyl}amino)phenyl]imidazo[1,2-b]pyridazin-7-yl}phenyl)propanamide

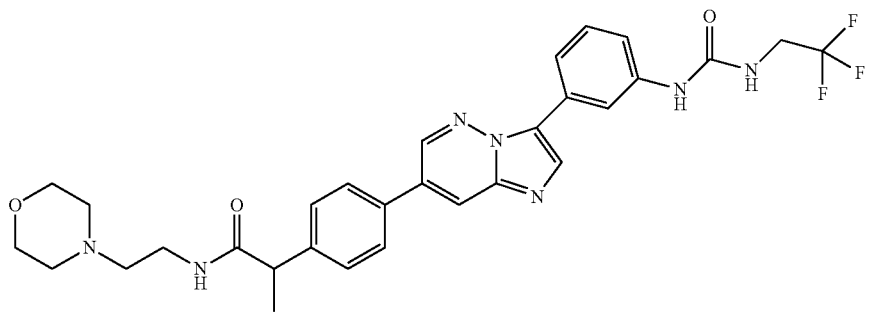 [SMILES: CC(C(=O)NCCN1CCOCC1)c1ccc(-c2cnn3c(-c4cccc(NC(=O)NCC(F)(F)F)c4)cnc3c2)cc1]

This compound was prepared by using procedure analogous to those described for the synthesis of Example 98, Step 9 starting from 2-(4-{3-[3-({[(2,2,2-trifluoroethyl)amino]carbonyl}amino)phenyl]imidazo[1,2-b]pyridazin-7-yl}phenyl)propanoic acid and N-(2-aminoethyl)morpholine. LCMS (M+H)$^+$: m/z=596.3.

Example A

FGFR3 Enzymatic Assay The inhibitor potency of compounds of the invention was measured in an enzyme assay that measures peptide phosphorylation using FRET measurements to detect product formation. Inhibitors were serially diluted in DMSO and a volume of 0.5 μL was transferred to the wells of a 384-well plate. A 10 μL volume of FGFR3 enzyme (Millipore) diluted in assay buffer (50 mM HEPES, 10 mM MgCl$_2$, 1 mM EGTA, 0.01% Tween-20, 5 mM DTT, pH 7.5) was added to the plate and pre-incubated for 5-10 minutes. Appropriate controls (enzyme blank and enzyme with no inhibitor) were included on the plate. The assay was initiated by the addition of a 10 μL solution containing biotinylated peptide and ATP (final concentrations of 500 nM and 140 μM respectively) in assay buffer to the wells. The plate was incubated at 25° C. for 1 hr. The reactions were ended with the addition of 10 μL/well of quench solution (50 mM Tris, 150 mM NaCl, 0.5 mg/ml BSA, pH 7.8; added fresh 30 mM EDTA and Perkin Elmer Lance Reagents for HTRF at 3.75 nM Eu-antibody PY20 and 180 nM APC-Streptavidin). The plate was allowed to equilibrate for ~1 hr before scanning the wells on a PheraStar plate reader.

GraphPad prism3 was used to analyze the data. The IC$_{50}$ values were derived by fitting the data to the equation for a sigmoidal dose-response with a variable slope. Y=Bottom+(Top-Bottom)/(1+10^(Log IC50-X)*HillSlope)) where X is the logarithm of concentration and Y is the response.

The compounds of the invention were found to be inhibitors of FGFR3 according to the above-described assay. IC$_{50}$ data is proved below in Table 1. The symbol "+" indicates an IC$_{50}$ less than 10 nM, the symbol "++" indicates an IC$_{50}$ of 10 to 25 nM, and the symbol "+++" indicates an IC$_{50}$ greater than 25 nM.

TABLE 1

| Ex. No. | IC50 (nM) |
| --- | --- |
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | + |
| 13 | + |
| 14 | + |
| 15 | + |
| 16 | + |
| 17 | + |
| 18 | + |
| 19 | + |
| 20 | + |
| 21 | + |
| 22 | + |
| 23 | + |
| 24 | + |

TABLE 1-continued

| Ex. No. | IC50 (nM) |
| --- | --- |
| 25 | + |
| 26 | + |
| 27 | + |
| 28 | + |
| 29 | + |
| 30 | + |
| 31 | + |
| 32 | + |
| 33 | + |
| 34 | + |
| 35 | + |
| 36 | + |
| 37 | + |
| 38 | + |
| 39 | + |
| 40 | + |
| 41 | + |
| 42 | + |
| 43 | + |
| 44 | + |
| 45 | + |
| 46 | + |
| 47 | + |
| 48 | + |
| 49 | + |
| 50 | + |
| 51 | ++ |
| 52 | ++ |
| 53 | + |
| 54 | + |
| 55 | + |
| 56 | + |
| 57 | + |
| 58 | + |
| 59 | + |
| 60 | + |
| 61 | + |
| 62 | + |
| 63 | + |
| 64 | + |
| 65 | + |
| 66 | + |
| 67 | + |
| 68 | + |
| 69 | + |
| 70 | + |
| 71 | + |
| 72 | + |
| 73 | + |
| 74 | + |
| 75 | + |
| 76 | + |
| 77 | + |
| 78 | + |
| 79 | + |
| 80 | + |
| 81 | + |
| 82 | + |
| 83 | ++ |
| 84 | + |
| 85 | + |
| 86 | + |
| 87 | + |
| 88 | + |
| 89 | + |
| 90 | + |
| 91 | + |
| 92 | + |
| 93 | + |
| 94 | ++ |
| 95 | ++ |
| 96 | +++ |
| 97 | +++ |
| 98 | + |
| 99 | + |
| 100 | + |
| 101 | + |
| 102 | + |

TABLE 1-continued

| Ex. No. | IC50 (nM) |
|---|---|
| 103 | + |
| 104 | + |
| 105 | + |
| 106 | + |
| 107 | + |

Example B

Cell Proliferation/Survival Assays

A recombinant cell line over-expressing human FGFR3 was developed by stable transfection of the mouse pro-B Ba/F$_3$ cells (obtained from the Deutsche Sammlung von Mikroorganismen und Zellkulturen) with a plasmid encoding the full length human FGFR3. Cells were sequentially selected for puromycin resistance and proliferation in the presence of heparin and FGF1. A single cell clone was isolated and characterized for functional expression of FGFR3. This Ba/F3-FGFR3 clone can be used in cell proliferation assays, and compounds are screened for their ability to inhibit cell proliferation/survival. The Ba/F3-FGFR3 cells are seeded into 96 well, black cell culture plates at 3500 cells/well in RPMI1640 media containing 2% FBS, 20 μg/mL Heparin and 5 ng/mL FGF1. The cells are treated with 10 μL of 10× concentrations of serially diluted compounds (diluted with medium lacking serum from 5 mM DSMO dots) to a final volume of 100 μL/well. After 72 hour incubation, 100 μL of Cell Titer Glo® reagent (Promega, # G7571) that measures cellular ATP levels is added to each well. After a 20 minute incubation with shaking, the luminescence is read on a Packard TopCount instrument. The luminescent readings are converted to percent inhibition relative to DMSO treated control wells, and the IC$_{50}$ values are calculated with the GraphPad Prism software. Compounds having an IC$_{50}$ of 10 μM or less are considered active. Other non-recombinant cancer cell lines representing a variety of tumor types including KMS-11 (multiple myeloma), RT112 (bladder cancer), KatoIII (gastric cancer), and KG-1 (leukemia) are used in similar proliferation assays.

Example C

Cell-Based FGFR Phosphorylation Assays

The inhibitory effect of compounds on FGFR phosphorylation in relevant cell lines (Ba/F3-FGFR3, KMS-11, RT112, KatoIII, KG-1, SNU-16 cancer cell lines and HUVEC cell line) can be assessed using immunoblotting analysis and ELISA-based FGFR phosphorylation assays. Cells are starved in media with reduced serum (0.5%) and no FGF1 for 4 to 48 h depending upon the cell line then treated with various concentrations of individual inhibitors for 1 hour. For some cell lines, such as Ba/F3-FGFR3 and KMS-11, cells are stimulated with Heparin (20 ug/mL) and FGF1 (10 ng/mL) for 10 min. Whole cell protein extracts are prepared by incubation in lysis buffer with protease and phosphatase inhibitors [50 mM HEPES (pH 7.5), 150 mM NaCl, 1.5 mM MgCl$_2$, 10% Glycerol, 1% Triton X-100, 1 mM sodium orthovanadate, 1 mM sodium fluoride, aprotinin (2 μg/mL), leupeptin (2 μg/mL), pepstatin A (2 μg/mL), and phenylmethylsulfonyl fluoride (1 mM)] at 4° C. Protein extracts are cleared of cellular debris by centrifugation at 14,000×g for 10 minutes and quantified using the BCA (bicinchoninic acid) microplate assay reagent (Thermo Scientific).

Phosphorylation of FGFR receptor in protein extracts can be determined by immunoblotting. Equal amounts of protein are resolved by electrophoresis using 4-12% MOPS-PAGE gels and electroblotted to a nitrocellulose (or PVDF) membrane. Relevant antibodies are obtained from commercial sources: Total FGFR1 (Cell Signaling Technologies #3472); Total FGFR2 (DYC-684); Total FGFR3 (Santa Cruz #123); phospho-FGFR3 pY724 (Santa Cruz #33041); phospho-FGFR pY653/654 (Cell Signaling Technologies #3471); phospho-FGFR2 (RnD Systems The membrane is blocked in PBS containing 4% milk and 0.1% Tween-20 for 1 hour, and then incubated with primary antibodies in blocking solution for overnight at 4° C. After 3 washes, the membrane is incubated with appropriate horseradish-conjugated secondary antibodies for 1 hour. After final wash, the blot is incubated with chemiluminescence detection reagent for 5 minutes and exposed to X-ray film or a chemiluminescence imager for quantification. The images are normalized with total FGFR, and IC$_{50}$ values are estimated. Compounds having an IC$_{50}$ of 1 μM or less are considered active.

Example D

Cell-Based Signaling Assays

Activation of FGFR leads to phosphorylation of Erk proteins. Detection of pErk can be monitored using the Cellu'Erk HTRF (Homogeneous Time Resolved Flurorescence) Assay (CisBio) according to the manufacturer's protocol. KMS-11 cells are seeded into 96-well plates at 40,000 cells/well in RPMI medium with 0.25% FBS and starved for 2 days. The medium is aspirated and cells are treated with 30 μL of 1× concentrations of serially diluted compounds (diluted with medium lacking serum from 5 mM DSMO dots) to a final volume of 30 μL/well and incubated for 45 min at room temperature. Cells are stimulated by addition of 10 μL of Heparin (100 ug/mL) and FGF1 (50 ng/mL) to each well and incubated for 10 min at room temperature. After lysis, an aliquot of cell extract is transferred into 384-well low volume plates, and 4 μL of detection reagents are added followed by incubation for 3 hr at room temperature. The plates are read on a PheraStar instrument with settings for HTRF. The normalized fluorescence readings are converted to percent inhibition relative to DMSO treated control wells, and the IC$_{50}$ values are calculated using the GraphPad Prism software. Compounds having an IC$_{50}$ of 1 μM or less are considered active.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating cancer in a patient comprising administering to said patient a therapeutically effective amount of a compound of Formula IIa:

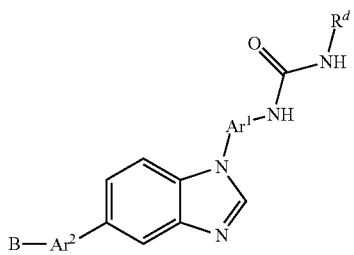

Iia or a pharmaceutically acceptable salt thereof, wherein:
Ar$^1$ is aryl, heteroaryl, cycloalkyl, or heterocycloalkyl, each optionally substituted by 1, 2, 3, or 4 independently selected R$^{A1}$ groups;
Ar$^2$ is aryl, heteroaryl, cycloalkyl, or heterocycloalkyl, each optionally substituted by 1, 2, 3, or 4 independently selected R$^{A2}$ groups;
B is:
(i) —(CR$^3$R$^4$)$_{m1}$—(CR$^1$R$^2$)—(CR$^3$R$^4$)$_{m2}$—X;
(ii) -L$^1$-(CR$^3$R$^4$)$_n$-Cy$^1$;
(iii) -Cy$^2$-(L$^2$)$_q$-(CR$^3$R$^4$)$_p$-Cy$^3$; or
(iv) -Cy$^4$-L$^3$-Y;
L$^1$ is C(O)NR, C(O)O, S(O)$_2$NR, NRC(O)NR, NRC(S)NR, S, or S(O);
L$^2$ and L$^3$ are each independently selected from CO, C(O)O, C(O)NR, S(O)$_2$NR, NR, NRC(O)NR, NRC(S)NR, O, S, S(O), and S(O)$_2$;
X is Cy$^5$, CN, C(O)NR$^5$R$^6$, NR$^5$C(O)R$^7$, NR$^5$S(O)$_2$R$^7$, NR$^5$S(O)$_2$NR$^5$R$^6$, NR$^5$C(O)OR$^8$, or S(O)$_2$NR$^5$R$^6$;
Y is:
(1) aryl, heteroaryl, or heterocycloalkyl, each optionally substituted by 1, 2, 3, 4, or 5 independently selected R$^{B1}$ groups;
(2) C$_{3-7}$ cycloalkyl substituted by 1, 2, 3, 4, or 5 independently selected R$^{B2}$ groups; or
(3) C$_{1-6}$ alkyl or C$_{1-6}$ haloalkyl, each substituted by 1, 2, 3, 4, or 5 independently selected R$^X$ groups;
Cy$^1$, Cy$^2$, Cy$^3$, Cy$^4$, and Cy$^5$ are each independently selected from aryl, heteroaryl, cycloalkyl, and heterocycloalkyl, each of which is optionally substituted by 1, 2, 3, 4, or 5 independently selected R$^{Cy}$ groups;
R is independently selected from H and C$_{1-4}$ alkyl;
R$^1$ is halo, cyano, hydroxy, C$_{1-4}$ alkyl, C$_{2-4}$ cyanoalkyl, C$_{2-4}$ alkoxyalkyl, C$_{1-4}$ haloalkyl, aryl, heteroaryl, cycloalkyl, or heterocycloalkyl, wherein said aryl, heteroaryl, cycloalkyl, or heterocycloalkyl is optionally substituted by 1, 2, 3, 4, or 5 independently selected R$^D$ groups;
R$^2$ and R$^4$ are each independently selected from H, halo, hydroxy, C$_{1-4}$ alkyl, C$_{2-4}$ cyanoalkyl, C$_{2-4}$ alkoxyalkyl, and C$_{1-4}$ haloalkyl;
R$^3$ is independently selected from H, halo, cyano, hydroxy, C$_{1-4}$ alkyl, C$_{2-4}$ cyanoalkyl, C$_{2-4}$ alkoxyalkyl, C$_{1-4}$ haloalkyl, aryl, heteroaryl, cycloalkyl, and heterocycloalkyl, wherein said aryl, heteroaryl, cycloalkyl, or heterocycloalkyl is optionally substituted by 1, 2, 3, 4, or 5 independently selected R$^D$ groups;
R$^5$ is independently selected from H, C$_{1-4}$ alkyl, C$_{2-4}$ cyanoalkyl, C$_{2-4}$ alkoxyalkyl, and C$_{1-4}$ haloalkyl;
R$^6$, R$^7$, and R$^8$ are each independently selected from H, C$_{1-4}$ alkyl, aryl, heteroaryl, cycloalkyl, and heterocycloalkyl, wherein said C$_{1-4}$ alkyl, aryl, heteroaryl, cycloalkyl, or heterocycloalkyl is optionally substituted with 1, 2, 3, 4, 5, or 6 independently selected R$^D$ groups;
or R$^5$ and R$^6$ together with the N atom to which they are attached form a 4-, 5-, 6-, or 7-membered heterocycloalkyl ring optionally substituted by 1, 2, 3, 4, or 5 independently selected R$^D$ groups;
each R$^{A1}$ is independently selected from halo, C$_{1-6}$ alkyl, C$_{2-6}$ alkenyl, C$_{2-6}$ alkynyl, C$_{1-6}$ haloalkyl, halosulfanyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said C$_{1-6}$ alkyl, C$_{2-6}$ alkenyl, C$_{2-6}$ alkynyl, C$_{1-6}$ haloalkyl, aryl, cycloalkyl, heteroaryl, and heterocycloalkyl are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;
each R$^{A2}$ is independently selected from halo, C$_{1-4}$ alkyl, C$_{2-4}$ alkenyl, C$_{2-4}$ alkynyl, C$_{1-4}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, C(=NR$^{e1}$)R$^{b1}$, C(=NR$^{e1}$)NR$^{c1}$R$^{d1}$, NR$^{c1}$C(=NR$^{e1}$)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$; wherein said C$_{1-4}$ alkyl, C$_{2-4}$ alkenyl, C$_{2-4}$ alkynyl, C$_{1-4}$ haloalkyl, are each optionally substituted with 1, 2, or 3 substituents independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;
each R$^{B1}$, R$^{B2}$, R$^{Cy}$, and R$^D$ is independently selected from halo, C$_{1-6}$ alkyl, C$_{2-6}$ alkenyl, C$_{2-6}$ alkynyl, C$_{1-6}$ haloalkyl, halosulfanyl, aryl, cycloalkyl, heteroaryl, heterocycloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^{e2}$)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$; wherein said C$_{1-6}$ alkyl, C$_{2-6}$ alkenyl, C$_{2-6}$ alkynyl, C$_{1-6}$ haloalkyl, aryl, cycloalkyl, heteroaryl, and heterocycloalkyl are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C (O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$;

- each R$^X$ is independently selected from C$_{1-6}$ alkyl, C$_{2-6}$ alkenyl, C$_{2-6}$ alkynyl, aryl, cycloalkyl, heteroaryl, heterocycloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NR$^{e3}$)NR$^{c3}$R$^{d3}$, NR$^{c3}$C(=NR$^{e3}$)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$; wherein said C$_{1-6}$ alkyl, C$_{2-6}$ alkenyl, C$_{2-6}$ alkynyl, C$_{1-6}$ haloalkyl, aryl, cycloalkyl, heteroaryl, and heterocycloalkyl are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$;

- each R$^a$, R$^b$, R$^c$, and R$^d$ is independently selected from H, C$_{1-6}$ alkyl, C$_{1-4}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from C$_{1-4}$ alkyl, C$_{1-4}$ haloalkyl, halo, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{f4}$)NR$^{c4}$R$^{d4}$, NR$^{c4}$C(=NR$^{f4}$)NR$^{c4}$R$^{d4}$, S(O)R$^{b4}$, S(O)NR$^{c4}$R$^{d4}$, S(O)$_2$R$^{b4}$, NR$^{c4}$S(O)$_2$R$^{b4}$, NR$^{c4}$S(O)$_2$NR$^{c4}$R$^{d4}$, and S(O)$_2$NR$^{c4}$R$^{d4}$;

- or any R$^c$ and R$^d$ together with the N atom to which they are attached form a 3-, 4-, 5-, 6-, or 7-membered heterocycloalkyl group or a heteroaryl group, each optionally substituted with 1, 2, or 3 substituents independently selected from C$_{1-6}$ alkyl, C$_{1-6}$ haloalkyl, halo, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{f4}$)NR$^{c4}$R$^{d4}$, NR$^{c4}$C(=NR$^{f4}$)NR$^{c4}$R$^{d4}$, S(O)R$^{b4}$, S(O)NR$^{c4}$R$^{d4}$, S(O)$_2$R$^{b4}$, NR$^{c4}$S(O)$_2$R$^{b4}$, NR$^{c4}$S(O)$_2$NR$^{c4}$R$^{d4}$, and S(O)$_2$NR$^{c4}$R$^{d4}$, wherein said C$_{1-6}$ alkyl is optionally substituted by 1, 2, or 3 substituents independently selected from halo, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{f4}$)NR$^{c4}$R$^{d4}$, NR$^{c4}$C(=NR$^{f4}$)NR$^{c4}$R$^{d4}$, S(O)R$^{b4}$, S(O)NR$^{c4}$R$^{d4}$, S(O)$_2$R$^{b4}$, NR$^{c4}$S(O)$_2$R$^{b4}$, NR$^{c4}$S(O)$_2$NR$^{c4}$R$^{d4}$, and S(O)$_2$NR$^{c4}$R$^{d4}$;

- each R$^e$ and R$^f$ is independently selected from H, C$_{1-4}$ alkyl, CN, OR$^{a4}$, SR$^{b4}$, S(O)$_2$R$^{b4}$, C(O)R$^{b4}$, S(O)$_2$NR$^{c4}$R$^{d4}$, and C(O)NR$^{c4}$R$^{d4}$;

- each R$^{a1}$, R$^{b1}$, R$^{c1}$, and R$^{d1}$ is independently selected from H, C$_{1-4}$ alkyl, C$_{2-4}$ alkenyl, C$_{2-4}$ alkynyl, aryl, cycloalkyl, heteroaryl, and heterocycloalkyl, wherein said C$_{1-4}$ alkyl, C$_{2-4}$ alkenyl, C$_{2-4}$ alkynyl, aryl, cycloalkyl, heteroaryl, or heterocycloalkyl is optionally substituted with 1, 2, or 3 substituents independently selected from C$_{1-6}$ alkyl, C$_{1-6}$ haloalkyl, halo, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{f4}$)NR$^{c4}$R$^{d4}$, NR$^{c4}$C(=NR$^{f4}$)NR$^{c4}$R$^{d4}$, S(O)R$^{b4}$, S(O)NR$^{c4}$R$^{d4}$, S(O)$_2$R$^{b4}$, NR$^{c4}$S(O)$_2$R$^{b4}$, NR$^{c4}$S(O)$_2$NR$^{c4}$R$^{d4}$, and S(O)$_2$NR$^{c4}$R$^{d4}$;

- or any R$^{c1}$ and R$^{d1}$ together with the N atom to which they are attached form a 3-, 4-, 5-, 6-, or 7-membered heterocycloalkyl group or a heteroaryl group, each optionally substituted with 1, 2, or 3 substituents independently selected from C$_{1-6}$ alkyl, C$_{1-6}$ haloalkyl, halo, CN, OR$^{a4}$SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{f4}$)NR$^{c4}$R$^{d4}$, NR$^{c4}$C(=NR$^{f4}$)NR$^{c4}$R$^{d4}$, S(O)R$^{b4}$, S(O)NR$^{c4}$R$^{d4}$, S(O)$_2$R$^{b4}$, NR$^{c4}$S(O)$_2$R$^{b4}$, NR$^{c4}$S(O)$_2$NR$^{c4}$R$^{d4}$, and S(O)$_2$NR$^{c4}$R$^{d4}$;

- each R$^{e1}$ and R$^{f1}$ is independently selected from H, C$_{1-4}$ alkyl, CN, OR$^{a4}$, SR$^{b4}$, S(O)$_2$R$^{b4}$, C(O)R$^{b4}$, S(O)$_2$NR$^{c4}$R$^{d4}$, and C(O)NR$^{c4}$R$^{d4}$;

- each R$^{a2}$, R$^{b2}$, R$^{c2}$, and R$^{d2}$ is independently selected from H, C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein said C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from C$_{1-4}$ alkyl, C$_{1-4}$ haloalkyl, halo, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{f4}$)NR$^{c4}$R$^{d4}$, NR$^{c4}$C(=NR$^{f4}$)NR$^{c4}$R$^{d4}$, S(O)R$^{b4}$, S(O)NR$^{c4}$R$^{d4}$, S(O)$_2$R$^{b4}$, NR$^{c4}$S(O)$_2$R$^{b4}$, NR$^{c4}$S(O)$_2$NR$^{c4}$R$^{d4}$, and S(O)$_2$NR$^{c4}$R$^{d4}$;

- or any R$^{c2}$ and R$^{d2}$ together with the N atom to which they are attached form a 3-, 4-, 5-, 6-, or 7-membered heterocycloalkyl group or a heteroaryl group, each optionally substituted with 1, 2, or 3 substituents independently selected from C$_{1-6}$ alkyl, C$_{1-6}$ haloalkyl, halo, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{f4}$)NR$^{c4}$R$^{d4}$, NR$^{c4}$C(=NR$^{f4}$)NR$^{c4}$R$^{d4}$, S(O)R$^{b4}$, S(O)NR$^{c4}$R$^{d4}$, S(O)$_2$R$^{b4}$, NR$^{c4}$S(O)$_2$R$^{b4}$, NR$^{c4}$S(O)$_2$NR$^{c4}$R$^{d4}$, and S(O)$_2$NR$^{c4}$R$^{d4}$, wherein said C$_{1-6}$ alkyl is optionally substituted by 1, 2, or 3 substituents independently selected from halo, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{f4}$)NR$^{c4}$R$^{d4}$, NR$^{c4}$C(=NR$^{f4}$)NR$^{c4}$R$^{d4}$, S(O)R$^{b4}$, S(O)NR$^{c4}$R$^{d4}$, S(O)$_2$R$^{b4}$, NR$^{c4}$S(O)$_2$R$^{b4}$, NR$^{c4}$S(O)$_2$NR$^{c4}$R$^{d4}$, and S(O)$_2$NR$^{c4}$R$^{d4}$;

- each R$^{e2}$ and R$^{f2}$ is independently selected from H, C$_{1-4}$ alkyl, CN, OR$^{a4}$, SR$^{b4}$, S(O)$_2$R$^{b4}$, C(O)R$^{b4}$, S(O)$_2$NR$^{c4}$R$^{d4}$, and C(O)NR$^{c4}$R$^{d4}$;

- each R$^{a3}$, R$^{b3}$, R$^{c3}$, and R$^{d3}$ is independently selected from H, C$_{1-6}$ alkyl, C$_{2-6}$ alkenyl, and C$_{2-6}$ alkynyl, wherein said $C_{1-6}$ alkyl, $C_{2-6}$ alkenyl, or $C_{2-6}$ alkynyl, is optionally substituted with 1, 2, 3, 4, or 5 substituents independently selected from $C_{1-4}$ alkyl, $C_{1-4}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{f4})NR^{c4}R^{d4}$, $NR^{c4}C(=NR^{f4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

or any $R^{c3}$ and $R^{d3}$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{f4})NR^{c4}R^{d4}$, $NR^{c4}C(=NR^{f4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

each $R^{e3}$ and $R^{f3}$ is independently selected from H, $C_{1-4}$ alkyl, CN, $OR^{a4}$, $SR^{b4}$, $S(O)_2R^{b4}$, $C(O)R^{b4}$, $S(O)_2NR^{c4}R^{d4}$, and $C(O)NR^{c4}R^{d4}$;

each $R^{a4}$, $R^{b4}$, $R^{c4}$, and $R^{d4}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{1-4}$ haloalkyl, $C_{2-4}$ alkenyl, or $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

or any $R^{c4}$ and $R^{d4}$ together with the N atom to which they are attached form a 3-, 4-, 5-, 6-, or 7-membered heterocycloalkyl group or heteroaryl group, each optionally substituted with 1, 2, or 3 substituents independently selected from OH, CN, amino, halo, $C_{1-6}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

each $R^{e4}$ and $R^{f4}$ is independently selected from H, $C_{1-4}$ alkyl, and CN;

a is 0 or 1;

m1 is 0, 1, 2, 3, or 4;

m2 is 0, 1, 2, 3, or 4;

n is 1, 2, 3, 4, 5, or 6; and p is 1, 2, 3, 4, 5, or 6 wherein aryl refers to a $C_{6-10}$ aromatic cyclic hydrocarbon group; wherein heteroaryl refers to a 5-6 membered aromatic heterocycle comprising 1, 2, 3, or 4 heteroatom ring members independently selected from nitrogen, sulfur and oxygen; wherein cycloalkyl refers to a $C_{3-14}$ non-aromatic cyclic hydrocarbon group; and wherein heterocycloalkyl refers to a 3-20 membered non-aromatic heterocycle comprising at least one heteroatom ring member independently selected from nitrogen, sulfur, oxygen, and phosphorus;

wherein said cancer is associated with elevated expression or activity of FGFR3; and wherein said cancer is selected from bladder cancer, breast cancer, cervical cancer, colorectal cancer, endometrial cancer, head and neck cancer, liver cancer, lung cancer, ovarian cancer, esophageal cancer, gall bladder cancer, multiple myeloma, acute myelogenous leukemia, glioblastoma, and kidney cancer.

2. The method of claim 1, wherein $Ar^1$ is phenyl optionally substituted by 1, 2, 3, or 4 independently selected $R^{A1}$ groups.

3. The method of claim 1, wherein $Ar^1$ is phenyl.

4. The method of claim 1, wherein $R^{A1}$ is independently selected from $NR^cR^d$, $NR^cC(O)R^b$, $NR^cC(O)OR^a$, $NR^cC(O)NR^cR^d$, $c(=NR^e)R^b$, $c(=NR^e)NR^cR^d$, $NR^cC(=NR^e)NR^cR^d$, $NR^cS(O)R^b$, $NR^cS(O)_2R^b$, and $NR^cS(O)_2NR^cR^d$.

5. The method of claim 1, wherein $Ar^2$ is aryl or heteroaryl, each optionally substituted by 1, 2, 3, or 4 independently selected $R^{A2}$ groups.

6. The method of claim 1, wherein $Ar^2$ is phenyl optionally substituted by 1, 2, 3, or 4 independently selected $R^{A2}$ groups.

7. The method of claim 1, wherein $Ar^2$ is pyrazolyl optionally substituted by 1, 2, or 3 independently selected $R^{A2}$ groups.

8. The method of claim 1, wherein $Ar^2$ is heterocycloalkyl optionally substituted by 1, 2, or 3 independently selected $R^{A2}$ groups.

9. The method of claim 1, wherein $Ar^2$ is 1,2,3,4-tetrahydroisoquinolinyl optionally substituted by 1, 2, 3, or 4 independently selected $R^{A2}$ groups.

10. The method of claim 1, wherein B is —$(CR^3R^4)_{m1}$—$(CR^1R^2)$—$(CR^3R^4)_{m2}$—X.

11. The method of claim 10, wherein X is $Cy^5$, CN, or $C(O)NR^5R^6$.

12. The method of claim 1, wherein B is -$L^1$-$(CR^3R^4)_n$-$Cy^1$.

13. The method of claim 12, wherein $L^1$ is C(O)NR.

14. The method of claim 12, wherein n is 1 or 2.

15. The method of claim 1, wherein B is -$Cy^2$-$(L^2)_a$-$(CR^3R^4)_p$-$Cy^3$.

16. The method of claim 15, wherein a is 1.

17. The method of claim 15, wherein a is 0.

18. The method of claim 15, wherein p is 1 or 2.

19. The method of claim 1, wherein B is -$Cy^4$-$L^3$-Y.

20. The method of claim 19, wherein Y is aryl, heteroaryl, or heterocycloalkyl, each optionally substituted by 1, 2, 3, 4, or 5 independently selected $R^{B1}$ groups.

21. The method of claim 19, wherein Y is $C_{3-7}$ cycloalkyl substituted by 1, 2, 3, 4, or 5 independently selected $R^{B2}$ groups.

22. The method of claim 19, wherein Y is $C_{1-6}$ alkyl or $C_{1-6}$ haloalkyl, each substituted by 1, 2, 3, 4, or 5 independently selected $R^x$ groups.

23. The method of claim 1, wherein the compound has Formula IIa:

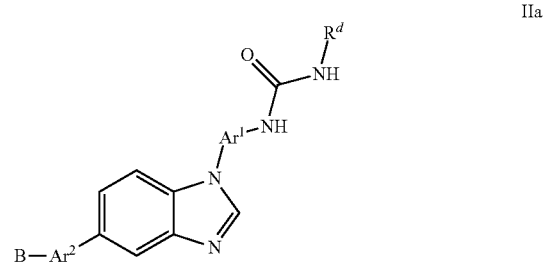

IIa or a pharmaceutically acceptable salt thereof, wherein $R^d$ is $C_{1-4}$ alkyl or $C_{1-4}$ haloalkyl.

24. The method of claim 1, wherein the compound has Formula IIb:

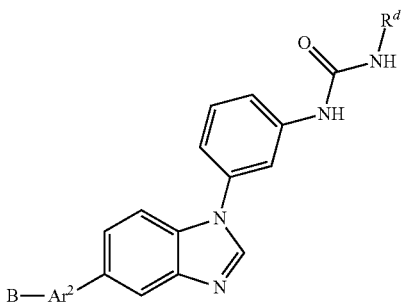

or a pharmaceutically acceptable salt thereof, wherein $R^d$ is $C_{1-4}$ alkyl or $C_{1-4}$ haloalkyl.

25. The method of claim 1, wherein the compound is selected from:

Cyclopropylmethyl 3-{1-[3-({[(2,2,2-trifluoroethyl)amino]carbonyl}amino)phenyl]-1H-benzimidazol-5-yl}benzoate;

N-(Tetrahydrofuran-2-ylmethyl)-3-{1-[3-({[(2,2,2-trifluoroethyl)amino]carbonyl}amino)phenyl]-1H-benzimidazol-5-yl}benzamide;

N-[(1-Methylpiperidin-4-yl)methyl]-3-{1-[3-({[(2,2,2-trifluoroethyl)amino]carbonyl}amino)phenyl]-1H-benzimidazol-5-yl}benzamide;

N-(2-Morpholin-4-ylethyl)-3-{1-[3-({[(2,2,2-trifluoroethyl)amino]carbonyl}amino)phenyl]-1H-benzimidazol-5-yl}benzamide;

N-(Pyridin-3-ylmethyl)-3-{1-[3-({[(2,2,2-trifluoroethyl)amino]carbonyl}amino)phenyl]-1H-benzimidazol-5-yl}benzamide;

N-[(1-Methyl-1H-imidazol-2-yl)methyl]-3-{1-[3-({[(2,2,2-trifluoroethyl)amino]carbonyl}amino)phenyl]-1H-benzimidazol-5-yl}benzamide;

N-(Cyclopropylmethyl)-4-{1-[3-({[(2,2,2-trifluoroethyl)amino]carbonyl}amino)phenyl]-1H-benzimidazol-5-yl}benzamide;

N-(Tetrahydrofuran-2-ylmethyl)-4-{1-[3-({[(2,2,2-trifluoroethyl)amino]carbonyl}amino)phenyl]-1H-benzimidazol-5-yl}benzamide;

N-[(2-Hydroxycyclohexyl)methyl]-4-{1-[3-({[(2,2,2-trifluoroethyl)amino]carbonyl}amino)phenyl]-1H-benzimidazol-5-yl}benzamide;

N-[(1-Methylpiperidin-4-yl)methyl]-4-{1-[3-({[(2,2,2-trifluoroethyl)amino]carbonyl}amino)phenyl]-1H-benzimidazol-5-yl}benzamide;

N-(2-Morpholin-4-ylethyl)-4-{1-[3-({[(2,2,2-trifluoroethyl)amino]carbonyl}amino)phenyl]-1H-benzimidazol-5-yl}benzamide;

N-(Pyridin-3-ylmethyl)-4-{1-[3-({[(2,2,2-trifluoroethyl)amino]carbonyl}amino)phenyl]-1H-benzimidazol-5-yl}benzamide;

N-[(1-Methyl-1H-imidazol-2-yl)methyl]-4-{1-[3-({[(2,2,2-trifluoroethyl)amino]carbonyl}amino)phenyl]-1H-benzimidazol-5-yl}benzamide;

N-Methyl-2-(4-{1-[3-({[(2,2,2-trifluoroethyl)amino]carbonyl}amino)phenyl]-1H-benzimidazol-5-yl}phenyl)propanamide;

N,N-Dimethyl-2-(4-{1-[3-({[(2,2,2-trifluoroethyl)amino]carbonyl}amino)phenyl]-1H-benzimidazol-5-yl}phenyl)propanamide;

N-(Cyclopropylmethyl)-2-(4-{1-[3-({[(2,2,2-trifluoroethyl)amino]carbonyl}amino)phenyl]-1H-benzimidazol-5-yl}phenyl)propanamide;

N-(3-{5-[4-(1-Methyl-2-oxo-2-pyrrolidin-1-ylethyl)phenyl]-1H-benzimidazol-1-yl}phenyl)-N'-(2,2,2-trifluoroethyl)urea;

N-(Tetrahydrofuran-2-ylmethyl)-2-(4-{1-[3-({[(2,2,2-trifluoroethyl)amino]carbonyl}amino)phenyl]-1H-benzimidazol-5-yl}phenyl)propanamide;

N-[3-(5-{4-[2-(3-Cyanopyrrolidin-1-yl)-1-methyl-2-oxoethyl]phenyl}-1H-benzimidazol-1-yl)phenyl]-N'-(2,2,2-trifluoroethyl)urea;

N-[(1-Methyl-1H-imidazol-2-yl)methyl]-2-(4-{1-[3-({[(2,2,2-trifluoroethyl)amino]carbonyl}amino)phenyl]-1H-benzimidazol-5-yl}phenyl)propanamide;

N-[3-(5-{1-[1-(Cyclopropylmethyl)piperidin-4-yl]-1H-pyrazol-4-yl}-1H-benzimidazol-1-yl)phenyl]-N'-(2,2,2-trifluoroethyl)urea;

N-[3-(5-{1-[1-(Cyanomethyl)-2,2,2-trifluoroethyl]-1H-pyrazol-4-yl}-1H-benzimidazol-1-yl)phenyl]-N'-(2,2,2-trifluoroethyl)urea;

N-{3-[5-{1-[(1-Methyl-1H-pyrazol-4-yl)carbonyl]piperidin-4-yl}-1H-pyrazol-4-yl)-1H-benzimidazol-1-yl]phenyl}-N'-(2,2,2-trifluoroethyl)urea;

N-{3-[5-(1-{1-[(1-Methyl-1H-pyrazol-3-yl) sulfonyl]piperidin-4-yl}-1H-pyrazol-4-yl)-1H-benzimidazol-1-yl]phenyl}-N'-(2,2,2-trifluoroethyl)urea;

N-Pyridin-3-yl-4-(4-{1-[3-({[(2,2,2-trifluoroethyl)amino]carbonyl}amino)phenyl]-1H-benzimidazol-5-yl}-1H-pyrazol-1-yl)piperidine-1-carboxamide;

N-[3-(5-{1-[1-(Pyrrolidin-1-ylcarbonyl)piperidin-4-yl]-1H-pyrazol-4-yl}-1H-benzimidazol-1-yl)phenyl]-N'-(2,2,2-trifluoroethyl)urea;

N-[3-(5-{1-[1-(Cyclopropylacetyl)piperidin-4-yl]-1H-pyrazol-4-yl}-1H-benzimidazol-1-yl)phenyl]-N'-(2,2,2-trifluoroethyl)urea;

N-[3-(5-{1-[1-(Cyanoacetyl)piperidin-4-yl]-1H-pyrazol-4-yl}-1H-benzimidazol-1-yl)phenyl]-N'-(2,2,2-trifluoroethyl)urea; and N-[3-(5-{1-[1-(Tetrahydrofuran-2-ylcarbonyl)piperidin-4-yl]-1H-pyrazol-4-yl}-1H-benzimidazol-1-yl)phenyl]-N'-(2,2,2-trifluoroethyl)urea;

or a pharmaceutically acceptable salt of any of the aforementioned.

26. The method of claim 1, wherein said cancer is bladder cancer.

27. The method of claim 1, wherein said cancer is breast cancer.

28. The method of claim 1, wherein said cancer is cervical cancer.

29. The method of claim 1, wherein said cancer is colorectal cancer.

30. The method of claim 1, wherein said cancer is endometrial cancer.

31. The method of claim 1, wherein said cancer is head and neck cancer.

32. The method of claim 1, wherein said cancer is liver cancer.

33. The method of claim 1, wherein said cancer is lung cancer.

34. The method of claim 33, wherein said lung cancer is non-small cell lung carcinoma.

35. The method of claim 33, wherein said lung cancer is adenocarcinoma or small cell lung cancer.

36. The method of claim 1, wherein said cancer is ovarian cancer.

37. The method of claim 1, wherein said cancer is esophageal cancer.

38. The method of claim 1, wherein said cancer is gall bladder cancer.

39. The method of claim 1, wherein said cancer is multiple myeloma.

40. The method of claim 1, wherein said cancer is acute myelogenous leukemia.

41. The method of claim 1, wherein said cancer is glioblastoma.

42. The method of claim 1, wherein said cancer is kidney cancer.

* * * * *